US010159816B2

(12) United States Patent
Tsai et al.

(10) Patent No.: US 10,159,816 B2
(45) Date of Patent: Dec. 25, 2018

(54) SYSTEMS AND METHODS FOR PREVENTING, MITIGATING, AND/OR TREATING DEMENTIA

(71) Applicant: Massachusetts Institute of Technology, Cambridge, MA (US)

(72) Inventors: Li-Huei Tsai, Cambridge, MA (US); Emery Brown, Brookline, MA (US); Hannah Iaccarino, Somerville, MA (US); Anthony James Martorell, Cambridge, MA (US); Chinnakkaruppan Adaikkan, Somerville, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 15/647,157

(22) Filed: Jul. 11, 2017

(65) Prior Publication Data

US 2017/0304584 A1 Oct. 26, 2017

Related U.S. Application Data

(63) Continuation of application No. 15/360,637, filed on Nov. 23, 2016.

(60) Provisional application No. 62/259,187, filed on Nov. 24, 2015.

(51) Int. Cl.
*A61M 21/00* (2006.01)
*A61H 23/00* (2006.01)
*A61N 5/06* (2006.01)

(52) U.S. Cl.
CPC ............ *A61M 21/00* (2013.01); *A61H 23/00* (2013.01); *A61N 5/062* (2013.01); *A61N 5/0622* (2013.01); *A61M 2021/0022* (2013.01); *A61M 2021/0027* (2013.01); *A61M 2021/0044* (2013.01); *A61N 2005/063* (2013.01); *A61N 2005/0651* (2013.01); *A61N 2005/0662* (2013.01)

(58) Field of Classification Search
CPC ...... A61M 21/00; A61N 5/062; A61N 5/0622
USPC .................................................... 600/27-28
See application file for complete search history.

(56) References Cited

U.S. PATENT DOCUMENTS

| 5,934,967 | A | 8/1999 | Brown et al. |
|---|---|---|---|
| 6,071,229 | A | 6/2000 | Rubins |
| 6,167,298 | A | 12/2000 | Levin |
| 6,234,953 | B1 | 5/2001 | Thomas et al. |
| 6,539,263 | B1 | 3/2003 | Schiff et al. |
| 7,715,910 | B2 | 5/2010 | Hargrove et al. |
| 7,769,439 | B2 | 8/2010 | Vesely et al. |
| 8,121,694 | B2 | 2/2012 | Molnar et al. |
| 8,267,851 | B1 | 9/2012 | Kroll |
| 8,280,502 | B2 | 10/2012 | Hargrove et al. |
| 8,380,314 | B2 | 2/2013 | Panken et al. |
| 8,423,144 | B2 | 4/2013 | Tass et al. |
| 8,543,219 | B2 | 9/2013 | Tass |
| 8,577,470 | B2 | 11/2013 | Assaf et al. |
| 8,591,392 | B2 | 11/2013 | Bentwich et al. |
| 8,636,640 | B2 | 1/2014 | Chang |
| 8,700,167 | B2 | 4/2014 | Sabel |
| 8,892,207 | B2 | 11/2014 | Nelson et al. |
| 8,914,119 | B2 | 12/2014 | Wu et al. |
| 8,932,218 | B1 | 1/2015 | Thompson |
| 8,942,809 | B2 | 1/2015 | Assaf et al. |
| 9,119,583 | B2 | 9/2015 | Tass |
| 9,302,069 | B2 | 4/2016 | Tass et al. |
| 2006/0263332 | A1 | 11/2006 | Li et al. |
| 2007/0225773 | A1 | 9/2007 | Shen et al. |
| 2008/0227139 | A1 | 9/2008 | Deisseroth et al. |
| 2009/0153800 | A1 | 6/2009 | Bassi et al. |
| 2009/0312624 | A1 | 12/2009 | Berridge et al. |
| 2011/0152967 | A1 | 6/2011 | Simon et al. |
| 2012/0065709 | A1 | 3/2012 | Dunning et al. |
| 2012/0271374 | A1 | 10/2012 | Nelson et al. |
| 2012/0289869 | A1 | 11/2012 | Tyler |
| 2013/0066392 | A1 | 3/2013 | Simon et al. |
| 2014/0135680 | A1 | 5/2014 | Peyman |
| 2015/0196762 | A1 | 7/2015 | Amurthur et al. |

FOREIGN PATENT DOCUMENTS

| WO | WO 2001/84141 | 11/2001 |
|---|---|---|
| WO | WO 2014/179331 | 11/2014 |

OTHER PUBLICATIONS

Aronov, D. et al., "Engagement of neural circuits underlying 2D spatial navigation in a rodent virtual reality system," Neuron, vol. 84 (Oct. 2014): 442-456.
Barton, A. "Sound vibration treatment may boost brain activity in Alzheimer's patients," The Globe and Mail (2016): http://www.theglobeandmail.com/life/health-and-fitness/health/sound-vibration-treatment-may-boost-brain-activity-in-alzheimers-patients/article29771676/.
Bartos, M. et al., "Synaptic mechanisms of synchronized gamma oscillations in inhibitory interneuron networks," Nature Reviews Neuroscience, vol. 8 (Januray 2007): 45-56.
Basar, E. et al., "Delay of cognitive gamma responses in Alzheimer's disease," NeuroImage: Clinical, vol. 11 (2016): 106-115.

(Continued)

*Primary Examiner* — John Lacyk
(74) *Attorney, Agent, or Firm* — Smith Baluch LLP

(57) ABSTRACT

The present disclosure provides systems and methods for at least one of preventing, reducing, and treating a level of or change in at least one of amyloid-β (Aβ) peptide, C-terminal fragment-β (β-CTF), β-secretase (BACE1), γ-secretase, neuroinflammation, and/or dementia (e.g., Alzheimer's disease or age-related decline) in a subject by inducing synchronized gamma oscillations in the brain of the subject using, for example, a stimulus-emitting device to emit a stimulus (e.g., light, sound, and/or haptic) at a frequency (e.g., about 40 Hz) that synchronously activates in vivo a specific cell type (e.g., fast-spiking-parvalbumin (FS-PV) immunoreactive interneurons) and/or brain region (e.g., a sensory cortex and/or hippocampus) of the subject.

28 Claims, 128 Drawing Sheets

(56) References Cited

OTHER PUBLICATIONS

Bero, A. et al., "Neuronal activity regulates the regional vulnerability to amyloid-β deposition," Nature Neuroscience, vol. 14 (May 2011): 750-756.

Boissonneault, V. et al., "Powerful beneficial effects of macrophage colony-stimulating factor on beta-amyloid deposition and cognitive impairment in Alzheimer's disease," Brain, vol. 132 (Apr. 2009): 1078-1092.

Bragin, A. et al., "Gamma (40-100 Hz) oscillation in the hippocampus of the behaving rat," Journal of Neuroscience, vol. 15 (Jan. 1995): 47-60.

Busche, M. et al., "Decreased amyloid-β and increased neuronal hyperactivity by immunotherapy in Alzheimer's models," Nature Neuroscience, vol. 18 (Dec. 2015): 1725-1727.

Buzsaki, G. "Theta oscillations in the hippocampus," Neuron, vol. 33 (Jan. 2002): 325-340.

Buzsaki, G. et al., "Hippocampal network patterns of activity in the mouse," Neuroscience, vol. 116 (2003): 201-211.

Buzsaki, G. "Rhythms of the Brain," Oxford University Press (2006).

Buzsaki et al., "Mechanisms of Gamma Oscillations," Rev. Neurosci. 35, 203-23 (2012).

Buzsaki, G. et al., "Scaling brain size, keeping timing: evolutionary preservation of brain rhythms," Neuron, vol. 80 (Oct. 2013): 751-764.

Cardin, J. et al., "Driving fast-spiking cells induces gamma rhythm and controls sensory responses," Nature, vol. 459 (Apr. 2009): 663-667.

Carr, M. et al., "Hippocampal replay in the awake state: a potential substrate for memory consolidation and retrieval," Nature Neuroscience, vol. 14 (Feb. 2011): 147-153.

Carr, M. et al., "Transient slow gamma synchrony underlies hippocampal memory replay," Neuron, vol. 75 (Aug. 2012): 700-713.

Cataldo, A. et al., "Endocytic pathway abnormalities precede amyloid beta deposition in sporadic Alzheimer's disease and Down syndrome: differential effects of APOE genotype and presenilin mutations," American Journal of Pathology, vol. 157 (2000): 277-286.

Chitu, V. et al., "Colony-stimulating factor-1 in immunity and inflammation," Current Opinion in Immunology, vol. 18 (Feb. 2006): 39-48.

Chiu, I. et al., "A neurodegeneration-specific gene-expression signature of acutely isolated microglia from an amyotrophic lateral sclerosis mouse model," Cell Reports, vol. 4 (Jul. 2013): 385-401.

Chung, K. et al., "Structural and molecular interrogation of intact biological systems," Nature, vol. 497 (May 2013): 332-337.

Cirrito, J. et al., "In vivo assessment of brain interstitial fluid with microdialysis reveals plaque-associated changes in amyloid-beta metabolism and half-life," The Journal of Neuroscience, vol. 23 (Oct. 2003): 8844-8853.

Clements-Cortes, A. "Sound Stimulation in Patients With Alzheimer's Disease," Annals of Long-Term Care: Clinical Care and Aging, vol. 23 (May 2015): 10-16.

Colgin, L. et al., "Frequency of gamma oscillations routes flow of information in the hippocampus," Nature, vol. 462 (Nov. 2009): 353-357.

Colgin, L. et al., "Gamma oscillations in the hippocampus," Physiology, vol. 25 (Oct. 2010): 319-329.

Cronk, J. et al., "Methyl-CpG binding protein 2 regulates microglia and macrophage gene expression in response to inflammatory stimuli," Immunity, vol. 42 (Apr. 2015): 679-691.

Crotti, A. et al., "Mutant Huntingtin promotes autonomous microglia activation via myeloid lineage-determining factors," Nature Neuroscience, vol. 17 (Apr. 2014): 513-521.

Das, U. et al., "Activity-induced convergence of App and Bace-1 in acidic microdomains via an endocytosis-dependent pathway," Neuron, vol. 79 (Aug. 2013): 447-460.

Eckhorn, R. et al., "Coherent Oscillations: a Mechanism of Feature Linking in the Visual Cortex," Biological Cybernetics, vol. 60 (1988): 121-130.

Erny, D. et al., "Host microbiota constantly control maturation and function of microglia in the CNS," Nature Neuroscience, vol. 18 (Jun. 2015): 965-977.

Foster, D. et al., "Reverse replay of behavioural sequences in hippocampal place cells during the awake state," Nature, vol. 440 (Mar. 2006):680-683.

Fries, P. et al., "The gamma cycle," Trends in Neurosciences, vol. 30 (Jul. 2007): 309-316.

Gillepsie, A. et al., "Apolipoprotein E4 Causes Age-Dependent Disruption of Slow Gamma Oscillations during Hippocampal Sharp-Wave Ripples," Neuron, vol. 90 (May 2016): 740-751.

Gjoneska, E. et al., "Conserved epigenomic signals in mice and humans reveal immune basis of Alzheimer's disease," Nature, vol. 518 (Feb. 2015): 365-369.

Gosselin, D. et al., "Environment drives selection and function of enhancers controlling tissue-specific macrophage identities," Cell, vol. 159 (Dec. 2014): 1327-1340.

Goutagny, R. et al., "Alterations in hippocampal network oscillations and theta-gamma coupling arise before Aβ overproduction in a mouse model of Alzheimer's disease," European Journal of Neuroscience, vol. 37 (Jun. 2013): 1896-1902.

Gray, C. et al., "Oscillatory responses in cat visual cortex exhibit inter-columnar synchronization which reflects global stimulus properties," Nature, vol. 338 (Mar. 1989): 334-337.

Gray, C. et al., "Chattering cells: superficial pyramidal neurons contributing to the generation of synchronous oscillations in the visual cortex," Science, vol. 274 (Oct. 1996): 109-113.

Harvey, C. et al., "Intracellular dynamics of hippocampal place cells during virtual navigation," Nature, vol. 461 (Oct. 2009): 941-946.

Helwig, M. et al., "The neuroendocrine protein 7B2 suppresses the aggregation of neurodegenerative disease-related proteins," The Journal of Biological Chemistry, vol. 288 (Jan. 2013): 1114-1124.

Hen Eka, M. et al., "Innate immune activation in neurodegenerative disease," Nature Reviews Immunology, vol. 14 (Jul. 2014): 463-477.

Hermann, C. et al., "Human EEG responses to 1-100 Hz flicker: resonance phenomena in visual cortex and their potential correlation to cognitive phenomena," Experimental Brain Research, vol. 137 (Apr. 2001): 346-353.

Hermann, C. et al., "Human Eeg gamma oscillation in neuropsychiatric disorders," Clinical Neurophysiology, vol. 116 (Sep. 2006): 2719-2733.

Hsiao, F. et al., "Altered Oscillation and Synchronization of Default-Mode Network Activity in Mild Alzheimer's Disease Compared to Mild Cognitive Impairment: an Electrophysiological Study," PLOS One, vol. 8 (Jul. 2013): 1-10.

Huang, S. et al., "Cell-intrinsic lysosomal lipolysis is essential for alternative activation of macrophages," Nature Immunology, vol. 15 (Sep. 2014): 846-855.

Iliff, J. et al., "A Paravascular Pathway Facilitates CSF Flow Through the Brain Parenchyma and the Clearance of Interstitial Solutes, Including Amyloid β," Science Trandlational Medicine, vol. 4 (Aug. 2012): 147.

Israel, M. et al., "Probing sporadic and familial Alzheimer's disease using induced pluripotent stem cells," Nature, vol. 482 (Jan. 2012): 216-220.

Jeong, J. "EEG dynamics in patients with Alzheimer's disease," Clinical Neurophysiology, vol. 115 (Aug. 2004): 1490-1505.

Koenig, T. et al., "Decreased EEG synchronization in Alzheimer's disease and mild cognitive impairment," Neurobiology of Aging, vol. 26 (Feb. 2005): 165-171.

Kurudenkandy, F. et al., "Amyloid-β-Induced Action Potential Desynchronization and Degradation of Hippocampal Gamma Oscillations Is Prevented by Interference with Peptide Conformation Change and Aggregation," The Journal of Neuroscience, vol. 34 (Aug. 2014): 11416-11425.

Kreutzberg, G. "Microglia: a sensor for pathological events in the CNS," Trends in Neurosciences, vol. 19 (Sep. 1996): 312-318.

Leinenga, G. et al., "Scanning ultrasound removes amyloid-β and restores memory in an Alzheimer's disease mouse model," Science Translational Medicine, vol. 7 (Mar. 2015): 278.

Li, F. et al., "Effect of electroacupuncture stimulation of "Baihui" (GV 20) and "Yongquan" (KI 1) on expression of hippocampal

(56) References Cited

OTHER PUBLICATIONS amyloid-β and low density lipoprotein receptor-related protein-1 in APP/PS 1 transgenic mice," Zhen Ci Yan Jiu, vol. 40 (Feb. 2015).
Lok, K. et al., "Characterization of the APP/PS1 mouse model of Alzheimer's disease in senescence accelerated background," Neuroscience Letters, vol. 557 (Dec. 2013): 84-89.
Mastrangelo, M. et al., "Detailed immunohistochemical characterization of temporal and spatial progression of Alzheimer's disease-related pathologies in male triple-transgenic mice," BMC Neuroscience, vol. 9 (Aug. 2008): 1-31.
Mitrasinovic, O. et al., "Microglial overexpression of the M-CSF receptor augments phagocytosis of opsonized Aβ," Neurobiology of Aging, vol. 24 (Oct. 2003): 807-815.
Oakley, H. et al., "Intraneuronal beta-amyloid aggregates, neurodegeneration, and neuron loss in transgenic mice with five familial Alzheimer's disease mutations: potential factors in amyloid plaque formation," Journal of Neuroscience, vol. 26 (Oct. 2006): 10129-10140.
Ohmi, K. et al., "Defects in the medial entorhinal cortex and dentate gyrus in the mouse model of Sanfilippo syndrome type B," Plos One, vol. 6 (Nov. 2011): 1-10.
Palop, J. et al., "Aberrant excitatory neuronal activity and compensatory remodeling of inhibitory hippocampal circuits in mouse models of Alzheimer's disease," Neuron, vol. 55 (Sep. 2007): 697-711.
Pericic, D. et al., "Sex differences in the response to GABA antagonists depend on the route of drug administration," Experimental Brain Research, vol. 115 (Jun. 1997): 187-190.
Raivich, G. et al., "Neuroglial activation repertoire in the injured brain: graded response, molecular mechanisms and cues to physiological function," Brain Research Reviews, vol. 30 (Aug. 1999): 77-105.
Ravassard, P. et al., "Multisensory control of hippocampal spatiotemporal selectivity," Science, vol. 340 (Jun. 2013): 1342-1346.
Sauer et al., "Impaired fast-spiking interneuron function in a genetic mouse modef of deperession,"eLIFE, vol. 4., Mar. 5, 2015, pp. 1-20.
Selkoe, D. et al., "The role of APP processing and trafficking pathways in the formation of amyloid beta-protein," Annals of the New York Academy of Sciences (Jan. 1996): 57-64.
Siegle, J. et al., "Enhancement of Encoding and retrieval functions through theta phase-specific manipulation of hippocampus," ELife Sciences Publications (Jul. 2014).
Stam, C. et al., "Generalized synchronization of MEG recordings in Alzheimer's Disease: evidence for involvement of the gamma band," Journal of Clinical Neurophysiology, vol. 19 (Dec. 2002): 562-574.
Subramanian, A. et al., "Gene set enrichment analysis: A knowledge-based approach for interpreting genorne-wide expression profiles," PNAS, vol. 102 (Aug. 2005): 15545-15550.
Sudol, K. et al., "Generating Differentially Targeted Amyloid-β Specific Intrabodies as a Passive Vaccination Strategy for Alzheimer's Disease," Molecular Therapy, vol. 17 (Dec. 2009): 2031-2040.
Thakurela, S. et al., "Dynamics and function of distal regulatory elements during neurogenesis and neuroplasticity," Genome Research, vol. 25 (Sep. 2015): 1309-1324.
Traub, R. et al., "Analysis of gamma rhythms in the rat hippocampus in vitro and in vivo," the Journal of Physiology, vol. 493 (Jun. 1996): 471-484.
Trapnell, C. et al., "Transcript assembly and quantification by RNA-Seq reveals unannotated transcripts and isoforrn switching during cell differentiation," Nature Biotechnology, vol. 28 (May 2010): 511-515.
Trapnell, C. et al., "Differential gene and transcript expression analysis of RNA-seq experiments with TopHat and Cufflinks," Nature Protocols, vol. 7 (2012): 562-578.
Verret, L. et al., "Inhibitory interneuron deficit links altered network activity and cognitive dysfunction in Alzheimer model," Cell, vol. 149 (Apr. 2012): 708-721.
Wang, Y. et al., "TREM2 lipid sensing sustains the microglial response in an Alzheimer's disease model," Cell, vol. 160 (Mar. 2015): 1061-1071.
Ylinen, A. et al., "Sharp wave-associated high-frequency oscillation (200 Hz) in the intact hippocampus: network and intracellular mechanisms," Journal of Neuroscience, vol. 15 (Jan. 1995): 30-46.
Yoshiyama, Y. et al., "Synapse loss and microglial activation precede tangles in a P301S tauopathy mouse model," Neuron, vol. 53 (Feb. 2007): 337-351.
Yu, H. et al., "Tet3 regulates synaptic transmission and homeostatic plasticity via Dna oxidation and repair," Nature Neuroscience, vol. 18 (Jun. 2015): 836-843.
Zhang, Y. et al., "An RNA-sequencing transcriptome and splicing database of glia, neurons, and vascular cells of the cerebral cortex," Journal of Neuroscience, vol. 34 (Sep. 2014): 11929-11947.
"Brainsway: Deep TMS Therapy," Brainsway (2014): http://www.brainsway.com/us.
International Search Report and Written Opinion issued by the International Searching Authority for Internaltional Application No. PCT/US16/63536, dated Mar. 27, 2017, 19 pages.
"40hz Light Therapy addressing Alzheimer's news!" Indiegogo https://www.indiegogo.com/projects/40hz-light-therapy-addressing-alzheimer-s-news#/, https://www.indiegogo.com, Internet Archive Wayback Machine earliest Internet archived date Oct. 29, 2017, 6 pages.
Fisher Wallace Stimulator http.//www.fisherwallace.com/, Internet Archive Wayback Machine earliest Internet archived date Jul. 13.2017, 7 pages.
"Good Vibrations Can Help Alzheimer's Patients," Awakening from Alzheimer's http://www.awakeningfromalzheimers.com/good-vibrations-can-help-alzheimers-patients/, Internet Archive Wayback Machine earliest Internet archived date Nov. 2, 2016, 8 pages.
Mind Alive Inc. http://mindalive.com/ Internet Archive Wayback Machine earliest Internet archived date Mar. 2, 2001, 2 pages.
Mind Gear http://Mindlightz.com, Internet Archive Wayback Machine earliest Internet archived date Mar. 1, 2015, 5 pages.
Mind Machines http://www.mindmachines.com/: Internet Archive Wayback Machine earliest Internet archived date Dec. 7, 1998, 4 pages.
Mind Mods http://www.mindmods.com/, Internet Archive Wayback Machine earliest. Internet archived date Mar. 12, 2008, 2 pages.
Mind Place http://mindplace.com/, Internet Archive Wayback Machine earliest Internet archived date Dec. 2, 1998, 4 pages.
Neuronix http://neuronixmedical.com, Internet Archive Wayback Machine earliest Internet archived date Nov. 16, 2009, 2 pages.
Neuronix http://neurotronics.eu/, Internet Archive Wayback Machine earliest Internet archived date Sep. 24, 2008, 2 pages.
Paro Therapeutic Robot http://www.parorobots.com/: Internet Archive Wayback Machine earliest Internet Archived date Dec. 4, 2008, 2 pages.
"PSIO Manual," PSiO http://www.psioplanet.com/download/manuals/manuel-psio-1.1-EN.pdf, http://www.psoplanet.com/, Internet Archive Wayback Machine earliest Internet archived date Mar. 2, 2013, 16 pages.
Transparent Corporation https://www.transparentcorp.com/, Internet Archive Wayback Machine earliest Internet archived date Jan. 10, 1998, 3 pages.
Final Office Action dated Jun. 4, 2018 for U.S. Appl. No. 15/360,637, 11 pages.

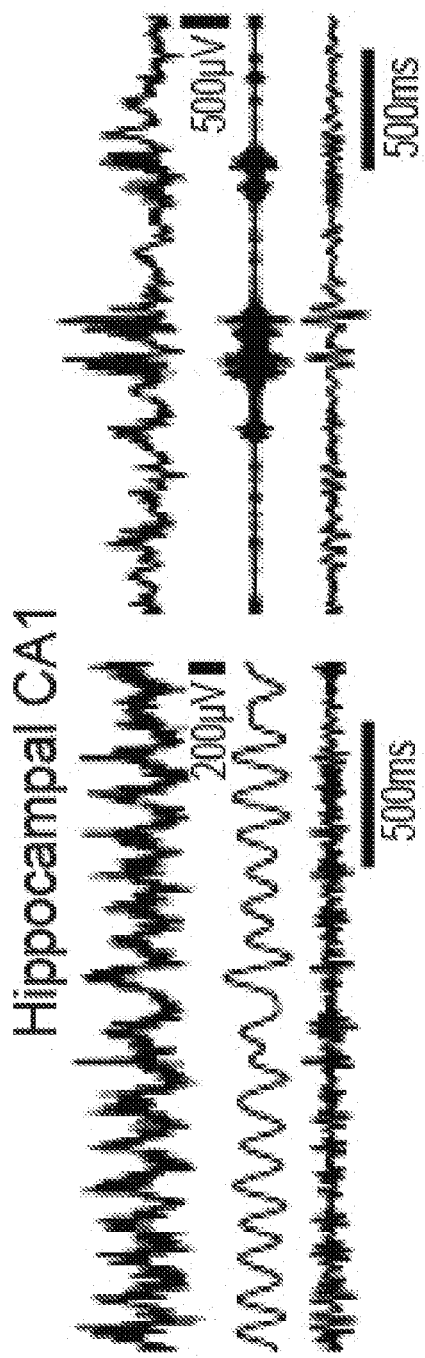

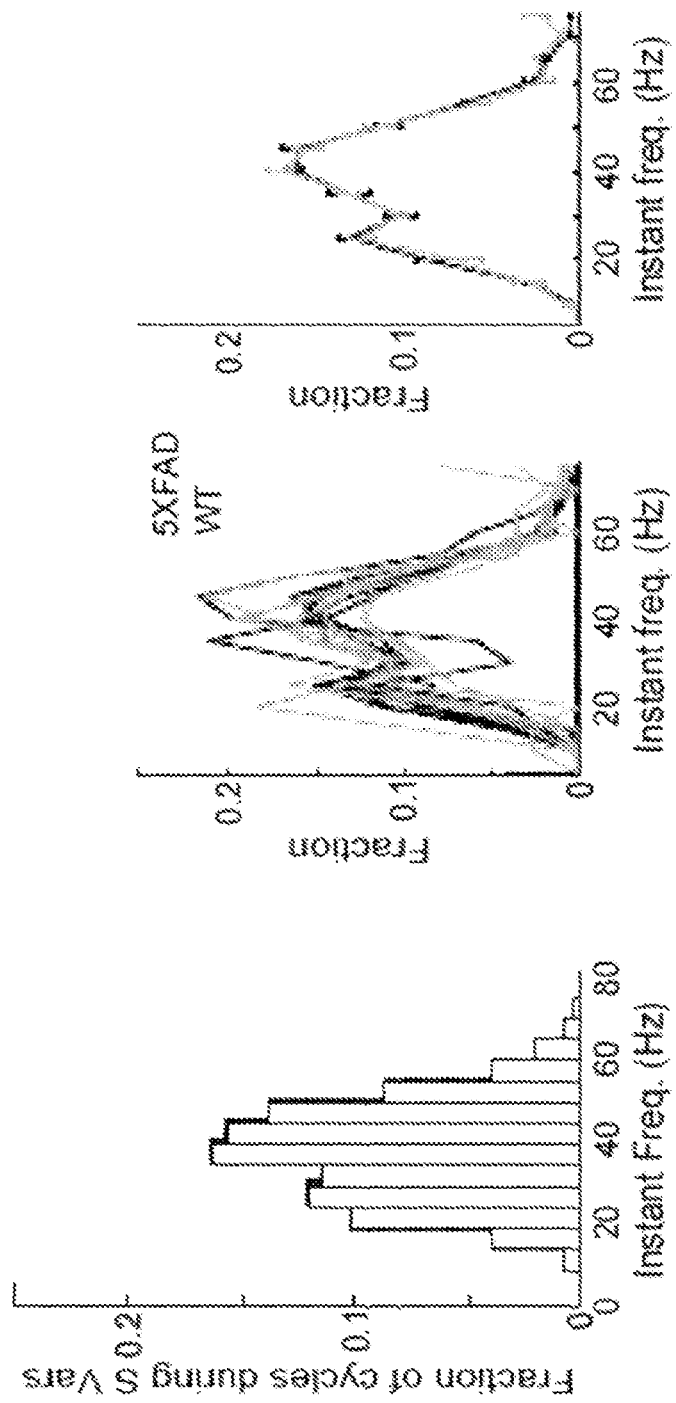

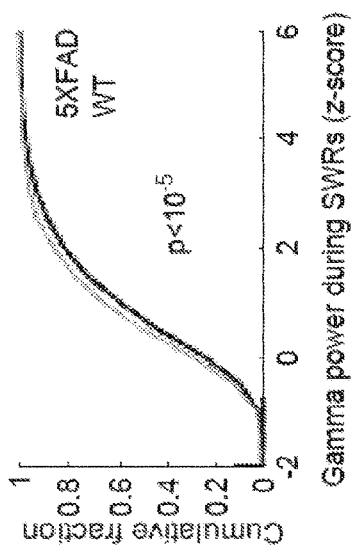
FIG. 6A
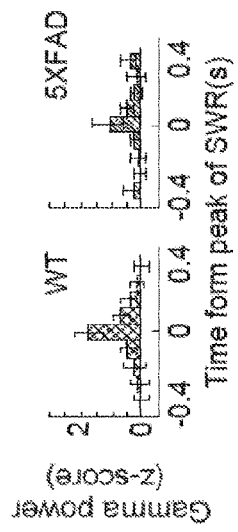
FIG. 6C
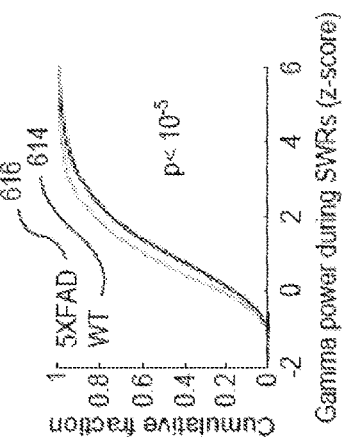
FIG. 6B
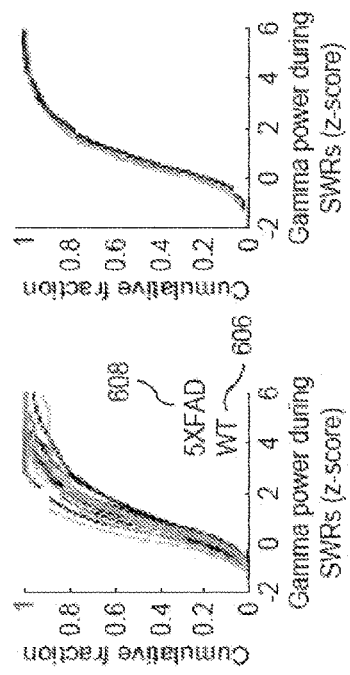
FIG. 6D
FIG. 6E

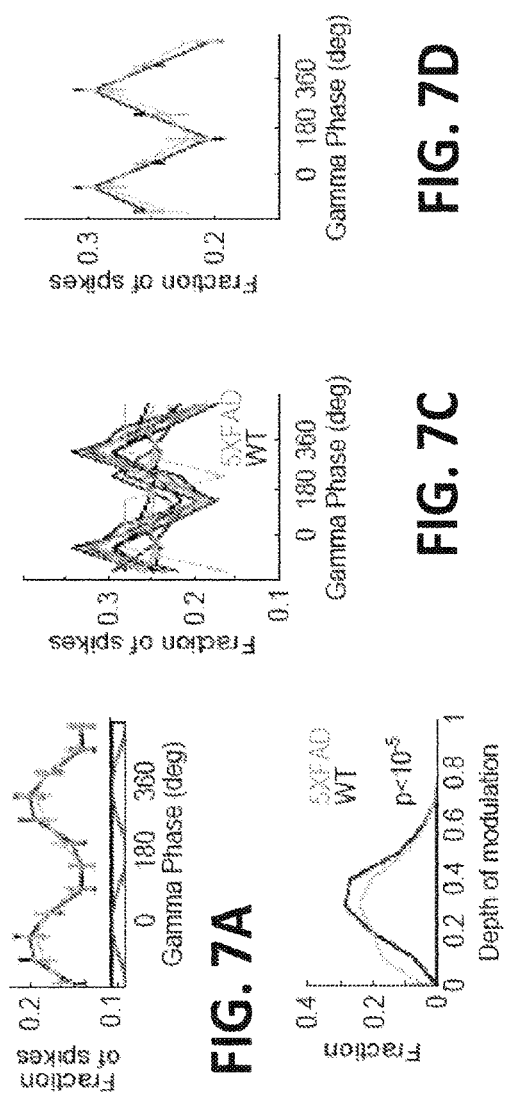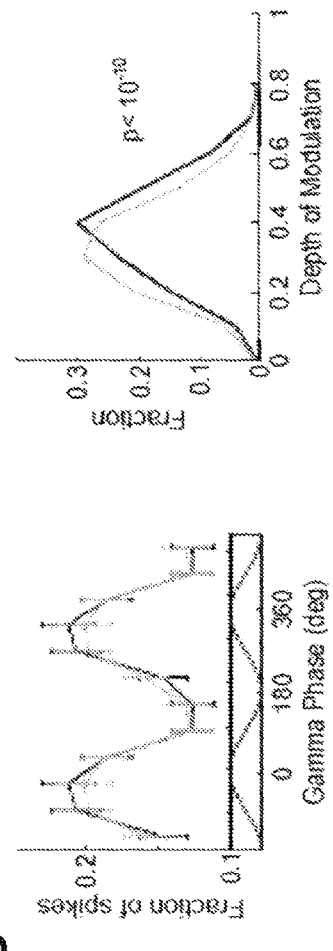
FIG. 7A FIG. 7B FIG. 7C FIG. 7D FIG. 7E FIG. 7F

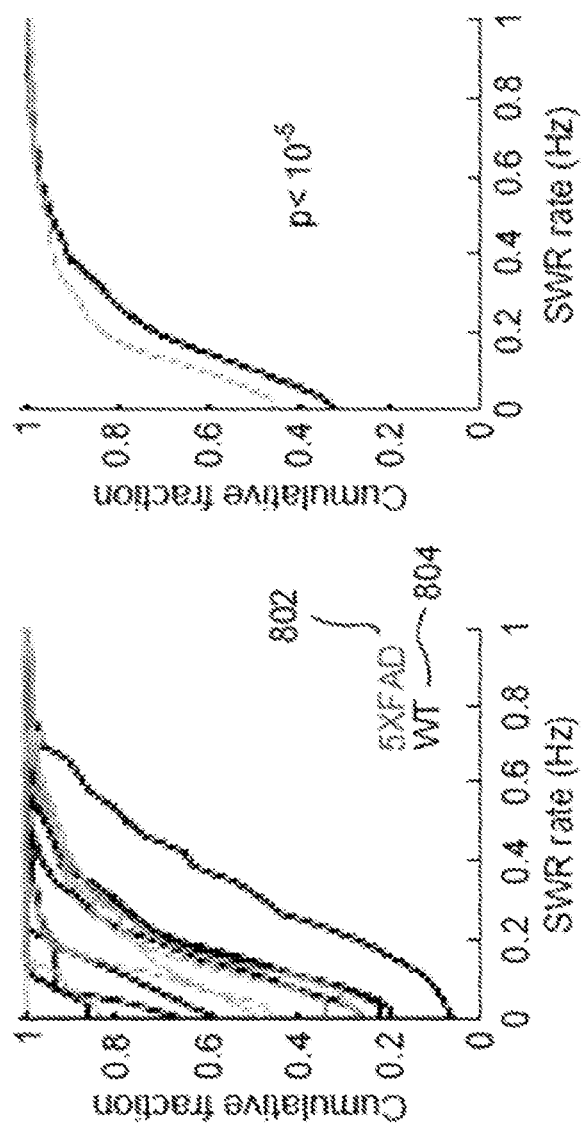

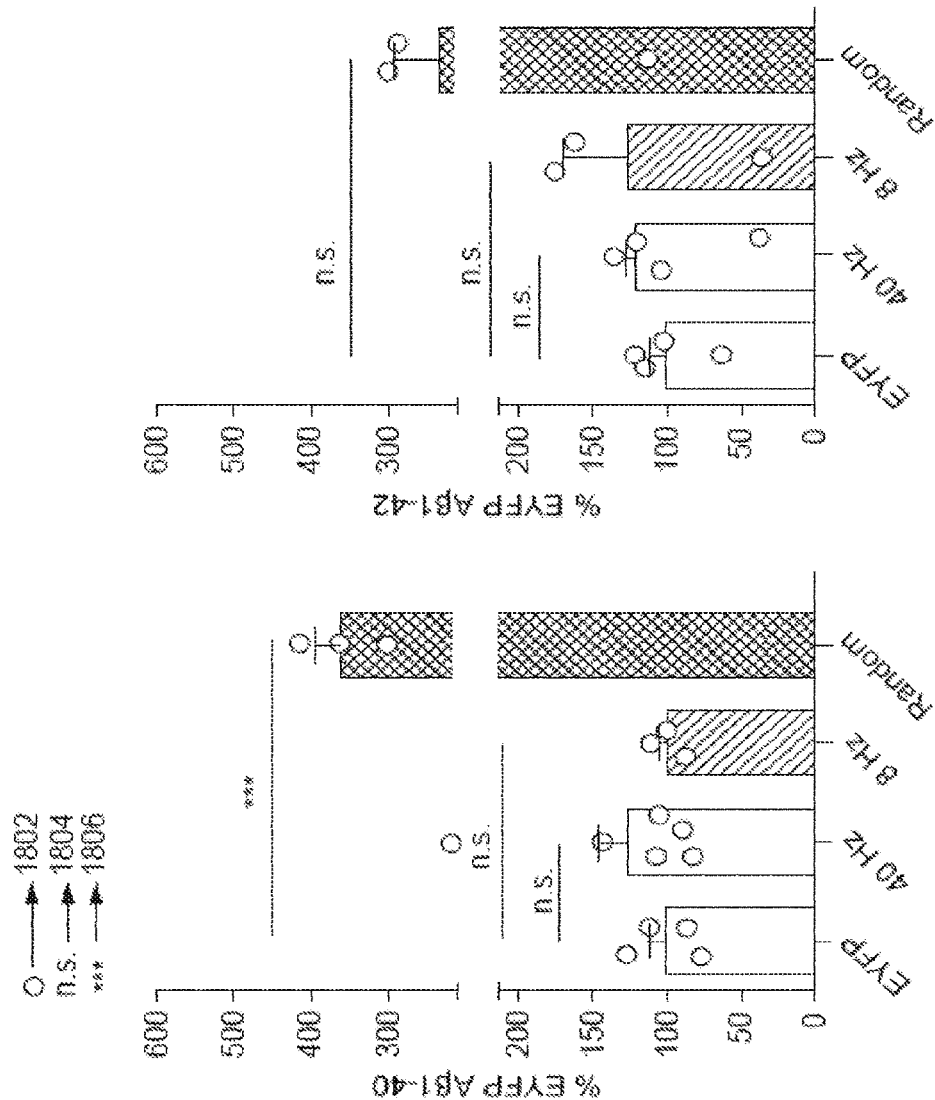

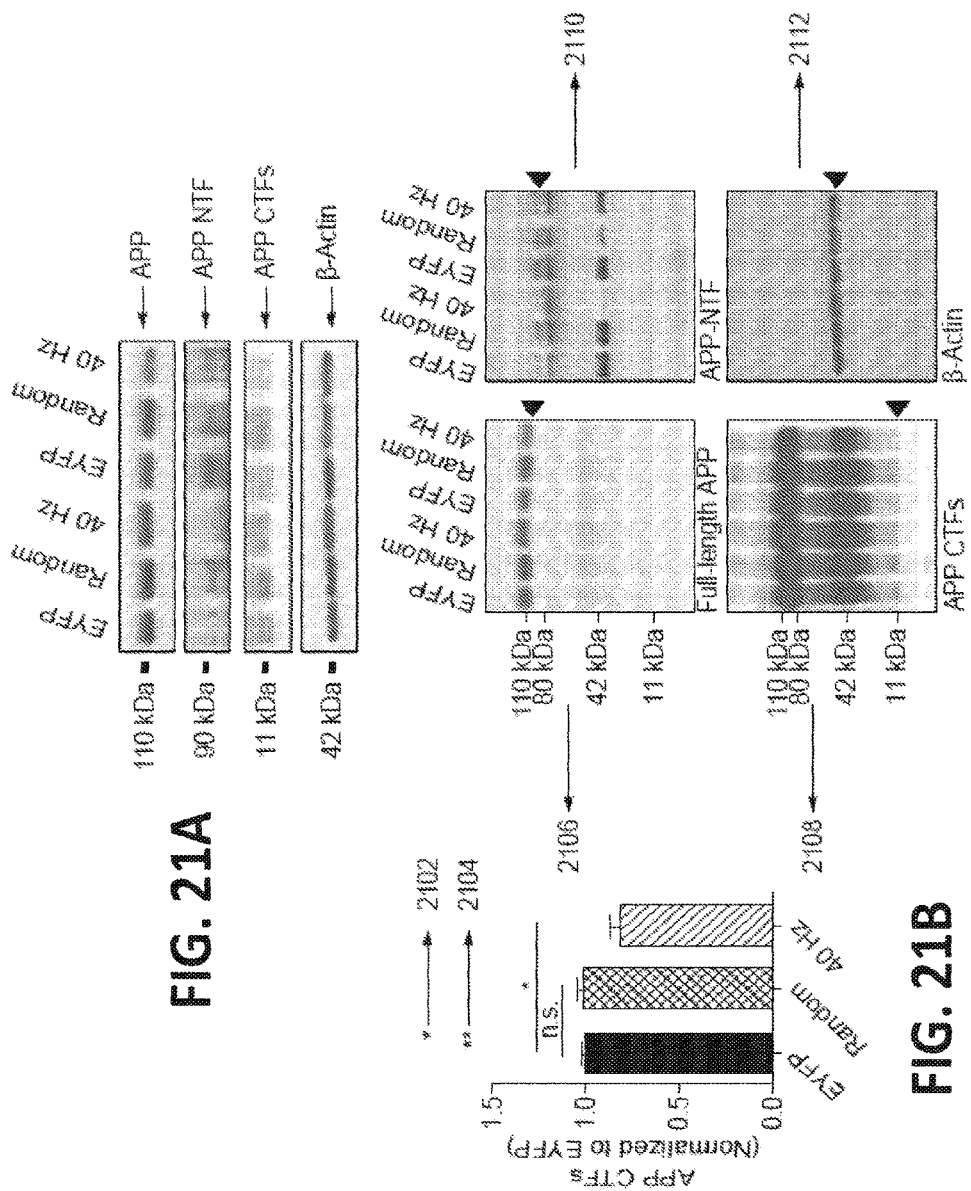

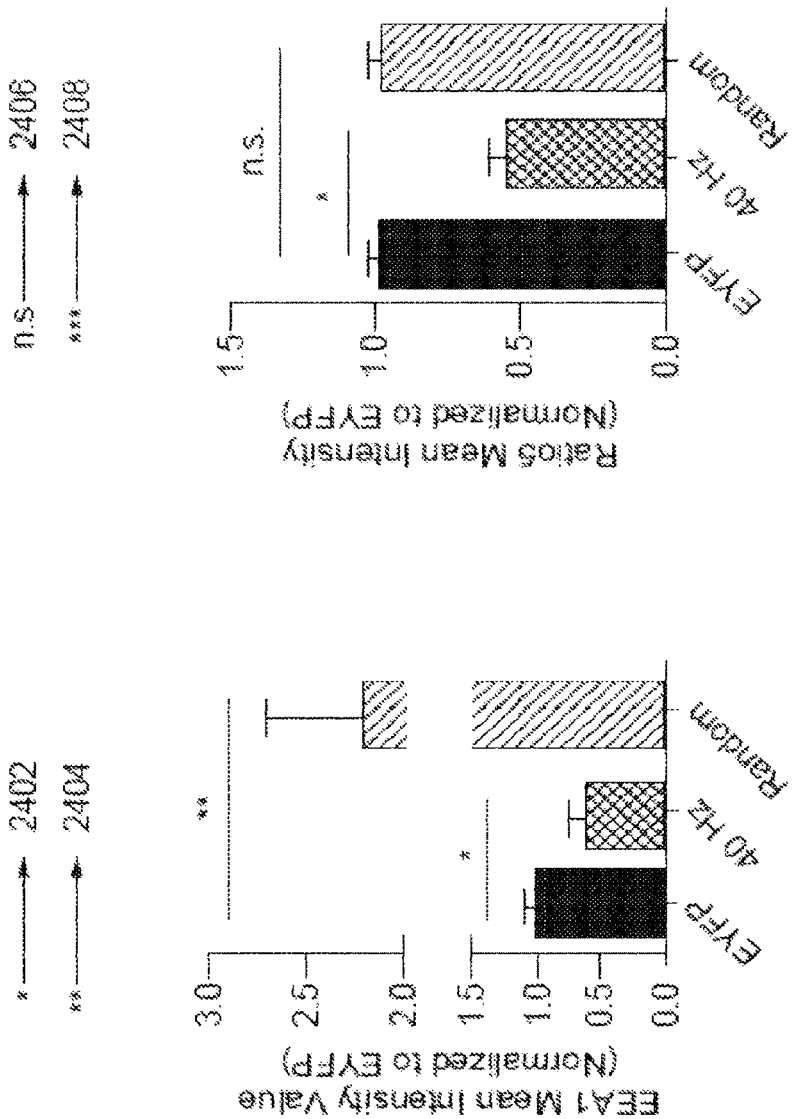

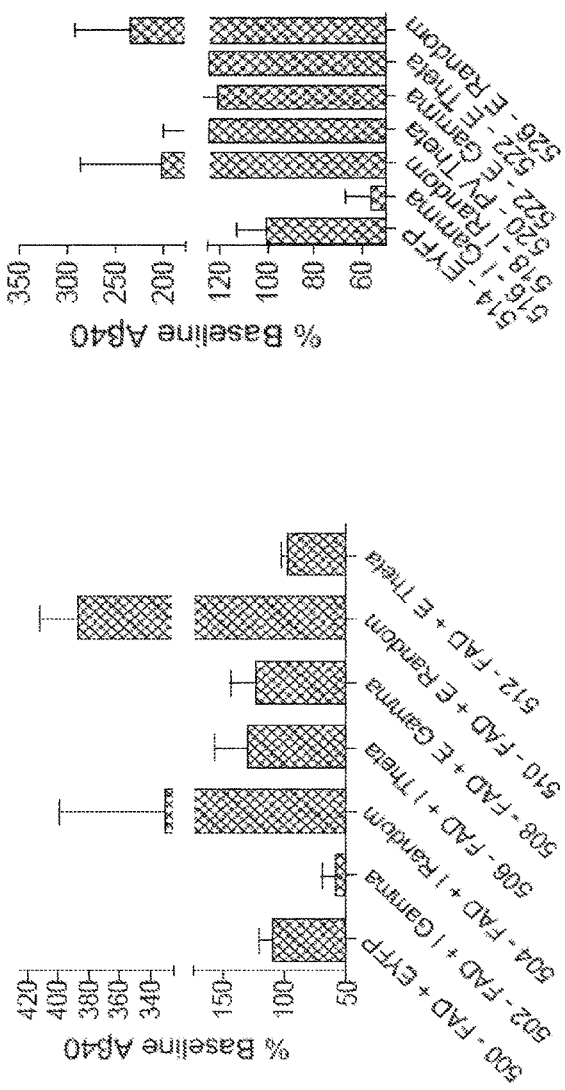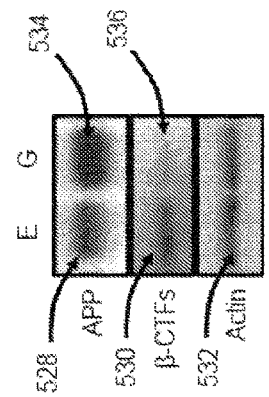

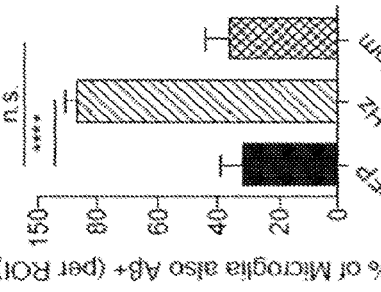
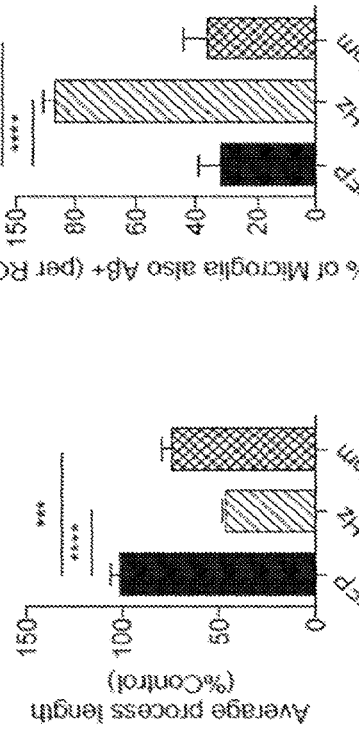
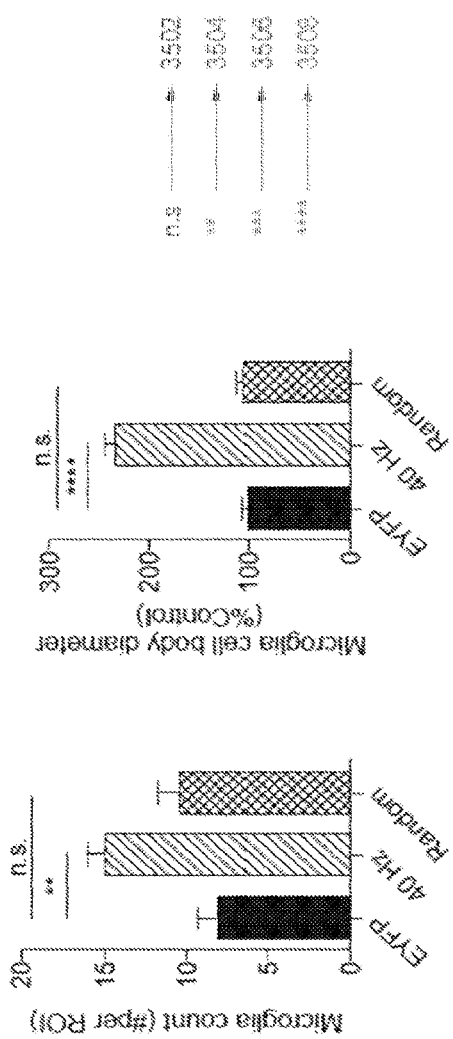
FIG. 35A, FIG. 35B, FIG. 35C, FIG. 35D

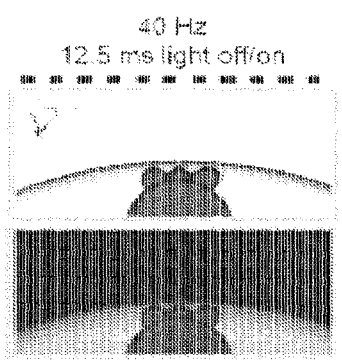
FIG. 43A
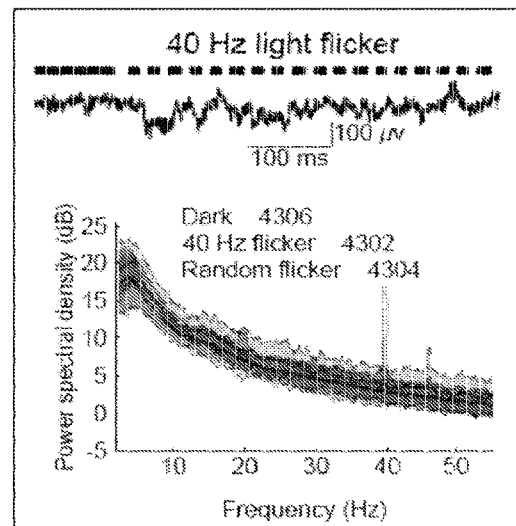
FIG. 43B
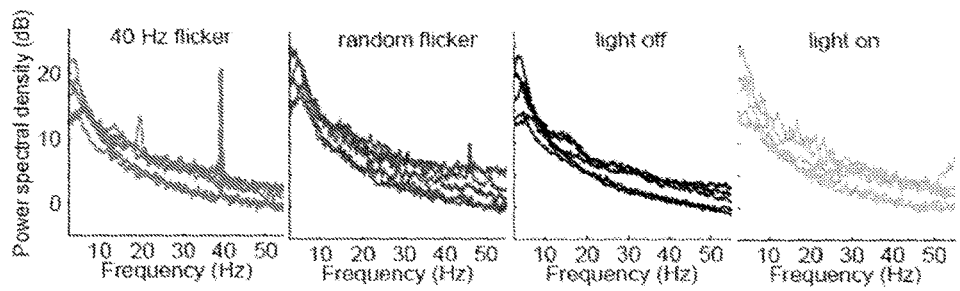
FIG. 43C FIG. 43D FIG. 43E FIG. 43F

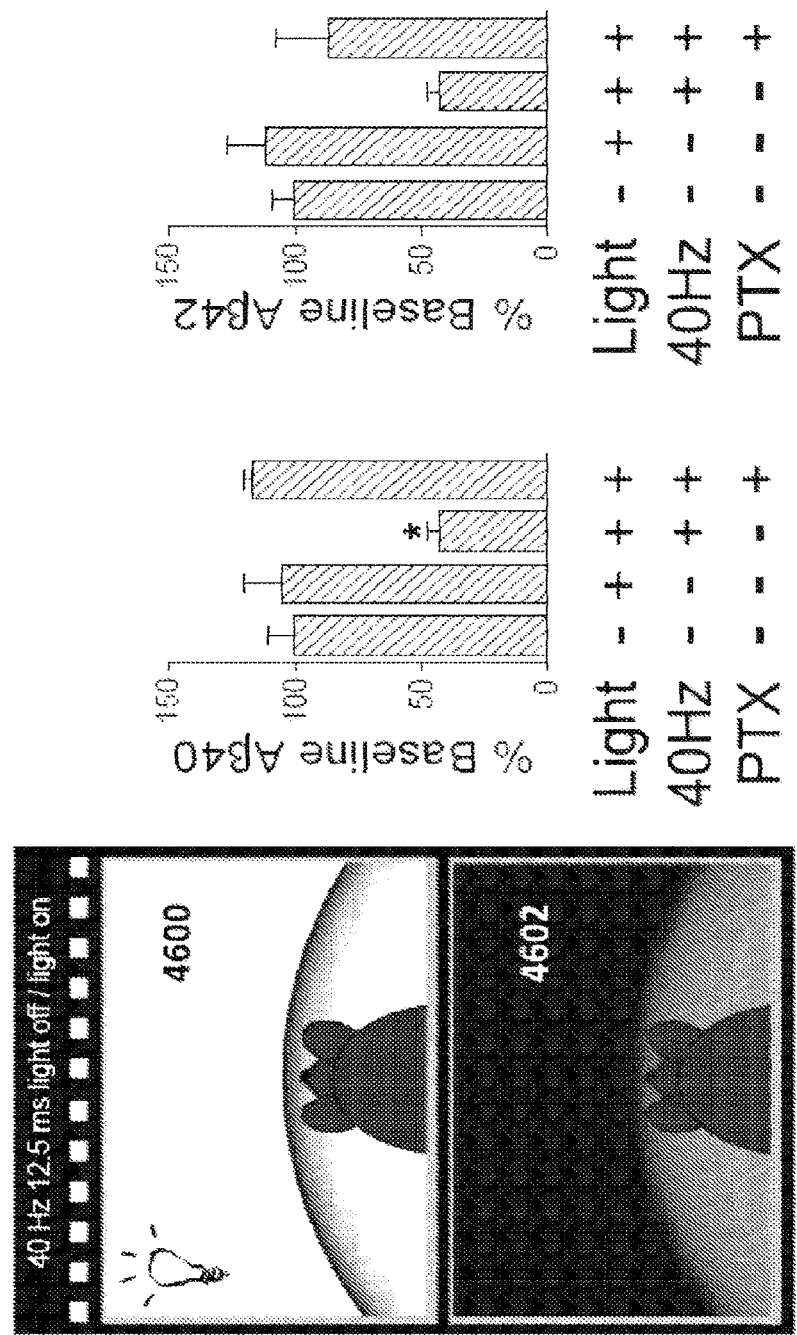

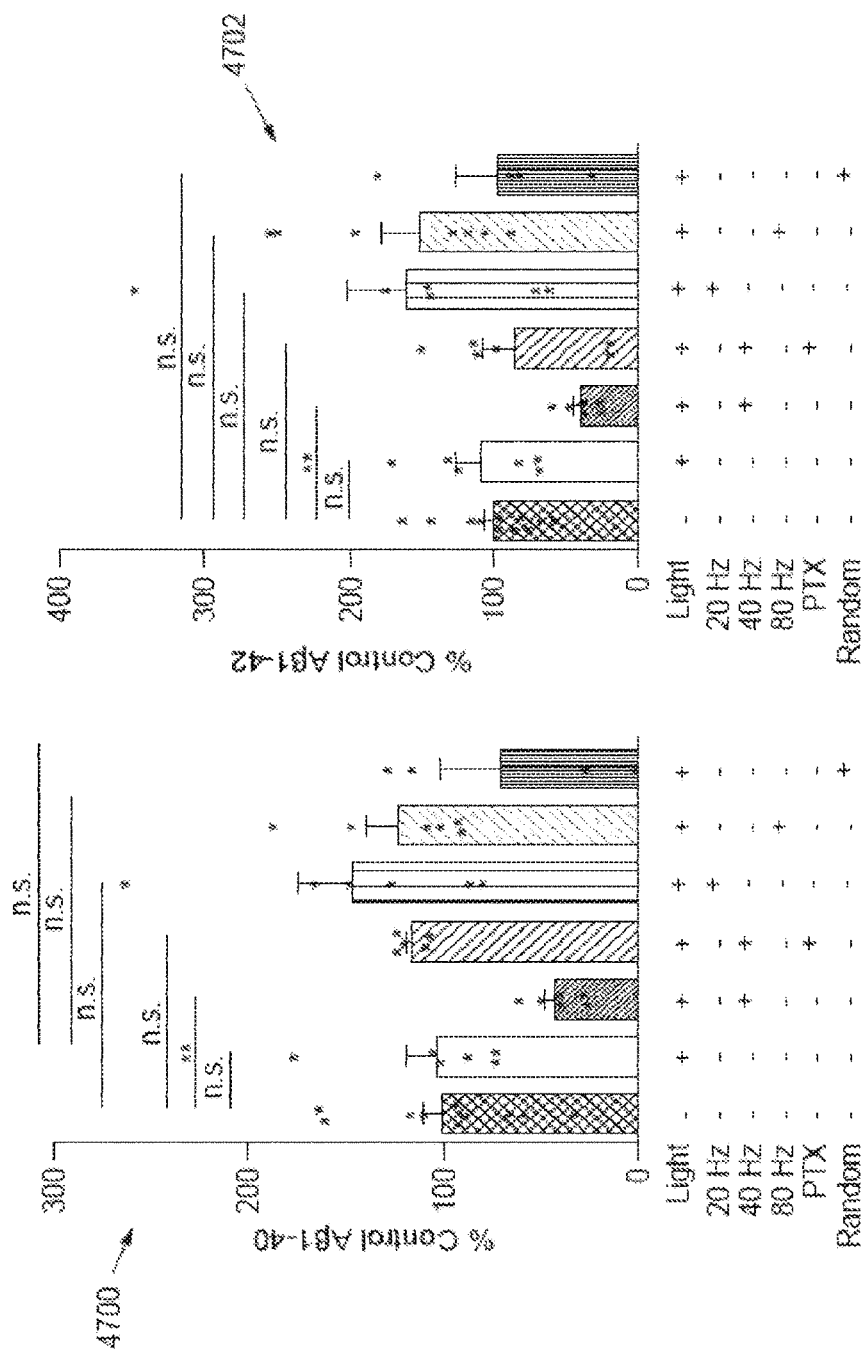

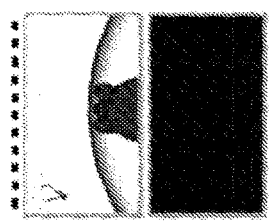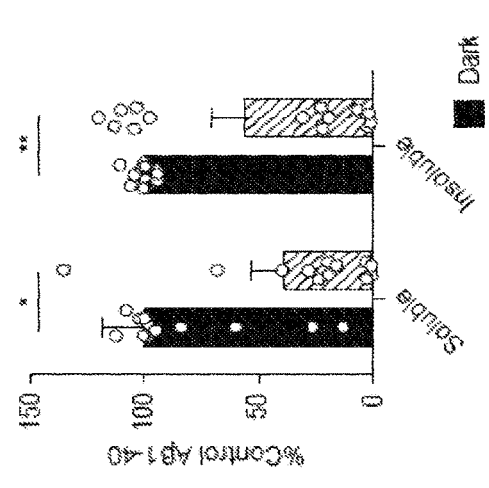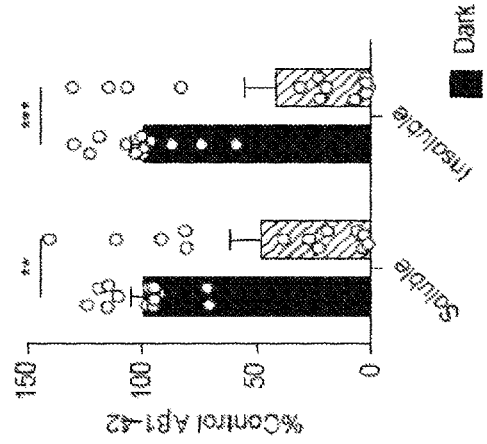

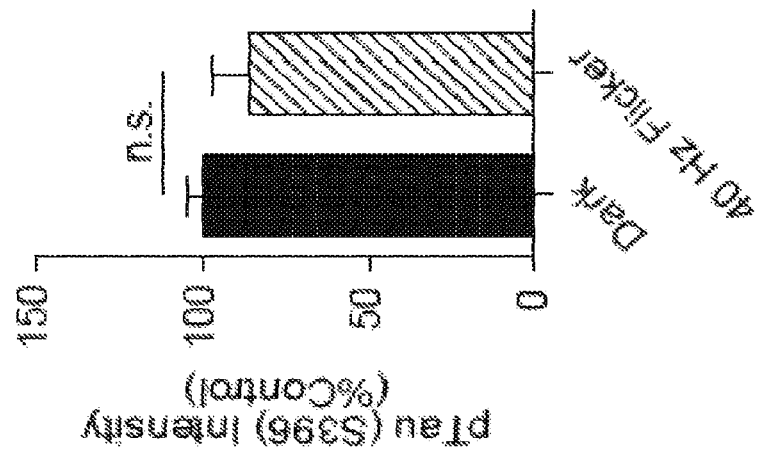
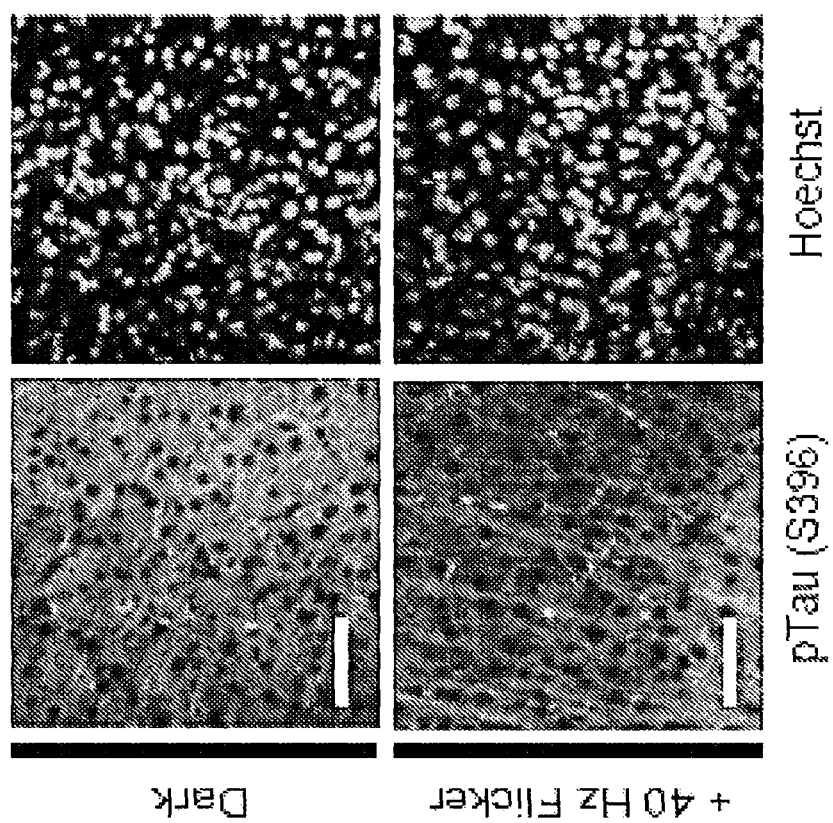
FIG. 63B
FIG. 63A

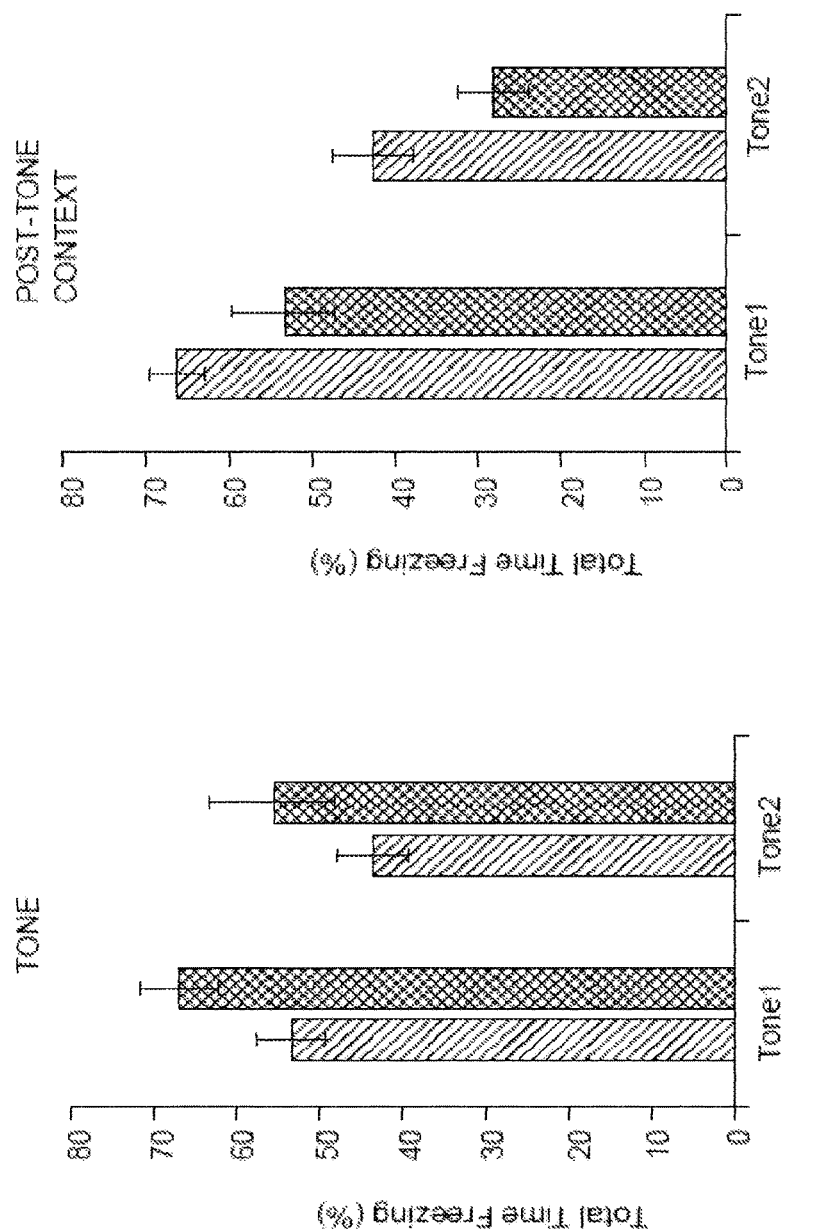

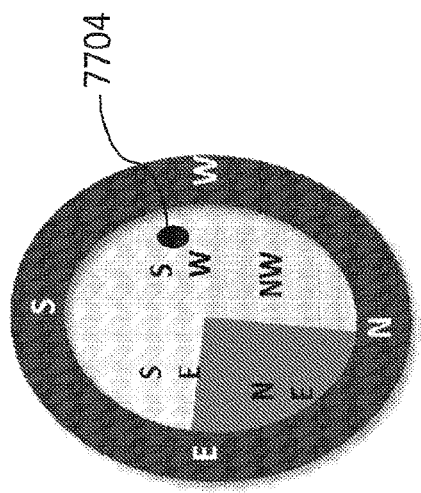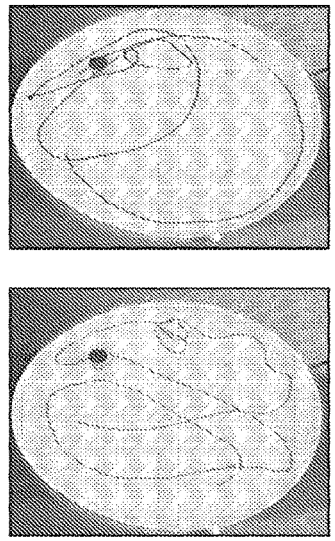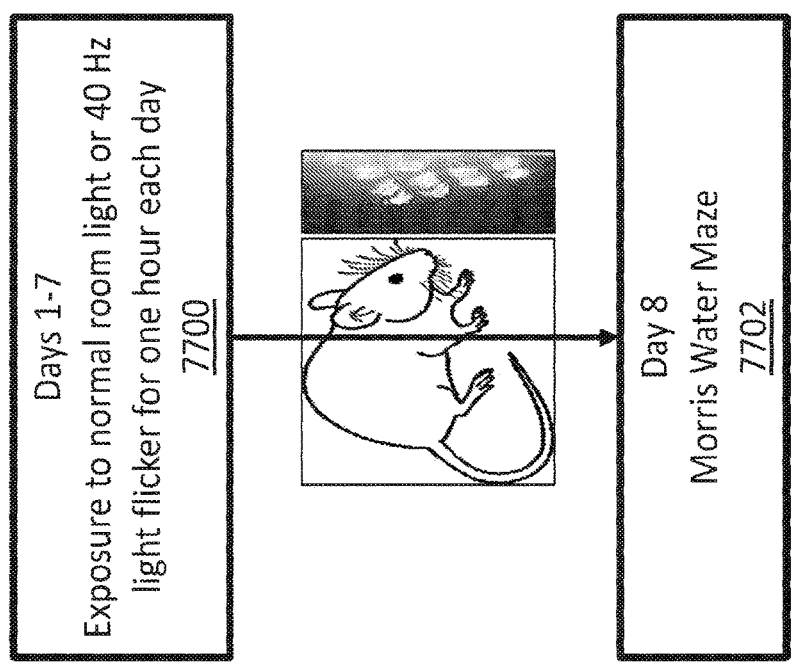
FIG. 77B
FIG. 77D
FIG. 77C
FIG. 77A

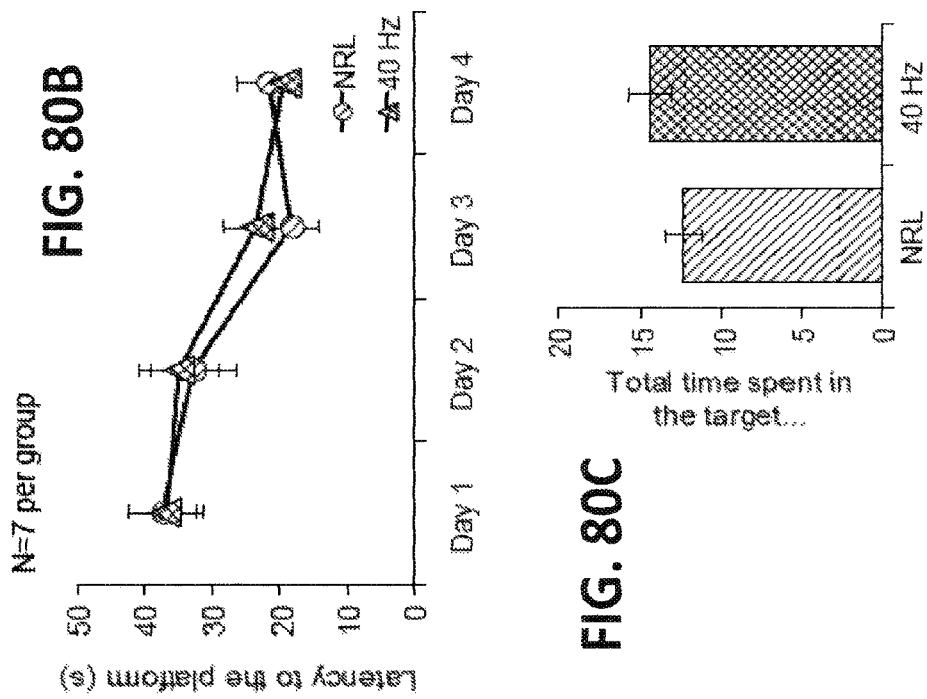
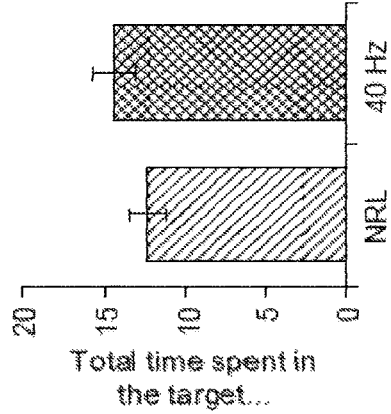
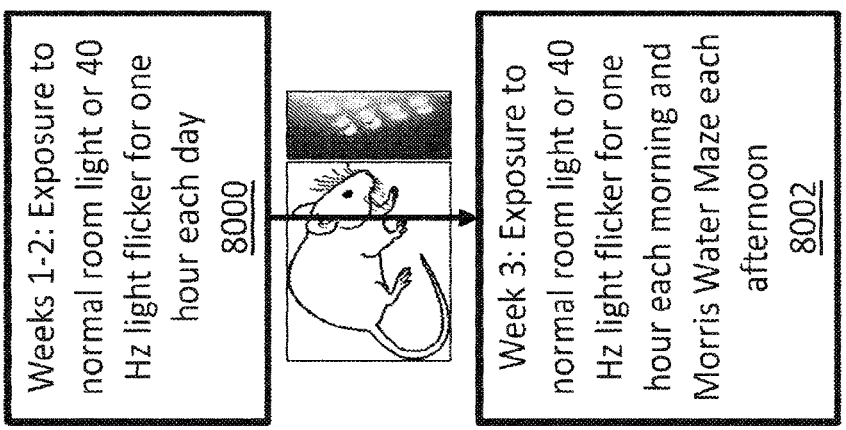
FIG. 80B
FIG. 80C
FIG. 80A

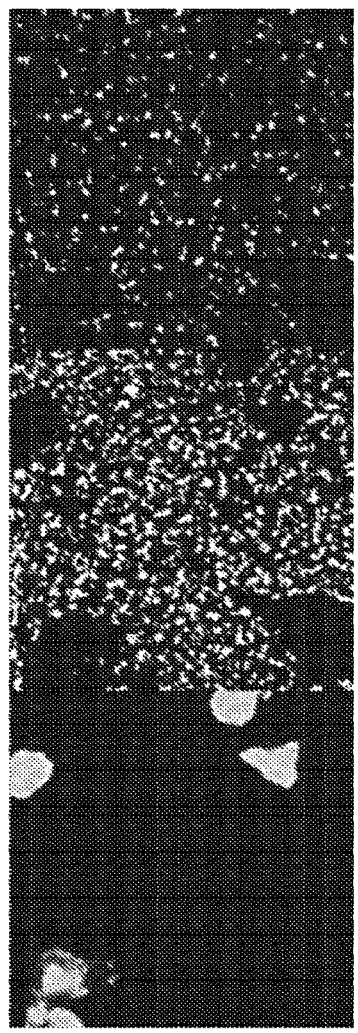
FIG. 113A  FIG. 113B  FIG. 113C  FIG. 113D  FIG. 113E  FIG. 113F

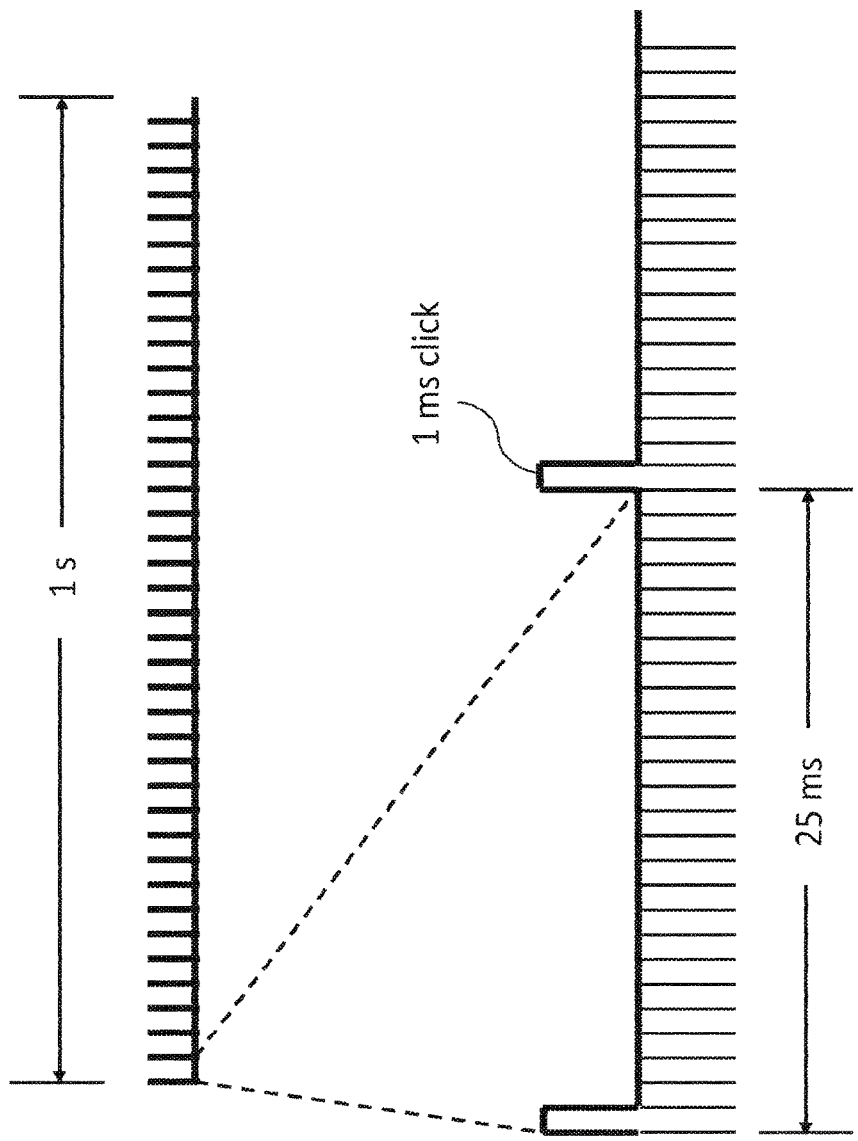

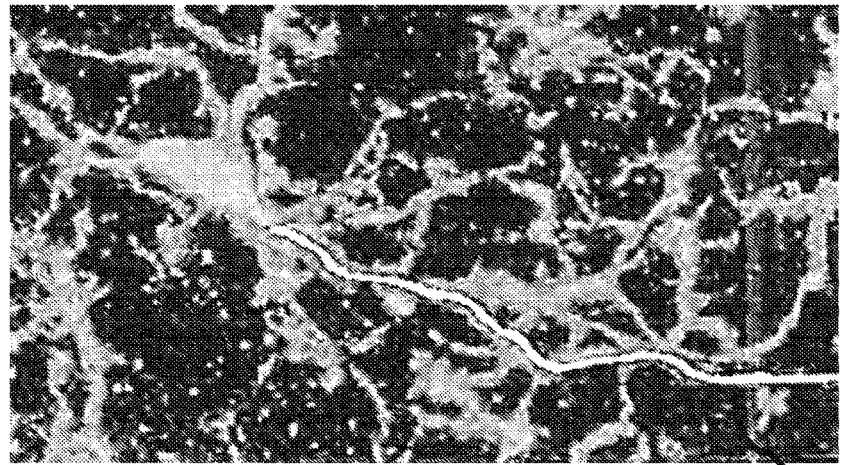
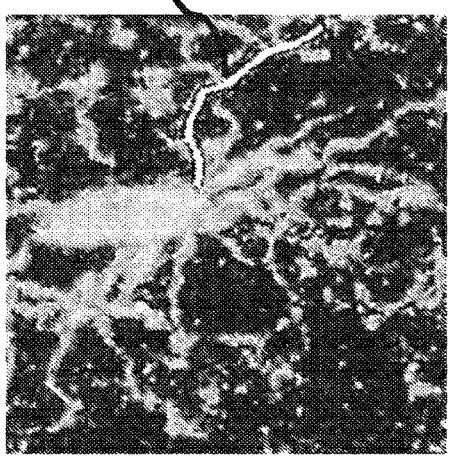
FIG. 118A
FIG. 118B

N = 6

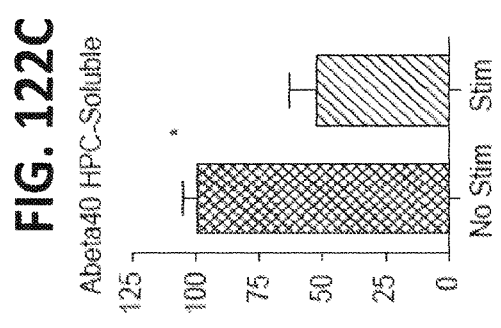
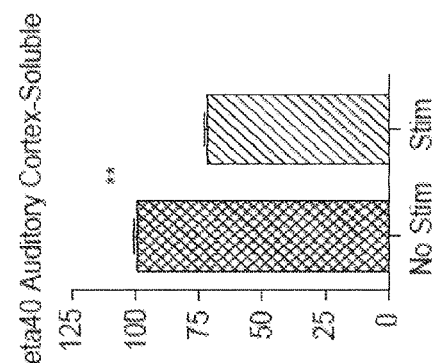
FIG. 122A  FIG. 122B  FIG. 122C  FIG. 122D

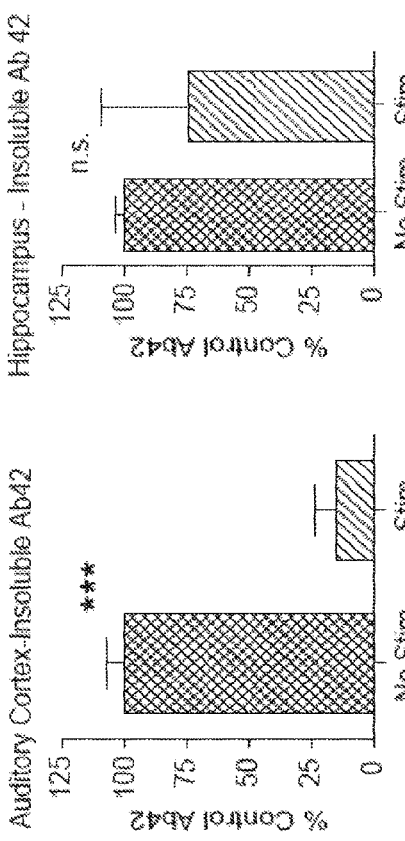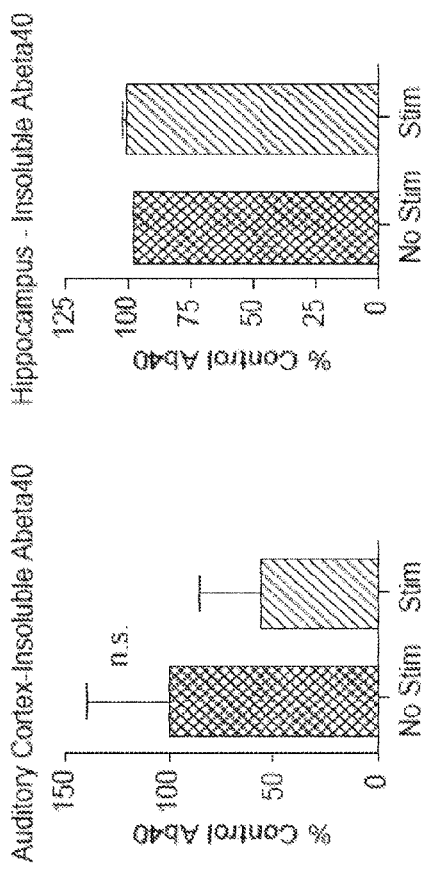
FIG. 123A
FIG. 123B
FIG. 123C
FIG. 123D

SYSTEMS AND METHODS FOR PREVENTING, MITIGATING, AND/OR TREATING DEMENTIA

CROSS-REFERENCE TO RELATED APPLICATION(S)

This application is a continuation application of U.S. application Ser. No. 15/360,637, filed Nov. 23, 2016, entitled "SYSTEMS AND METHODS FOR PREVENTING, MITIGATING, AND/OR TREATING DEMENTIA," and claims priority to U.S. provisional application Ser. No. 62/259,187, entitled "SYSTEM AND METHODS FOR PREVENTING, MITIGATING, AND/OR TREATING DEMENTIA," filed on Nov. 24, 2015. Each of the foregoing applications is incorporated herein by reference in its entirety.

GOVERNMENT SUPPORT STATEMENT

This invention was made with Government support under Grant No. AG047661 awarded by the National Institutes of Health. The Government has certain rights in the invention.

TECHNICAL FIELD

The present disclosure relates generally to systems and methods for preventing, mitigating, and/or treating dementia in a subject. More specifically, the present disclosure relates to systems and methods for inducing synchronized gamma oscillations in at least one brain region of subject.

BACKGROUND

Alzheimer's disease (AD) is a progressive neurodegenerative disease characterized by a decline in memory, orientation, and reasoning. It is the most common form of dementia in the world, affecting approximately one in eight people over the age of 65, and the sixth leading cause of death in the United States. The prevalence of this progressive neurodegenerative disorder is estimated to increase by 40% in the next ten years.

Histopathologically, AD may be characterized by the accumulation of amyloid plaques comprising the amyloid-β (Aβ) peptide and neurofibrillary tangles (NFTs) made of the tau protein. The Aβ peptide is a 36-43 amino acid protein whose normal physiological function remains unidentified. The Aβ peptide is formed by the sequential proteolytic cleavage of the amyloid precursor protein (APP) by β-secretase 1 (BACE1) and γ-secretase. C-terminal fragment β (β-CTF) is an APP derivative produced during amyloidogenic cleavage of APP by BACE1 and thus another indicator of Aβ peptide production. Under normal conditions, the soluble Aβ peptide is produced and secreted by neurons and subsequently cleared from the brain via cerebral spinal fluid (CSF) pathways. However, in subjects with AD, the Aβ peptide appears to aggregate into higher-order species to form soluble oligomers and insoluble plaques in a concentration-dependent manner. This aggregation may initiate many neurotoxic events including disrupted brain metabolism, neuroinflammation, reduced functional connectivity, synaptic and neuronal loss, and/or formation of NFTs.

A fundamental relationship between Aβ concentration and neuronal activity has been demonstrated. First, treatment of organotypic hippocampal slices prepared from transgenic (Tg) mice overexpressing APP with tetrodotoxin decreased neuronal activity and subsequently Aβ levels. Then, the opposite effect—increased neuronal activity—was observed upon treatment with picrotoxin. Dynamic modulation of the Aβ peptide concentration and eventual plaque deposition in vivo also has been demonstrated using neuronal activity. In human AD patients, neural imaging shows that the most severe plaque deposition may align with the most consistently active brain areas, known as the "default-mode network."

Currently AD has no cure, and treatment options do not inhibit the pathological progression of AD, are mainly palliative, and/or may have multiple, troubling side effects. For example, preventative and/or therapeutic strategies targeting the Aβ peptide and/or its precursors (e.g., Aβ immunotherapy and inhibition of β- and γ-secretases) have been toxic and/or ineffective at reducing AD pathology in clinical trials. Clinical trials involving amyloid beta vaccines (e.g., bapineuzumab) have failed due to lack of cognitive benefit. Gamma-secretase inhibitors (e.g., semagacestat) have failed clinical trials for worsening of cognitive deficits in subjects. Even existing medications like acetylcholinesterase inhibitors (e.g., donepezil and rivastigmine) and N-methyl-D-aspartate (NMDA)-receptor antagonists (e.g., memantine) demonstrate only mild cognitive benefits.

SUMMARY

Key microscopic pathological hallmarks of AD include the presence of amyloid plaques, NFTs, and extensive neuronal loss. This accumulation of neuronal insults occurs over a length of time and induces macroscopic circuit dysfunctions in the brain, specifically gamma power deficits during memory and attention tasks. These gamma oscillations (e.g., about 20 Hz to about 100 Hz, about 20 Hz to about 80 Hz, or about 20 Hz to about 50 Hz) primarily originate, and are modulated by, fast-spiking-parvalbumin (FS-PV)-interneurons.

In one aspect, the present disclosure provides devices, methods, and systems for preventing, mitigating, and/or treating dementia in a subject comprising inducing synchronized gamma oscillations in at least one brain region of the subject. In some embodiments, the dementia is associated with AD, vascular dementia, frontal temporal dementia, Lewy Body dementia, and/or age-related cognitive decline. The subject may be a human or an animal.

In some embodiments, the synchronized gamma oscillations have a frequency of about 20 Hz to about 50 Hz, such as about 40 Hz. The synchronized gamma oscillations may be induced in a cell-type specific manner. For example, the oscillations may correspond to synchronized activation of FS-PV-interneurons. The synchronized gamma oscillations may be induced in a brain-region specific manner. For example, the oscillations may correspond to synchronized activation in at least one of a hippocampus region and a sensory cortex region.

In one embodiment, a method for preventing, mitigating, and/or treating dementia in a subject includes the steps of controlling a stimulus-emitting device to emit a stimulus and exposing the subject to the stimulus and/or administering the stimulus to the subject, thereby inducing in vivo synchronized gamma oscillations in at least one brain region of the subject. The stimulus may have a frequency of about 35 Hz to about 45 Hz, such as a frequency of about 40 Hz. The stimulus-emitting device may be a haptic device, a light-emitting device, and/or a sound-emitting device. For example, the light-emitting device may be a fiber optic device. The duration of the exposure of the subject to the stimulus and/or the administration of the stimulus to the subject may be about one hour. The exposure of the subject to the stimulus and/or the administration of the stimulus to the subject may be repeated over a time period. For example, the exposure of the subject to the stimulus and/or the administration of the stimulus to the subject may be repeated at least once per day over the time period. The time period may include, but is not limited to, 1 day, 2 days, 3 days, 4 days, 5 days, 6 days, one week, two weeks, three weeks, and/or one month (or longer, such as once daily for the rest of the subject's life).

In one aspect, a method for reducing a level (e.g., an amount or rate) of Aβ peptide in at least one brain region of a subject includes inducing synchronized gamma oscillations in the at least one brain region of the subject. The Aβ peptide may include one or more isoforms of Aβ peptide (e.g., isoform A$\beta_{1-40}$, isoform A$\beta_{1-42}$, and/or isoform A$\beta_{1-43}$), soluble Aβ peptide, and/or insoluble Aβ peptide.

In some embodiments, the synchronized gamma oscillations reduce production of Aβ peptide in the at least one brain region of the subject by, for example, reducing a level (e.g., an amount or rate) of C-terminal fragments (CTFs) and/or N-terminal fragments (NTFs) of APP in the at least one brain region of the subject. The synchronized gamma oscillations may reduce cleavage of APP into CTFs and NTFs by BACE1 and/or γ-secretase in the at least one brain region of the subject. The synchronized gamma oscillations may reduce a level (e.g., an number or rate) of endosomes in the at least one brain region of the subject. For example, the endosomes may be positive for early endosomal antigen 1 (EEA1) and/or Ras-related protein encoded by the RAB5A gene (Rab5). In some embodiments, the synchronized gamma oscillations promote clearance of Aβ peptide in the at least one brain region of the subject. The synchronized gamma oscillations may increase uptake of Aβ peptide by microglia in the at least one brain region of the subject.

In one aspect, a method for increasing a level (e.g., a number or rate) of microglial cells, a morphologic change in the microglial cells consistent with a neuroprotective state, and/or an activity of the microglial cells in at least one brain region of a subject comprising inducing synchronized gamma oscillations in the at least one brain region of the subject. The synchronized gamma oscillations may upregulate at least one differentially expressed gene, such as Nr4a1, Arc, Npas4, Cd68, B2m, Bsr2, Icam1, Lyz2, Irf7, Spp1, Csf1r, and/or Csf2ra, involved in the microglia activity in the at least one brain region of the subject. The morphologic change in the microglial cells consistent with the neuroprotective state may include an increase in cell body size and/or a decrease in process length.

In one aspect, a method for reducing a level (e.g., an amount or rate) of Aβ peptide in a hippocampus of a subject includes optogenetically stimulating FS-PV-interneurons in the hippocampus with a plurality of light pulses, the FS-PV-interneurons expressing an optogenetic actuator, thereby entraining in vivo synchronized gamma oscillations measured by local field potentials in the excitatory neurons (e.g., FS-PV-interneurons) that reduce the level of Aβ peptide in the hippocampus. The light pulses may have a pulse frequency of about 40 pulses/s. Each light pulse may have a duration of about 1 ms. At least one light pulse may have a wavelength of about 473 nm. The optogenetic actuator may include channelrhodopsin, halorhodopsin, and/or archaerhodopsin. For example, the optogenetic actuator may be channelrhodopsin-2 (ChR2).

In one aspect, a method for reducing a level (e.g., an amount or rate) soluble and/or insoluble Aβ peptide in a visual cortex of a subject includes stimulating the subject with a plurality of light pulses at a pulse frequency of about 40 pulses/s, thereby inducing in vivo synchronized gamma oscillations in the visual cortex that reduce the level of the soluble and/or insoluble Aβ peptide in the visual cortex.

In one aspect, a method for reducing a level of (e.g., an amount or rate) tau phosphorylation in a visual cortex of a subject includes stimulating the subject with a plurality of light pulses at a pulse frequency of about 40 pulses/s, thereby inducing in vivo synchronized gamma oscillations in the visual cortex that reduce tau phosphorylation in the visual cortex.

In one aspect, a method for reducing a level (e.g., an amount or rate) of Aβ peptide in a hippocampus and/or an auditory cortex of a subject includes stimulating the subject with a plurality of sound pulses at a pulse frequency of about 40 pulses/s, thereby inducing in vivo synchronized gamma oscillations in the at least one of the hippocampus and the auditory cortex that reduce the level of Aβ peptide in the at least one of the hippocampus and the auditory cortex.

In one aspect, a system for preventing, reducing, and/or treating a level (e.g., an amount or rate) of or change in Aβ peptide, neuroinflammation, and/or cognitive function in a subject includes a stimulus-emitting device for in vivo synchronized activation of a brain region of the subject, at least one memory for storing stimulus parameters and processor executable instructions, and at least one processor communicatively connected to the stimulus-emitting device and the at least one memory. Upon execution of the processor executable instructions, the at least one processor controls the stimulus-emitting device to emit the stimulus according to the stimulus parameters, the parameters including a frequency that synchronously activates the brain region at the frequency, whereby the Aβ peptide, the neuroinflammation, and/or the dementia in the subject is prevented, reduced, and/or treated. The frequency may be from about 35 Hz to about 45 Hz, such as about 40 Hz. The in vivo synchronized activation may be regulated by an enzyme and/or occur in a specific cell type, such as immunoreactive FS-PV-interneurons. The enzyme may include an optogenetic activator, a microbial opsin, ChR2, and/or vector AAV-DIO-ChR2-EYFP.

In one aspect, a system for preventing, reducing, and/or treating a level (e.g., an amount or rate) of or change in Aβ peptide, neuroinflammation, and/or cognitive function in a subject includes a light occlusion device for reducing ambient light to at least one eye of the subject and/or a noise-canceling device for reducing ambient noise to at least one ear of the subject. The light occlusion device may include a light-emitting unit for emitting a light stimulus to the at least one eye for in vivo synchronized activation of at least one of a visual cortex and a hippocampus of the subject. The noise-canceling device may include a speaker unit for emitting a sound stimulus to the at least one ear for in vivo synchronized activation of at least one of an auditory cortex and a hippocampus of the subject. The system also includes at least one memory for storing processor executable instructions and at least one processor communicatively connected to the light occlusion device and/or the noise-canceling device and the at least one memory. Upon execution of the processor executable instructions, the at least one processor may control the light occlusion device such that the light-emitting unit emits the light stimulus at a frequency that synchronously activates the at least one of the visual cortex and the hippocampus at the frequency. Alternatively, or in addition, the at least one processor may control the noise-canceling device such that the speaker unit actuates the sound stimulus at the frequency that synchronously activates the at least one of the auditory cortex and the hippocampus at the frequency.

In one aspect, a method for improving cognitive function in a subject includes controlling at least one electroacoustic transducer to convert an electrical audio signal into a corresponding sound stimulus. In some embodiments, the sound stimulus includes a click train with a click frequency of about 35 clicks/s to about 45 clicks/s. The method further includes exposing the subject to the sound stimulus and/or administering the stimulus to the subject to induce synchronized gamma oscillations in at least one brain region of the subject, the synchronized gamma oscillations resulting in an improvement of the cognitive function in the subject. The cognitive function may include recognition, discrimination, and/or spatial memory.

In one aspect, a method for preventing, reducing, and/or treating a level (e.g., an amount or rate) of or change in Aβ peptide, neuroinflammation, and/or cognitive function in a subject includes controlling at least one electroacoustic transducer to convert an electrical audio signal into a corresponding sound stimulus, the sound stimulus including a click train with a click frequency of about 35 clicks/s to about 45 clicks/s, and exposing the subject to the sound stimulus and/or administering the stimulus to the subject to induce synchronized gamma oscillations in at least one brain region of the subject, the synchronized gamma oscillations resulting in the prevention, the reduction, and/or the treatment of the level of Aβ peptide, neuroinflammation, and/or dementia in the subject.

The Aβ peptide may include one or more isoforms of Aβ peptide (e.g., isoform $Aβ_{1-40}$, isoform $Aβ_{1-42}$, and/or isoform $Aβ_{1-43}$), soluble Aβ peptide, and/or insoluble Aβ peptide. The synchronized gamma oscillations may prevent, reduce, and/or treat the level of Aβ peptide, neuroinflammation, and/or dementia in the subject by increasing a number of microglial cells in the at least one brain region of the subject and/or enhancing uptake of Aβ peptide by the microglial cells in the at least one brain region. The at least one brain region may include the auditory cortex and/or the hippocampus.

The click frequency may be about 40 clicks/s. Each click in the click train may have a duration of about 1 ms. Each click in the click train may have a frequency of about 10 Hz to about 100 kHz, about 12 Hz to about 28 kHz, about 20 Hz to about 20 kHz, and/or about 2 kHz to about 5 kHz. Each click in the click train may have a sound pressure level of about 0 dB to about 85 dB, about 30 dB to about 70 dB, and about 60 dB to about 65 dB.

The at least one electroacoustic transducer may include at least one headphone, in which case the method may include applying the at least one headphone around, on, and/or in at least one ear of the subject to direct the sound stimulus into the at least one ear of the subject. The method also may include reducing ambient noise using passive noise isolation and/or active noise cancellation.

In one aspect, a system for preventing, reducing, and/or treating a level (e.g., an amount or rate) of or change in Aβ peptide, neuroinflammation, and/or cognitive function in a subject includes at least one electroacoustic transducer for converting an electrical audio signal into a corresponding sound stimulus, the sound stimulus including a click train with a click frequency of about 35 clicks/s to about 45 clicks/s, at least one memory device for storing the electrical audio signal and processor executable instructions, and at least one processor communicatively connected to the at least one electroacoustic transducer and the at least one memory device. Upon execution of the processor executable instructions, the at least one processor controls the electroacoustic transducer to output the sound stimulus to at least one ear of the subject to induce synchronized gamma oscillations in at least one brain region of the subject, the synchronized gamma oscillations resulting in the prevention, the reduction, and/or the treatment of the level of Aβ peptide, neuroinflammation, and/or dementia in the subject.

The system may be stationary or portable. If the at least one electroacoustic transducer includes at least one headphone for the subject to wear around, on, and/or in the at least one ear to direct the sound stimulus into the at least one ear of the subject and reduce ambient noise, the system further may include a headphone interface for communicating the electrical audio signal to the at least one headphone. Alternatively, or in addition, the system may include a neuroimaging scanner to monitor function in the at least one brain region of the subject before, during, and/or following the output of the sound stimulus.

In one aspect, a method for preventing, mitigating, and/or treating dementia in a subject includes providing a device that induces synchronized gamma oscillations in at least one brain region of the subject.

In one aspect, a method for maintaining and/or reducing a blood level (e.g., an amount) of a glucocorticoid involved in a stress response in a subject includes providing a device that induces synchronized gamma oscillations in at least one brain region of the subject.

In one aspect, a method for preventing and/or reducing anxiety in a subject includes providing a device that induces synchronized gamma oscillations in at least one brain region of the subject.

In one aspect, a method for maintaining and/or enhancing a memory association includes providing a device that induces synchronized gamma oscillations in at least one brain region of the subject. The memory association may be based in spatial memory.

In one aspect, a method for a maintaining and/or enhancing cognitive flexibility includes providing a device that induces synchronized gamma oscillations in at least one brain region of the subject.

In one aspect, a method for maintaining and/or reducing changes to anatomy and/or morphology in at least one brain region of a subject includes providing a device that induces synchronized gamma oscillations in the at least one brain region of the subject. The anatomy and/or morphology may include brain weight, lateral ventricle size, a thickness of a cortical layer, a thickness of a neuronal layer, and/or a blood vessel diameter. The at least one brain region may include a visual cortex, a somatosensory cortex, and/or an insular cortex of the subject.

In one aspect, a method for maintaining and/or reducing changes to a number of neurons, a quality of DNA in the neurons, and/or a synaptic puncta density in at least one brain region of a subject includes providing a device that induces synchronized gamma oscillations in the at least one brain region of the subject. The at least one brain region may include a visual cortex, a somatosensory cortex, an insular cortex, and/or a hippocampus of the subject.

In one aspect, a device that induces synchronized gamma oscillations in at least one brain region of a subject can prevent, mitigate, and/or treat dementia and/or anxiety in the subject, maintain and/or enhance a memory association and/or cognitive flexibility of the subject, and/or maintain and/or reduce changes to anatomy, morphology, cells, and molecules in the at least one brain region of the subject.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally see, e.g., like features (e.g., functionally similar and/or structurally similar elements).

FIGS. 2A and 2B are electrical traces recorded from hippocampal CA1 and illustrating theta oscillations and sharp-wave ripples (SWRs) in accordance with some embodiments.

FIGS. 5A-5C are plots depicting the distribution of instantaneous gamma frequencies during SWRs in accordance with some embodiments.

FIG. 6A is a series of graphs depicting the Z-scored gamma power as a function of the time from the peak of the SWRs in 5XFAD and WT mice in accordance with some embodiments. FIG. 6B is a plot depicting the cumulative distribution of gamma power during SWRs in 5XFAD and WT mice in accordance with some embodiments. FIGS. 6C and 6D are plots depicting the cumulative distribution of the Z-scored gamma power during the 100 ms around the peak of the SWRs for WT and 5XFAD mice in accordance with some embodiments. FIG. 6E is a plot depicting the cumulative distribution of gamma power during large SWRs in 5XFAD and WT mice in accordance with some embodiments.

FIG. 7A is a plot depicting fraction of spikes as function of phase of gamma oscillation, and FIG. 7B is a plot depicting depth of modulation of spiking during SWRs in accordance with some embodiments. FIGS. 7C and 7D are plots illustrating fraction of spikes in hippocampal CA1 during SWRs as a function of phase of gamma oscillations in accordance with some embodiments. FIG. 7E is a plot depicting fraction of spikes as function of phase of gamma oscillation, and FIG. 7F is a plot depicting depth of modulation of spiking during large SWRs in accordance with some embodiments.

FIGS. 8A and 8B are plots depicting SWR rate per non-theta period in 5XFAD and WT animals for each animal and all animals combined in accordance with some embodiments.

FIGS. 18A and 18B are bar graphs depicting relative $A\beta_{1-40}$ and $A\beta_{1-42}$ levels of 5XFAD/αCamKII-Cre CA1 by one-way ANOVA in accordance with some embodiments.

FIG. 21A is a representative western blot depicting levels of APP (CT695), APP NTF (A8967), APP CTFs (CT695), and β-Actin (A5316) (loading control) in CA1 in accordance with some embodiments. FIG. 21B is a bar graph depicting relative (normalized to actin) immunoreactivity of APP CTFs in 40-Hz vs. EYFP and Random conditions in accordance with some embodiments. FIG. 21C is a series of western blots depicting levels of full-length APP 2106 (CT695), APP CTFs 2108 (CT695) and β-Actin 2112 (A5316, loading control) in CA1 in accordance with some embodiments.

FIG. 24A is a bar graph representing the relative immunoreactivity of EEA1 normalized to EYFP, and FIG. 24B is a bar graph depicting relative Rab5 intensity levels of CA1 from 5XFAD/PV-Cre under EYFP, 40 Hz, and random stimulation conditions in accordance with some embodiments.

FIG. 25A is a bar graph depicting levels of the Aβ peptide isoform $A\beta_{1-40}$ following different types of stimulation of the CA1 region of the hippocampus of a subject in accordance with some embodiments. FIG. 25B is a bar graph depicting a decrease in the Aβ peptide isoform $A\beta_{1-42}$ following stimulation of a specific cell type in the CA1 region of the hippocampus of a subject with gamma oscillations in accordance with some embodiments. FIG. 25C is a series of images illustrating a decrease in the level of CTFs (e.g., β-CTF) and an increase in the level of full-length APP (normalized to actin) following stimulation of a specific cell type in the CA1 region of the hippocampus of a subject with gamma oscillations in accordance with some embodiments.

FIG. 35A is a bar graph depicting the number of microglia in EYFP and 40-Hz conditions in accordance with some embodiments. FIG. 35B is a bar graph depicting the diameter of microglial cell bodies normalized to EYFP in EYFP, 40-Hz, and Random stimulation conditions in accordance with some embodiments. FIG. 35C is a bar graph depicting the average length of microglia primary processes normalized to EYFP in EYFP, 40-Hz, and Random stimulation conditions in accordance with some embodiments. FIG. 35D is a bar graph depicting the percent of Iba1-positive (microglia) cell bodies that are also Aβ-positive in EYFP and 40-Hz stimulation conditions in accordance with some embodiments.

FIG. 43A is a schematic diagram illustrating a mouse exposed to light flicker stimulation in accordance with some embodiments. FIG. 43B includes a local field potential trace in the visual cortex before and during 40-Hz light flicker and a plot of power spectral density in accordance with some embodiments. FIGS. 43C-43F are plots depicting power spectral densities of local field potentials in the visual cortex in accordance with some embodiments.

FIG. 46A is a schematic diagram illustrating an experimental paradigm in accordance with some embodiments. FIGS. 46B-46C are plots further illustrating changes in baseline levels of Aβ peptide isoforms $A\beta_{1-40}$ and $A\beta_{1-42}$, respectively, following the experimental paradigm in FIG. 46A in accordance with some embodiments.

FIGS. 47A and 47B are bar graphs depicting changes in baseline levels of $A\beta_{1-40}$ and $A\beta_{1-42}$, respectively, in 5XFAD visual cortex in accordance with some embodiments.

FIG. 59A is a schematic diagram illustrating a study in accordance with some embodiments. FIG. 59B is a bar graph depicting relative $A\beta_{1-42}$ levels in visual cortices of six-month-old 5XFAD mice after seven days of one hour/day under dark or 40-Hz flicker conditions in accordance with some embodiments. FIG. 59C is a bar graph illustrating relative $A\beta_{1-40}$ levels in visual cortices of six-month-old 5XFAD mice after seven days of one hour/day under dark or 40-Hz flicker conditions in accordance with some embodiments.

FIG. 63A is a series of immunofluorescence images illustrating immunohistochemistry with anti-pTau 6302 (S396) antibodies in four-month-old P301S mice after seven days of one hour/day under dark and 40-Hz flicker conditions in accordance with some embodiments. FIG. 63B is a bar graph depicting relative pTau (S396) fluorescence intensity levels of P301S visual cortex after seven days of one hour/day under dark and 40-Hz flicker conditions in accordance with some embodiments.

FIGS. 76A and 76B are bar graphs demonstrating enhanced memory in subjects in accordance with some embodiments.

FIG. 77A is a flow diagram illustrating a study conducted to examine whether gamma exposure and/or administration improves memory in subjects in accordance with some embodiments. FIG. 77B is a diagram illustrating a Morris water maze with a platform hidden in a target quadrant. FIGS. 77C and 77D are images illustrating representative tracks of the subjects during a Morris water maze probe test.

FIG. 80A is a flow diagram illustrating a study conducted to examine whether chronic gamma exposure and/or administration in accordance with some embodiments influences spatial learning and memory in subjects. FIG. 80B is a plot depicting the average amount of time the subjects spent finding the hidden platform in the Morris water maze test on each day. FIG. 80C is a bar graph depicting the average amount of time the subjects spent searching for the removed platform in the target quadrant during a thirty-second trial.

FIGS. 113A-113D are images illustrating a Hoechst stain, VGluT1 markers, and/or GAD65 markers in a representative sample in accordance with some embodiments. FIGS. 113E and 113F are images illustrating a method of puncta quantification in accordance with some embodiments.

FIG. 114 is a stimulus diagram illustrating a click-train stimulus in accordance with some embodiments.

FIGS. 118A and 118B are magnified images of microglial projection length from FIGS. 117A and 117B in accordance with some embodiments.

FIGS. 119A and 119B are magnified images of microglial soma size from FIGS. 117A and 117B in accordance with some embodiments.

Figures 120A, 120B, 120C:
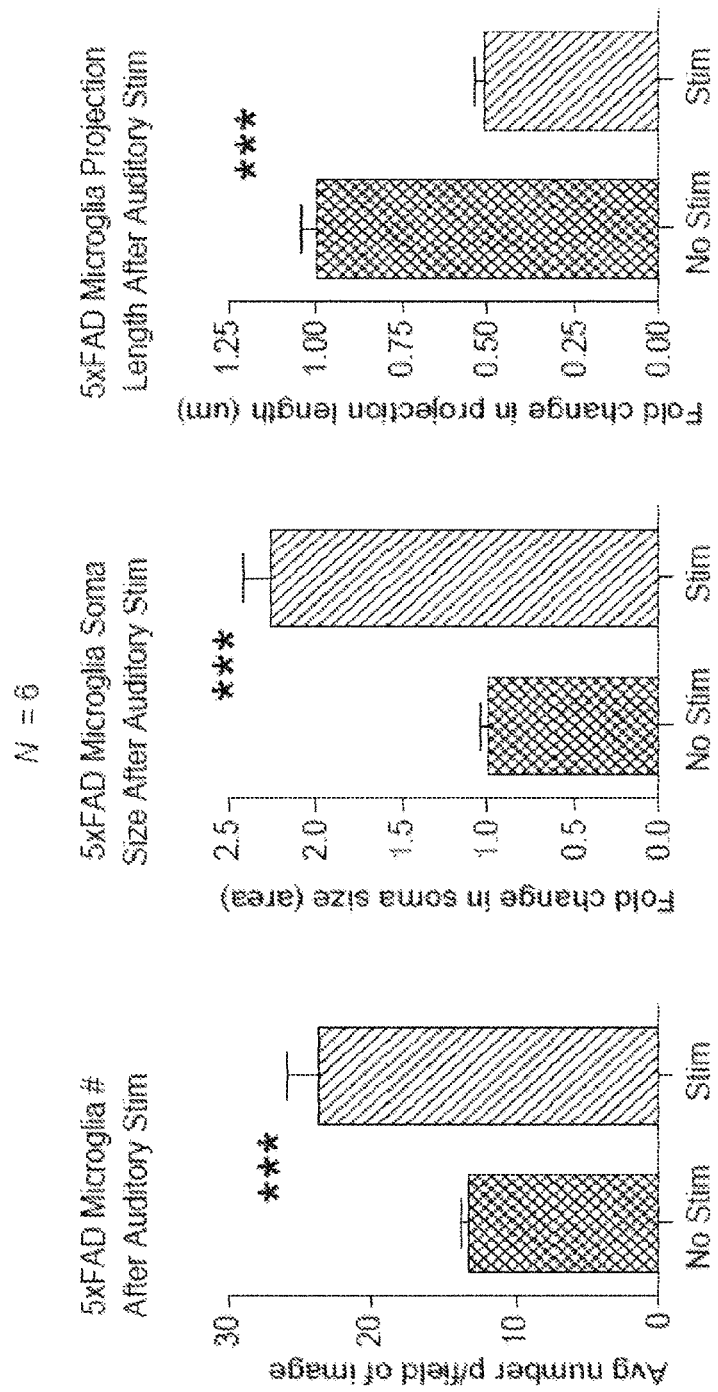

FIG. 120A is a bar graph depicting the average number of microglia per image field in the auditory cortices of subjects in accordance with some embodiments. FIG. 120B is a bar graph depicting the average fold change in soma size of microglia in the auditory cortices of subjects in accordance with some embodiments. FIG. 120C is a bar graph depicting the average fold change in projection length of microglia in the auditory cortices of subjects in accordance with some embodiments.

Figure 121B:
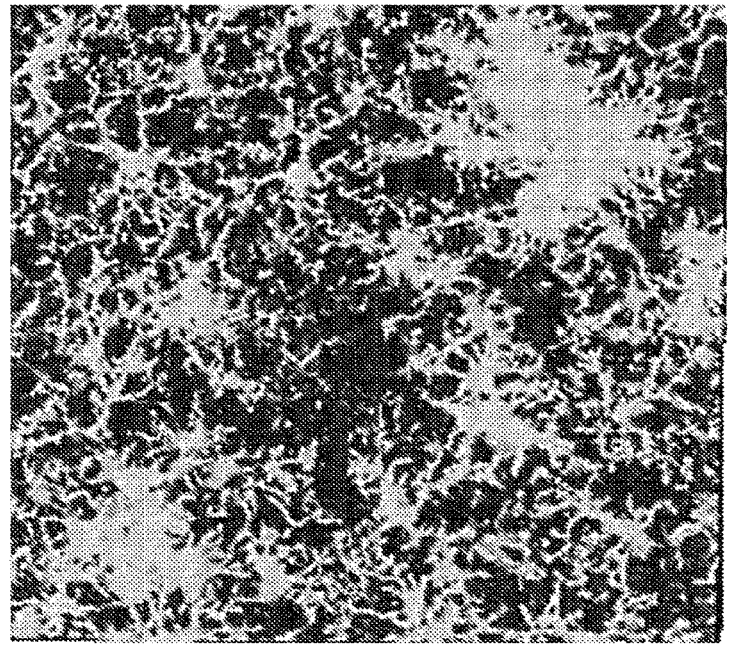
Figure 121A:
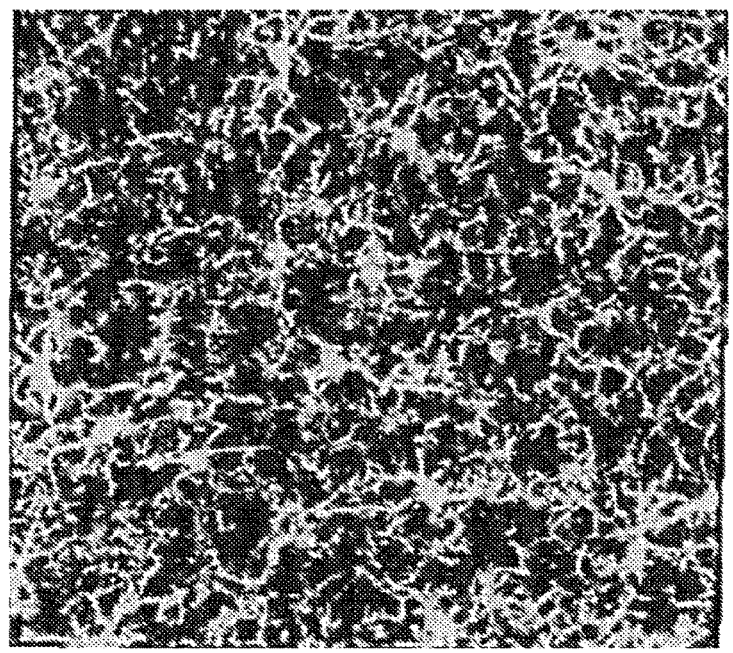

FIGS. 121A and 121B are representative images of microglia in the auditory cortices of subjects in accordance with some embodiments.

FIGS. 122A-122D are bar graphs depicting levels of soluble Aβ isoforms $A\beta_{1-40}$ and $A\beta_{1-42}$ in the auditory cortices and hippocampuses of subjects in accordance with some embodiments.

FIGS. 123A-123D are bar graphs depicting levels of insoluble Aβ isoforms $A\beta_{1-40}$ and $A\beta_{1-42}$ in the auditory cortices and hippocampuses of subjects in accordance with some embodiments.

FIGS. 124A-124D are representative images of microglia in the auditory cortices of subjects in accordance with some embodiments.

Figures 125A, 125B:
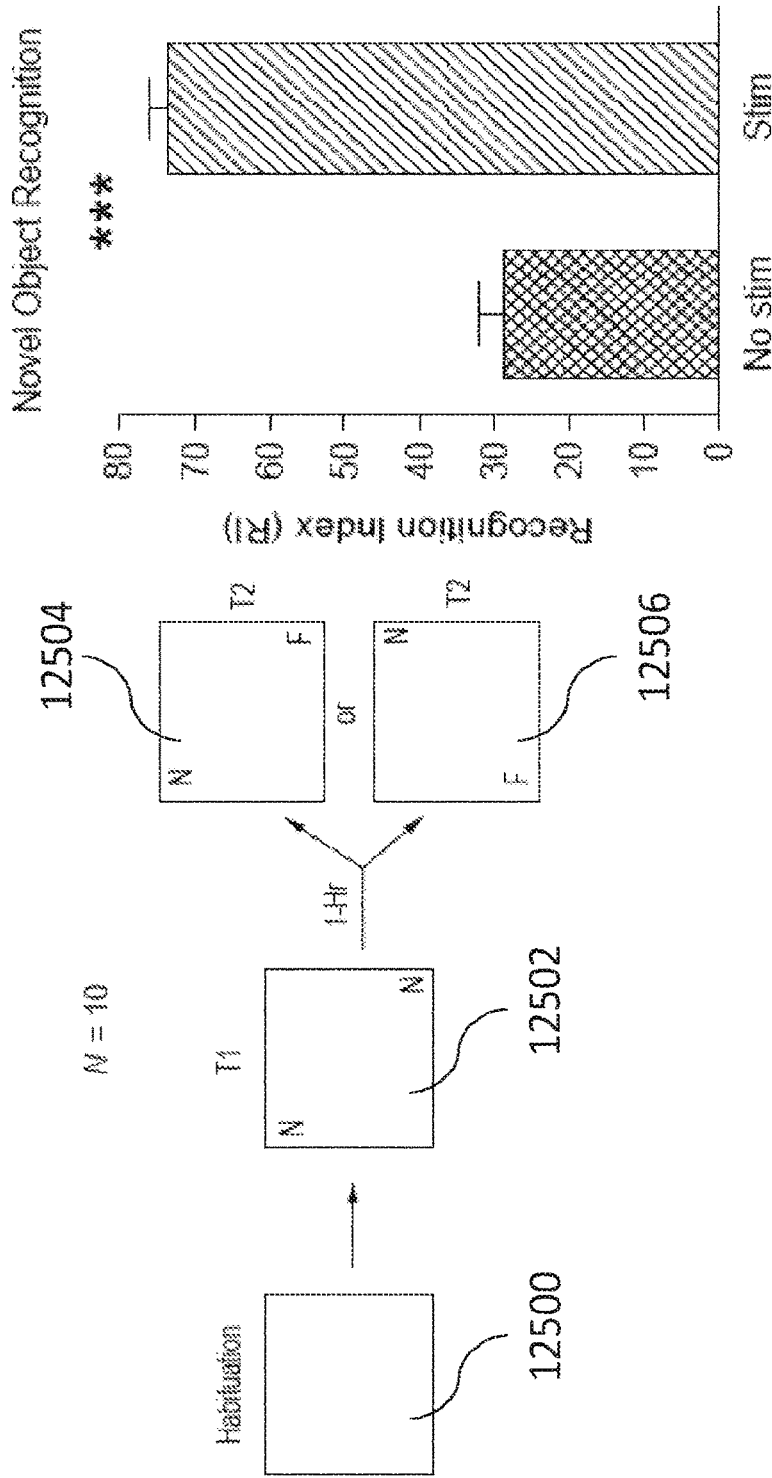

FIG. 125A is a flow diagram illustrating a novel object recognition test. FIG. 125B is a bar graph demonstrating improvements in memory in accordance with some embodiments.

Figures 126A, 126B:
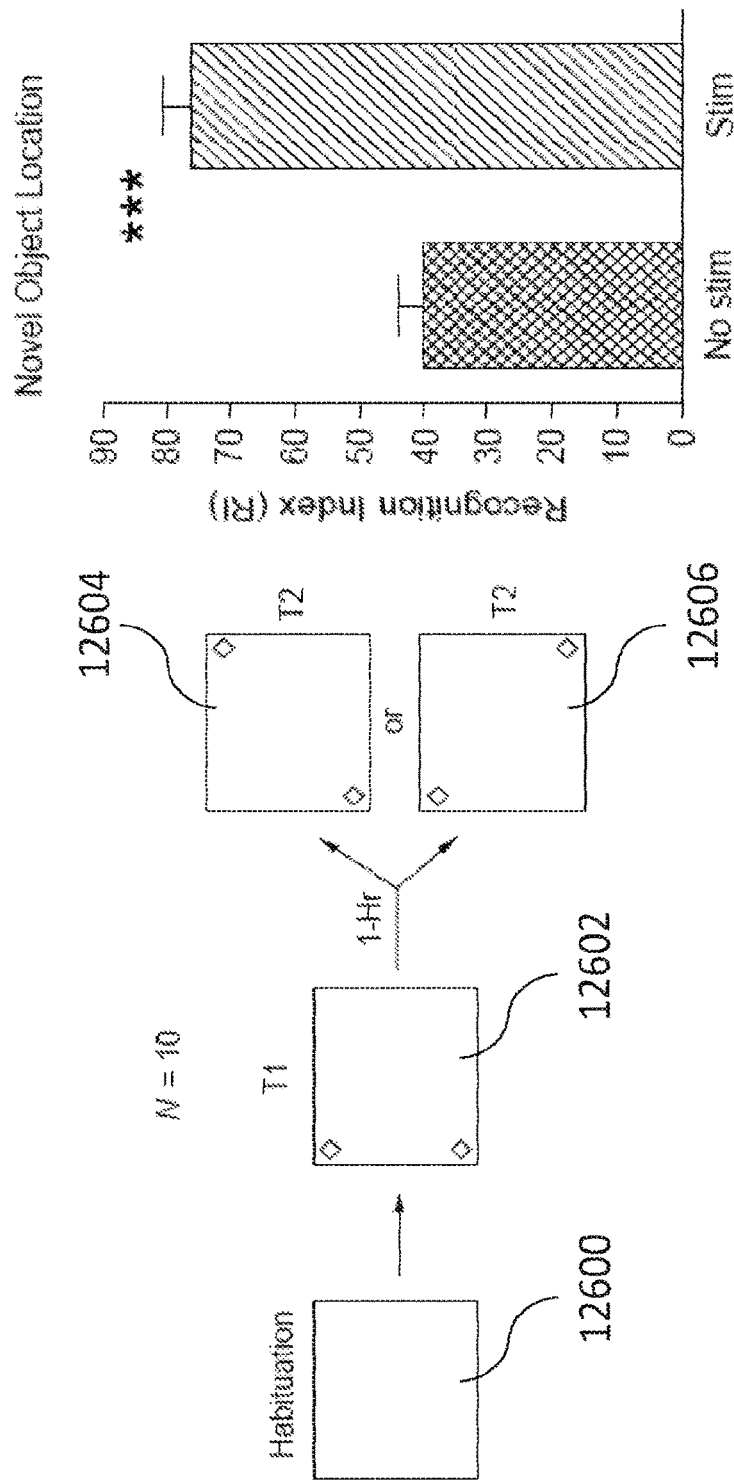

FIG. 126A is a flow diagram illustrating a novel object location test. FIG. 126B is a bar graph demonstrating improvements in memory and/or discrimination in accordance with some embodiments.

Figures 127A, 127B:
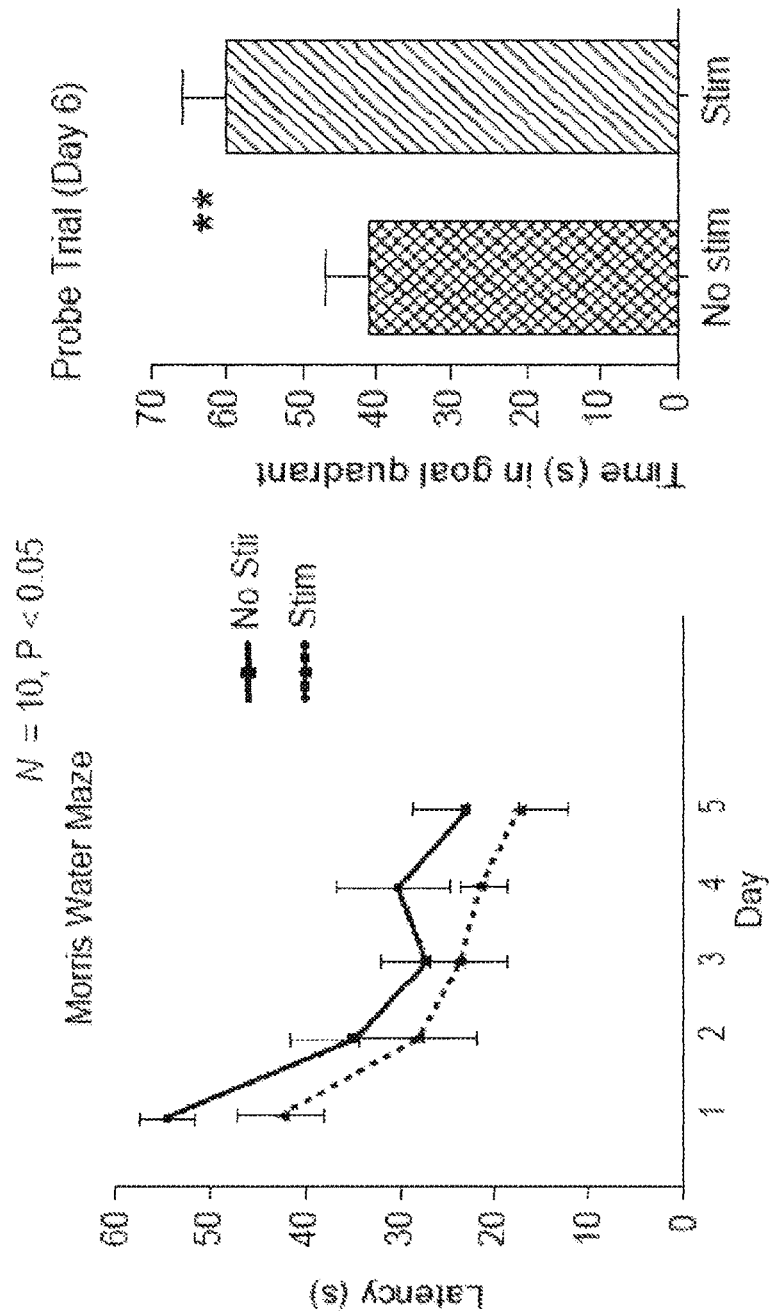

FIG. 127A is a plot depicting the average amount of time the subjects spent finding the hidden platform in the Morris water maze test on each day. FIG. 127B is a bar graph depicting the average amount of time the subjects spent searching for the removed platform in the target quadrant during a probe test.

Figures 128A, 128B:
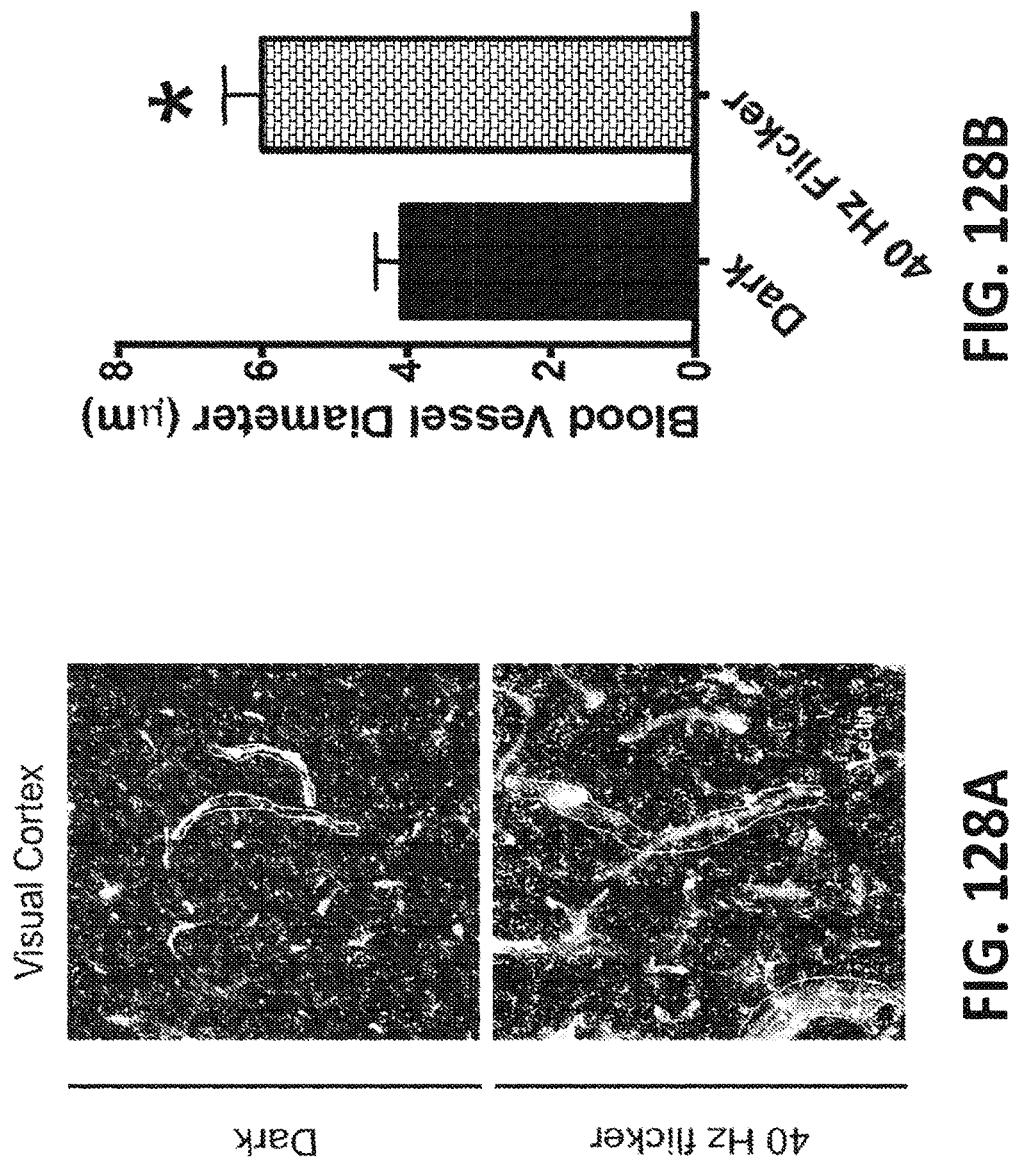

FIG. 128A is a series of representative immunofluorescence images illustrating enlarged vasculature in the visual cortex in accordance with some embodiments. FIG. 128B is a bar graph depicting blood vessel diameter in the visual cortex and illustrating an increase in blood vessel diameter following gamma exposure in accordance with some embodiments.

DETAILED DESCRIPTION

In one aspect, the present disclosure provides methods, devices, and systems for preventing, mitigating, and/or treating a brain disorder or cognitive dysfunction/deficit in a subject. In some embodiments, the brain disorder is a dementia.

Cognitive function critically depends on the precise timing of oscillations in neural network activity, specifically in the gamma frequency, a rhythm (e.g., about 20 Hz to about 100 Hz, about 20 Hz to about 80 Hz, or about 20 Hz to about 50 Hz) linked to attention and working memory. Because these oscillations emerge from synaptic activity, they provide a direct link between the molecular properties of neurons and higher level, coherent brain activity. Importantly, gamma oscillatory activity is disrupted in neural circuits compromised by molecular neuropathology in AD and may represent a key determinant of memory impairment in the disease. It has yet to be determined whether there is a causal relationship between pathology and impairment of brain oscillations. However, driving brain rhythms can serve as a multi-target therapy for the treatment of a dementia, such as AD, and can be achieved via non-invasive therapies.

In one aspect, the present disclosure provides devices, methods, and systems for enhancing or inducing gamma oscillations. In some embodiments, the enhancement or induction of gamma oscillations is by optogenetic methods. In other embodiments, the enhancement or induction of gamma oscillations is by behavioral methods. The present disclosure provides that the enhancement and/or induction of gamma oscillations by optogenetic, behavioral, or other methods reduces AD pathology.

In one aspect, the present disclosure provides devices, systems, and methods for restoration or induction of the gamma oscillatory rhythms in subjects having dementia. In some embodiments, the dementia is AD, vascular dementia, frontal temporal dementia (FTD), and/or Lewy Body dementia. Thus, in some embodiments, the present disclosure provides devices, systems, and methods for treating dementia.

As used herein, the terms "treatment" or "treating" refers to both therapeutic treatment and prophylactic or preventive measures. In some embodiments, subjects in need of treatment include those subjects that already have the disease or condition as well as those subjects that may develop the disease or condition and in whom the object is to prevent, delay, or diminish the disease or condition. For example, in some embodiments, the devices, methods, and systems disclosed herein may be employed to prevent, delay, or diminish a disease or condition to which the subject is genetically predisposed, such as AD. In some embodiments, the devices, methods, and systems disclosed herein may be employed to treat, mitigate, reduce the symptoms of, and/or delay the progression of a disease or condition with which the subject has already been diagnosed, such as AD.

As used herein, the term "subject" denotes a mammal, such as a rodent, a feline, a canine, or a primate. Preferably, a subject according to the invention is a human.

The term "about," as used herein, refers to plus or minus ten percent of the object that "about" modifies.

Dementias are disorders characterized by loss of intellectual abilities and/or memory impairments. Dementias include, for example, AD, vascular dementia, Lewy body dementia, Pick's disease, fronto-temporal dementia (FTD), AIDS dementia, age-related cognitive impairments, and age-related memory impairments. Dementias may also be associated with neurologic and/or psychiatric conditions such as, for example, brain tumors, brain lesions, epilepsy, multiple sclerosis, Down's syndrome, Rett's syndrome, progressive supranuclear palsy, frontal lobe syndrome, schizophrenia, and traumatic brain injury.

AD is the most frequent neurodegenerative disease in developed countries. AD is histopathologically characterized by the accumulation of amyloid plaques comprised of the Aβ peptide and NFTs made of the tau protein. Clinically, AD is associated with progressive cognitive impairment characterized by loss of memory, function, language abilities, judgment, and executive functioning. AD often leads to severe behavioral symptoms in its later stages.

Vascular dementia can also be referred to as cerebrovascular dementia and refers to cerebrovascular diseases (e.g., infarctions of the cerebral hemispheres), which generally have a fluctuating course with periods of improvement and stepwise deterioration. Vascular dementia can include one or more symptoms of disorientation, impaired memory and/or impaired judgment. Vascular dementia can be caused by discrete multiple infarctions, or other vascular causes including, for example, autoimmune vasculitis, such as that found in systemic lupus erythematosus; infectious vasculitis, such as Lyme's disease; recurrent intracerebral hemorrhages; and/or strokes.

Frontal temporal dementia (FTD) is a progressive neurodegenerative disorder. Subjects with FTD generally exhibit prominent behavioral and personality changes, often accompanied by language impairment.

Lewy body dementia is characterized by one or more symptoms of the development of dementia with features overlapping those of AD; development of features of Parkinson's disease; and/or early development of hallucinations. Lewy body dementia is generally characterized by day-to-day fluctuations in the severity of the symptoms.

In some aspects, the present disclosure provides methods for preventing, mitigating, and/or treating dementia in a subject, comprising inducing synchronized gamma oscillations in the brain of the subject. In some embodiments, the induction of gamma oscillations in the subject suffering from a neurological disease or disorder or age-related decline acts to restore gamma oscillatory rhythms that are disrupted in the subject as a result of or in association with the disease or disorder or age-related decline.

In some embodiments, the induction of gamma oscillations reduces generation of isoforms $A\beta_{1-40}$ and $A\beta_{1-42}$. In some embodiments, the induction of gamma oscillations enhances clearance of Aβ (e.g., isoforms $A\beta_{1-40}$ and $A\beta_{1-42}$) from the brain of the subject. In some embodiments, the induction of gamma oscillations prevents accumulation of Aβ in the brain of the subject. In some embodiments, the methods provided herein reduce the level of Aβ in the brain of the subject by about 10%, about 20%, about 30%, about 40%, about 50%, about 60%, about 70%, or more, relative to the level of Aβ in the brain of the subject prior to treatment. In some embodiments, the level of Aβ in the brain of the subject is reduced by at least about 50% relative to the level of Aβ in the brain of the subject prior to treatment.

In some embodiments, the level of Aβ in the brain of the subject is reduced via reduction in the cleavage of APP in the brain of the subject. In some embodiments, the methods provided herein reduce the cleavage of APP in the brain of the subject by about 10%, about 20%, about 30%, about 40%, about 50%, about 60%, about 70%, or more, relative to the level of APP cleavage in the brain of the subject prior to treatment. In some embodiments, the level of APP cleavage in the brain of the subject is reduced by at least about 50% relative to the level of APP cleavage in the brain of the subject prior to treatment. In some embodiments, the level of APP cleavage is measured by the level of C-terminal fragment β (β-CTF) in the brain of the subject. In some embodiments, the level of APP cleavage in the brain is reduced via inhibition of β- and/or γ-secretases, such as by increasing the level of inhibition of β- and/or γ-secretase activity. In some embodiments, the methods provided herein reduce the aggregation of Aβ plaques in the brain of the subject.

In some embodiments, the methods improve cognitive ability and/or memory in the subject.

In another aspect, the present disclosure provides methods for inducing a neuroprotective profile or neuroprotective environment in the brain of a subject, comprising inducing synchronized gamma oscillations in the brain of the subject. For example, in some embodiments, the neuroprotective profile is associated with a neuroprotective microglial cell profile. In further embodiments, the neuroprotective profile is induced by or associated with an increase in activity of the M-CSF pathway. In some embodiments, the neuroprotective environment is associated with anti-inflammatory signaling pathways. For example, in some embodiments, the anti-inflammatory signaling pathways are anti-inflammatory microglia signaling pathways.

In some embodiments, the neuroprotective profile is associated with a reduction in or a lack of pro-inflammatory glial cell activity. Pro-inflammatory glial cell activity is associated with an M1 phenotype in microglia, and includes production of reactive species of oxygen (ROS), neurosecretory protein Chromogranin A, secretory cofactor cystatin C, NADPH oxidase, nitric oxide synthase enzymes such as iNOS, NF-κB-dependent inflammatory response proteins, and pro-inflammatory cytokines and chemokines (e.g., TNF, IL-1β, IL-6, and IFNγ).

In contrast, an M2 phenotype of microglia is associated with downregulation of inflammation and repair of inflammation-induced damage. Anti-inflammatory cytokines and chemokines (IL-4, IL-13, IL-10, and/or TGFβ) as well as an increase in phagocytic activity are associated with an M2 phenotype. Thus, in some embodiments, the methods provided herein elicit a neuroprotective M2 phenotype in microglia. In some embodiments, the methods provided herein increase the phagocytic activity in the brain of the subject. For example, in some embodiments, the methods provided herein increase phagocytic activity of microglia such that the clearance of Aβ is increased.

Gamma oscillations may include about 20 Hz to about 100 Hz. Thus, in some embodiments, the present disclosure provides methods for preventing, mitigating, or treating dementia in a subject comprising inducing gamma oscillations of about 20 Hz to about 100 Hz, or about 20 Hz to about 80 Hz, or about 20 Hz to about 50 Hz, or about 30 to about 60 Hz, or about 35 Hz to about 45 Hz, or about 40 Hz, in the brain of the subject. Preferably, the gamma oscillations are about 40 Hz.

A stimulus may include any detectable change in the internal or external environment of the subject that directly or ultimately induces gamma oscillations in at least one brain region. For example, a stimulus may be designed to stimulate electromagnetic radiation receptors (e.g., photoreceptors, infrared receptors, and/or ultraviolet receptors), mechanoreceptors (e.g., mechanical stress and/or strain), nociceptors (i.e., pain), sound receptors, electroreceptors (e.g., electric fields), magnetoreceptors (e.g., magnetic fields), hydroreceptors, chemoreceptors, thermoreceptors, osmoreceptors, and/or proprioceptors (i.e., sense of position). The absolute threshold or the minimum amount of sensation needed to elicit a response from receptors may vary based on the type of stimulus and the subject. In some embodiments, a stimulus is adapted based on individual sensitivity.

In some embodiments, gamma oscillations are induced in a brain region specific manner. For example, in some embodiments, the gamma oscillations are induced in the hippocampus, the visual cortex, the barrel cortex, the auditory cortex, or any combination thereof. By way of example, in some embodiments, the gamma oscillations are induced in the visual cortex using a flashing light; and in other embodiments, the gamma oscillations are induced in the auditory cortex using auditory stimulation at particular frequencies. In some embodiments, the gamma oscillations are induced in multiple brain regions simultaneously using a combination of visual, auditory, and/or other stimulations. In some embodiments, the gamma oscillations are induced in a virtual reality system.

In some embodiments, the subject receives a stimulus via an environment configured to induce gamma oscillations, such as a chamber that passively or actively blocks unrelated stimuli (e.g., light blocking or noise canceling). Alternatively or in addition, the subject may receive a stimulus via a system that includes, for example, light blocking or noise canceling aspects. In some embodiments, the subject receives a visual stimulus via a stimulus-emitting device, such as eyewear designed to deliver the stimulus. The device may block out other light. In some embodiments, the subject receives an auditory stimulus via a stimulus-emitting device, such as headphones designed to deliver the stimulus. The device may cancel out other noise.

In addition to at least one interface for emitting a stimulus, some embodiments may include at least one processor (to, e.g., generate a stimulus, control emission of the stimulus, monitor emission of the stimulus/results, and/or process feedback regarding the stimulus/results), at least one memory (to store, e.g., processor-executable instructions, at least one stimulus, a stimulus generation policy, feedback, and/or results), at least one communication interface (to communicate with, e.g., the subject, a healthcare provider, a caretaker, a clinical research investigator, a database, a monitoring application, etc.), and/or a detection device (to detect and provide feedback regarding, e.g., the stimulus and/or the subject, including whether gamma oscillations are induced, subject sensitivity, cognitive function, physical or chemical changes, stress, safety, etc.).

In some embodiments, the gamma oscillations are induced by a visual stimulus such as a flashing light at about 20 Hz to about 100 Hz. In particular embodiments, the gamma oscillations are induced by flashing light at about 20 Hz to about 50 Hz. In further embodiments, the gamma oscillations are induced by flashing light at about 35 Hz to about 45 Hz. In yet further embodiments, the gamma oscillations are induced by flashing light at about 40 Hz. In some embodiments, the subject receives (e.g., is placed in a chamber with or wears a light blocking device emitting) about 20 Hz to about 100 Hz flashing light, or about 20 Hz to about 50 Hz flashing light or about 35 Hz to about 45 Hz flashing light, or about 40 Hz flashing light.

In some embodiments, the gamma oscillations are induced by an auditory stimulus such as a sound at a frequency of about 20 Hz to about 100 Hz, or about 20 Hz to about 80 Hz, or about 20 Hz to about 50 Hz, or about 35 Hz to about 45 Hz, or about 40 Hz. In some embodiments, the subject receives (e.g., is placed in a chamber with or wears a noise canceling device emitting) an auditory stimulus of about 20 Hz to about 100 Hz, about 20 Hz to about 80 Hz, about 20 Hz to about 50 Hz, about 35 Hz to about 45 Hz, or about 40 Hz.

In some embodiments, the subject receives (e.g., is placed in a chamber with or wears a light blocking device emitting) the visual and/or auditory stimuli for about one hour, about 2 hours, about 3 hours, about 4 hours, about 5 hours, or more. In some embodiments, the subject receives (e.g., is placed in a chamber with or wears a light blocking device emitting) the stimuli for no more than about 6 hours, no more than about 5 hours, no more than about 4 hours, no more than about 3 hours, no more than about 2 hours, or no more than about one hour. In some embodiments, the subject receives (e.g., is placed in a chamber with or wears a light blocking device emitting) the stimuli for less than an hour.

In some embodiments, the subject undergoes with the methods provided herein. In other embodiments, the subject undergoes treatment with the methods provided herein on multiple separate occasions. Subjects may be treated on a regular schedule or as symptoms arise or worsen. In some embodiments, chronic treatment may be effective at reducing soluble Aβ peptide and/or insoluble Aβ peptide (i.e., plaques).

In some embodiments, the gamma oscillations are induced in a cell-type specific manner. In some embodiments, the gamma oscillations are induced in FS-PV-interneurons. The term "fast-spiking" (FS) when used to describe a class of neurons refers to the capacity of the neurons to discharge at high rates for long periods with little spike frequency adaptation or attenuation in spike height. Thus, these neurons are capable of sustained high frequency (e.g., equal to or greater than about 100 Hz or about 150 Hz) discharge without significant accommodation. This property of FS neurons is attributable in large measure to their expression of fast delayed rectifier channels, in other words, channels that activate and deactivate very quickly.

In one aspect, the stimulations may be non-invasive. The term "non-invasive," as used herein, refers to devices, methods, and systems which do not require surgical intervention or manipulations of the body such as injection or implantation of a composition or a device. For example, the stimulations may visual (e.g., flickering light), audio (e.g., sound vibrations), and/or haptic (mechanical stimulation with forces, vibrations, or motions).

In another aspect, the stimulations may be invasive or at least partially invasive. For example, visual, audio, and/or haptic stimulations may be combined with an injection or implantation of a composition (e.g., a light-sensitive protein) or a device (e.g., an integrated fiber optic and solid-state light source).

Experimental Data

Gamma Oscillations are Decreased During Hippocampal SWR in 5XFAD Mice Early in Disease.

Deficits in gamma have been observed in multiple brain regions in several neurological and psychiatric disorders including a reduction in spontaneous gamma synchronization in human patients with AD. Intriguingly, reduced spontaneous gamma has also been found in two mouse models of AD (a human amyloid precursor protein (hAPP) Tg mouse and an Apolipoprotein E4 allele (APOE4) knock-in mouse) in vivo and in in vitro slice studies in another mouse model (Tg CRND8 mouse). However, it is unclear if gamma oscillations are altered in other mouse models of AD, if it occurs early in disease progression, and if gamma disruption affects disease progression.

Figure 1:
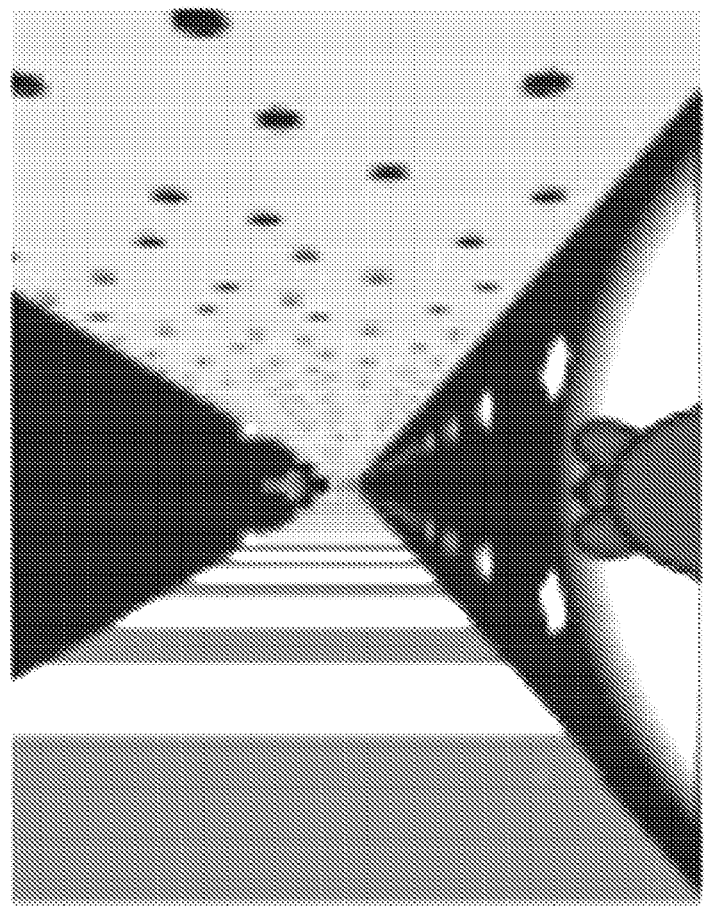
FIG. 1 is a schematic diagram illustrating a mouse running through a virtual linear maze on a spherical treadmill in accordance with some embodiments.

To address these questions, neural activity from awake behaving 5XFAD mice, a well-established model of AD that carries five familial AD mutations was recorded. In particular, 5XFAD mice express five different alleles of familial AD including APP KM670/671NL (Swedish), APP I716V (Florida), APP V717I (London), PSEN1 M146L (A>C), and PSEN1 L286V. Thus, 5XFAD mice were used as a model of AD amyloid pathology. In some embodiments, the neural activity is recorded from the mice at approximately 3 months of age, when they have elevated levels of Aβ, but before the onset of major plaque accumulation and manifestation of learning and memory deficits. FIG. 1 is a schematic diagram illustrating a mouse running through a virtual linear maze on a spherical treadmill in accordance with some embodiments. Food-restricted mice may receive reward for running back and forth through a virtual linear maze on a spherical treadmill.

Neural activity from hippocampal subregion CA1 may be recorded. FIGS. 2A and 2B are electrical traces recorded from hippocampal CA1 and illustrating theta oscillations and sharp-wave ripples (SWRs) in accordance with some embodiments. In some embodiments, gamma oscillations in CA1 may be present during distinct periods of activity such as, during running, when theta oscillations (4-12 Hz) are observed, as illustrated in FIG. 2A, and during quiescent and exploratory behavior, when SWRs occur, as illustrated in FIG. 2B.

Figures 3A, 3B:
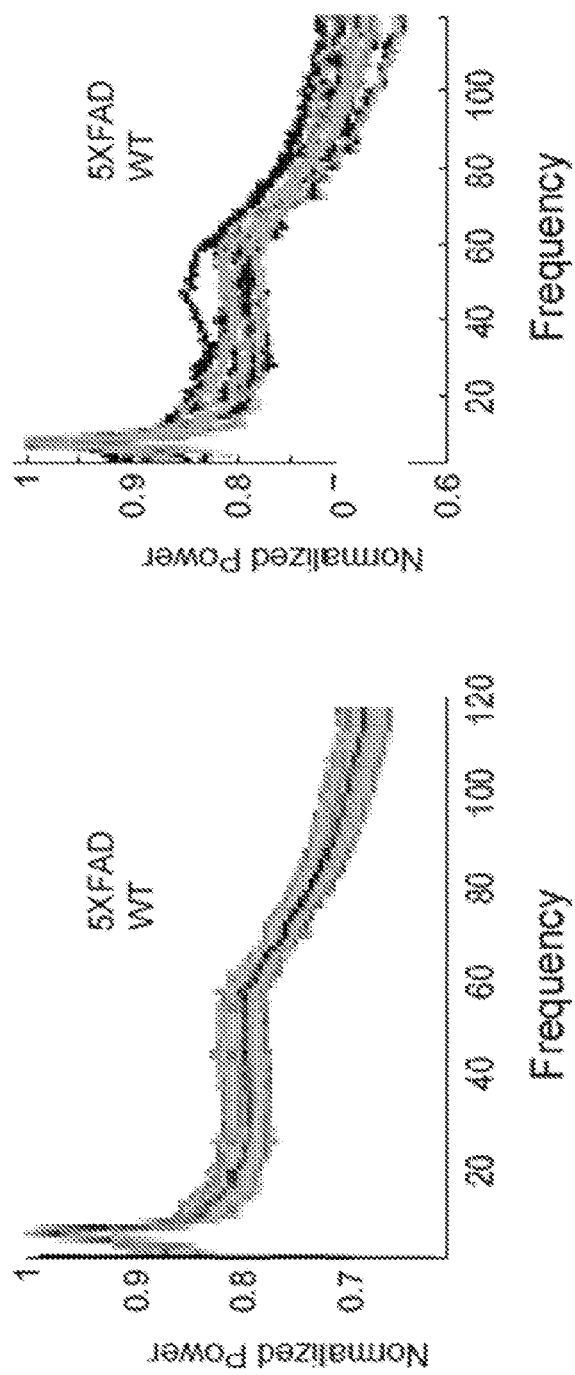
FIGS. 3A and 3B are plots illustrating the mean and standard deviation of normalized power spectrum and normalized power spectral densities during theta periods in three-month-old Tg 5XFAD and wild-type (WT) mice in accordance with some embodiments.

Power spectral densities during theta oscillations were examined and no clear differences were found in slow gamma power (20 Hz to 50 Hz range) between 5XFAD mice and WT littermates. FIGS. 3A and 3B are plots illustrating the mean and standard deviation of normalized power spectrum and normalized power spectral densities during theta periods in three-month-old Tg 5XFAD and WT mice in accordance with some embodiments. FIG. 3A illustrates the mean and standard deviation of the normalized power spectrum during theta periods in three-month-old 5XFAD (n=6 mice) and WT (n=6 mice) mice. In some embodiments, each animal's power spectral density may be normalized to its peak (in theta). FIG. 3B illustrates the normalized power spectral densities during theta periods in three-month-old 5XFAD (n=6 mice) and WT (n=6 mice) mice.

As a next step, in some embodiments, gamma oscillations during SWRs, high frequency oscillations of 150-250 Hz that last around 50-100 ms were examined. SWRs are associated with bursts of population activity during which patterns of spiking activity are replayed across the hippocampus. Prior work has shown that slow gamma is elevated during SWRs and synchronized across CA3 and CA1. As a result, neurons across these hippocampal subregions are more likely to fire together during SWRs because neurons are more likely to fire phase locked to gamma. A study was conducted in which SWRs (defined as periods when power in the ripple band, about 150 Hz to about 250 Hz, exceeded four standard deviations above the mean) were identified and spectrograms were plotted to examine power across a range of frequencies during these SWRs. In the spectrograms, increased power above 100 Hz indicative of the high frequency oscillations characteristic of SWRs, as well as increased power below approximately 50 Hz, indicative of a concurrent increase in gamma power may be observed.

Figures 4A, 4B:
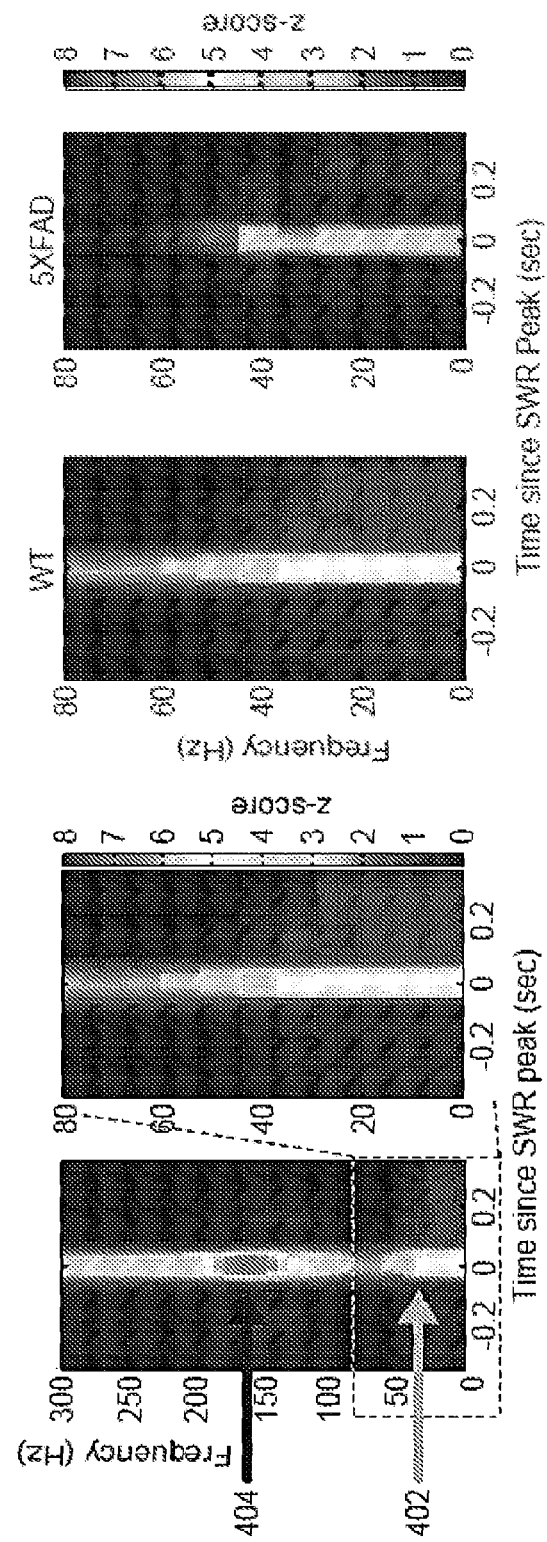
FIGS. 4A and 4B are spectrograms illustrating SWRs for a WT mouse and a 5XFAD mouse in accordance with some embodiments.

FIGS. 4A and 4B are spectrograms illustrating SWRs for a WT mouse and a 5XFAD mouse in accordance with some embodiments. FIG. 4A illustrates that average SWR-triggered spectrograms for one WT mouse shows an increase in the gamma band 402, during SWRs 404 with frequencies below 80 Hz enlarged in the right plot. FIG. 4B illustrates that average SWR-triggered spectrograms for one 5XFAD mouse shows an increase in the gamma band during SWRs though this increase is lower than in the WT mouse as illustrated in FIG. 4A.

In some embodiments, the study found that the instantaneous frequencies of these slower oscillations (10-50 Hz range, as described further herein) were a unimodal distribution centered around 40 Hz. FIGS. 5A-5C are plots depicting the distribution of instantaneous gamma frequencies during SWRs in accordance with some embodiments. FIG. 5A illustrates the distribution of instantaneous gamma frequencies during SWRs for the same mouse shown in FIG. 4A peak around 40 Hz (n=370 SWRs). FIG. 5B illustrates that the distribution of instantaneous gamma frequencies during SWRs in 5XFAD and WT mice show distributions around 40 Hz for each recording session, and FIG. 5C illustrates the mean and standard error of mean (SEM) across animals (n=820, 800, 679, 38, 1875, 57 gamma cycles per session in six 5XFAD animals and 181, 1075, 919, 1622, 51, 1860, 1903 gamma cycles session in six WT animals).

In some embodiments, these gamma oscillations during SWRs in WT mice were then compared to those in 5XFAD littermates and a deficit was found in gamma during SWRs: while gamma power did increase from baseline during SWRs in 5XFAD mice, gamma power during SWRs was significantly smaller in 5XFAD than in WT mice, as described further herein.

FIG. 6A is a series of graphs depicting the z-scored gamma power as a function of the time from the peak of the SWRs in 5XFAD and WT mice, respectively, in accordance with some embodiments. FIG. 6A shows mean and SEM, and illustrates gamma power increases during SWRs relative to baseline.

FIG. 6B is a plot depicting the cumulative distribution of gamma power during SWRs in 5XFAD and WT mice in accordance with some embodiments. The cumulative distribution of gamma power during SWRs shows significantly smaller increases in 5XFAD than WT mice (ranksum test, $p<10^{-5}$; n=2166 SWRs in six 5XFAD mice and 3085 SWRs in six WT mice; z-score median 1.02 (0.39-1.87, $25^{th}$-$75^{th}$ percentiles) in 5XFAD mice and z-score median 1.18 (0.53-2.15, $25^{th}$-$75^{th}$ percentiles) in WT mice).

FIGS. 6C and 6D are plots depicting the cumulative distribution of the z-scored gamma power during the 100 ms around the peak of the SWRs for WT mice 606 and 5XFAD mice 608 and the mean and SEM (shaded) across animals (n=514, 358, 430, 22, 805, 37 SWRs per session in six 5XFAD animals and 82, 311, 370, 776, 18, 710, 818 SWRs per session in six WT animals) in accordance with some embodiments.

FIG. 6E is a plot depicting the cumulative distribution of z-scored gamma power during the 100 ms around the peaks of large SWRs (detection threshold greater than 6 standard deviations above the mean) in WT mice 614 and 5XFAD mice 616 in accordance with some embodiments. Ranksum tests were performed throughout for data that was not normally distributed, as described further herein. FIG. 6E shows significantly smaller increases in WT mice 614 and 5XFAD mice 616 (ranksum test, $p<10^{-5}$, n=1000 SWRs in six 5XFAD mice and 1467 SWRs in six WT mice).

In some embodiments, spiking was phase modulated by these gamma oscillations in both groups, however modulation of spiking by gamma phase was weaker in 5XFAD than in WT animals. The study found that the depth of modulation may be significantly smaller in 5XFAD than in WT animals.

FIG. 7A is a plot depicting fraction of spikes as function of phase of gamma oscillation, and FIG. 7B is a plot depicting depth of modulation of spiking during SWRs as a function of gamma phase during SWRs in three-month-old 5XFAD (n=6 mice) and WT (n=6 mice) mice in accordance with some embodiments (ranksum test, bootstrap resampling, $p<10^{-5}$, which is significant when controlling for multiple comparisons, n=2500 5XFAD spike-gamma phase distributions and 3000 WT distributions, depth of modulation median 0.35 (0.21-0.44, $25^{th}$-$75^{th}$ percentiles) in 5XFAD mice and depth of modulation median 0.38 (0.29-0.47, $25^{th}$-$75^{th}$percentiles) in WT mice). Error bars indicate mean+/−SEM. Plot 704 illustrates histogram of the depth of modulation of spiking FIGS. 7C and 7D are plots illustrating fraction of spikes in hippocampal CA1 during SWRs as a function of phase of gamma oscillations in 5XFAD and WT animals for each animal and the mean and SEM across animals (n=2475, 1060, 3092, 25, 6521, 123 spikes during SWRs per session in six 5XFAD animals and 360, 4741, 1564, 2961, 88, 3058, 4270 spikes during SWRs per session in six WT animals) in accordance with some embodiments.

FIG. 7E is a plot depicting fraction of spikes as function of phase of gamma oscillation, and FIG. 7F is a plot depicting depth of modulation of spiking during large SWRs (detection threshold greater than 6 standard deviations above the mean, as described further herein) in three-month-old 5XFAD (n=6 mice) and WT (n=6 mice) mice (ranksum test, bootstrap resampling one asterisk indicates $p<10^{-10}$, n=2500

5XFAD spike-gamma phase distributions and 3000 WT distributions) in accordance with some embodiments. Error bars indicate mean+/−SEM.

The study also found that there may be fewer SWRs per time in non-theta periods in 5XFAD mice compared to WT (ranksum test, p<10$^{-5}$, n=634 non-theta periods in six 5XFAD mice and 750 non-theta periods in six WT mice, median 0.07 Hz (0-0.17, 25$^{th}$-75$^{th}$ percentiles) in 5XFAD mice and median 0.12 Hz (0-0.24, 25$^{th}$-75$^{th}$ percentiles) in WT mice), further reducing the periods when gamma power is elevated as disclosed above).

FIGS. 8A and 8B are plots depicting SWR rate per non-theta period in 5XFAD mice 802 and WT mice 804 animals for each animal (FIG. 8A) and all animals combined (FIG. 8B) in accordance with some embodiments (ranksum test, p<10$^{-10}$, n=117, 210, 151, 55, 100, 1 non-theta periods per session in six 5XFAD animals and 80, 68, 115, 95, 15, 159, 218 non-theta periods per session in six WT animals). These results reveal deficits in gamma oscillations and modulation of hippocampal CA1 spiking in a mouse model of AD prior to development of major amyloid plaque accumulation and evidence of cognitive deficits.

Optogenetic Stimulation of FS-PV-Interneurons at Gamma Frequency Drove Gamma Oscillations in the CA1 Region of the Hippocampus.

The observation of gamma deficits during SWRs early in the progression of the disease in this mouse model of AD prompts the question of whether gamma oscillations could affect molecular and cellular AD pathophysiology. To test that, gamma oscillations were optogenetically driven by expressing ChR2 in a Cre-dependent manner using a double-floxed inverted open reading frame (DIO) ChR2-EYFP adeno-associated virus (AAV) in FS-PV-interneurons in hippocampal CA1 of 2.5-month-old 5XFAD/PV-Cre bi-transgenic mice. A study was conducted to determine if genetic induction of hippocampal gamma oscillations in mice affects molecular pathology in a mouse model of AD. Hippocampal gamma oscillations were genetically induced in awake, behaving WT and 5XFAD mice.

Figure 9:
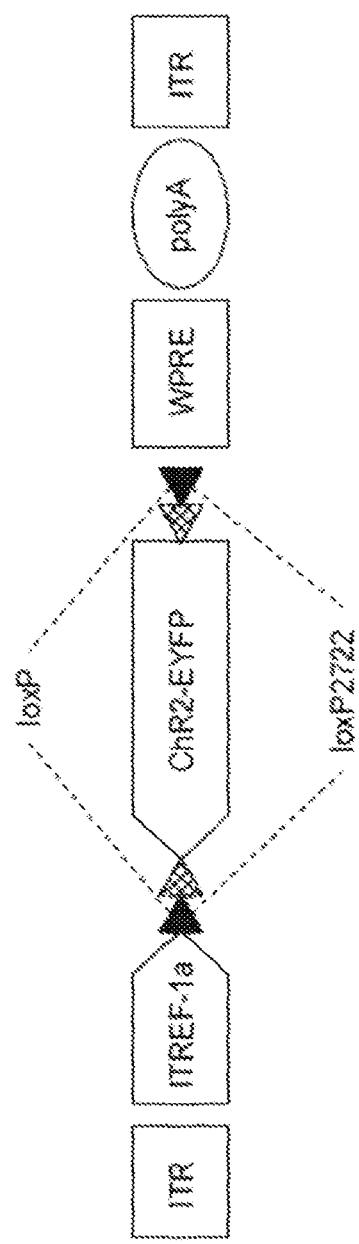
FIG. 9 is a schematic diagram illustrating a viral vector for regulating activation of a specific cell type in the brain of a subject in accordance with some embodiments.

An adeno-associated virus (i.e., an AAV5 virus) with a double-floxed, inverted, open-reading-frame (DIO) ChR2 coupled to enhanced yellow fluorescent protein (EYFP) driven by the EF1α promoter was generated. FIG. 9 is a schematic diagram illustrating a viral vector (i.e., AAV5-DIO-ChR2-EYFP) for regulating activation of a specific cell type in the brain of a subject in accordance with some embodiments. Viral expression was targeted to the CA1 region of the hippocampus in a cell-type-specific manner. In the presence of Cre-recombinase, one of two incompatible loxP variants flips to allow expression of ChR2.

The CA1 region of the hippocampuses of 5XFAD mice were infected with either the AAV-DIO-ChR2-EYFP or an EYFp-only construct using a stereotaxic viral injection method allowing precise regional targeting of viral infection. In one embodiment, at the time of injection, a ferrule containing a fiber optic cable (white bar) was placed about 0.3 mm above the targeted brain region. After two weeks, which provided time for the mice to recover and the virus to express in the PV cells, CA1 interneurons were optogenetically manipulated.

Figure 10A:
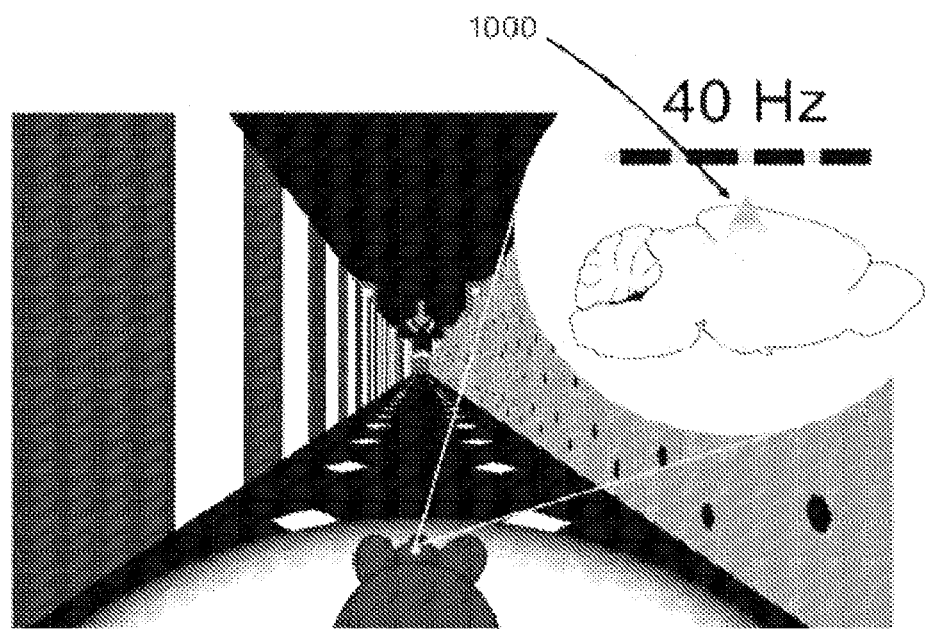
FIGS. 10A and 10B are schematic diagrams illustrating delivery of a signal to the CA1 region of the hippocampus of a subject in accordance with some embodiments.
Figure 10B:
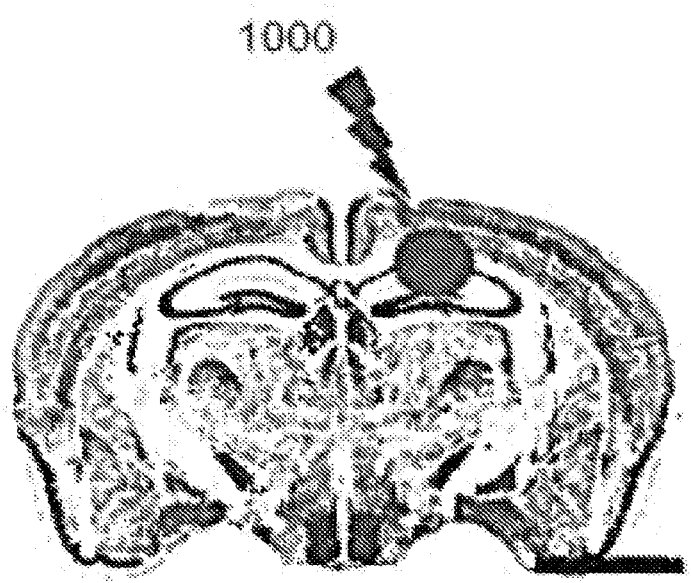

FIGS. 10A and 10B are schematic diagrams illustrating delivery of a signal to the CA1 region of the hippocampus of a subject in accordance with some embodiments. In FIG. 10A, a mouse is shown running on a ball through a maze while undergoing gamma stimulation via optogenetics in the hippocampus in accordance with some embodiments. As shown in FIGS. 10A and 10B, arrow 1000 indicates the blue light that flickers at about 40 Hz to activate the brain region.

In the example, a 200-mW 493-nm DPSS laser was connected to a patch cord with a fiber channel/physical contact connector at each end. During the experiment, about 1 mW of optical stimulation was delivered for about one hour. More specifically, blue light (e.g., 473 nm) was delivered at various frequencies, including theta (e.g., about 8 Hz), gamma (e.g., about 40 Hz), and also randomly at about 40 Hz through an optical fiber positioned just above the CA1 region of the hippocampus. In some embodiments, no stimulation conditions were tested. The theta condition served as a frequency control, and the random condition controlled for rhythmicity specificity in accordance with some embodiments.

Figure 11:
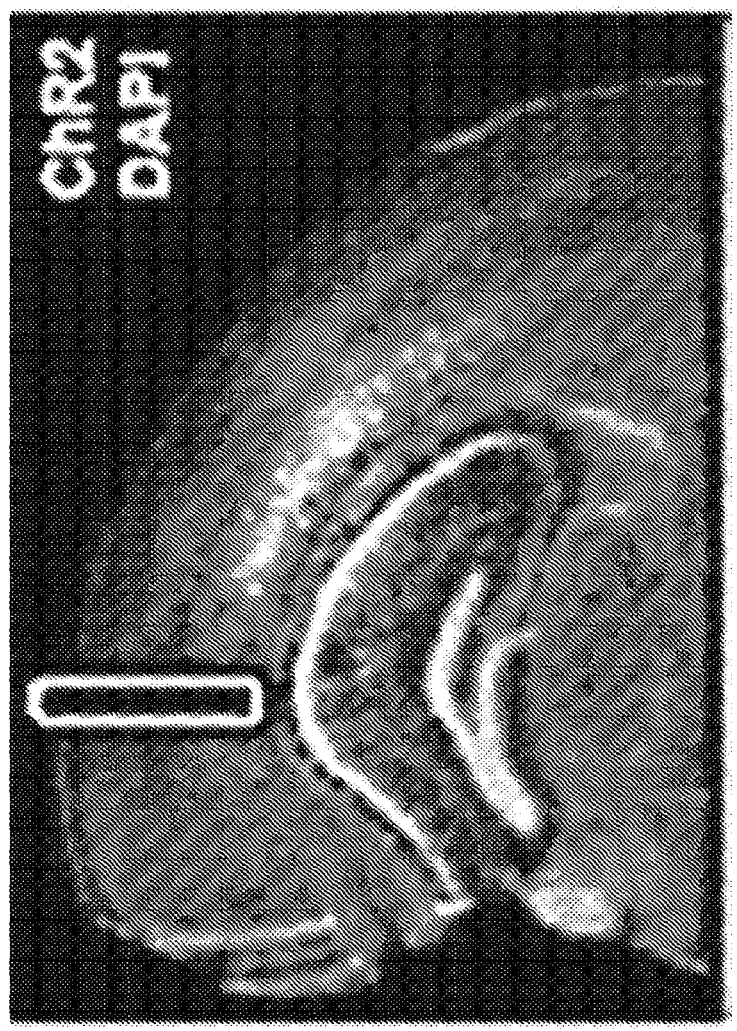
FIG. 11 is an immunofluorescence image illustrating immunostaining of neural tissue in a subject with ChR2 and DAPI in accordance with some embodiments.

Following the completion of the one-hour stimulation, brain tissue was dissected and frozen at −80° C. for staining and enzyme-linked immunosorbent assay (ELISA) analyses. FIG. 11 is an immunofluorescence image illustrating immunostaining of neural tissue in a subject with ChR2 and DAPI in accordance with some embodiments. In the example, FIG. 11 shows the DAPI (nuclei) and ChR2 staining in the hippocampus.

Figure 12A:
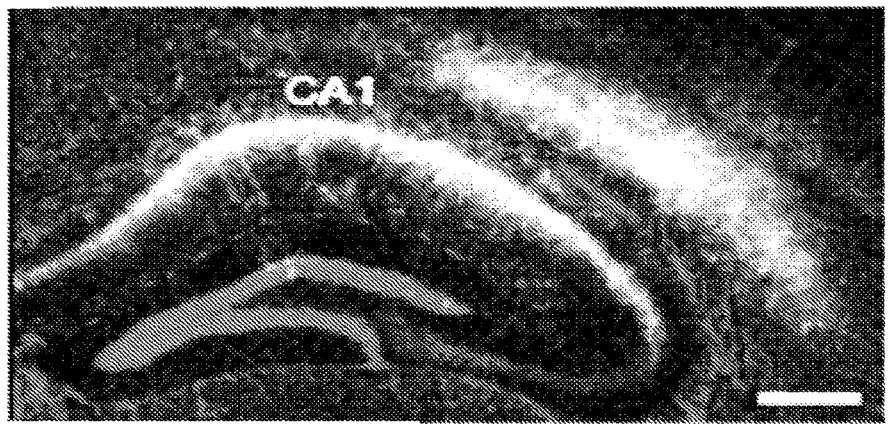
FIG. 12A is an immunofluorescence image illustrating ChR2-EYFP expressed in PV+ interneurons in accordance with some embodiments.
Figure 12B:
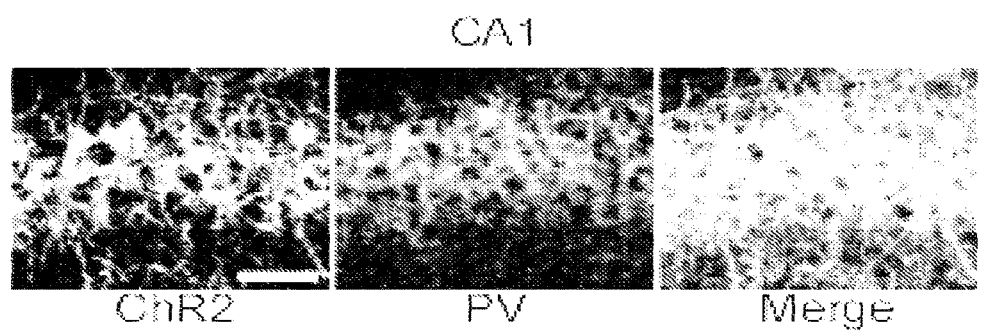
FIG. 12B is a series of immunofluorescence images illustrating immunohistochemistry with anti-EYFP and anti-PV antibodies in accordance with some embodiments.

FIG. 12A is an immunofluorescence image illustrating ChR2-EYFP expressed in PV+ interneurons in accordance with some embodiments. FIG. 12A shows ChR2-EYFP was strongly expressed in PV+ interneurons in CA1 of three-month-old 5XFAD/PV-Cre mice (scale bar=100 μm). FIG. 12B is a series of immunofluorescence images illustrating immunohistochemistry with anti-EYFP and anti-PV antibodies in three-month-old 5XFAD/PV-Cre CA1 expressing AAV DIO ChR2-EYFP that shows EYFP expression only in PV+ cells (scale bar=50 μm). To compare 5XFAD and WT mice, ChR2 was expressed in FS-PV-interneurons in 5XFAD-negative littermates. As a control for the non-specific effects of light stimulation, 5XFAD/PV-Cre bi-transgenic mice expressing AAV-DIO, which contained EYFP only was used. In these mice, with an identical genetic background and light delivery conditions, light delivery does not result in optogenetic stimulation. In some embodiments, the FS-PV-interneurons at 40 Hz were chosen for two reasons. First, previous studies have shown that driving FS-PV-interneurons at 40 Hz produced the largest LFP responses. Second, in some embodiments, deficits in gamma during SWRs was found, and instantaneous gamma frequencies during SWRs formed a distribution centered around 40 Hz as illustrated in FIGS. 5A-5C. In some embodiments, for electrophysiological recordings, periods of 40-Hz stimulation were interleaved with periods of no stimulation or periods with stimulation delivered at a randomized interval selected from a Poisson distribution centered at 40 Hz as described further herein.

Figure 13A:
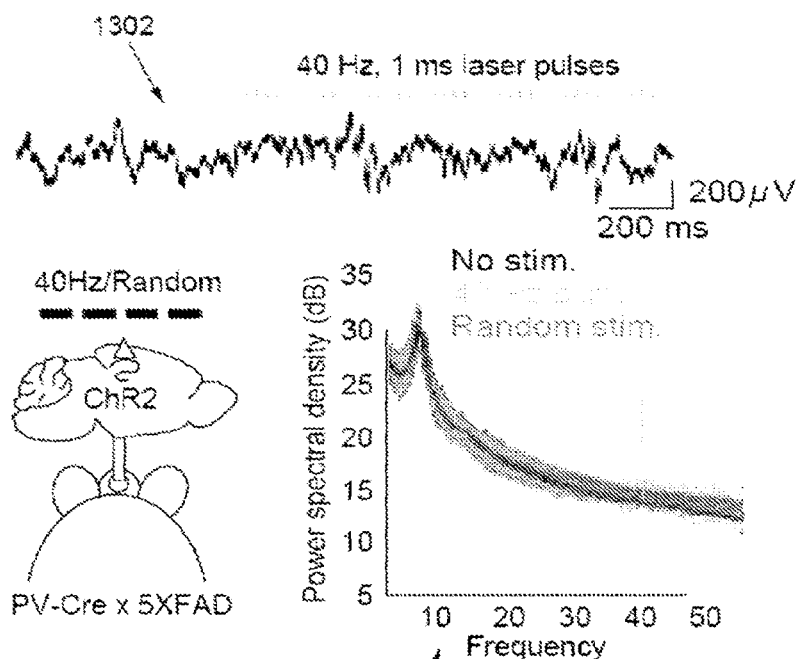
FIGS. 13A and 13B include a schematic diagram of a study, an electrical trace of a local field potential, and power spectral density of FS-PV-interneurons in accordance with some embodiments.
Figure 13B:
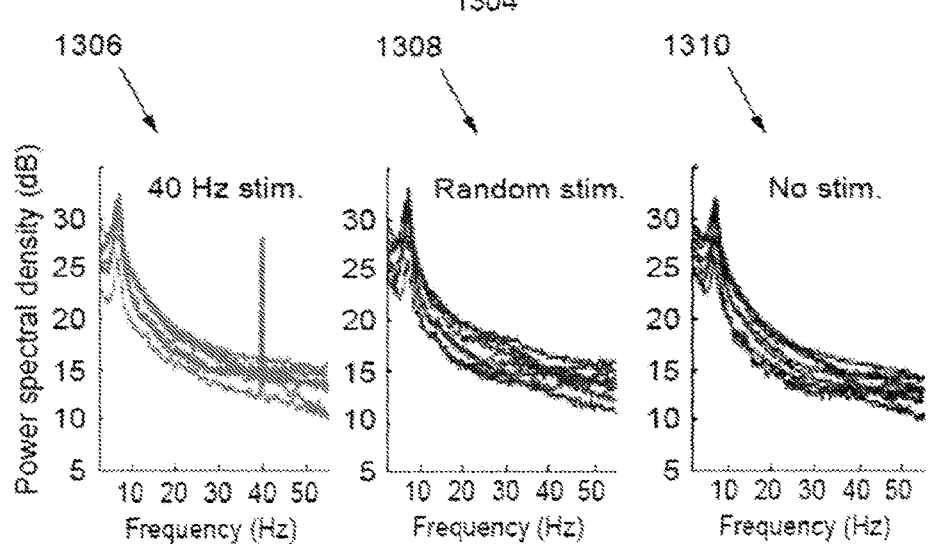

FIGS. 13A and 13B include a schematic diagram of a study, an electrical trace of a local field potential, and power spectral density of FS-PV-interneurons in accordance with some embodiments. Referring to FIG. 13A, 1302 is an electrical trace of a local field potential in CA1 before and during 40 Hz optogenetic drive of FS-PV-interneurons. Plot 1304 illustrates the mean and standard deviation of power spectral density during 40-Hz stimulation, random stimulation (stimulation with a randomized interval selected from a Poisson distribution centered at 40 Hz), or no stimulation of FS-PV-interneurons in CA1 (n=four 5XFAD and three WT mice). FIG. 13B illustrates power spectral density during 40-Hz stimulation 1306, random stimulation 1308, or no stimulation 1310 of FS-PV-interneurons in CA1 for each mouse (n=four 5XFAD mice with 169, 130, 240, 73 40 Hz, 143, 129, 150, 72 random, and 278, 380, 52, 215 no stimulation periods per animal; and n=three WT mice with 65, 93, 91 40 Hz, 64, 93, 90 random, and 187, 276, 270 no stimulation periods per animal). Delivering 1 ms of 473-nm-light pulses at 40 Hz resulted in increased power at 40 Hz in the LFPs as illustrated in FIG. 13A and in plot 1306 of FIG. 13B, while random stimulation did not result in increased power at 40-Hz, as illustrated in FIG. 13A and in plot 1308 of FIG. 13B.

Figures 14A, 14B:
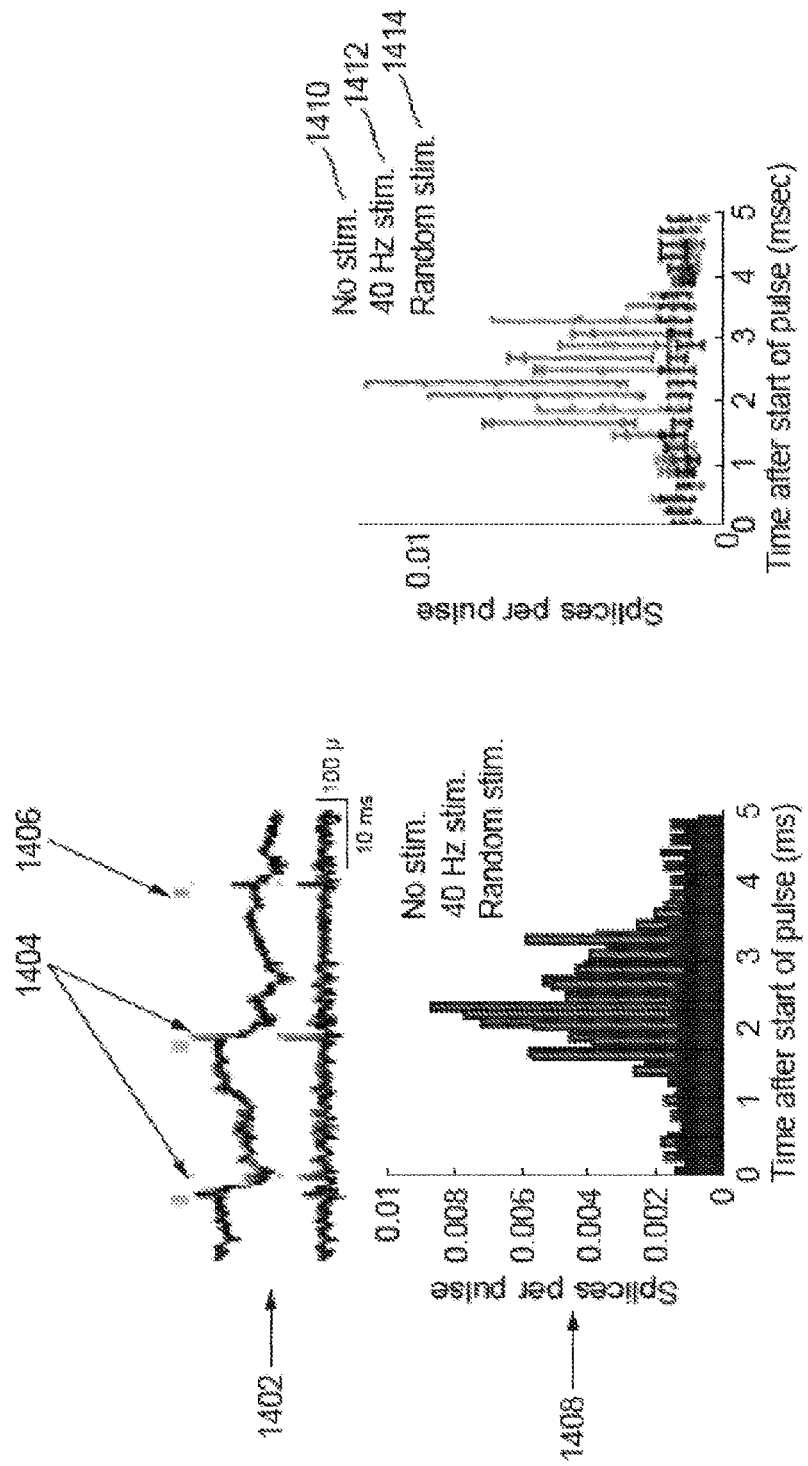
FIGS. 14A and 14B include a raw electrical trace, the trace filtered for spikes after optogenetic stimulation, and plots of spike probability after the onset of 1 ms laser pulse in accordance with some embodiments.

Furthermore, in some embodiments, light pulses effectively drove spikes 2-3 ms after light onset, and spikes per pulse were similar in both random and 40-Hz conditions. FIGS. 14A and 14B include a raw electrical trace, the trace filtered for spikes after optogenetic stimulation, and plots of spike probability after the onset of 1 ms laser pulse in accordance with some embodiments. FIG. 14A illustrates an example raw trace 1402 and the trace filtered for spikes (300-6000 Hz) 1404 after optogenetic stimulation 1406. Plot 1408 illustrates histogram of spikes per pulse after the onset of the 1 ms laser pulse during 40-Hz stimulation, random stimulation, or no stimulation (n=345762 40-Hz stimulation, 301559 random pulse stimulation, and 32350 no stimulation times at least 500 ms apart from 552 40-Hz stimulation, 543 random stimulation, and 1681 no stimulation periods in four 5XFAD and three WT mice). FIG. 14B shows spike probability after the onset of the 1 ms laser pulse in response to 40-Hz stimulation 1412, random stimulation 1414, or no stimulation 1410 with an increase in spiking around 2-3 ms after the laser pulse onset (n=four 5XFAD with 87, 130, 8, 73 40-Hz stimulation, 85, 129, 5, 72 random stimulation, and 251, 379, 15, 215 no stimulation periods per animal; and n=three WT with 65, 93, 91 40-Hz stimulation periods per animal, 64, 93, 90 random stimulation periods per animal, and 187, 277, 270 no stimulation periods per animal). Error bars show mean+/−SEM.

Thus, 40-Hz oscillations in CA1 were effectively driven via optogenetic stimulation of FS-PV-interneurons. Previous studies have shown that Aβ peptide levels were elevated following increases in neural activity and reduced following silencing of neural activity. In some embodiments, the random stimulation condition was used to control for overall changes in spiking activity caused by stimulation. In some embodiments, multi-unit firing rates were compared during interleaved periods of 40 Hz and random stimulation and no significant differences were found between firing rates in these conditions.

Figures 15A, 15B:
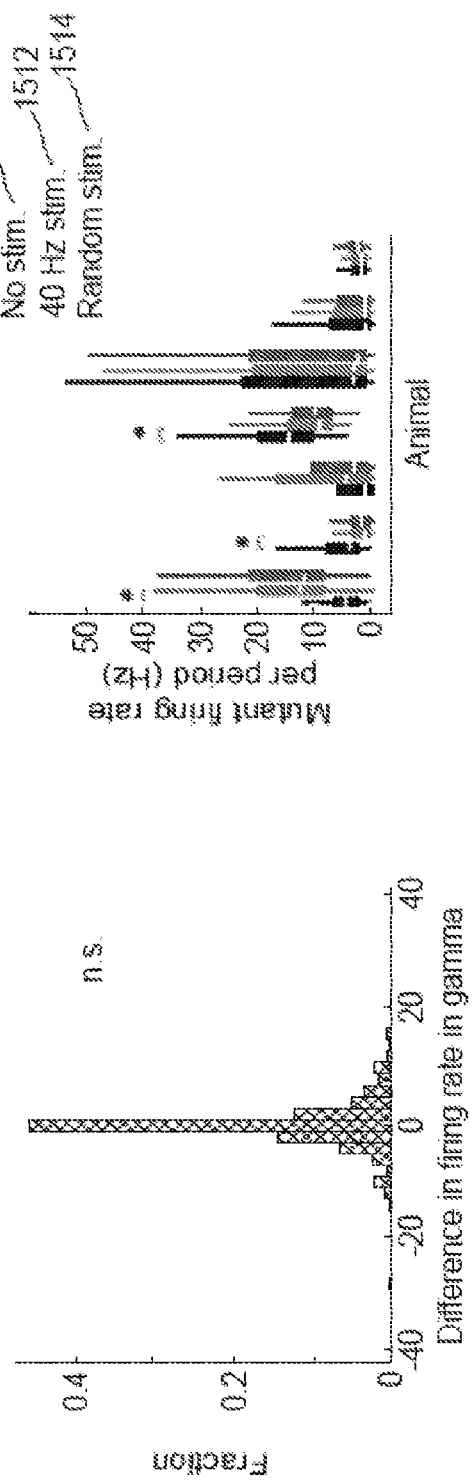
FIG. 15A is a histogram illustrating the difference in firing rates between 40-Hz stimulation and random stimulation periods in accordance with some embodiments.
FIG. 15B is a bar graph illustrating multiunit firing rates per 40-Hz stimulation, random stimulation, and no stimulation periods for each animal in accordance with some embodiments.

FIG. 15A is a histogram illustrating the difference in firing rates between 40-Hz stimulation and random stimulation periods in accordance with some embodiments. FIG. 15A shows that both types of stimulation elicit similar amount of spiking activity (Wilcoxon signed rank test for zero median, p>0.6, n=538 stimulation periods from four 5XFAD and three WT mice, "n.s." indicates not significant). Wilcoxon signed rank test for zero median of the distribution of differences between firing rates during 40 Hz and random stimulation for all mice together p>0.6: median $-1.75 \times 10^{-5}$ Hz ($-1.28$-$1.18$ Hz, $25^{th}$-$75^{th}$ percentiles) n=538 stimulation periods.

FIG. 15B is a bar graph illustrating multiunit firing rates per 40-Hz stimulation 1512, random stimulation 1514, and no stimulation 1510 periods for each animal (ranksum tests for each animal, three WT and four 5XFAD mice, p>0.09, median and quartiles shown in figure, n=87, 130, 8, 65, 93, 91, 73 40-Hz stimulation periods and 85, 129, 5, 64, 93, 90, 72 random stimulation periods per mouse). Box and whisker plots show median (white lines in box) and quartiles (top and bottom of box). In all animals firing rates between 40 Hz and random stimulation were not significantly different showing that the random stimulation condition serves as a control for spiking activity (ranksum tests for each animal, three WT and four 5XFAD mice, p>0.09, median and quartiles shown in figure, n=87, 130, 8, 65, 93, 91, 73 40-Hz stimulation periods and 85, 129, 5, 64, 93, 90, 72 random stimulation periods per animal). Whether 40-Hz stimulation caused neuronal hyperactivity relative to no stimulation was also examined. In most animals the firing rates between 40 Hz or random stimulation and no stimulation were not significantly different (ranksum tests for each animal, 2 WT and two 5XFAD, p>0.25, n=8, 93, 91, 73 40-Hz stimulation periods and 15, 277, 270, 215 baseline periods per animal) or the firing rates during 40-Hz or random stimulation were lower than during no stimulation (ranksum tests for each animal, 1 WT and 1 5XFAD, $p<10^{-5}$, which is significant, when corrected for performing multiple comparisons, n=130, 65 40-Hz stimulation periods and 379, 187 baseline periods per animal) indicating that 40-Hz stimulation did not cause neuronal hyperactivity. In one animal there was significantly more activity with 40 Hz or random stimulation than during baseline (ranksum test for 1 5XFAD, mouse, $p<10^{-5}$, n=87 40-Hz stimulation periods and 251 baseline periods per animal). Therefore in six out of seven animals there is no evidence that the 40 Hz optogenetic stimulation of FS-PV-interneurons causes hyperactivity. Therefore, in some embodiments while the random condition did not induce gamma oscillations, it did result in similar amounts of multi-unit spiking activity as illustrated in FIG. 15A.

Figure 16A:
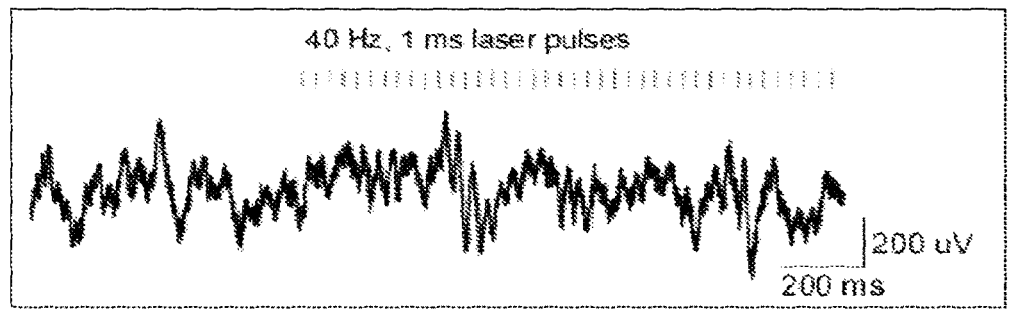
FIG. 16A is an electrical trace recorded from a hippocampus of a subject during a frequency-specific increase in the stimulation of a specific cell type in the CA1 region of the hippocampus of a subject in accordance with some embodiments.

FIG. 16A is an electrical trace recorded from a hippocampus of a subject during a frequency-specific increase in the stimulation of a specific cell type in the CA1 region of the hippocampus of a subject in accordance with some embodiments. More specifically, FIG. 16A was recorded from the hippocampus of a subject during the frequency-specific increase in the stimulation of the FS-PV+ (i.e., the gamma condition) in accordance with some embodiments.

Figure 16B:
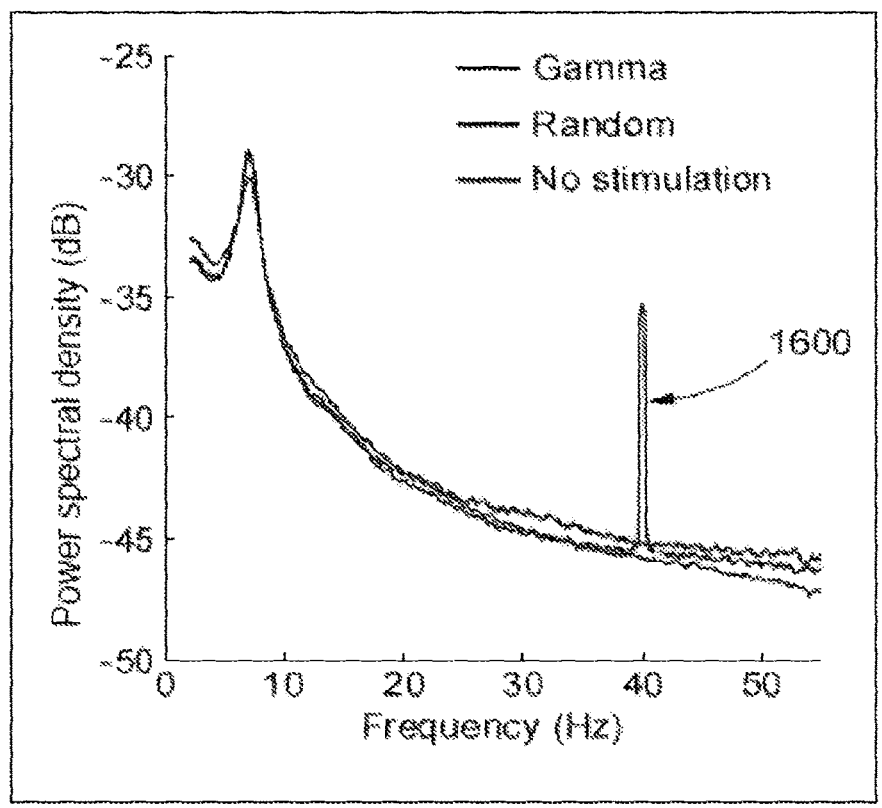
FIG. 16B is a plot of power spectral density illustrating a frequency-specific increase in the local field potential power in the stimulation of a specific cell type in the CA1 region of the hippocampus of a subject in accordance with some embodiments.

FIG. 16B is a plot of power spectral density illustrating a frequency-specific increase in the local field potential power in the stimulation of a specific cell type in the CA1 region of the hippocampus of a subject in accordance with some embodiments. In particular, the power spectral density graph in FIG. 16B verifies the specificity of the stimulation. Local field potential (LFP) power was enhanced only in the 40 Hz band 1600 during the gamma stimulation condition when the FS-PV+ are activated by 40-Hz blue light pulses (n=4 mice per group). Neither baseline nor random stimulation conditions showed enhancement at this frequency 1600.

Gamma Stimulation Reduced Aβ Production in the CA1 Region of the Hippocampus.

Accumulation of Aβ may initiate multiple neurotoxic events typical for AD pathology. Therefore, in some embodiments, gamma stimulation affects in overall Aβ peptide levels in 5XFAD mice were examined. Mice that were three months old were used because plaques are not present in the hippocampus at this stage in these mice, allowing soluble Aβ dynamics independent of plaque load to be investigated. In some embodiments, it was found that one hour of stimulation of FS-PV-interneurons reduced $A\beta_{1-40}$ by 53.22% and $A\beta_{1-42}$ by 44.62% in the 40 Hz group compared to the EYFP control group in the CA1 region of the hippocampus, as measured by Aβ ELISA analyses.

Figures 17A, 17B:
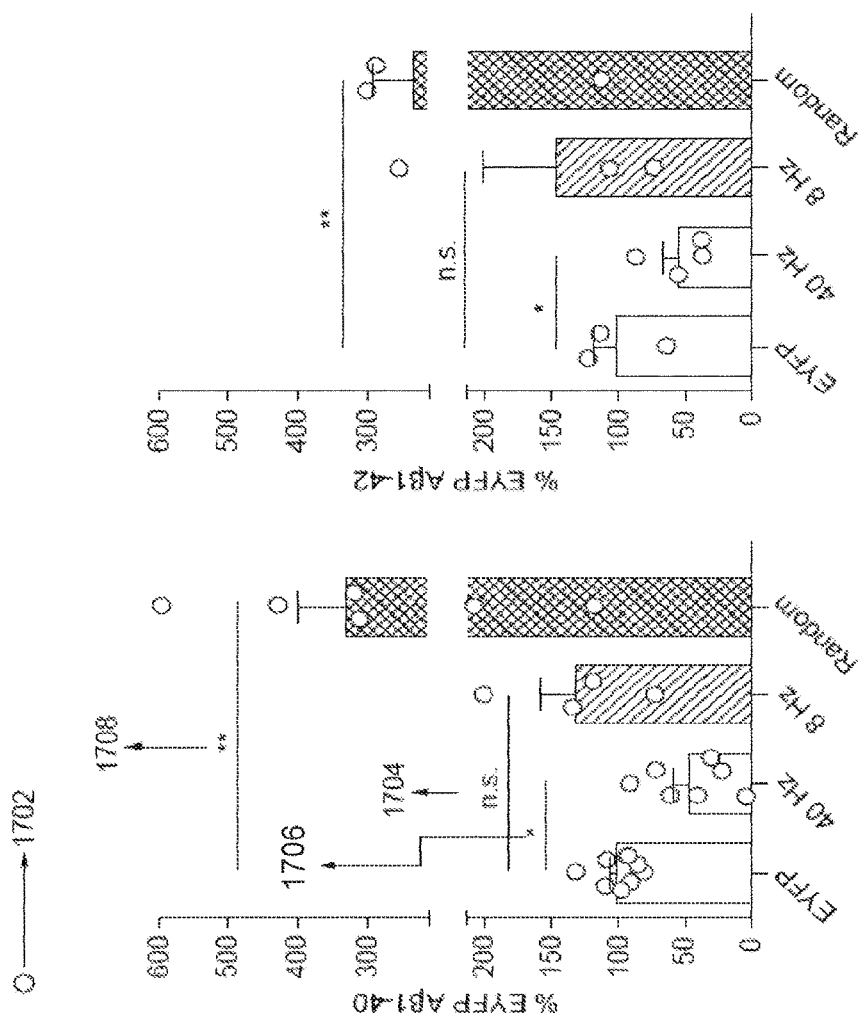
FIGS. 17A and 17B are bar graphs depicting relative $A\beta_{1-40}$ and $A\beta_{1-42}$ levels of 5XFAD/PV-Cre CA1 by one-way ANOVA in accordance with some embodiments.

FIGS. 17A and 17B are bar graphs depicting relative $A\beta_{1-40}$ and $A\beta_{1-42}$ levels of 5XFAD/PV-Cre CA1 by one-way ANOVA grouping all mice together in accordance with some embodiments (n=8 EYFP mice and 740 Hz mice for $A\beta_{1-40}$, n=4 mice per group for $A\beta_{1-42}$). The bar graph in FIG. 17A represents relative $A\beta_{1-40}$ levels of 5XFAD/PV-Cre CA1 in each stimulation condition. Circles 1702 superimposed on bars in bar graphs indicate individual data points in each group (n=8 EYFP, n=7 40-Hz, n=4 8-Hz, n=6 random 5XFAD/PV-Cre mice per group). Notation "n.s." 1704 indicates not significant, asterisk 1706 indicates p<0.05, double asterisks 1708 indicate p<0.01 by one-way ANOVA for all bar graphs in this figure. FIG. 17B represent relative $A\beta_{1-42}$ levels of 5XFAD/PV-Cre CA1 in each simulation condition (n=4 EYFP, n=4 40-Hz, n=3 8 Hz n=3 random 5XFAD/PV-Cre mice per group). FIGS. 17A and 17B show mean and SEM.

TABLE 1 (below) depicts significantly different p<0.05 by Student's t-test, raw concentration (pg/ml) values when mice from the same litter that receive different conditions are compared. TABLE 1 displays raw $A\beta_{1-40}$ and $A\beta_{1-42}$ levels with ELISA dilution for each experimental group.

TABLE 1

| Treatment | Dilution Factor | Average $A\beta_{1-40}$ Concentration (pg/ml) | Average $A\beta_{1-42}$ Contentration (pg/ml) |
|---|---|---|---|
| Optogenetics | | | |
| PV-Cre EYFP | 1:2 | 100.01, 61.598, 65.462, 82.509, 69.023, 70.831, 82.152, 74.314 | 58.777, 54.546, 30.585 |
| PV-Cre 40 Hz | 1:2 | 46.604, 31.041, 26,639, 55.612, 69.326, 17.711, 3.9951 | 27.271, 41.950, 18.790, 18.262 |
| PV-Cre 8 Hz | 1:2 | 101.268, 54.283, 90.190, 151.690 | 50.699, 122.85, 35.507 |
| PV-Cre Random | 1:2 | 235.68, 89.962, 157.37, 323.902, 451.78, 241.63 | 54.029, 137.78, 144.63 |
| αCaMKII-Cre EYFP | 1:2 | 45.813, 59.069, 40.404, 66.810 | 72.052, 36.573, 67.243, 59.295 |
| αCaMKII-Cre 40 Hz | 1:2 | 55.942, 44.270, 57.498, 47.382, 115.08, 75.673 | 70.847, 79.683, 61.429 |
| αCaMKII-Cre 8 Hz | 1:2 | 52.829, 46.604, 57.720 | 95.939, 21.640, 102.987 |
| αCaMKII-Cre Random | 1:2 | 218.00, 191.72, 159.07 | 66.203, 168.867, 176.404 |
| Light Flicker | | | |
| Dark one hour VC | 1:2 | 343.8, 245.3, 210.6, 343.8, 588.4, 394.9, 151.5, 334.4, 301.1, 185.6 | 449.5, 320.7, 275.2, 449.5, 769.2, 516.2 |
| Light one hour VC | 1:2 | 366.9, 632.4, 378.2, 314.1, 266.9, 264.1 | 616.4, 592.3, 802.9, 394.5, 330.7, 337.8 |
| 20 Hz one hour VC | 1:2 | 944.4, 313.2, 595.9, 530.9, 456.5, 289.9 | 1624, 302.4, 816.9, 687.2, 676.6, 343.0 |
| 40 Hz one hour VC | 1:2 | 146.4, 143.6, 104.9, 99.6, 179.7, 219.8, 100.4, 98.46, 71.96, 68.31, 123.3, 150.7 | 191.4, 187.7, 137.2, 130.2, 234.9, 287.3 |
| 80 Hz one hour VC | 1:2 | 332.5, 328.7, 363.5, 390.6, 530.0, 673.3 | 558.3, 418.9, 510.7, 609.5, 1186, 921.9 |
| 40 Hz + PTX one hour VC | 1:2 | 367.2, 431.4, 445.2, 392.4, 386.7, 445.2 | 396.6, 540.5, 532.7, 705.0, 104.5, 104.5 |
| Random one hour VC | 1:2 | 461.8, 100.2, 9.819, 416.6 | 423.9, 157.9, 389.9, 841.5 |
| Dark one hour HPC | 1:2 | 97.949, 107.33, 119.92, 139.33 | 499.30, 355.13, 469.53, 598.03 |
| 40 Hz one hour HPC | 1:2 | 88.136, 104.78, 161.52, 197.36 | 364.53, 408.41, 436.62, 873.83 |
| Random one hour HPC | 1:2 | 95.816, 136.77, 70.004, 125.47 | 466.39, 500.87, 311.26, 582.355 |
| Dark seven days soluble | 1:50 | 1216.9, 1181.3, 1173.4, 1199.5, 134.73, 151.34, 113.26, 145.14, 127.91, 127.48, 143.02, 127.48, 141.07 | 5217.2, 8057.9, 9051.3, 6773.7, 244.11, 236.96, 235.38, 240.62, 286.19, 8.382, 11.21, 14.03, 13.56 |
| Dark seven days insoluble | 1:100 | 1173.2, 1208.2, 1205.3, 1214.6, 994.86, 1059.2, 1176.6, 1065.4, 1002.9, 306.16, 690.70, 3442.7, 152.73 | 8572.7, 9127.1, 6349.3, 10138, 6852.2, 7056.7, 7039.7, 7094.2, 7289.0, 748.21, 1117.1, 1055.5, 504.95 |
| 40 Hz seven days soluble | 1:50 | 476.71, 283.83, 336.87, 237.22, 7.0175, 4.1480, 4.0580, 1.5205, 91.864, 152.73, 148.84, 141.07, 162.44 | 419.7, 248.1, 242.7, 90.974, 95.626, 56.936, 67.577, 47.586, 200.87, 13.56, 9.794, 15.44, 3.677 |
| 40 Hz seven days insoluble | 1:100 | 281.97, 270.37, 86.199, 239.71, 23.557, 15.166, 22.714, 1038.9, 1099.8, 1760.8, 1558.8, 187.69, 22.64 | 202.96, 130.71, 195.73, 193.70, 1646.89, 1579.1, 503.44, 1400.0, 7536.62, 955.23, 1208.8, 694.57, 784.91 |
| Dark one hour BC | 1:2 | 81.874, 18.343, 86.554 | 391.95, 883.69, 604.97 |
| 40 Hz one hour BC | 1:2 | 81.307, 27.986, 30.113 | 300.34, 1152.5, 616.92 |
| 40 Hz one hour wait 4 hours | 1:2 | 91.06, 141.8, 111.2, 12.30 | 108.0, 168.1, 157.3, 35.158 |

TABLE 1-continued

| Treatment | Dilution Factor | Average Aβ$_{1-40}$ Concentration (pg/ml) | Average Aβ$_{1-42}$ Contentration (pg/ml) |
| --- | --- | --- | --- |
| 40 Hz one hour wait 12 hours | 1:2 | 167.2, 101.6, 89.31, 119.9 | 236.1, 134.6, 124.8, 152.4 |
| 40 Hz one hour wait 24 hours | 1:2 | 246.7, 177.6, 281.2, 175.0, 257.3, 204.2 | 231.8, 107.0, 402.7, 184.6, 245.1, 179.7 |
| Dark APP/PS1 | 1:2 | 1050.16, 1085.25, 1522.45, 1153.69, 1750.77 | 19.22, 30.68, 28.08, 14.25, 25.30 |
| 40 Hz APP/PS1 | 1:2 | 512.42, 947.80, 850.45, 793.63 | 18.85, 15.58, 18.92, 11.44 |
| Dark WT | 1:1 | 0.038, 0.813, 2.016, 1.913, 0.313, 4.11, 7.23, 20.2, 40.4, 38.7, 11.9 | N/A |
| 40 Hz WT | 1:1 | 0.139, 0.325, 0.346, 0.390, 8.92, 12.1, 6.34, 12.4, 13.1 | N/A |

In some embodiments, a comprehensive set of control experiments were performed to determine whether the effect was specific to frequency, cell-type, and/or rhythmicity. To determine frequency specificity, FS-PV-interneurons of the 5XFAD/PV-Cre bi-transgenic mice at 8 Hz were driven and no change in Aβ levels was observed. Then, FS-PV-interneurons were driven at random and the effect was specific to rhythmic stimulation. Indeed, amyloid levels were not reduced following random stimulation, and in fact, Aβ$_{1-40}$ instead increased by 230.1% and Aβ$_{1-42}$ by 133.8% (see, e.g., FIGS. 17A and 17B, $p<0.01$ by one-way ANOVA grouping all mice together, n=8 EYFP mice and n=4 random mice for Aβ$_{1-40}$, n=3 mice per group for Aβ$_{1-42}$. Mice from the same litter that received different conditions were compared and significantly different $p<0.01$ by Student's t-test were observed).

Finally, cell-type specificity of the effect by stimulating at 8 Hz and 40 Hz in CamKII+ excitatory neurons in hippocampal CA1 using 5XFAD/αCamKII-Cre bi-transgenic mice was tested. FIGS. 18A and 18B are bar graphs depicting relative Aβ$_{1-40}$ and Aβ$_{1-42}$ levels of 5XFAD/αCamKII-Cre CA1 by one-way ANOVA in accordance with some embodiments. FIG. 18A represents relative Aβ$_{1-40}$ levels of 5XFAD/αCamKII-Cre CA1 in each simulation condition. Circles 1802 superimposed on bars in bar graphs indicate individual data points in each group (n=6 40-Hz, n=3 8-Hz, n=3 random 5XFAD/αCamKII-Cre mice per group, notation "n.s." 1804 indicates not significant, asterisks 1806 indicate $p<0.001$ by one-way ANOVA).

FIG. 18B represents relative Aβ$_{1-42}$ levels of 5XFAD/αCamKII-Cre CA1 in each simulation condition (n=3 αCamKII-Cre mice per group). In some embodiments, it was found that driving CamKII+ excitatory neurons at 8 Hz or 40 Hz did not produce significant differences in Aβ$_{1-40}$ and Aβ$_{1-42}$ levels (see, e.g., FIGS. 18A and 18B, right, $p>0.05$ by one-way ANOVA, n=6 40 Hz mice and 3 8 Hz mice (Aβ$_{1-40}$), n=3 mice per group (Aβ$_{1-42}$). If mice from the same litter that received different conditions are compared, they are not significantly different $p>0.05$ by Student's t-test). Similarly to 5XFAD/PV-Cre mice, driving CamKII+ neurons with random stimulation also resulted in a 257.6% elevation of Aβ$_{1-40}$ and 133.3% increase of Aβ$_{1-42}$ (see, e.g., FIGS. 18A and 18B, right, $p<0.001$ by one-way ANOVA, n=5 40 Hz mice and 3 random mice for Aβ$_{1-40}$, n=3 mice per group for Aβ$_{1-42}$. If mice from the same litter that received different conditions are compared then Aβ$_{1-40}$ is significantly different $p<0.001$ by Student's t-test and Aβ$_{1-42}$, $p=0.13$ by Student's t-test).

Thus, the reduction of Aβ peptide levels following 40-Hz stimulation may be specific to driving the FS-PV-interneurons. In some embodiments, to confirm these ELISA findings with immunohistochemistry, Aβ-labeling was performed using a β-amyloid C-terminal end-specific antibody that does not cross react with APP in CA1.

Figures 19A, 19B:
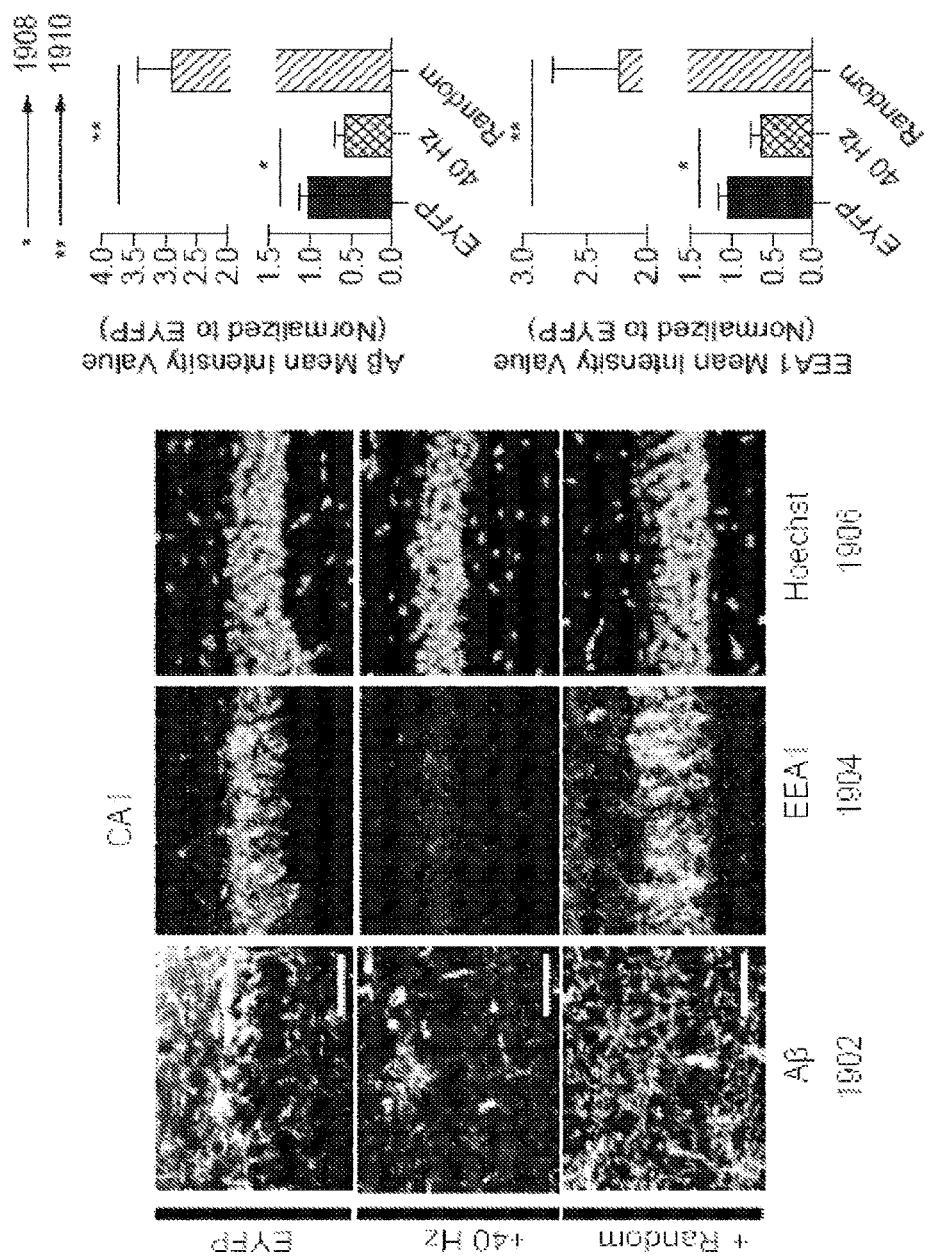
FIG. 19A is a series of images illustrating immunohistochemistry with anti-Aβ and anti-EEA1 antibodies in hippocampal CA1 region in accordance with some embodiments.
FIG. 19B is a series of bar graphs depicting the relative immunoreactivity of Aβ normalized to EYFP in accordance with some embodiments.

FIG. 19A is a series of images illustrating immunohistochemistry with anti-Aβ and anti-EEA1 antibodies in hippocampal CA1 region in accordance with some embodiments. In particular, FIG. 19A is a series of immunofluorescence images illustrating immunohistochemistry with anti-Aβ 1902 (D54D2) and anti-EEA1 1904 (610457) antibodies in hippocampal CA1 region of 5XFAD/PV-Cre in EYFP, 40-Hz and random simulation conditions (scale bar=50 μm). FIG. 19B is a series of bar graphs depicting the relative immunoreactivity of Aβ normalized to EYFP in accordance with some embodiments. In particular, FIG. 19B illustrates the relative immunoreactivity of Aβ normalized to EYFP (n=4 mice per group, 1908 indicates $p<0.05$ and 1920 indicates $p<0.01$ by one-way ANOVA).

Figure 20B:
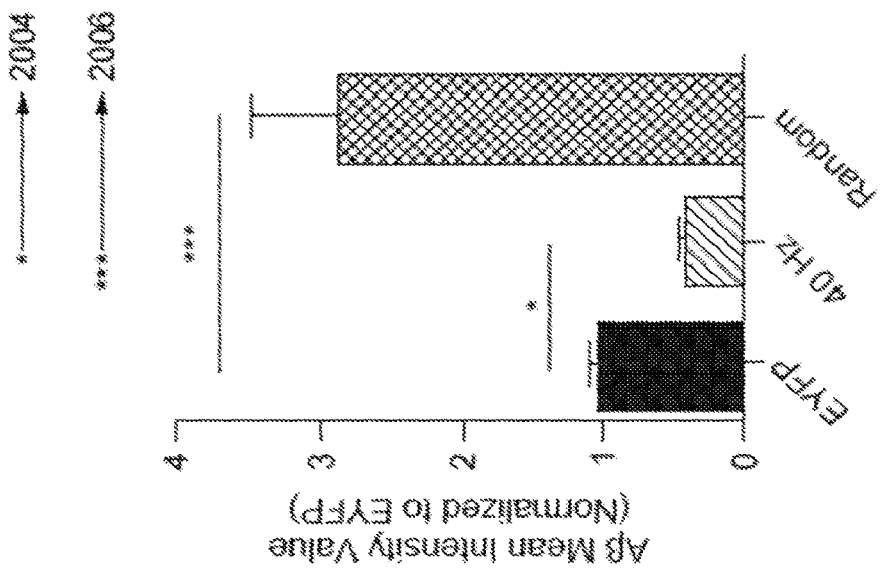
FIG. 20B is a bar graph depicting the relative immunoreactivity of Aβ normalized to EYFP in accordance with some embodiments.
Figure 20A:
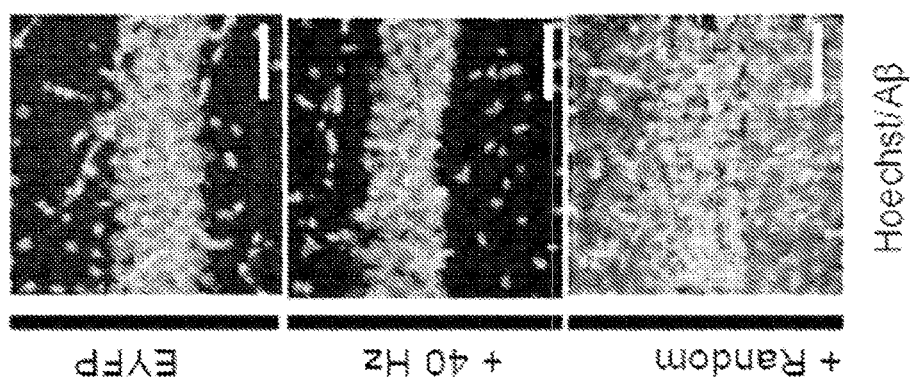
FIG. 20A is a series of immunofluorescence images illustrating immunohistochemistry with anti-Aβ antibodies in hippocampal CA1 region of 5XFAD/PV-Cre in accordance with some embodiments.

FIG. 20A is a series of immunofluorescence images illustrating immunohistochemistry with anti-Aβ antibodies in hippocampal CA1 region of 5XFAD/PV-Cre in accordance with some embodiments. In particular, FIG. 20A is a series of immunofluorescence images illustrating immunohistochemistry with anti-Aβ 2002 (12F4) antibodies in hippocampal CA1 region of 5XFAD/PV-Cre in EYFP, 40-Hz, and Random stimulation conditions (scale bar=50 μm). FIG. 20B is a bar graph depicting the relative immunoreactivity of Aβ normalized to EYFP in accordance with some embodiments. In particular, FIG. 20B illustrates the relative immunoreactivity of Aβ normalized to EYFP (n=4 mice per group, 2004 indicates $p<0.05$ and 2006 indicates $p<0.001$ by one-way ANOVA). The intensity of Aβ-labeling was reduced by 39.5% following 40-Hz stimulation of FS-PV-interneurons in the three-month-old 5XFAD/PV-Cre bi-transgenic mice and was significantly increased by 187.0% following random stimulation, when compared to the EYFP group (see, e.g., FIGS. 19A, 19B, 20A, and 20B, $p<0.05$ and $p<0.01$ by one-way ANOVA, n=4 mice per group).

Brain amyloid concentration may depend on Aβ production and clearance rates. In some embodiments, the Aβ peptides are produced by sequential proteolytic cleavage of APP by β- and γ-secretases. When BACE1 cleaves APP holoprotein, the CTFs and NTFs of APP may be produced. In some embodiments, to elucidate how 40-Hz stimulation reduced Aβ levels, gamma affected APP cleavage was examined by measuring levels of the cleavage intermediates of APP, CTFs and NTFs, following FS-PV-interneuron stimulation. Following 40-Hz stimulation, a significant reduction was found of CTFs by 18.6% following 40-Hz stimulation compared to the EYFP group and by 19.7% compared to the random group (p<0.05 and p<0.01 by one-way ANOVA, n=6 mice per group).

FIG. 21A is a representative western blot, in accordance with some embodiments, depicting levels of APP (CT695), APP NTF (A8967), APP CTFs (CT695), and β-Actin (A5316) (loading control) in CA1 in EYFP, Radom, and 40-Hz stimulation conditions, one mouse per lane, with two biological replicates of each condition. FIG. 21B is a bar graph depicting relative immunoreactivity of APP CTFs in accordance with some embodiments. In particular, FIG. 21B illustrates relative (normalized to actin) immunoreactivity of APP CTFs in 40-Hz versus EYFP and Random conditions (n=6 mice per group, one asterisk 2102 indicates p<0.05, and two asterisks 2104 indicate p<0.01 by one-way ANOVA). FIG. 21C is a series of western blots depicting levels of full-length APP 2106 (CT695), APP CTFs 2108 (CT695) and β-Actin 2112 (A5316, loading control) in CA1 in accordance with some embodiments. In particular, FIG. 21C illustrates levels of full-length APP 2106 (CT695), APP CTFs 2108 (CT695) and β-Actin 2112 (A5316, loading control) in CA1 in EYFP, Random, and 40-Hz stimulation conditions, one mouse per lane, with two biological replicates of each condition.

Figure 22A:
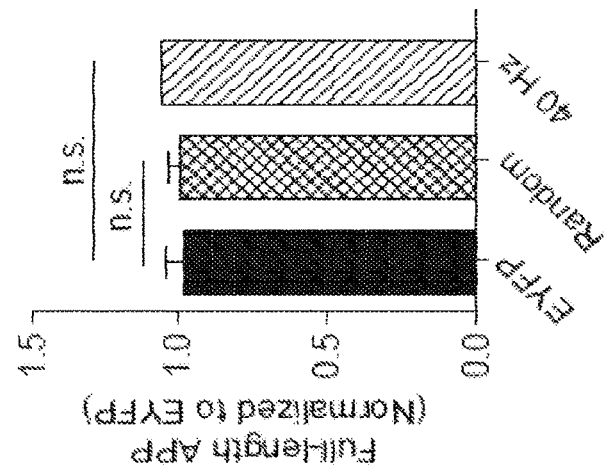
FIG. 22A is a bar graph depicting relative (normalized to actin) immunoreactivity of APP NTFs in 40-Hz versus EYFP and Random conditions in accordance with some embodiments.
Figure 22B:
FIG. 22B is a bar graph depicting relative (normalized to actin) immunoreactivity of full-length APP in EYFP, random, and 40-Hz conditions in accordance with some embodiments.

FIG. 22A is a bar graph depicting relative (normalized to actin) immunoreactivity of APP NTFs in 40-Hz versus EYFP and Random conditions (n=6 mice per group, notation "n.s" 2204 indicates not significant and 2202 indicates p<0.05, by one-way ANOVA). FIG. 22B is a bar graph depicting relative (normalized to actin) immunoreactivity of full-length APP in EYFP, random, and 40-Hz conditions (n=6 mice per group by one-way ANOVA).

In some embodiments, following 40-Hz stimulation significant reduction of APP NTF levels were found by 28.5% compared to the EYFP group and by 28.2% compared to the random group (see, e.g., FIGS. 21A, 22A, and 21C, p<0.05 by one-way ANOVA, n=6 mice per group). Moreover, the levels of full-length APP appeared to be similar among the various groups, showing that the decrease in Aβ was not due to a change in precursor levels (see, e.g., FIGS. 21A, 22B, 21C, n=6 mice per group in APP experiments). In some embodiments, because of the relatively high abundance of APP compared to its cleavage products in this mouse model, changes in full-length APP may be difficult to detect.

Figure 23:
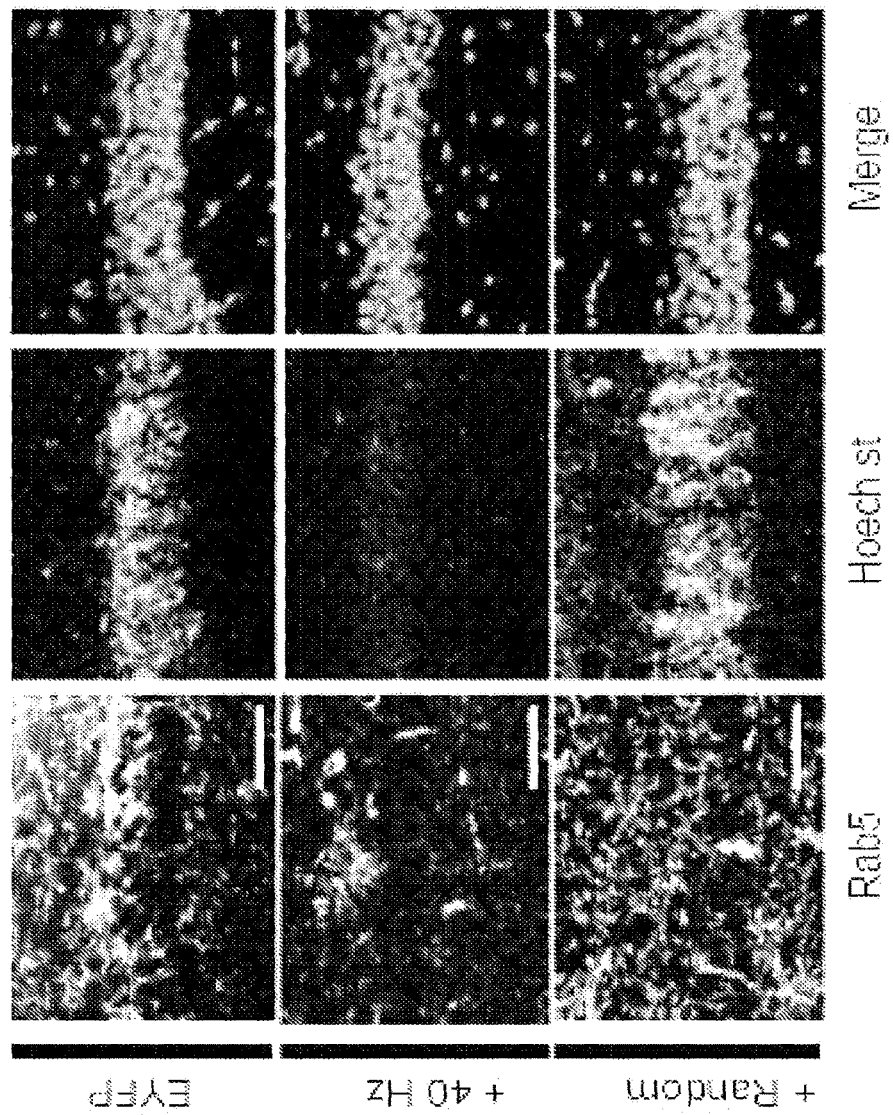
FIG. 23 is a series of immunofluorescence images illustrating immunohistochemistry with anti-Rab5 (ADI-KAp-GP006-E) antibody in accordance with some embodiments.

In some embodiments, processing of APP takes place within the vesicular trafficking pathway, and prior work has shown APP is transported into recycling endosomes following activity stimulation. Moreover, enlarged early endosomes have been observed in brain tissue from AD patients and in human neurons derived from AD patients. In some embodiments, to test whether gamma stimulation affected endosomal abundance in the experimental animals, early endosomes have been characterized in CA1 following 40 Hz and random stimulation using two markers, EEA1 (early endosomal antigen 1) and Rab5 (Ras-related protein encoded by the RAB5A gene). FIG. 23 is a series of immunofluorescence images illustrating immunohistochemistry with anti-Rab5 (ADI-KAp-GP006-E) antibody in three-month-old 5XFAD/PV-Cre mice in EYFP, 40-Hz, and random stimulation conditions (scaled bar=50 µm).

FIG. 24A is a bar graph representing the relative immunoreactivity of EEA1 normalized to EYFP in accordance with some embodiments (n=4 mice per group, one asterisk 2402 indicates p<0.05 and two asterisks 2402 indicate p<0.01 by one-way ANOVA). FIG. 24B is a bar graph depicting relative Rab5 intensity levels of CA1 from 5XFAD/PV-Cre under EYFP, 40-Hz, and random stimulation conditions in accordance with some embodiments (n=3 mice per group, three asterisks 2408 indicate p<0.001 by one-way ANOVA). In some embodiments, EEA1 staining produced a punctate cytoplasmic and juxtamembrane pattern in the neuronal cell bodies, typical for early endosomes (see, e.g., FIG. 19A). In some embodiments, Rab5 labeling has been mostly restricted to the cell bodies and plasma membrane, represented by small, thin puncta concentrated within endosomal and membrane compartments (see, e.g., FIG. 23). Altogether, early endosomal labeling of CA1 neurons demonstrated a significant decrease in both EEA1 (39.7%) and Rab5 (40.1%) staining intensity following 40-Hz stimulation compared to EYFP controls (see, e.g., FIGS. 19A, 23, 24A, p<0.05 and p<0.001 by one-way ANOVA, n=2 sections from 3 mice per group). By contrast, random stimulation of FS-PV-interneurons increased EEA1 staining intensity by 122% compared to EYFP controls (see, e.g., FIGS. 19A and 24A, p<0.01 by one-way ANOVA, n=2 sections from 3 mice per group). In some embodiments, the treatment-dependent changes in EEA1 staining intensity paralleled those of Aβ in CA1 (see, e.g., FIGS. 19A-B, 20A-B, 23, and 24A-B, p<0.05 by one-way ANOVA, n=2 sections from 3 mice per group). These results suggest that in addition to observed changes in CTFs, 40-Hz stimulation alters EEA1 and Rab5, indicating differences in general endosomal processing.

FIG. 25A is a bar graph depicting levels of the Aβ peptide isoform $A\beta_{1-40}$ following different types of stimulation of the CA1 region of the hippocampus of a subject in accordance with some embodiments. In the experiment, one hour of optogenetic stimulation of FS-PV+ at about 40 Hz 502 decreased $A\beta_{1-40}$ levels in hippocampal CA1. Excitatory pyramidal stimulation at 8 Hz 506 and excitatory pyramidal stimulation at 40 Hz 508 did not significantly affect $A\beta_{1-40}$ levels. Random 40-Hz stimulation 504, and particularly random excitatory pyramidal stimulation 510, significantly increased $A\beta_{1-40}$ levels (n=4-9 animals per group).

FIG. 25B is a bar graph depicting a decrease in the Aβ peptide isoform $A\beta_{1-42}$ following stimulation of a specific cell type in the CA1 region of the hippocampus of a subject with gamma oscillations in accordance with some embodiments. In the experiment, one hour of optogenetic stimulation of FS-PV+ at about 40 Hz 516 decreased $A\beta_{1-42}$ levels in hippocampal CA1 (n=2-4 animals per group). Stimulation at 8 Hz 520, excitatory pyramidal stimulation at 40 Hz 522, and excitatory pyramidal stimulation at 8 Hz 524 increased $A\beta_{1-42}$ levels. Random 40-Hz stimulation 518, and particularly random excitatory pyramidal stimulation 526, significantly increased $A\beta_{1-42}$ levels).

FIG. 25C is a series of images illustrating an increase in the level of full-length APP 528, 534 (normalized to actin 532) and a decrease in the level of CTFs (e.g., β-CTF) 530, 536 (normalized to actin 532) following stimulation of a specific cell type in the CA1 region of the hippocampus of a subject with gamma oscillations in accordance with some embodiments. Compared to the random 40-Hz control condition, FS-PV+ stimulation at 40-Hz decreased APP β-CTF levels and increased full-length APP levels (n=4-6 animals per group). Because β-CTF is an APP derivative produced during amyloidogenic cleavage of APP by BACE1, higher β-CTF levels represent increased Aβ production.

Figures 26A, 26B:
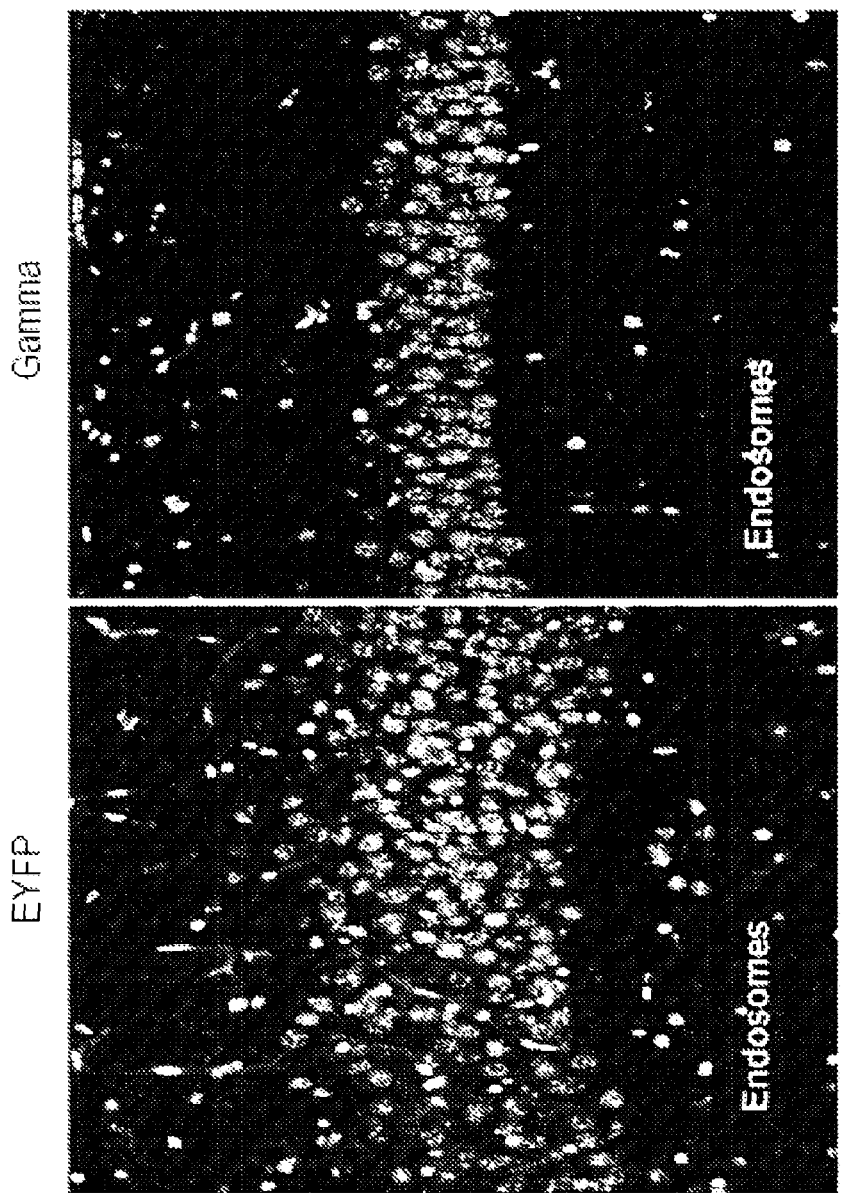
FIGS. 26A-26B are immunofluorescence images illustrating endosome levels (based on EEA1 levels) following different types of stimulation of the CA1 region of the hippocampus of a subject in accordance with some embodiments.

FIGS. 26A-26B are immunofluorescence images illustrating endosome levels (based on EEA1 levels) following different types of stimulation of the CA1 region of the hippocampus of a subject in accordance with some embodiments. In particular, a comparison of FIG. 26B to FIG. 26A shows that induction of gamma oscillations through FS-PV+

40-Hz stimulation reduces EEA1 levels (a marker for endosome levels) compared to random FS-PV+ stimulation 900 as measured by immunofluorescence (n=3 mice per group, p=0.007). Decreased endosome levels in the cells indicate decreased interaction between APP and β-secretase, which results in decreased APP cleavage and Aβ production. Thus, the study showed that, because increased endosome levels indicates increased APP processing and therefore Aβ production, gamma oscillations reduce AP production in an AD mouse model.

Figure 27:
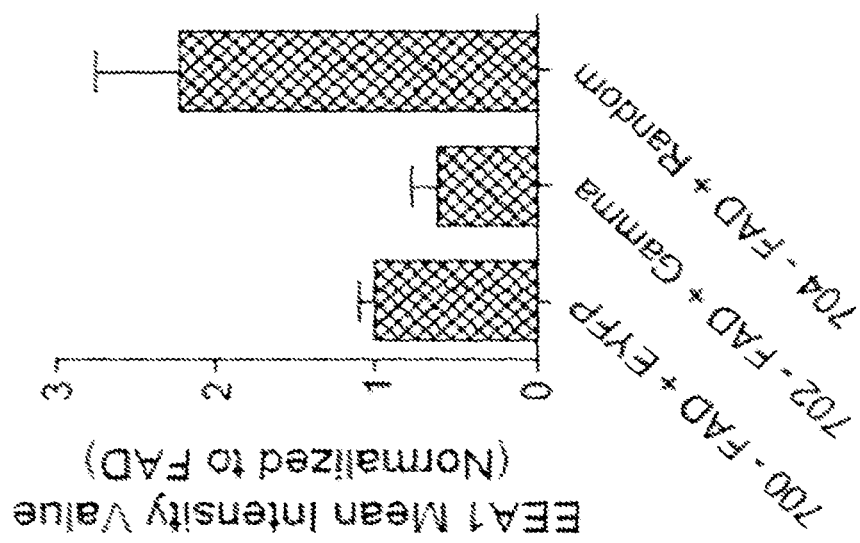
FIG. 27 is a bar graph depicting mean intensity values (normalized to FAD) for the immunofluorescence images in FIGS. 6A-6B following different types of stimulation of the CA1 region of the hippocampus of a subject in accordance with some embodiments.

FIG. 27 is a bar graph depicting mean intensity values (normalized to FAD) for the immunofluorescence images in FIGS. 26A-26B following different types of stimulation of the CA1 region of the hippocampus of a subject in accordance with some embodiments.

Gamma Stimulation Induced Morphological Transformation of Microglia.

In some embodiments, to further explore the cellular and molecular effects of 40-Hz stimulation in an unbiased manner, genome-wide RNA-seq of hippocampal CA1 tissue following one hour of 40-Hz FS-PV-interneuron stimulation, or no stimulation (EYFP) of the 5XFAD/PV-Cre bitransgenic mice was performed. In RNA-seq experiments, an average of 26,518,345 sequencing reads was obtained from three stimulated and three non-stimulated mice. Data QC analysis revealed an average value of 183 for exon/intron ratio, an average value of 272 for exon/intergenic ratio, and an average value of 3.6% for the percentage of ribosomal RNA reads. The analysis identified 523 differentially expressed genes (DEGs), with 130 of them up-regulated and 393 down-regulated in response to 40-Hz stimulation.

Figure 28:
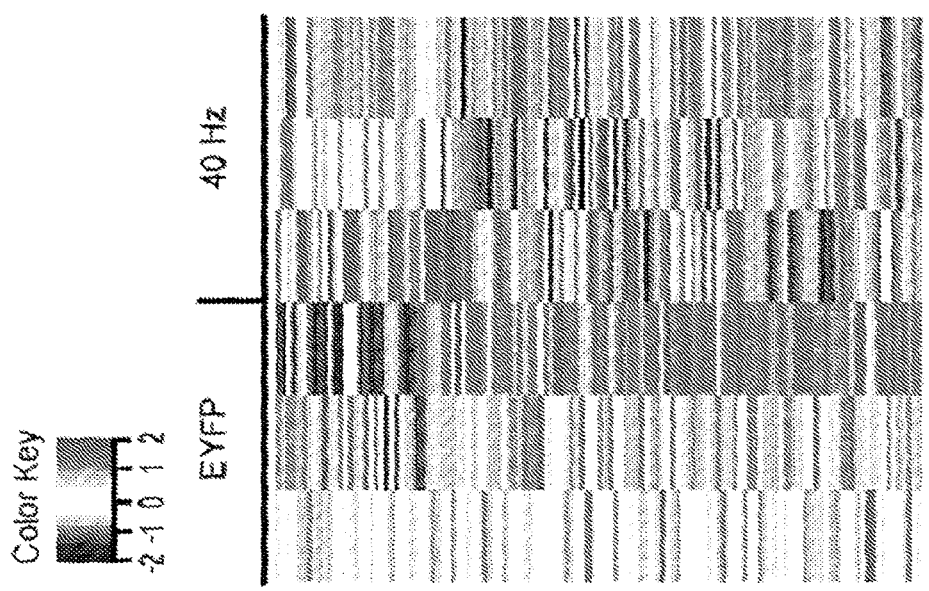
FIG. 28 is a heat map presenting differentially expressed genes determined by whole transcriptome ribonucleic acid sequencing (RNA-seq) of mouse hippocampal CA1 region with and without 40-Hz stimulation in accordance with some embodiments.

FIG. 28 is a heat map presenting differentially expressed genes determined by whole transcriptome RNA-seq of mouse hippocampal CA1 region with and without 40-Hz stimulation. Normalized z-score values were calculated for each differentially expressed gene (row). Colors represent relatively low and high levels of gene expression. TABLE 2 (below) presents 130 genes up-regulated by 40-Hz FS-PV-interneuron stimulation (p<0.05 using Cufflinks 2.2 software (available from the Trapnell Lab at the University of Washington, Seattle, Wash., for assembling transcripts, estimating their abundances, and testing for differential expression and regulation in RNA-seq samples)).

TABLE 3 (below) presents 393 genes down-regulated by 40-Hz FS-PV-interneuron stimulation (p<0.05 by Cufflinks 2.2 software (available from the Trapnell Lab at the University of Washington, Seattle, Wash.)).

TABLE 2

Genes Up-Regulated by 40-Hz FS-PV-Interneuron Stimulation

| | |
|---|---|
| 2010002N04Rik | Junb |
| 2010300C02Rik | Kcnc4 |
| 2410018L13Rik | Kcnh3 |
| Adra2c | Kcnj4 |
| Agfg2 | Klf16 |
| Agxt2l1 | Lag3 |
| Arc | Lcat |
| Atf3 | Lefty1 |
| B2m | Lgals3bp |
| BC018242 | Lingo3 |
| Beta-s | Lrg1 |
| Bst2 | Ltbp4 |
| C1ga | Lyz2 |
| C1gb | Metrn |
| C1gc | Mmp12 |
| C1ql2 | Mpped1 |
| C1qtnf4 | Mt1 |
| C3ar1 | Mt2 |
| C4b | Mtap1s |
| Car7 | Npy |
| Card10 | Nr1d1 |
| Cd68 | Nr4a1 |

TABLE 2-continued

Genes Up-Regulated by 40-Hz FS-PV-Interneuron Stimulation

| | |
|---|---|
| Cebpb | Oasl2 |
| Cebpd | Palm |
| Cirbp | Parp14 |
| Cnn2 | Pcsk1n |
| Cotl1 | Pdzd2 |
| Crip2 | Pgls |
| Cst3 | Phyhd1 |
| Ctxn1 | Pitpnm2 |
| Cyp2d22 | Plekhg5 |
| Dcakd | Pnpla7 |
| Egr4 | Pou3f1 |
| Erf | Ppp1r1a |
| F730043M19Rik | Prr7 |
| Fam107a | Prrt1 |
| Fam163b | Rab40b |
| Fmo2 | Rara |
| Fn1 | Rasl11b |
| Gbp3 | Rbm3 |
| Gldc | Rpph1 |
| Gm129 | Rprml |
| Gm2115 | Sbk1 |
| Gng7 | Scara3 |
| Gpnmb | Sh3bgrl3 |
| Gpr25 | Slc12a9 |
| Gpr37l1 | Slc25a34 |
| Grm2 | Slc29a4 |
| Gstm1 | Spp1 |
| Gstm6 | Spsb1 |
| H1fx | Ssbp4 |
| H2-D1 | Sstr4 |
| H2-k1 | Tfcp2l1 |
| Hipk4 | Thbs4 |
| Hmox1 | Thrsp |
| I830012O16Rik | Tmem198 |
| Icam1 | Tpst2 |
| Icam5 | Trim30a |
| Ifit1 | Ttr |
| Ifit3 | Unc5a |
| Igfbp4 | Ugcr11 |
| Igfbpl1 | Usp18 |
| Irf7 | Vwf |
| Irf9 | Wfs1 |
| Itpka | Xdh |

TABLE 3

Genes Down-Regulated by 40-Hz FS-PV-Interneuron Stimulation

| | | |
|---|---|---|
| 1700003M02Rik | Galnt13 | Prkcg |
| 1700007K13Rik | Gap43 | Prkg2 |
| 1700009P17Rik | Gatm | Prokr2 |
| 1700026D08Rik | Gdpd5 | Prr51 |
| 1700027A23Rik | Gfra1 | Prrg4 |
| 1700028P14Rik | Gm6300 | Ptgds |
| 1700040L02Rik | Gm7609 | Ptpn14 |
| 1700094D03Rik | Gm973 | Pvrl2 |
| 1810041L15Rik | Gng8 | Pyrl3 |
| 2310039L15Rik | Gpr115 | Rab37 |
| 2410004P03Rik | Gpr123 | Ramp3 |
| 3110047P20Rik | Gpr139 | Ranbp3I |
| 3632451O06Rik | Gpr151 | Rap1gap |
| 4930451C15Rik | Gpr153 | Rasgef1b |
| 4932411L15 | Gpr26 | Rassf9 |
| 4932425I24Rik | Gpr4 | Rbms3 |
| 5730508B09Rik | Gprasp2 | Resp18 |
| 6330406I15Rik | Gpx3 | Ret |
| A2m | Grb10 | Rgs16 |
| A330021E22Rik | Gria4 | Rgs3 |
| A630089N07Rik | Grid2ip | Rgs4 |
| AF529169 | Grin3a | Rgs6 |
| AU021034 | Grk4 | Rims3 |

TABLE 3-continued

Genes Down-Regulated by 40-Hz FS-PV-Interneuron Stimulation

| | | | | | |
|---|---|---|---|---|---|
| AW551984 | Grm4 | Rit2 | Efcab1 | Ntng1 | Unc13c |
| Adamts15 | Gucy1a3 | Rnf152 | Efna5 | Nudt4 | Vangl1 |
| Adamts9 | Hcn4 | Robo1 | Eif5a2 | Olfm3 | Vat1 |
| Adbyap1 | Hdc | Rorb | Elavl2 | Optn | Vat1l |
| Adra1b | Hhip | Ros6ka6 | Elavl4 | Otx2 | Vav2 |
| Aebp1 | Hivep1 | Rsph1 | Elfn1 | Pamr1 | Vav3 |
| Agt | Hs6st2 | Rsph4a | Emb | Pbx3 | Vwa5b1 |
| Aif1l | Hsp90aa1 | Rspo2 | Enkur | Pcp4 | Wbscr27 |
| Ak4 | Hsp90b1 | Scn1a | Eno4 | Pcsk1 | Wdr16 |
| Ak7 | Hspa4l | Scube1 | Enox2 | Pdp1 | Wdr52 |
| Akap12 | Htr2c | Scube3 | Epha8 | Peg10 | Wdr6 |
| Amigo2 | Htr5b | Sema3d | Epn3 | Pgap1 | Wdr78 |
| Amotl1 | Htr7 | Sema6a | Ermn | Pgbd1 | Wdr96 |
| Ankrd29 | Hydin | Serpinf1 | Etv1 | Phactr2 | Wfikkn2 |
| Ankrd34c | Inadl | Sgpp2 | Exph5 | Pirt | Wif1 |
| Ano1 | Igca | Sh3bgrl2 | Fabp7 | Pkib | Wls |
| Agp4 | Igub | Shox2 | Fam149a | Plagl1 | Wnt3 |
| Arhgap24 | Irx1 | Shroom3 | Fam196b | Plcb4 | Ysk4 |
| Asb2 | Irx2 | Slc12a2 | Fam198b | Plch1 | Zcchc12 |
| Aspa | Irx3 | Slc17a6 | Fam19a4 | Plch2 | Zdbf2 |
| Baiap3 | Itga3 | Slc38a1 | Fbln7 | Plcxd2 | Zdhhc22 |
| Bbox1 | Kcnc2 | Slc39a4 | Fgf1 | Pld5 | Zfhx3 |
| Bmp7 | Kcng4 | Slc5a3 | Fgf10 | Plekhg1 | Zfp474 |
| Btbd11 | Kcnip1 | Slc5a7 | Fhdc1 | Plxnc1 | Zfp618 |
| C530008M17Rik | Kcni12 | Slc6a9 | Foxj1 | Popdc3 | Zfp941 |
| Cacna2d2 | Kcni16 | Slc7a11 | Foxp2 | Pou4f1 | Zic1 |
| Calb2 | Kcnma1 | Slc9a4 | Frem3 | Ppp1r32 | Zic2 |
| Calr3 | Kcnn3 | Slco2a1 | Fstl5 | Ppp1r36 | Zic3 |
| Camk2d | Kcnq1ot1 | Slit2 | Fzd1 | Prkcd | Zic4 |
| Car10 | Kctd12b | Slitrk6 | Fzd10 | Prkch | Zic5 |
| Cast | Kctd8 | Sncg | | | |
| Cbln1 | Kif9 | Sntn | | | |
| Cbln2 | Kit | Socs2 | | | |
| Cbln4 | Kitl | Sox5 | | | |
| Ccdc108 | Klhl1 | Spag16 | | | |
| Ccdc135 | Lars2 | Spata18 | | | |
| Ccdc136 | Lbh | Spock1 | | | |
| Ccdc141 | Lbp | Spock3 | | | |
| Ccdc153 | Ldhd | Srgap1 | | | |
| Ccdc19 | Lect1 | St8sia2 | | | |
| Ccdc3 | Lef1 | Strbp | | | |
| Ccdc40 | Lhfpl1 | Sv2b | | | |
| Ccdc81 | Lhfpl3 | Synpo2 | | | |
| Cd109 | Lhx9 | Syt15 | | | |
| Cd24a | Lrguk | Syt4 | | | |
| Cdh26 | Lrrc23 | Syt6 | | | |
| Cdhr3 | Lrrc48 | Syt9 | | | |
| Cdr1 | Lrrc55 | Tac1 | | | |
| Cdr2 | Malat1 | Tac2 | | | |
| Chat | Mcf2 | Tacr1 | | | |
| Chgb | Megf11 | Tcf7l2 | | | |
| Chrdl1 | Mgat4c | Tekt1 | | | |
| Chrna3 | Mlf1 | Tex15 | | | |
| Chrna4 | Mme | Tex9 | | | |
| Chrnb3 | Mob3b | Tgfb2 | | | |
| Chrnb4 | Mreg | Th | | | |
| Cit | Mrvi1 | Timp2 | | | |
| Cited2 | Msi2 | Tm4sf1 | | | |
| Clec18a | Mtfr1 | Tmem130 | | | |
| Clic6 | Mum1l1 | Tmem132c | | | |
| Cntn6 | Musk | Tmem163 | | | |
| Cntnap4 | Myb | Tmem176a | | | |
| Cobl | Mycbpap | Tmem212 | | | |
| Coch | Myoc | Tmem56 | | | |
| Col12a1 | Ndn | Tnc | | | |
| Col8a2 | Necab1 | Tnnt1 | | | |
| Cpne4 | Necab2 | Trhde | | | |
| Cpne9 | Necab3 | Trim36 | | | |
| Dach1 | Nexn | Trim66 | | | |
| Dcn | Nfam1 | Trpc3 | | | |
| Dcd | Ngb | Trps1 | | | |
| Dnahc5 | Nhlh2 | Tsku | | | |
| Dnahc6 | Nppa | Ttc18 | | | |
| Dpp10 | Npr1 | Ttc21a | | | |
| Dpy19l1 | Nr4a2 | Ttc39a | | | |
| Dvnlrb2 | Nrip3 | Tyrp1 | | | |
| Ebf1 | Nrp2 | Ubxn10 | | | |
| Edil3 | Nrsn2 | Ugt8a | | | |

Figure 29:
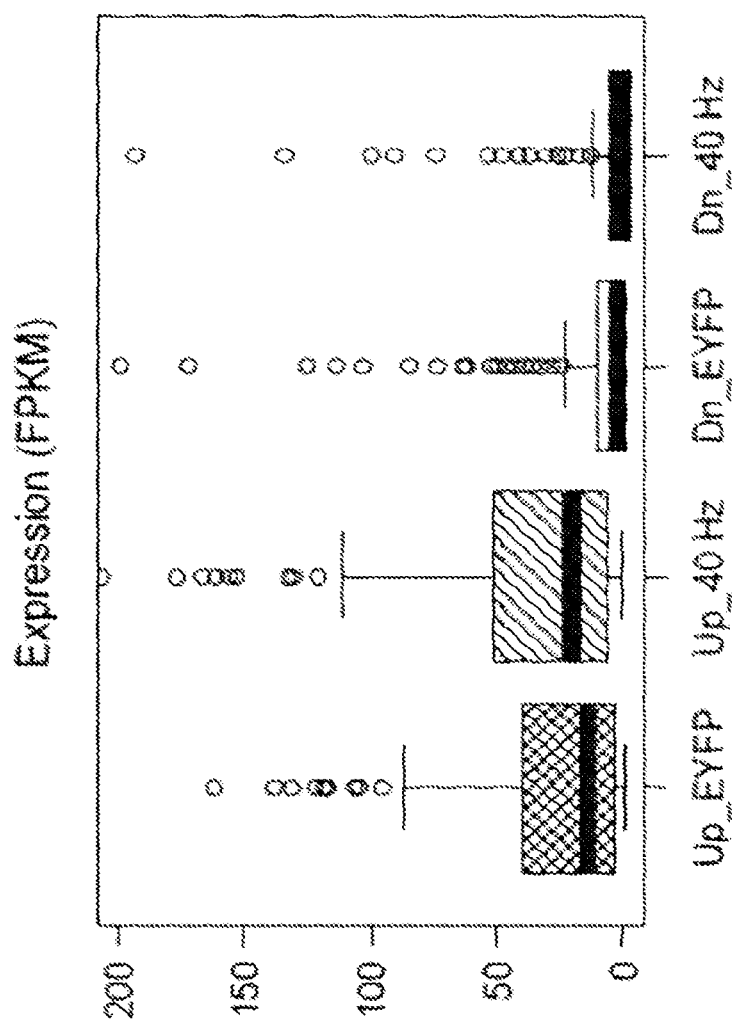
FIG. 29 is a box plot illustrating FPKM values of up- and down-regulated genes in EYFP and 40-Hz conditions in accordance with some embodiments.

In some embodiments, up-regulated genes had generally higher expression values than down-regulated genes. FIG. 29 is a box plot showing FPKM values of up- and down-regulated genes in EYFP and 40-Hz conditions according to some embodiments. The box shows median (black lines in box) and quartiles (top and bottom of box), whiskers represent minimum and maximum values, and circles represent outliers. Up-regulated genes may have been highly enriched in microglia. Specifically, about 35% of all up-regulated genes had their highest expression in microglia (with about 19% in neurons, about 17% in endothelial cells, about 14% in astrocytes, about 9% in myelinating oligodendrocytes, about 5% in oligodendrocyte precursor cells, and about 1% in newly formed oligodendrocytes).

Figure 30:
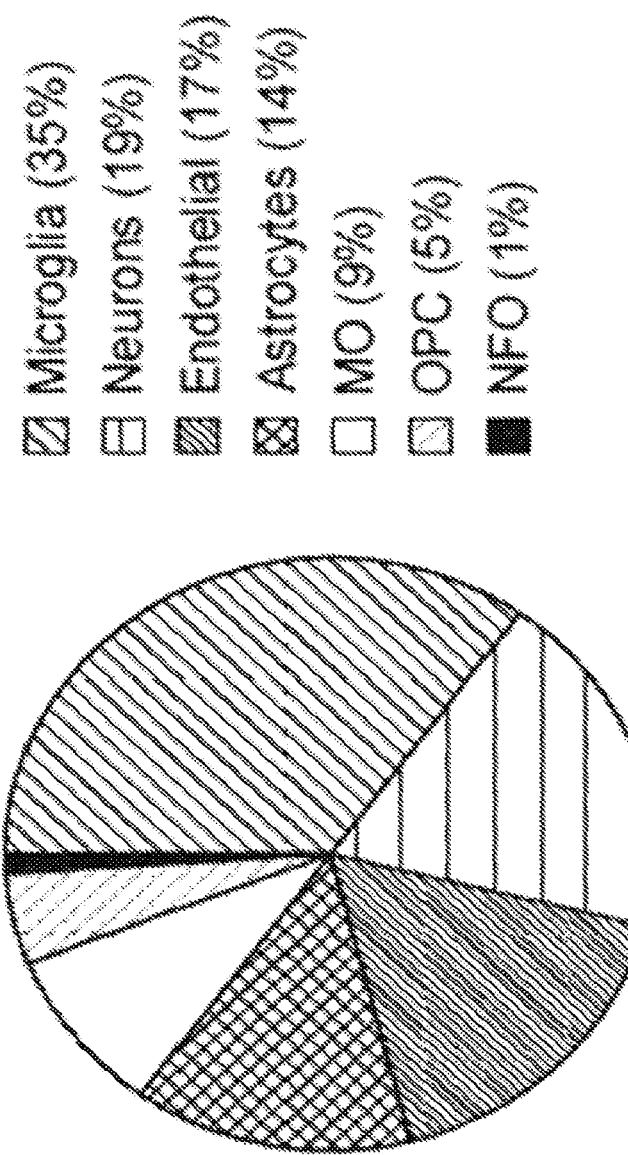
FIG. 30 is a pie chart illustrating cell-type specific expression patterns of identified up-regulated genes following 40-Hz stimulation in accordance with some embodiments.

FIG. 30 is a pie chart illustrating cell-type specific expression patterns of identified up-regulated genes following 40-Hz stimulation in accordance with some embodiments. Gene FPKM values were calculated from the publicly available RNA-seq data from different brain cell types, including astrocytes, endothelial cells, microglia, myelinating oligodendrocytes (MO), neurons, newly formed oligodendrocytes (NFo), and oligodendrocyte precursor cells (OPC). Thus, RNA-seq analysis strongly suggests that one hour of 40-Hz stimulation of FS-PV-interneurons caused an alteration of the cellular state of microglia, which is significant given the accumulating evidence that these cells play a role in AD pathology.

In some embodiments, to further explore the potential effects of 40-Hz stimulation on microglia, a series of publicly available RNA-seq datasets from microglia, peripheral macrophages, and neurons under different chemical and genetic perturbations were compared to the gene lists from characterization described in some embodiments herein using Gene Set Enrichment Analysis. TABLE 4 (below) illustrates GSEA-based statistical significance of correlation between genes up- or down-regulated by 40-Hz stimulation and publicly available neuron, microglia and macrophage specific RNA-seq data under different chemical and genetic perturbations.

TABLE 4

| Name of Perturbed Transcriptome | NES | Nominal p-value | FDR q-value |
|---|---|---|---|
| MCSF treated microglia | 1.76 | 0.000 | 0.000 |
| NMDA treated neurons | 1.62 | 0.000 | 0.000 |
| IL34 treated microglia | 1.59 | 0.000 | 0.000 |
| GMCSF treated microglia | 1.49 | 0.005 | 0.004 |
| Bicuculline treated neurons | 1.49 | 0.016 | 0.013 |
| ALS SOD1 mutant microglia | −1.26 | 0.050 | 0.028 |
| LPS&IFNg treated macrophage (M1) | 1.18 | 0.122 | 0.081 |
| MeCP2 null microglia | 1.16 | 0.164 | 0.127 |
| IL4 treated macrophage (M2) | −1.19 | 0.101 | 0.147 |
| Huntington HTT mutant microglia | 1.03 | 0.371 | 0.361 |
| Germ-free microglia | 0.94 | 0.604 | 0.667 |
| Tetrodotoxin treated neurons | −0.76 | 0.941 | 0.970 |

Figure 31:
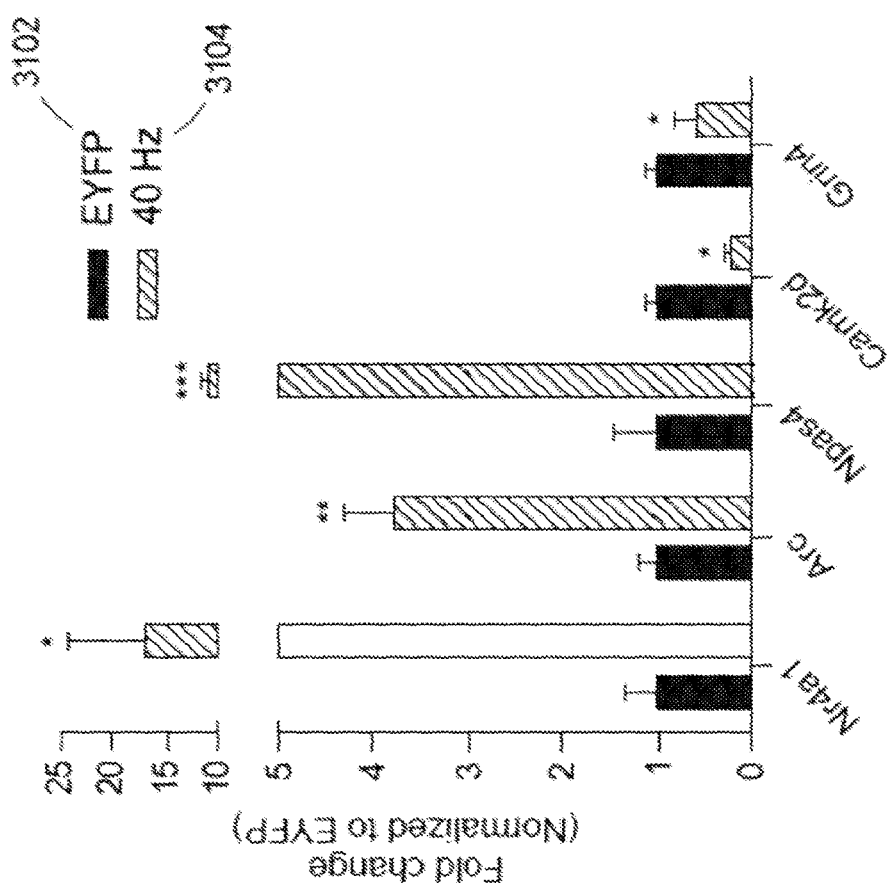
FIG. 31 is a bar graph illustrating RT-qPCR verification of specific gene targets in the RNA-seq data set in accordance with some embodiments.

Interestingly, the transcriptomic changes following 40-Hz stimulation were more similar to those due to increased neural activity (by NMDA and bicuculline) and less similar to those due to silencing activity (by tetrodotoxin). These findings further support the observation that 40-Hz stimulation of FS-PV-interneurons does not decrease neuronal activity. Moreover, immediate early genes Nr4a1, Arc, and Npas4 that are known to be up-regulated by neuronal activity, were elevated following one hour of 40-Hz stimulation shown by both RNA-seq and RT-qPCR. FIG. 31 is a bar graph illustrating RT-qPCR verification of specific gene targets in the RNA-seq data set in accordance with some embodiments. The bar graph shows relative RNA levels (fold change) from EYFP 3102, and 40-Hz stimulation 3104 conditions (one asterisk indicates p<0.05, two asterisks indicate p<0.01, and three asterisks indicate p<0.001 by Student's t-test, n=3 mice per group). Top down-regulated genes were Grin4 and Camk2d (see, e.g., FIG. 31, p<0.05, n=3 mice per group).

Figure 32:
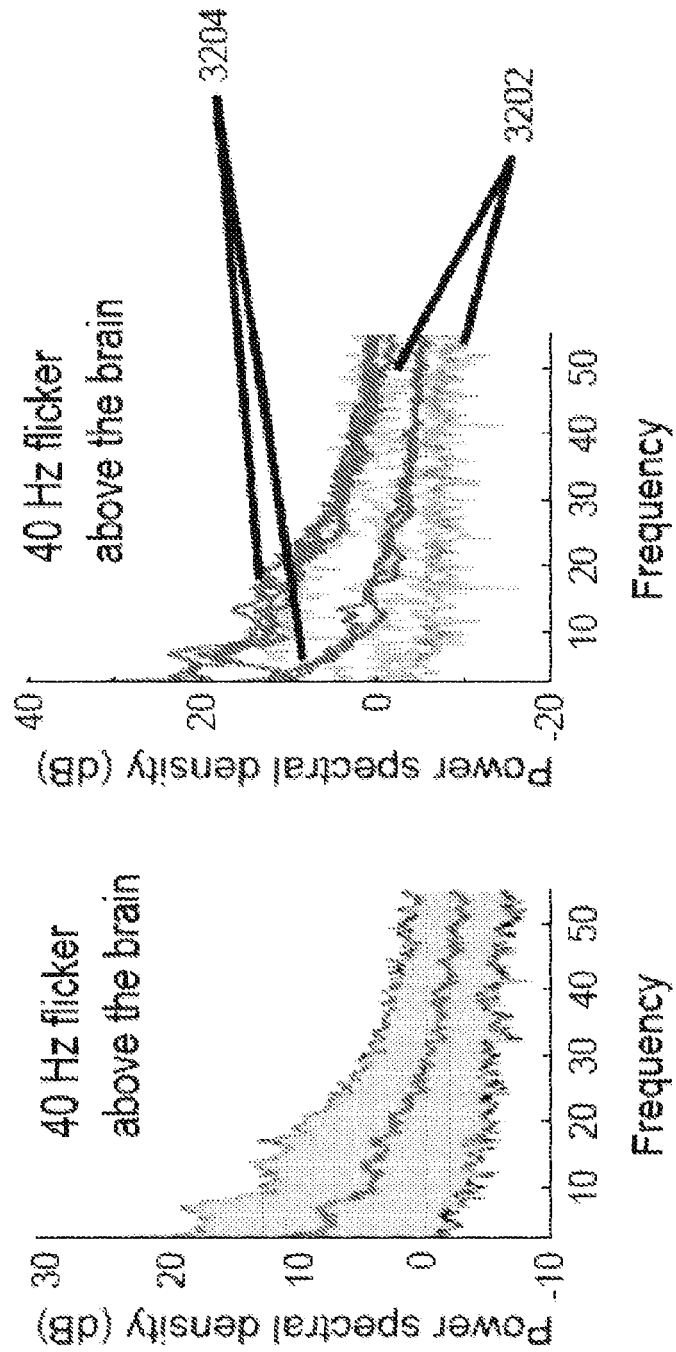
FIGS. 32A and 32B are plots illustrating power spectral densities of local field potentials recoded above the brain during 40-Hz light flicker show in accordance with some embodiments.

Additionally, the transcriptomic results suggest a more phagocytic state of microglia. In some embodiments, the up-regulated genes positively correlated with genomic changes induced by macrophage colony-stimulating factor (MCSF) and granulocyte macrophage colony-stimulating factor (GMCSF), both known to promote microglial Aβ uptake. FIGS. 32A and 32B are plots illustrating power spectral densities of local field potentials recoded above the brain during 40 Hz light flicker in accordance with some embodiments. FIGS. 32A and 32B show no increase in power at 40 Hz, therefore the effect is not due to photoelectric effects on recording equipment or electrical noise (n=4, 2, 1, 1, 17, 42, 36, 55, 53 40-Hz flicker periods from 4 recording sessions in three 5XFAD animals undergoing visual cortex recordings and from 5 recording sessions in two 5XFAD and three WT mice undergoing hippocampal recordings). Mean (solid line) and standard deviation (shaded area) across recordings are shown on the left (FIG. 32A) and per animal on the right (FIG. 32B). Recordings with less than 3 flicker periods 3202 resulted in noisier power spectral densities than recordings with more data 3204 but none showed evidence of peaks at 40 Hz. In some embodiments, RT-qPCR was carried out to validate the up-regulated genes involved in known microglia functions. It was confirmed that the genes associated with microglial engulfment including Cd68, B2m, Bst2, Icam1, and Lyz2, were up-regulated in hippocampal CA1 region following 40-Hz stimulation.

Figure 33:
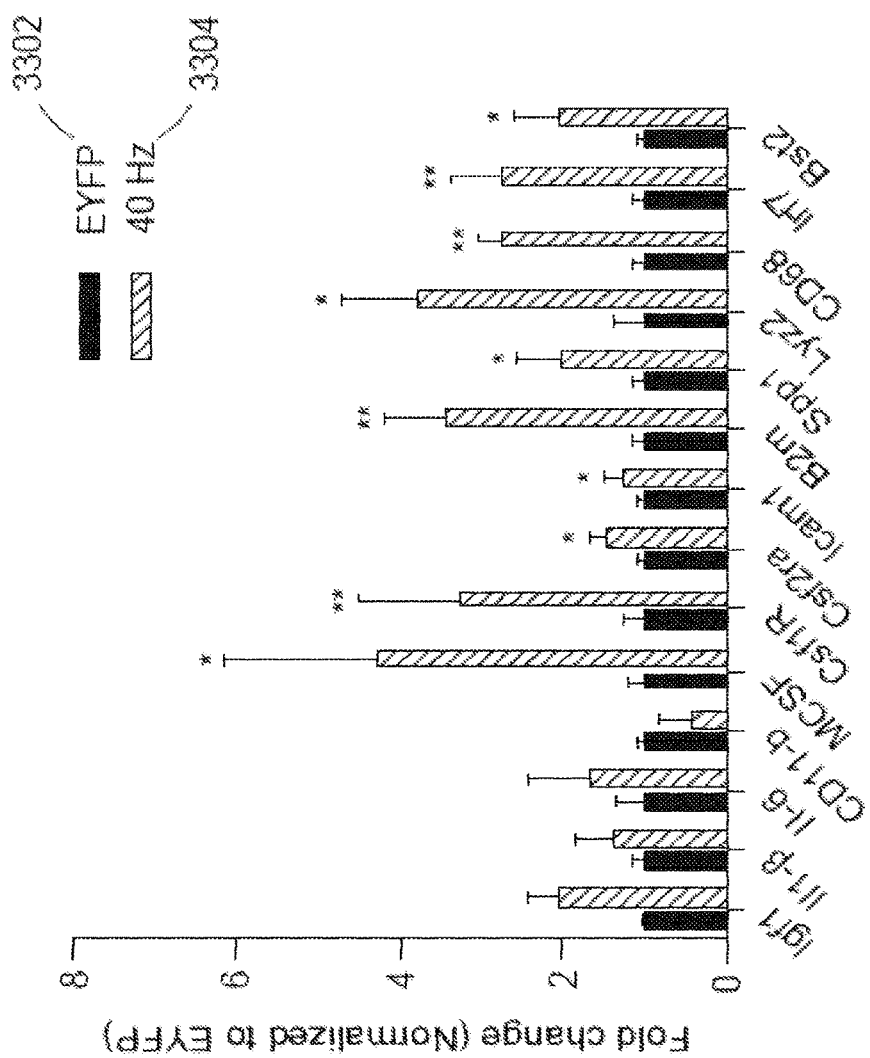
FIG. 33 is a bar graph depicting RT-qPCR verification of specific gene targets in the RNA-seq data set in accordance with some embodiments.

FIG. 33 is a bar graph depicting RT-qPCR verification of specific gene targets in the RNA-seq data set in accordance with some embodiments. FIG. 33 shows relative RNA levels (fold change) in EYFP 3302 and 40-Hz stimulation 3304 conditions (one asterisk indicates p<0.05 and two asterisks indicate p<0.01 by Student's t-test, n=6 mice per group). Other notable up-regulated genes included microglia-enriched transcriptional regulator Irf7, cell adhesion and migration regulator Spp1, as well as microglia proliferation markers Csf1r and Csf2ra (see, e.g., FIG. 33, p<0.05 and p<0.01 by Student's t-test, n=6 mice per group). RT-qPCR also showed that the expression levels of pro-inflammatory genes Il6, Il1b (Il1-β), Itgam (CD11-b) and an anti-inflammatory gene Igf1 were not changed (see, e.g., FIG. 33, p>0.05 by Student's t-test, n=6 mice per group). Thus the transcriptomic results described herein suggest that 40 Hz neuronal stimulation induced microglia into a state that promotes uptake.

Figure 34:
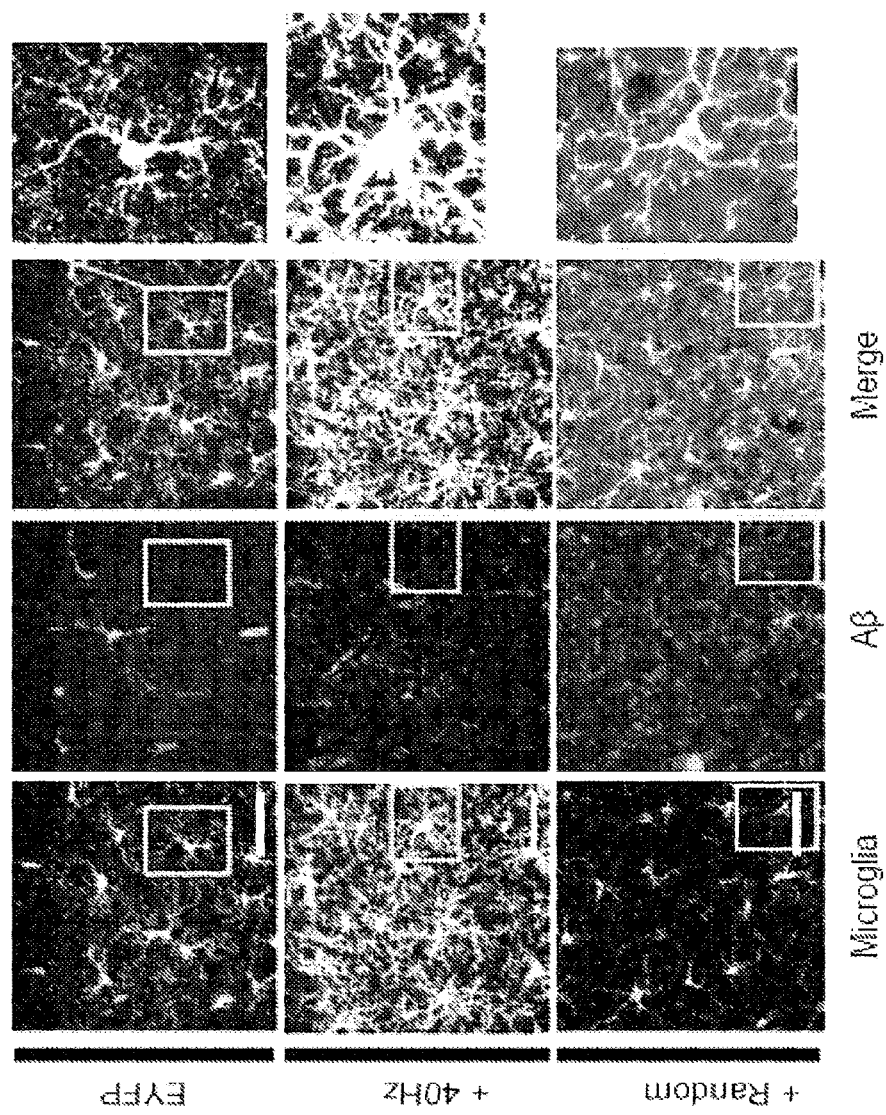
FIG. 34 is a series of immunofluorescence images illustrating immunohistochemistry with anti-Iba1 (019-19741) and anti-Aβ (12F4) antibodies in hippocampal CA1 region of 5XFAD/PV-Cre mice in EYFP, 40-Hz, and Random stimulation conditions in accordance with some embodiments.

Given the observations that 40-Hz stimulation up-regulated both phagocytosis-related and migration/cell adhesion-related genes, the morphological features of microglia activation was examined. In some embodiments, an antibody that recognizes the microglial marker Iba1 to label microglia in hippocampal CA1 sections from the 5XFAD/PV-Cre mice after one hour of 40 Hz, random or no stimulation (EYFP mice) was used. FIG. 34 is a series of immunofluorescence images illustrating immunohistochemistry with anti-Iba1 3402 (019-19741) and anti-Aβ 3404 (12F4) antibodies in hippocampal CA1 region of 5XFAD/PV-Cre mice in EYFP, 40-Hz, and Random stimulation conditions. Images were taken with 40× objective scale bar=50 μm). Arrows indicate +Iba1/+Aβ signal in cell body.

FIG. 35A is a bar graph depicting the number of microglia in EYFP and 40-Hz conditions in accordance with some embodiments (n=2 sections from 4 mice per group). FIG. 35B is a bar graph depicting the diameter of microglial cell bodies normalized to EYFP in EYFP, 40-Hz, and Random stimulation conditions in accordance with some embodiments (n=2 sections from 4 mice per group). FIG. 35C is a bar graph depicting the average length of microglia primary processes or projections normalized to EYFP in EYFP, 40-Hz, and Random stimulation conditions EYFP, 40 Hz and Random. FIG. 35D is a bar graph depicting the percent of Iba1-positive (microglia) cell bodies that are also Aβ-positive in EYFP and 40-Hz stimulation conditions in accordance with some embodiments (n=2 sections from 4 mice group). Notation "n.s." 3502 indicates not significant, two asterisks 3504 indicate p<0.01, three asterisks 3506 indicate p<0.001, and four asterisks 3508 indicate p<0.0001 by one-way ANOVA.

First, the number of Iba1+ microglia in 6 animals per condition were counted and almost twice as many microglial cells in the 40 Hz group were observed (15 microglial cells per 212.55 μm×212.55 μm region of interest (ROI)) compared to the unstimulated EYFP condition (mean of 8 microglial cells per ROI) (see, e.g., FIGS. 34 and 35A, p<0.01 by one-way ANOVA, n=2 sections from 4 mice per group) and compared to the random condition (mean of 10 microglial cells per ROI) (see, e.g., FIGS. 34 and 35A, p<0.05 by one-way ANOVA, n=2 sections from 4 mice per group). Previous studies may have shown that two primary characteristics of phagocytic microglia are increased cell body size and decreased process length, therefore how these characteristics were affected by 40-Hz stimulation were examined. In some embodiments, the diameter of each clearly labeled Iba1+ cell body in the field of view was measured. It was found that microglial cell body diameter increased by 135.3% following 40-Hz stimulation compared to no stimulation and by 138.7% compared to the random condition (see, e.g., FIGS. 34 and 35B, p<0.0001 by one-way ANOVA, n=2 sections from 4 mice per group). The length of primary processes of microglia in each condition was measured and a 54.0% reduction in primary microglia process length in the 40-Hz stimulation condition compared to EYFP controls and a 38.5% reduction compared to random stimulation was observed (see, e.g., FIGS. 34 and 35C, p<0.0001 by one-way ANOVA, n=2 sections from 4 mice per group). These findings were not affected by Iba1 levels as differences in Iba1 expression between conditions were not observed in gene expression analysis described herein (see, e.g., TABLES 2 and 3). Thus, the increase in cell body size and decrease in process length observed after 40-Hz stimulation are morphological changes consistent with a shift towards a phagocytic state for these microglia. Upon co-immunostaining with an Aβ antibody (12F4, which does not cross-react with APP), potential co-localization of Aβ within microglia was evaluated as a means to evaluate microglia Aβ uptake. The ratio of the number of microglia with Aβ/Iba1 co-localization in the cell body (ImageJ, Fuji co-localization plug-in) to the total number of microglia increased by 54.9% following 40-Hz stimulation compared to EYFP controls, and by 50.3% compared to random conditions, in CA1 neuropil where the Iba1+ cells are primarily located (see, e.g., FIGS. 34 and 35D, p<0.01 by one-way ANOVA, n=2 sections from 4 mice per group). Iba1/signal overlap in microglial processes was excluded to avoid including potentially random, non-engulfment co-localization.

Figure 36:
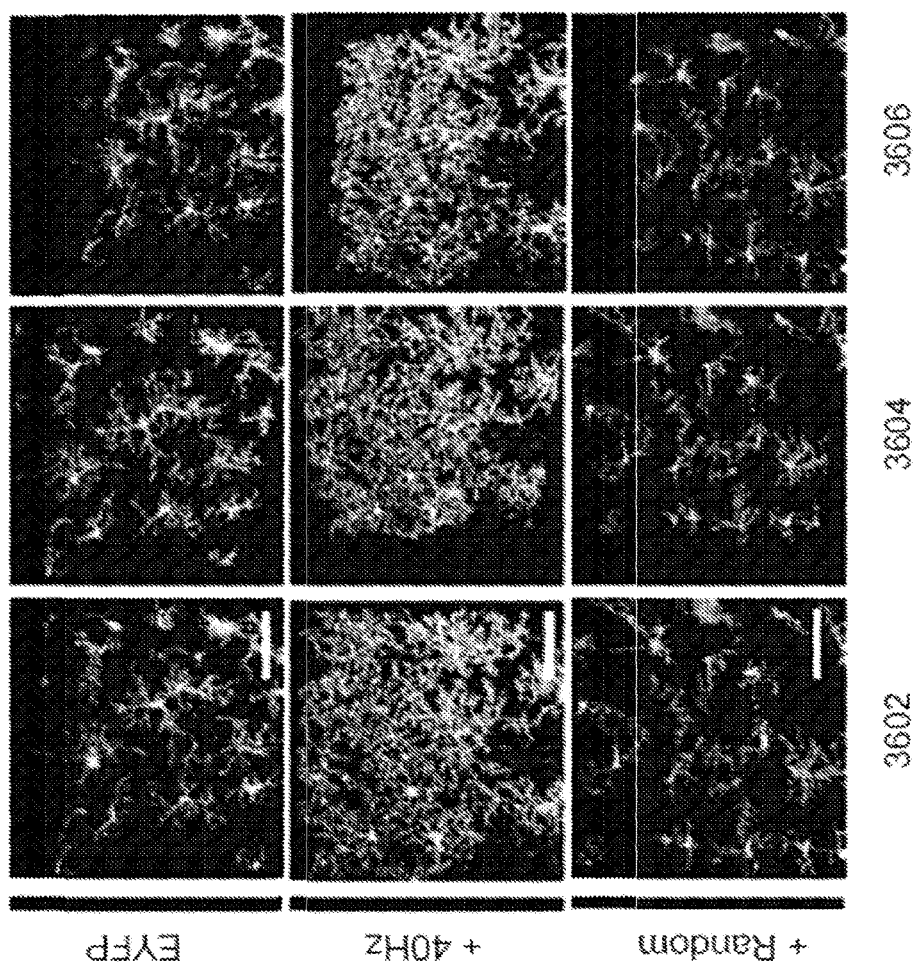
FIG. 36 is a series of 3D rendering formed by merging immunofluorescence images from FIG. 34 in accordance with some embodiments.

In some embodiments, to provide better resolution of the presence of Aβ signal within microglia, 3D renderings of microglia from this tissue and videos from these renderings were created. FIG. 36 is a series of 3D rendering formed by merging immunofluorescence images from FIG. 34 rotated 0 degrees 3602, −25 degrees around the Y-axis 3604, and 30 degrees around the X-axis 3606 in accordance with some embodiments. Images were taken with 40× objective (scale bar=50 μm). Altogether, gene expression and morphological analysis suggest that 40-Hz stimulation affects microglia activity by increasing recruitment of microglial cells to the site of stimulation and enhancing their engulfing activity, leading to an increased association with Aβ Importantly, in some embodiments, evidence of neuronal loss by measuring thickness of the CA1 cellular layer using nuclear staining with Hoechst was not found. The mean CA1 volume was not significantly different between EYFP and 40-Hz stimulation groups.

Figure 37B:
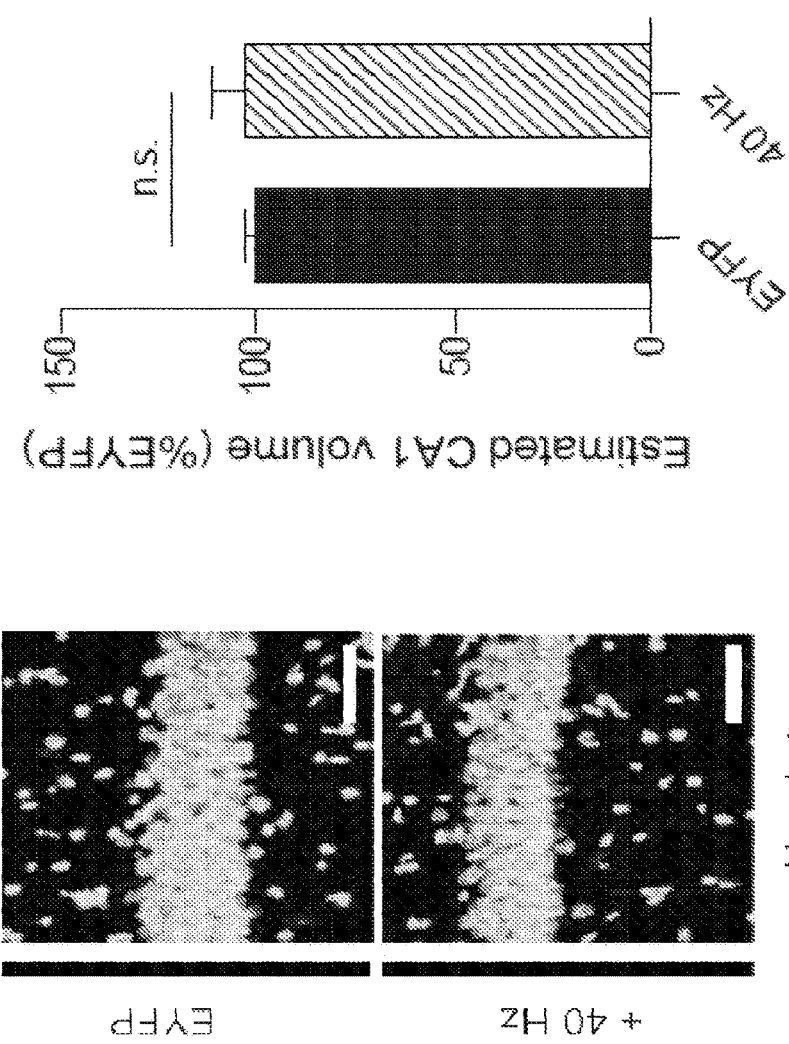
FIG. 37B is a bar graph depicting the estimated CA1 thickness of 5XFAD/PV-Cre in EYFP and 40-Hz stimulation conditions in accordance with some embodiments.
Figure 37A:
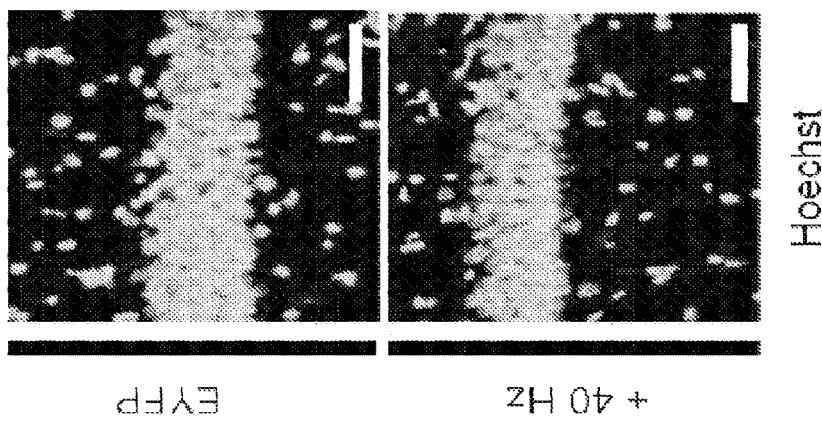
FIG. 37A is a series of immunofluorescence images illustrating immunohistochemistry with Hoechst in hippocampal CA1 region of 5XFAD/PV-Cre in accordance with some embodiments.

FIG. 37A is a series of immunofluorescence images illustrating immunohistochemistry with Hoechst in hippocampal CA1 region of 5XFAD/PV-Cre in EYFP and 40-Hz stimulation conditions in accordance with some embodiments. FIG. 37B is a bar graph depicting the estimated CA1 thickness of 5XFAD/PV-Cre in EYFP and 40-Hz stimulation conditions in accordance with some embodiments (n=4 mice per group, "n.s." indicates not significant by Student's t-test).

Figure 38A:
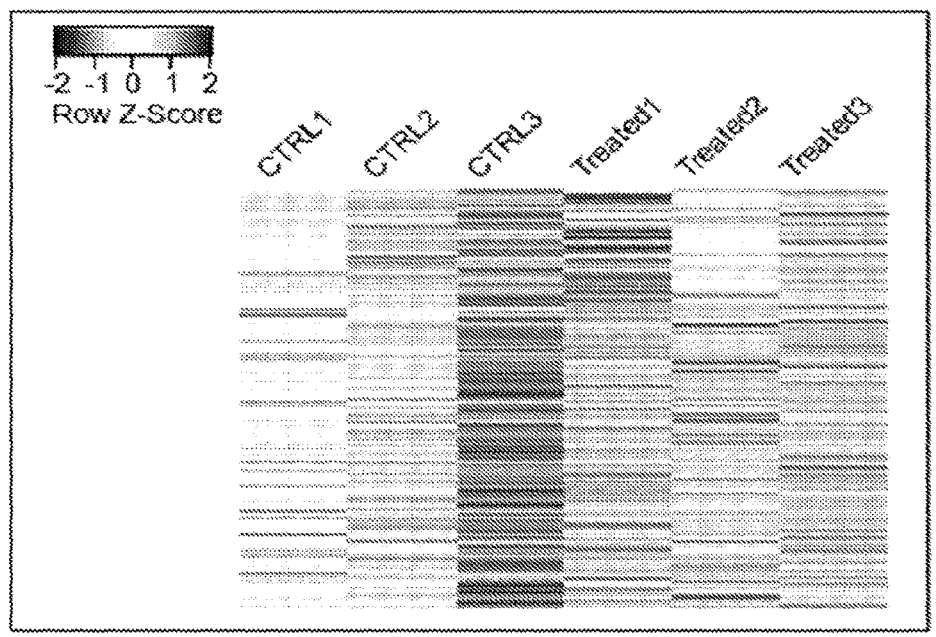
FIG. 38A is a heat map displaying differentially expressed genes (DEGs) determined by genome-wide RNA-seq of hippocampal CA1 upon 40-Hz FS-PV+ stimulation or control stimulation in accordance with some embodiments.

Next, differential gene expression in 5XFAD mice infected with the AAV-DIO-ChR2-EYFP and stimulated with 40-Hz FS-PV+ stimulation (TREAT) or control stimulation (CTRL) was assessed by genome-wide RNA-seq of hippocampal CA1 following one hour of stimulation according to some embodiments. FIG. 38A is a heat map displaying 523 differentially expressed genes (DEGs) determined by genome-wide RNA-seq of hippocampal CA1 upon TREAT or CTRL in accordance with some embodiments. Each row in FIG. 38A represents a DEG, and the columns in FIG. 38A represent the transcriptomic profiles of three individual control animals and three individual treated (40-Hz FS=PV+ stimulated) animals.

Figure 38B:
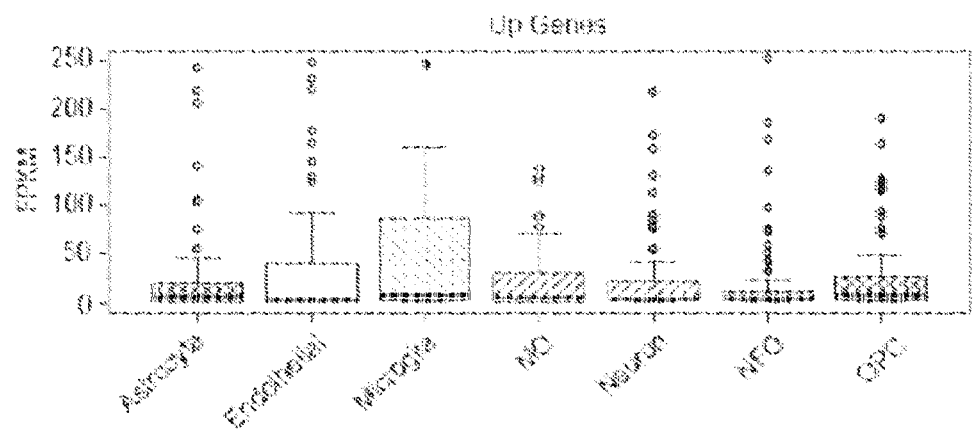
FIG. 38B is a chart illustrating overlap between DEGs up-regulated in the TREAT condition in FIG. 38A in accordance with some embodiments.

FIG. 38B is a chart illustrating overlap between DEGs up-regulated in the TREAT condition in FIG. 38A in accordance with some embodiments. In FIG. 38B, the induction of gamma oscillations through FS-PV+ 40-Hz stimulation reduces Iba1 levels compared to random FS-PV+ stimulation as measured by immunofluorescence (n=3 mice per group, p=0.006). FIG. 38B shows that the up-regulated genes in the TREAT condition overlap significantly and specifically with microglia genes up-regulated by anti-inflammatory microglia activation (i.e., MCSF genes). Genes were upregulated in microglial cells to a greater extent than in astrocytes, endothelial cells, myelinating oligodendrocytes (MOs), neurons, newly formed oligodendrocytes (NFOs), and oligodendrocyte precursor cells (OPCs). TABLE 5 (below) presents microglia/macrophage pathways for up-regulated genes.

TABLE 5

| Name of Perturbed Transcriptome | NES | Nominal p-value | FDR q-value |
| --- | --- | --- | --- |
| MCSF treated microglia | 1.76 | 0.000 | 0.000 |
| IL34 treated microglia | 1.59 | 0.000 | 0.000 |
| GMCSF treated microglia | 1.49 | 0.005 | 0.004 |
| LPS&IFNg treated macrophage (M1) | 1.18 | 0.122 | 0.081 |
| IL4 treated macrophage (M2) | −1.2 | 0.101 | 0.147 |

Figure 39:
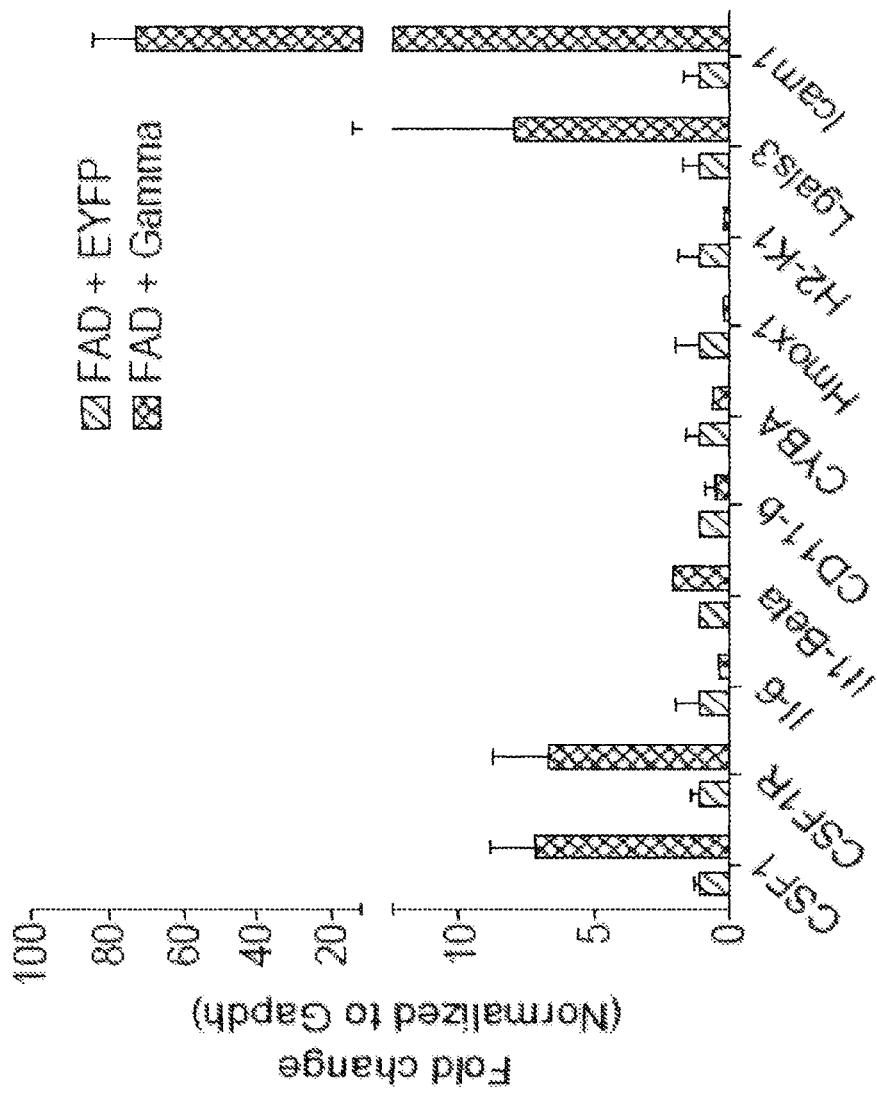
FIG. 39 is a bar graph depicting RT-qPCR verification of specific gene targets in the RNA-seq data set of FIG. 38A in accordance with some embodiments.

According to some embodiments, RT-qPCR was conducted to verify specific gene targets from the RNA-seq data set. FIG. 39 is a bar graph depicting RT-qPCR verification of specific gene targets in the RNA-seq data set of FIG. 38A in accordance with some embodiments. In particular, FIG. 39 shows the fold change (normalized to GAPDH) of specific gene targets in control and treated conditions, including the genes CSF1, CSF1R, ll-6, ll1-Beta, CD11-b, CYBA, Hmox1, H2-K1, Lgals3, and Icam1.

Figure 40:
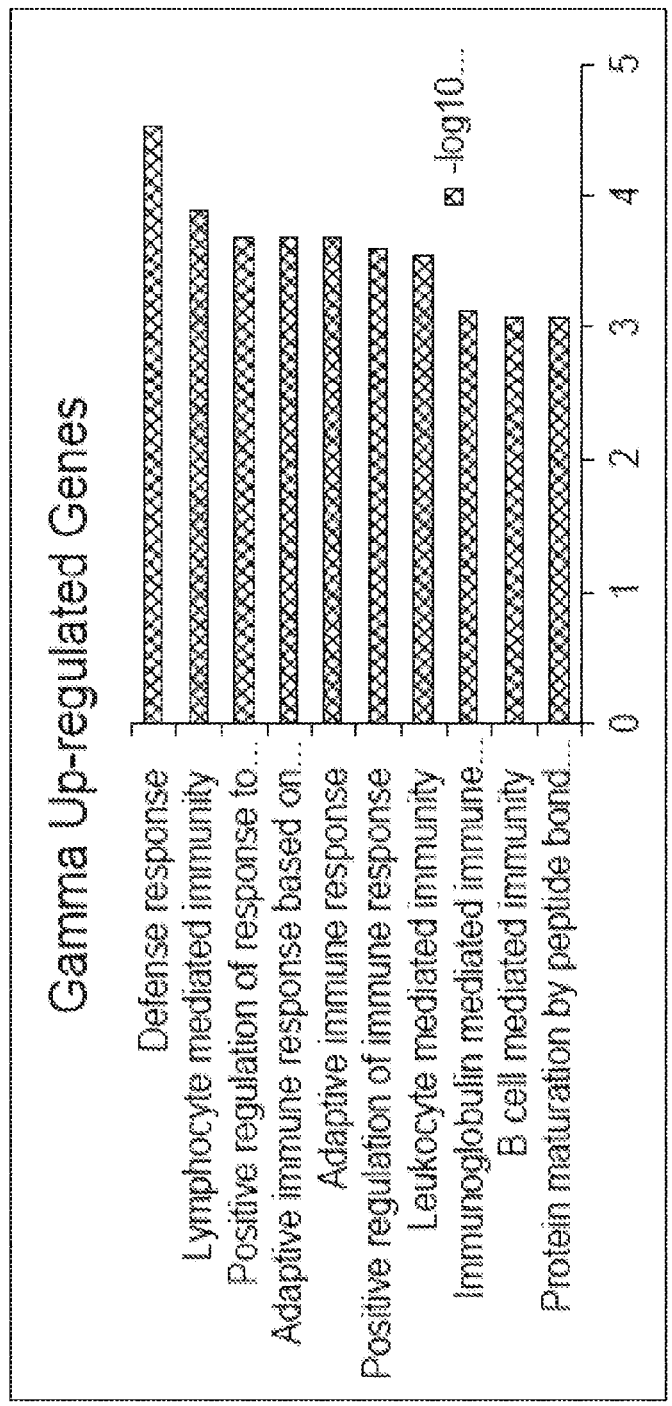
FIG. 40 is a plot illustrating the biological processes to which the up-regulated genes of FIG. 38A relate in accordance with some embodiments.
Figure 41:
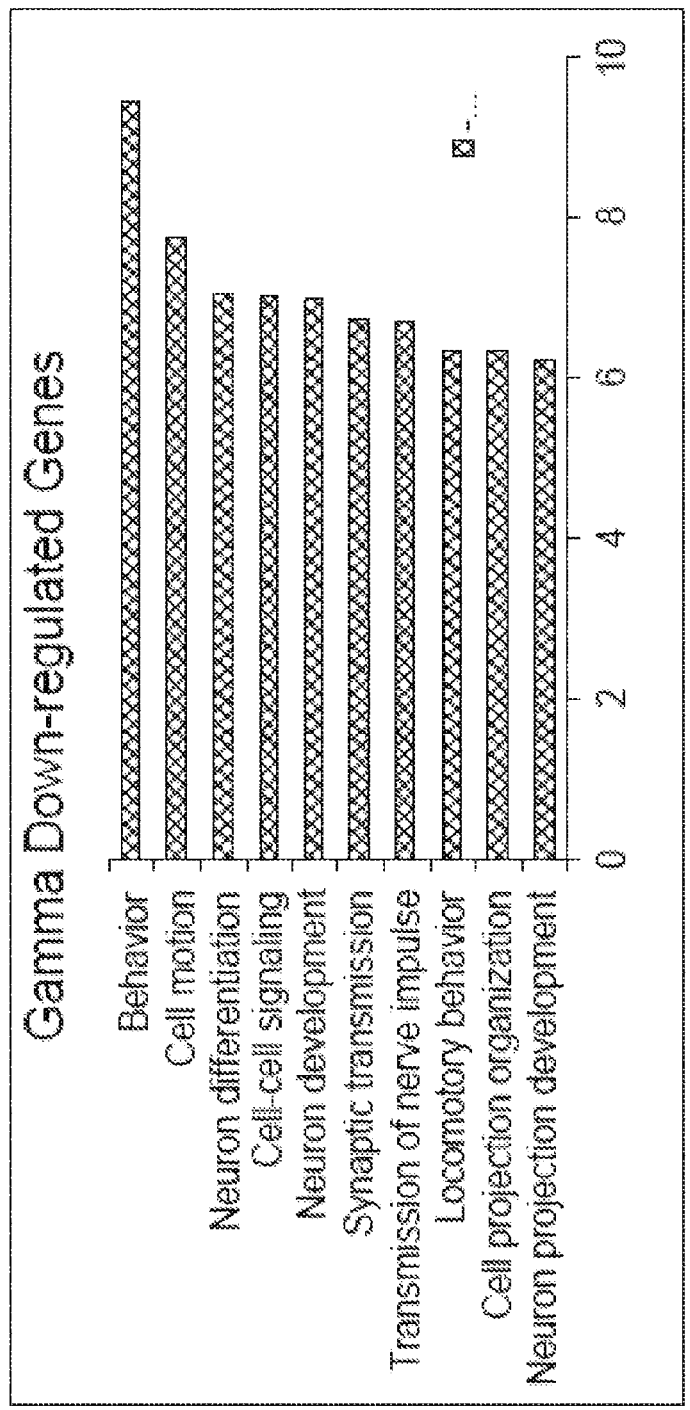
FIG. 41 is a plot illustrating the biological processes to which the down-regulated genes of FIG. 38A relate in accordance with some embodiments.

FIG. 40 is a plot illustrating the biological processes to which the up-regulated genes of FIG. 38A relate in accordance with some embodiments. Importantly, the up-regulated genes in FIG. 40 are specifically associated with immune-related processes. Upregulated genes belonged to immune-related biological processes including lymphocyte-mediated, adaptive immune, and immunoglobulin-mediated processes. FIG. 41 is a plot illustrating the biological processes to which the down-regulated genes of FIG. 38A relate in accordance with some embodiments. Down-regulated genes belonged to biological processes including cell motion, cell-cell signaling, synaptic transmission, locomotory behavior, and neuron projection, as shown in FIG. 41.

Figures 42A, 42B:
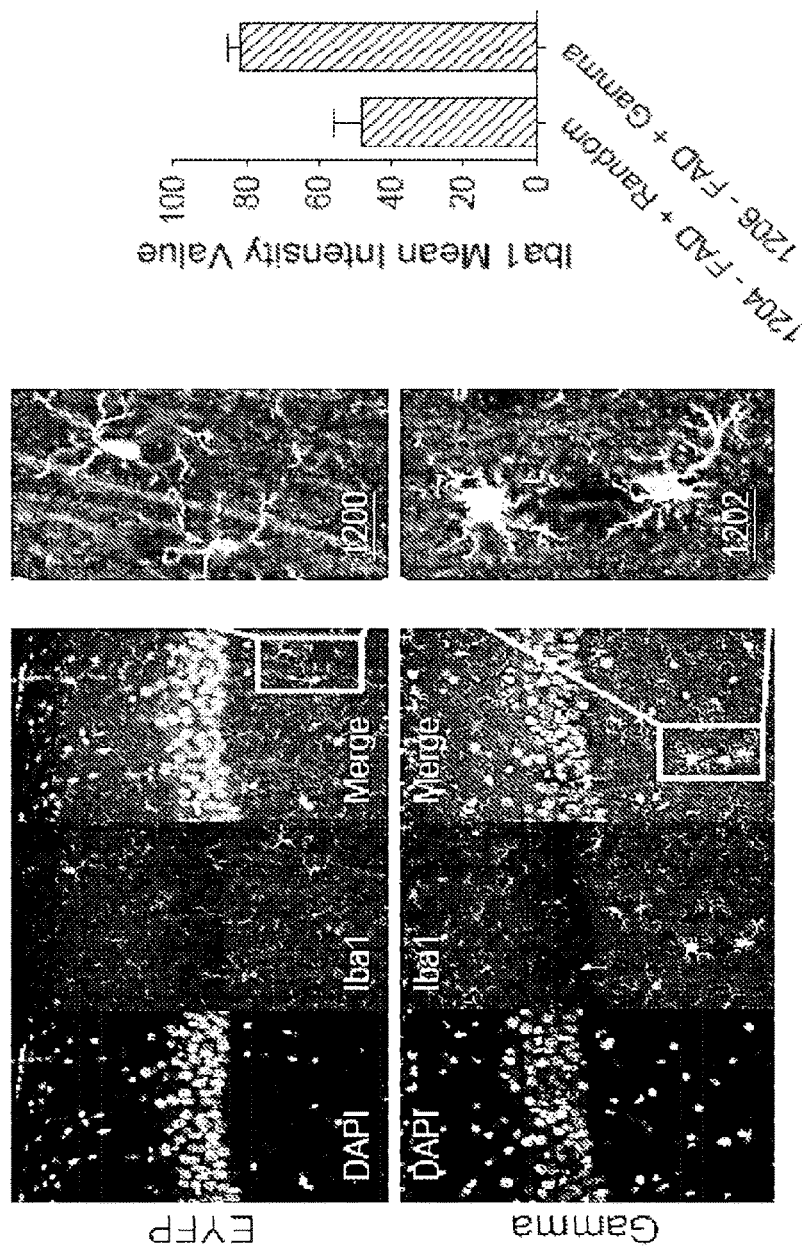
FIG. 42A is a series of immunofluorescence images illustrating levels of Iba1 following different types of stimulation of the CA1 region of the hippocampus of a subject in accordance with some embodiments.
FIG. 42B is a bar graph depicting mean intensity values for the immunofluorescence images in FIG. 42A in accordance with some embodiments.

FIG. 42A is a series of immunofluorescence images illustrating levels of Iba1 following different types of stimulation of the CA1 region of the hippocampus of a subject in accordance with some embodiments. FIG. 42B is a bar graph depicting mean intensity values for the immunofluorescence images in FIG. 42A in accordance with some embodiments. FIG. 42A shows that the endosome levels are reduced by optogenetic enhancement of gamma rhythm. Induction of gamma oscillations through FS-PV+ 40-Hz stimulation reduced levels of EEA1 (a marker for endosomes) as measured by immunofluorescence (n=3 mice per group, p=0.08). The results showed that, because increased endosome levels indicate increased APP processing and therefore Aβ production, gamma oscillations reduce Aβ production in the AD mouse model.

Taken together, the results of the study showed that restoration or induction of gamma rhythms recovered molecular pathology in a mouse model of AD. The cell-type specific and temporally precise reintroduction of gamma oscillations through optogenetics both reduced generation and enhanced clearance of isoforms $A\beta_{1-40}$ and $A\beta_{1-42}$, peptides which aggregate to initiate many degenerative cascades involved in AD neuropathology. Furthermore, this treatment induced anti-inflammatory microglia signaling pathways, counteracting immune mechanisms linked to neurodegeneration.

According to some embodiments, cell-type specific and temporally controlled gamma oscillations may be induced in the hippocampus, the visual cortex, the barrel cortex, and/or the auditory cortex without optogenetics.

Visual Stimulation at Gamma Frequency Non-Invasively Drove Gamma Oscillations in the Visual Cortex.

The profound reduction of $A\beta$ levels by optogenetic stimulation at 40 Hz led to exploring other ways to induce 40-Hz oscillations in the brain to ensure this effect was not somehow specific to optogenetic manipulations or invasive procedures. In order to examine whether light flickering could be used as a non-invasive approach to induce 40-Hz oscillations in the visual cortex, in some embodiments, animals were exposed to periods of 40 Hz or random flickering, and continuous lights on interleaved with periods of darkness.

FIG. 43A is a schematic diagram illustrating a mouse exposed to light flicker stimulation in accordance with some embodiments. To determine if this light flickering altered $A\beta$, the animals were exposed to 40-Hz light flickering for one hour, consistent with the duration of optogenetic stimulation that reduced $A\beta$ as described herein. Light flickering covered the animals' entire field of view. As controls for molecular and cellular assays, the three-month-old 5XFAD mice were maintained in constant dark for three days or were treated for one hour with either constant light or 20-Hz flickering lights, or 80-Hz flickering lights (see, e.g., FIG. 43A).

FIG. 43B includes a local field potential trace in the visual cortex before and during 40-Hz light flicker and a plot of power spectral density in accordance with some embodiments. Mean (solid line) and standard deviation (shaded area) of power spectral density are indicated during 40-Hz light flicker 4302, random light flicker 4304, or dark 4306 in visual cortex (n=4 5FXFAD mice from 5 recording sessions). FIGS. 43C-43F are plots depicting power spectral densities of local field potentials in the visual cortex during 40-Hz light flicker, random light flicker, constant dark, and constant light, respectively, for each recording session for each mouse in accordance with some embodiments (n=5 recordings from four 5XFAD mice with 47, 51, 61, 49, 16 40-Hz flicker, 47, 50, 64, 50, 16 random flicker, 279, 302, 382, 294, 93 dark, and 47, 50, 64, 49, 15 light periods). In visual cortex, it was found that light flickering at 40 Hz increased power in the LFPs at 40 Hz (see, e.g., FIGS. 43B and 43C), while random interval light flickering and dark did not (see, e.g., FIGS. 43B, 43D, and 43E).

Figure 44A:
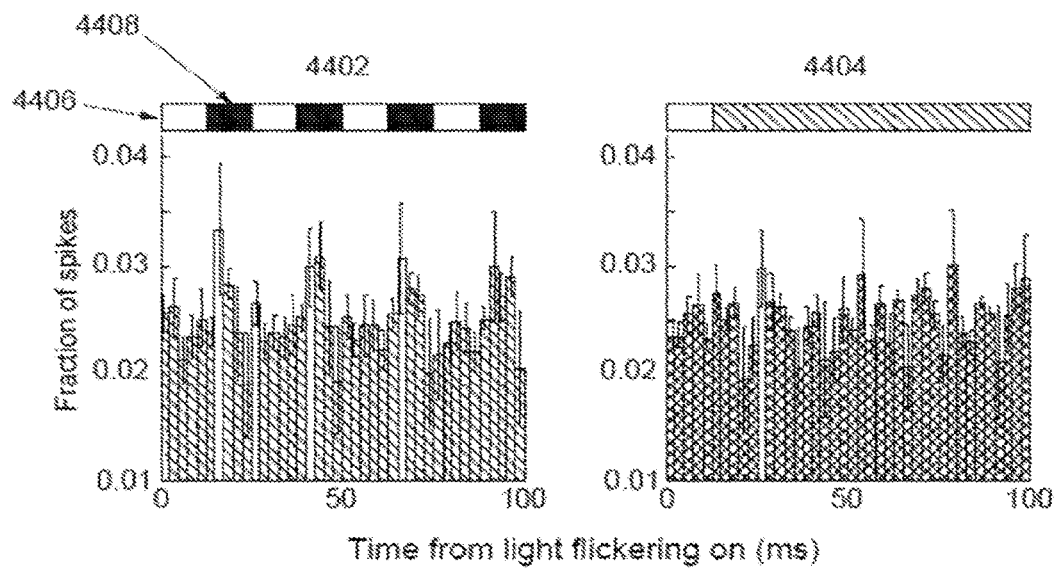
FIG. 44A is a series of histograms depicting fraction of spikes in visual cortex as a function of time for four cycles of 40-Hz light flicker and an equivalent period of time for random light flicker in accordance with some embodiments.

FIG. 44A is a series of histograms depicting fraction of spikes in visual cortex as a function of time for four cycles of 40-Hz light flicker and an equivalent period of time for random light flicker in accordance with some embodiments. FIG. 44A illustrates a histogram of fraction of spikes in visual cortex as a function of time for 4 cycles of 40-Hz light flicker 4402 or equivalent period of time of random light flicker 4404 (n=four 5XFAD mice from five recording sessions, bar indicates mean and error bars indicate SEM across animals). Bar above indicates when light was on 4406 or off 4408. In some embodiments, spiking increased and decreased as the light flickered on and off resulting in spiking phase locked to the 40-Hz frequency during 40-Hz stimulation (histogram 4402 in FIG. 44A) but no clear frequency emerged during random stimulation (histogram 4404 in FIG. 44A).

Figure 44B:
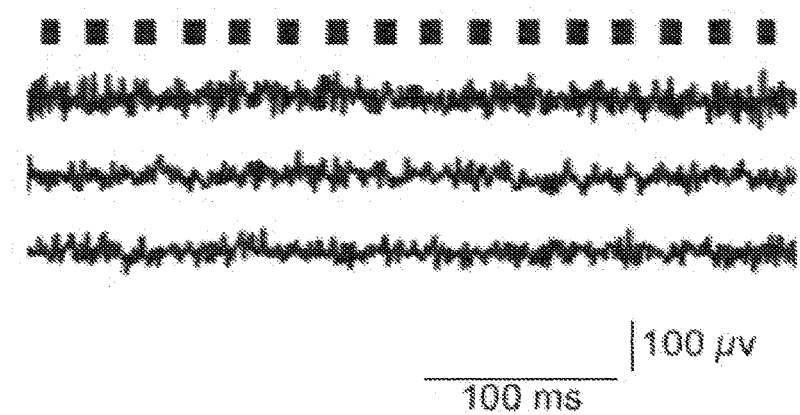
FIG. 44B is a series of electrical traces of local field potentials recorded above the brain during light flicker in accordance with some embodiments.

FIG. 44B is a series of electrical traces of local field potentials recorded above the brain during light flicker in accordance with some embodiments. In some embodiments, no increase in 40 Hz power during 40-Hz flicker was found when recorded from saline just above the brain, showing that this effect was not due to photoelectric effects or electrical noise (see, e.g., FIGS. 32 and 44B). As with optogenetic stimulation, the random flicker provided a control for overall changes in activity due to light flicker.

Figures 45A, 45B:
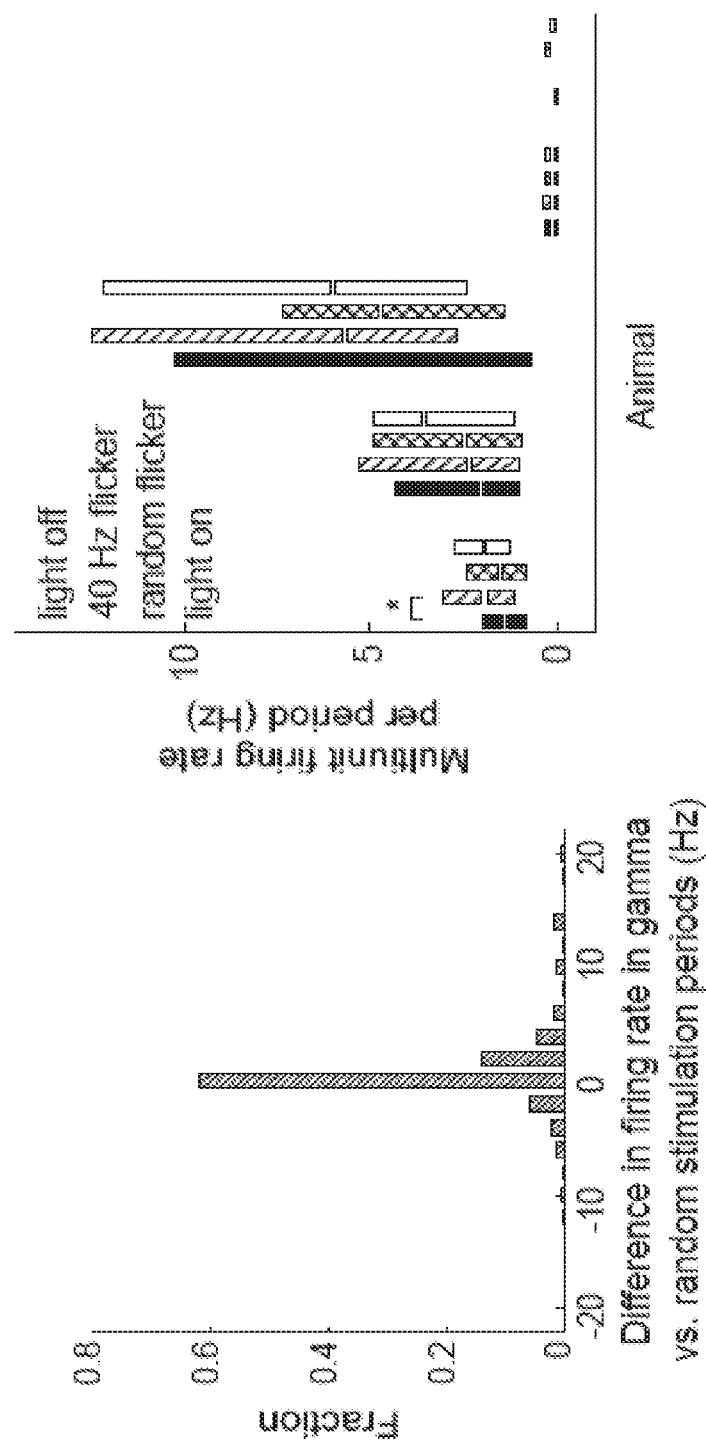
FIG. 45A is a histogram illustrating the difference in firing rates between 40-Hz light flicker and random light flicker in accordance with some embodiments.
FIG. 45B is a plot illustrating multi-unit firing rates in visual cortex in accordance with some embodiments.

FIG. 45A is a histogram illustrating the difference in firing rates between 40-Hz light flicker and random light flicker in accordance with some embodiments (n=226 stimulation periods from five recording sessions in four 5XFAD mice). FIG. 45B is a plot illustrating multi-unit firing rates in visual cortex during 40-Hz light flicker, random light flicker, dark, and light periods in accordance with some embodiments FIG. 45B illustrates multiunit firing rates in visual cortex. Box and whisker plots show median (white lines in box) and quartiles (top and bottom of box). In all animals firing rates between 40-Hz flicker and random flicker conditions were not significantly different showing that the random stimulation condition serves as a control for spiking activity (ranksum tests for each of 5 recording session from four 5XFAD mice, p>0.06, median and quartiles shown in figure, n=47, 51, 64, 49, 16 40-Hz flicker periods and 47, 50, 64, 50, 16 random flicker periods per recording). There were no significant differences in firing rates between 40-Hz flicker and light conditions indicating that 40-Hz light flicker generally did not cause neuronal hyper-excitability (ranksum tests for each of 5 recording session from four 5XFAD mice, p>0.2 for 4 recording sessions, p<0.01 for 1 recording session, which is not significant, when corrected for performing multiple comparisons, median and quartiles shown in figure, n=47, 51, 64, 49, 16 40 Hz periods and 47, 50, 64, 49, 16 light periods per recording). In one session, there was more activity in the 40-Hz stimulation than in the dark condition. Differences in multi-unit firing rates between 40 Hz and random flicker periods tended to be near zero (see, e.g., 45A); and comparing these periods within animals no significant differences were found (see, e.g., FIG. 45B, ranksum tests for each of 5 recording session from four 5XFAD mice, p>0.06, median and quartiles shown in figure, n=47, 51, 64, 49, 16 gamma flicker periods and 47, 50, 64, 50, 16 random flicker periods per recording).

Visual Stimulation at Gamma Frequency Decreased $A\beta$ Levels in the Visual Cortex.

Given the efficacy of the optogenetic method, a translational, non-invasive amyloid reduction treatment was designed. FIG. 46A is a schematic diagram illustrating an experimental paradigm in accordance with some embodiments. As shown in FIG. 46A, a first subset of AD model mice were placed in a first chamber 4600 with a 40-Hz flashing light, and a second subset of AD model mice were placed in a second chamber 4602 that was kept dark. The animals in the first chamber 4600 were exposed to the 40-Hz flashing light for about one hour.

FIGS. 46B and 46C are plots further illustrating changes in baseline levels of $A\beta$ peptide isoforms $A\beta_{1-40}$ and $A\beta_{1-42}$, respectively, following the experimental paradigm in FIG. 46A in accordance with some embodiments. FIG. 46B shows that 40-Hz light exposure in the visual cortex V1 of 5XFAD mice significantly reduced $A\beta_{1-40}$ and $A\beta_{1-42}$ levels. Levels of $A\beta_{1-40}$ and $A\beta_{1-42}$ are presented as pg/mL (n=6 animals per group).

Given that 40-Hz light flicker drives 40-Hz oscillations in the primary visual cortex and that optogenetic induction of 40-Hz oscillations reduced hippocampal Aβ levels, the aim was to determine whether 40-Hz light flicker could reduce Aβ levels in the visual cortex. For these experiments, in some embodiments, pre-symptomatic three-month-old 5XFAD mice were used. The mice were placed in a dark box and exposed to either 40-Hz light flicker, constant light on (light), or constant light off (dark) for one hour.

FIGS. 47A and 47B are bar graphs depicting changes in baseline levels of $A\beta_{1-40}$ and $A\beta_{1-42}$, respectively, in 5XFAD visual cortex in dark, light, 40-Hz flicker, 20-Hz flicker, 80-Hz flicker, 40-Hz flicker with picrotoxin (PTX) and Random flicker conditions in accordance with some embodiments (n=12 mice per group for dark; n=6 mice per group for light, 40-Hz flicker, 20-Hz flicker, 80-Hz flicker, and PTX; n=4 mice per group for Random flicker; "n.s." indicates not significant, one asterisk indicates p<0.05, and two asterisks indicate p<0.01 by one-way ANOVA). FIGS. 47 and 47B show mean and SEM. Circles superimposed on bars in the bar graphs indicate individual data points in each group. Following one hour after light exposure, it was observed that $A\beta_{1-40}$ levels in visual cortex were reduced by 57.96% and $A\beta_{1-42}$ levels by 57.97% compared to the dark condition (as measured by Aβ ELISA, see, e.g., FIGS. 47A and 47B, p<0.05 by one-way ANOVA, n=6 mice per group). Compared to light controls, amyloid levels were reduced by 62.47% ($A\beta_{1-40}$) and 68.55% ($A\beta_{1-42}$) following one hour of 40-Hz flicker (as measured by Aβ ELISA, see, e.g., FIG. 47, p<0.05 by one-way ANOVA, n=6 mice per group). Furthermore, the effect was specific to 40-Hz flicker as neither 20-Hz, 80-Hz, nor random flicker significantly reduced Aβ levels compared to dark and light controls (see, e.g., FIG. 47, "n.s." indicates not significant, n=6 mice per group).

Figures 48A, 48B, 48C:
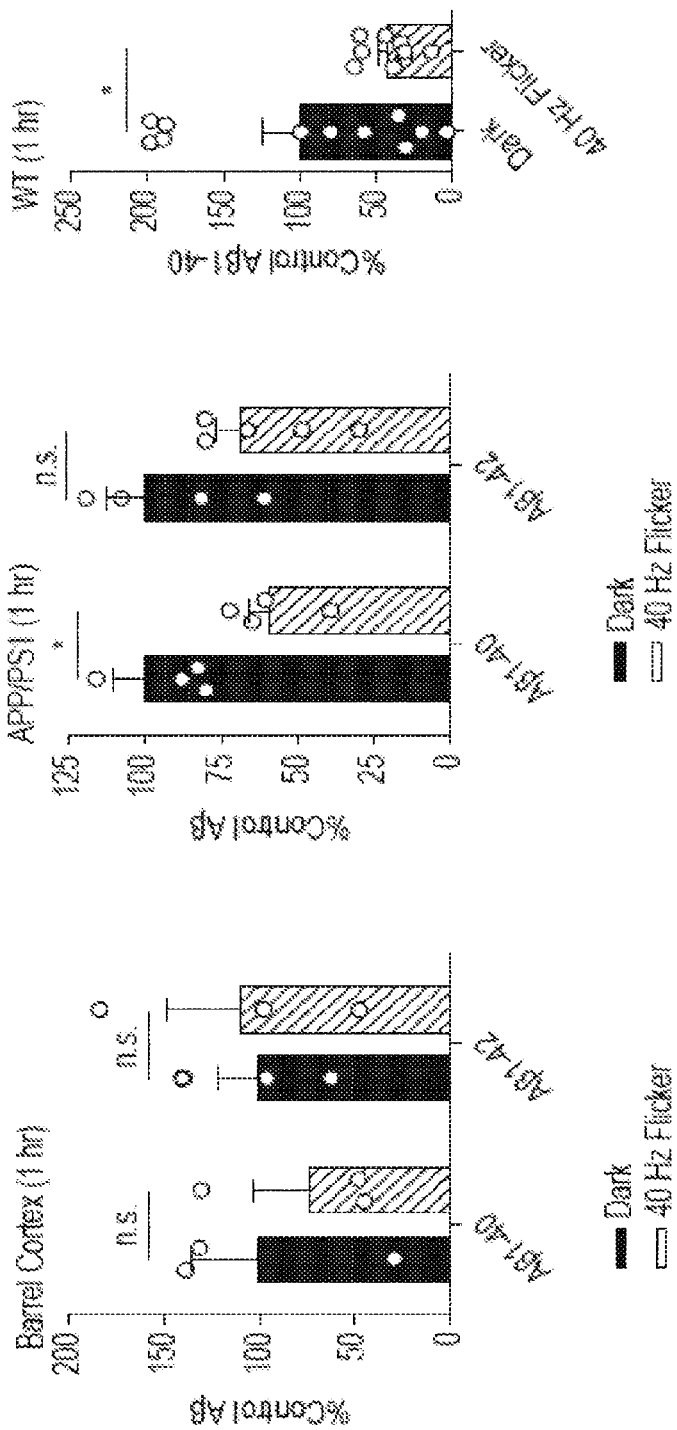
FIG. 48A is a bar graph depicting changes in baseline levels of $A\beta_{1-40}$ and $A\beta_{1-42}$ in 5XFAD barrel cortex under dark and 40-Hz flicker conditions in accordance with some embodiments.
FIG. 48B is a bar graph depicting changes in baseline levels of $A\beta_{1-40}$ and $A\beta_{1-42}$ in APP/PS1 visual cortex under dark and 40-Hz flicker conditions in accordance with some embodiments.
FIG. 48C is a bar graph depicting changes in baseline levels of $A\beta_{1-40}$ and $A\beta_{1-42}$ in WT visual cortex under dark and 40-Hz flicker conditions in accordance with some embodiments.

In some embodiments, to test regional specificity Aβ levels in the somatosensory barrel cortex (BC) was examined and no significant differences were found. FIG. 48A is a bar graph depicting relative $A\beta_{1-40}$ and $A\beta_{1-42}$ levels of 5XFAD barrel cortex under dark and 40-Hz flicker conditions in accordance with some embodiments (n=3 mice per group; "n.s." indicates not significant by Student's t-test). When 5XFAD mice were pretreated with a low dose GABA-A antagonist (picrotoxin, 0.18 mg/kg, which does not induce epileptic activity), the effects of 40-Hz flicker on Aβ levels were completely abrogated, indicating that GABAergic signaling, most likely from the FS-PV-interneurons, is necessary for this effect (see, e.g., FIG. 47, "n.s." indicates not significant, n=6 mice per group).

To demonstrate the effect was not specific to the 5XFAD mouse, this result was replicated in a different AD model, the APP/PS1 mouse, a well validated model with two familial AD mutations (APP Swedish and PSEN1 deltaE9). FIG. 48B is a bar graph depicting changes in baseline levels of $A\beta_{1-40}$ and $A\beta_{1-42}$ in APP/PS1 visual cortex under dark and 40-Hz flicker conditions in accordance with some embodiments (n=5 mice per group for dark and n=4 mice per group for 40-Hz flicker conditions; "n.s." indicates not significant and one asterisk indicates p<0.05, by Student's t-test).

FIG. 48C is a bar graph depicting changes in baseline levels of $A\beta_{1-40}$ and $A\beta_{1-42}$ in WT visual cortex under dark and 40-Hz flicker conditions in accordance with some embodiments (n=11 mice per group for dark and n=9 mice per group for 40-Hz flicker conditions; one asterisk indicates p<0.05, by Student's t-test). In some embodiments, in the APP/PS1 mice following 40-Hz flicker treatment, significantly reduced $A\beta_{1-40}$, by 20.80%, and a trend of reduced $A\beta_{1-42}$, by 37.68% was found, though the latter was not significantly different from dark conditions (see, e.g., FIG. 48B, $A\beta_{1-40}$ p<0.05, $A\beta_{1-42}$ p<0.09—not significant by Student's t-test, n=5 mice per group for dark, n=4 mice per group for 40-Hz flicker). In addition in aged WT mice, a 58.2% reduction in endogenous mouse $A\beta_{1-40}$ following one hour 40-Hz flicker was found (see, e.g., FIG. 48C, p<0.05 by Student's t-test, n=11 dark mice and n=9 40-Hz flicker mice). $A\beta_{1-42}$ was below detectable levels for both flicker and control groups in these animals. The reduction of endogenous mouse $A\beta_{1-40}$ in WT animals reveals these results may not be restricted to Tg APP expression or mutant APP; rather they may extend to Aβ produced from APP with expression driven by its endogenous promoter. FIGS. 48A-48C show mean and SEM.

Figure 49:
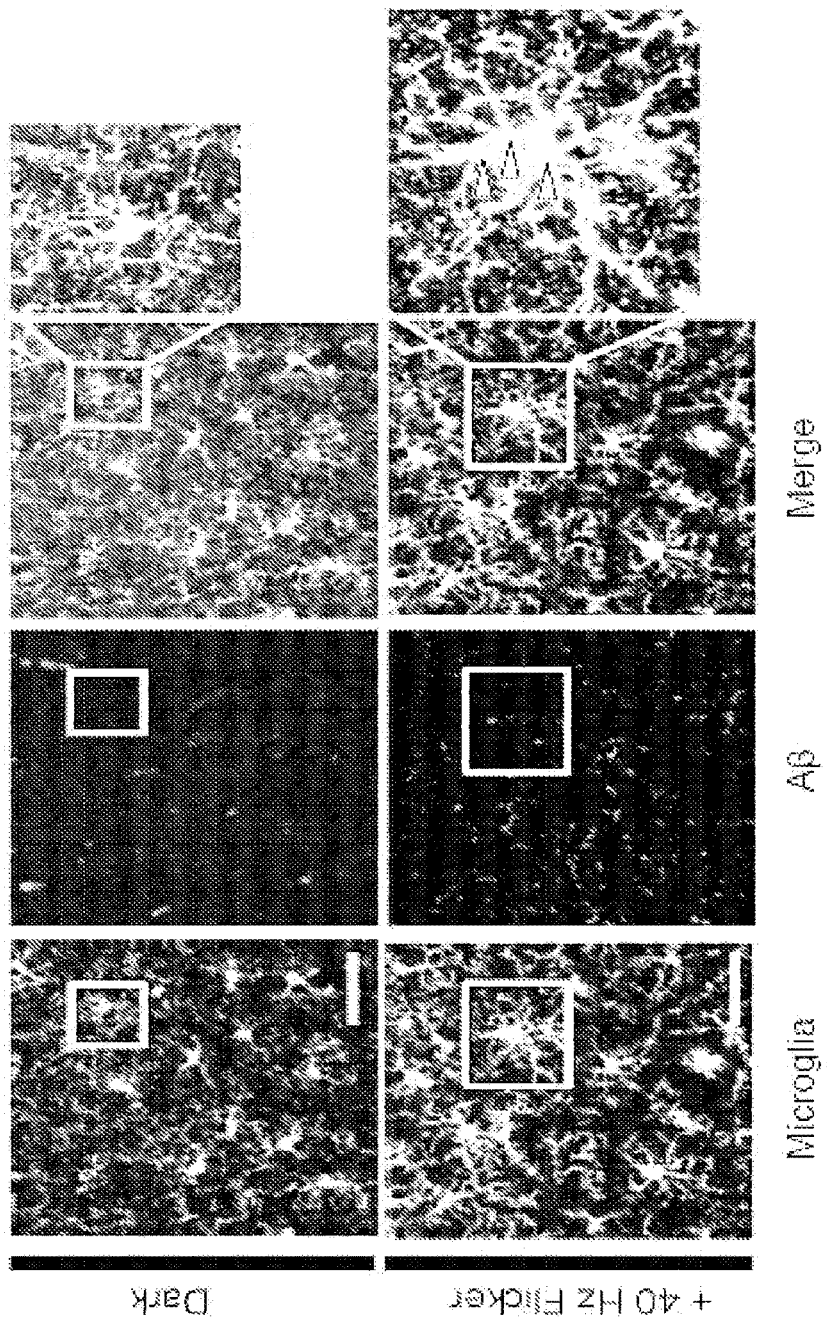
FIG. 49 is a series of immunofluorescence images illustrating immunohistochemistry with anti-Iba1 (019-19741) and anti-Aβ (12F4) antibodies in 5XFAD visual cortex under dark and 40-Hz flicker conditions in accordance with some embodiments.

Next, in some embodiments, an investigation as to whether 40-Hz flicker alters microglia activity in the visual cortex in the same manner that 40 Hz optogenetic FS-PV-interneuron stimulation altered hippocampal CA1 microglia was conducted. FIG. 49 is a series of immunofluorescence images illustrating immunohistochemistry with anti-Iba1 (019-19741) and anti-Aβ 4904 (12F4) antibodies in 5XFAD visual cortex under dark and 40-Hz flicker conditions in accordance with some embodiments. The images were taken with 40× objective (scale bar=50 μm). Right: 120× zoom; arrows indicate +Iba1/+Aβ signal in cell body.

Figure 50A:
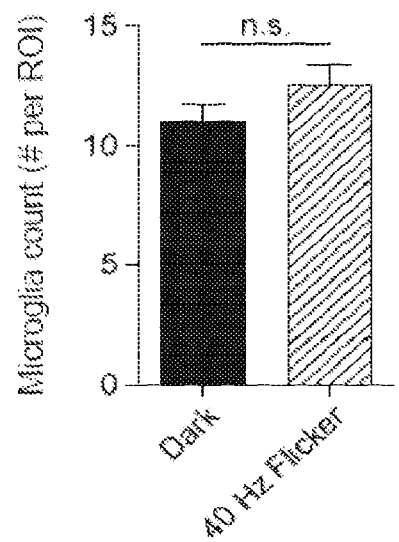
FIG. 50A is a bar graph depicting the number Iba1-positive cells (microglia) in accordance with some embodiments.
Figure 50B:
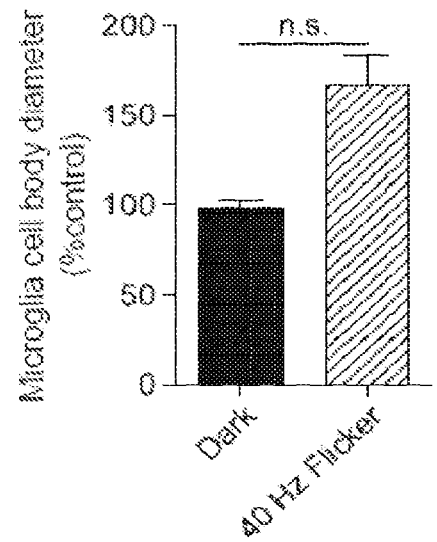
FIG. 50B is a bar graph depicting the diameter of microglial cell bodies normalized to control under dark and 40-Hz flicker conditions in accordance with some embodiments.
Figure 50C:
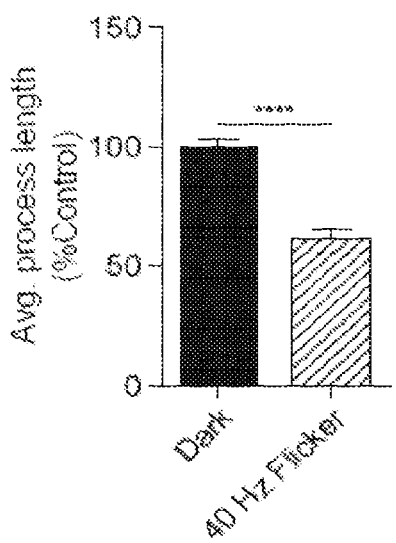
FIG. 50C is a bar graph depicting the average length of microglia primary processes normalized to control under dark and 40-Hz flicker conditions in accordance with some embodiments.
Figure 50D:
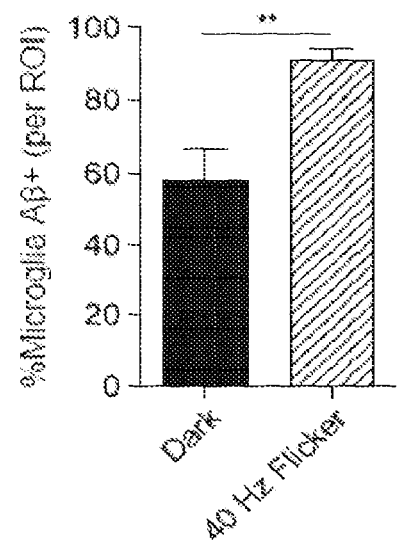
FIG. 50D is a bar graph depicting the percentage of microglia that are also Aβ-positive under dark and 40-Hz flicker conditions in accordance with some embodiments.

FIG. 50A is a bar graph depicting the number of microglia in dark and 40-Hz flicker conditions in accordance with some embodiments (n=2 sections from 4 mice per group; "n.s." indicates not significant by Student's t-test). FIG. 50B is a bar graph depicting the diameter of microglial cell bodies normalized to control in dark and 40-Hz flicker conditions in accordance with some embodiments (n=2 sections from 4 mice per group; two asterisks indicate p<0.01 by Student's t-test). FIG. 50C is a bar graph depicting the average length of microglia primary processes normalized to control in dark and 40-Hz flicker conditions in accordance with some embodiments (n=2 sections from 4 mice per group; four asterisks indicate p<0.0001 by Student's t-test). FIG. 50D is a bar graph depicting the percent of Iba1-positive (microglia) cell bodies that are also Aβ-positive under dark and 40-Hz flicker conditions in accordance with some embodiments (n=2 sections from 4 mice per group; two asterisks indicate p<0.01 by Student's t-test). FIGS. 50A-50D show mean and SEM.

In some embodiments, Iba1 was used to label microglia in visual cortex sections of 5XFAD mice after one hour of 40-Hz flicker or dark conditions (see, e.g., FIG. 49). While microglia number was not different between dark and 40-Hz flicker conditions (see, e.g., FIGS. 49 and 50A, "n.s." indicates not significant, n=2 sections from 4 mice per group) the microglial cell body diameter increased by 65.8% following 40-Hz flicker in the visual cortex compared to dark controls (see, e.g., FIGS. 49 and 50B, p<0.01 by Student's t-test, n=2 sections from 4 mice per group). The lengths of microglia primary processes were reduced by 37.7% in 40-Hz flicker conditions compared to dark controls (see, e.g., FIGS. 49 and 50C, p<0.0001 by Student's t-test, n=2 sections from 4 mice per group). Because the microglia in the visual cortex had morphology indicative of enhanced engulfment activity, in some embodiments, the number of Aβ-bearing microglia was examined. For this experiment, visual cortex sections were co-labeled with Iba1 and Aβ(12F4) antibodies. Aβ/Iba1 co-localization in the cell body was increased by 33.5% in 40-Hz flicker conditions, which indicated that 40-Hz flicker resulted in more Aβ-bearing microglia than dark control conditions (see, e.g., FIGS. 49 and 50D, p<0.01 by Student's t-test, n=2 sections from 4 mice per group).

Figure 51:
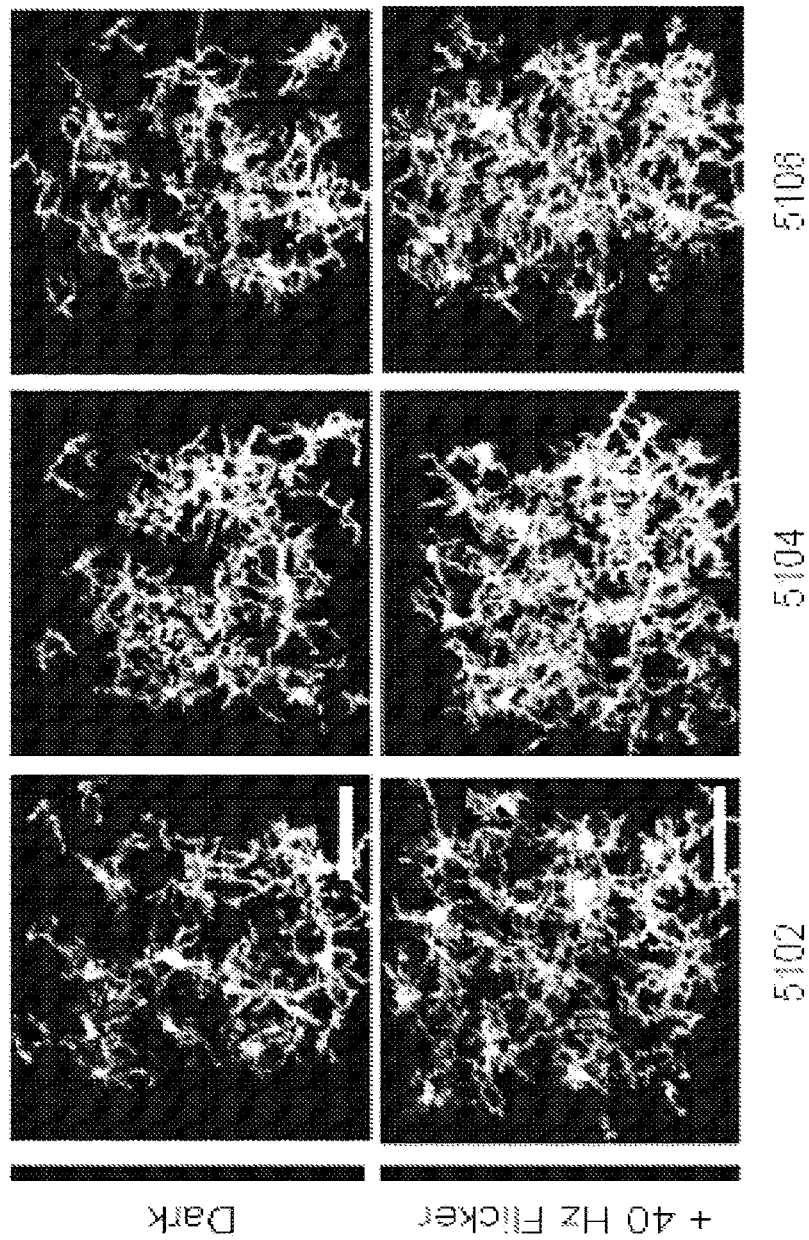
FIG. 51 is a series of 3D renderings (from immunofluorescence images) of Iba+ microglia under dark and 40-Hz flicker conditions from CLARITY-treated 100 μm tissue sections in accordance with some embodiments. CLARITY is a method of making brain tissue transparent using, e.g., acrylamide-based hydrogels built from within, and linked to, the tissue.

In some embodiments, to provide better resolution of the morphological change in microglia, CLARITY was used to create 3D renderings of microglia from 100 μm sections of visual cortex and videos were created from these renderings. FIG. 51 is a series of 3D renderings (from immunofluorescence images) of Iba+ microglia under dark and 40-Hz flicker conditions from CLARITY-treated 100 μm tissue sections rotated 0° 5102, 45° around the X-axis 5104, and 45° around the Y-axis 5106. Images were taken with 63× objective (scale bar=15 μm). Finally, to demonstrate that microglia indeed engulf Aβ in the 5XFAD mouse, microglia from 5XFAD and WT animals were purified using fluorescence-activated cell sorting (FACS) and Aβ levels were analyzed via ELISA.

Figures 52A, 52B:
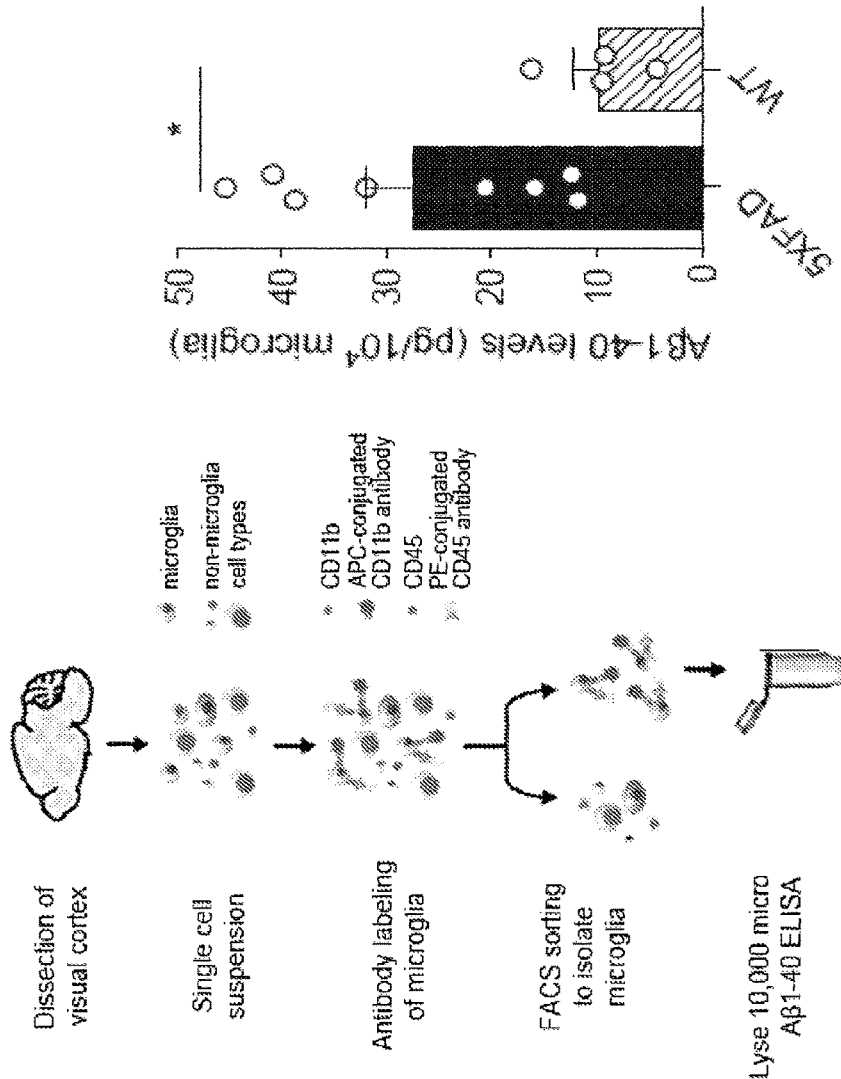
FIG. 52A is a flow diagram illustrating a method of isolating microglia from a visual cortex using fluorescence-activated cell sorting (FACS) in accordance with some embodiments.
FIG. 52B is a bar graph depicting $A\beta_{1-40}$ levels in microglia isolated from the visual cortices of three-month-old 5XFAD and WT control animals using the method of FIG. 52A in accordance with some embodiments.

FIG. 52A is a flow diagram illustrating a method of isolating microglia from a visual cortex using fluorescence-activated cell sorting (FACS) in accordance with some embodiments. Visual cortex was dissected, and then single cells were suspended and labeled with CD11b and CD45 antibodies. Subsequently, cells were sorted via fluorescence-activated cell sorting (FACS) and lysed. $A\beta_{1-40}$ levels were analyzed by ELISA. FIG. 52B is a bar graph depicting $A\beta_{1-40}$ levels in microglia isolated from the visual cortices of three-month-old 5XFAD and WT control animals using the method of FIG. 52A in accordance with some embodiments (n=8 mice per group for 5XFAD and n=4 mice per group for WT mice; one asterisk indicates p<0.05 by Student's t-test). Circles superimposed on bars in bar graphs indicate individual data points in each group.

Figure 53B:
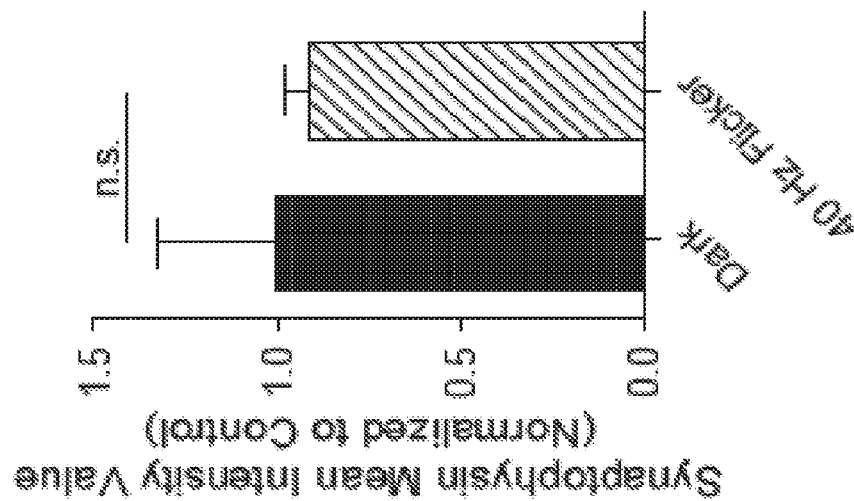
FIG. 53B is a bar graph depicting relative SVP38 intensity levels of 5XFAD visual cortex after dark and 40-Hz light flicker conditions in accordance with some embodiments.
Figure 53A:
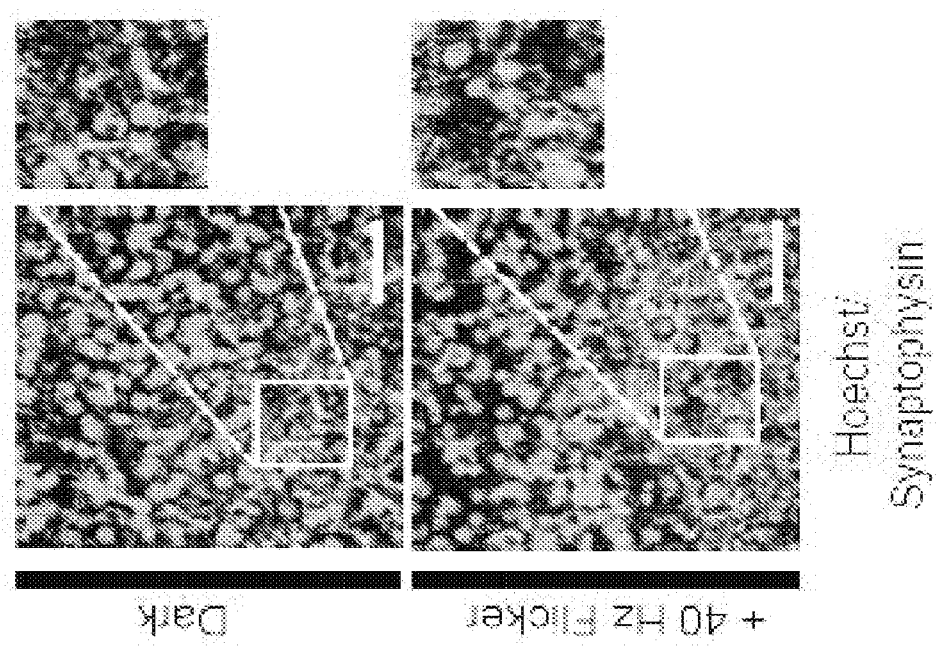
FIG. 53A is a series of immunofluorescence images illustrating immunohistochemistry with SVP38 antibodies to detect synaptophysin in three-month-old 5XFAD visual cortex under dark and 40-Hz flicker conditions in accordance with some embodiments.

FIG. 53A is a series of immunofluorescence images illustrating immunohistochemistry with SVP38 antibodies to detect synaptophysin in three-month-old 5XFAD visual cortex under dark and 40-Hz flicker conditions in accordance with some embodiments. Images were taken with 40× objective (scale bar=50 μm). Right: 100× of dark and 40-Hz flicker conditions. FIG. 53B is a bar graph depicting relative SVP38 intensity levels of 5XFAD visual cortex after in dark and 40 Hz flicker conditions in accordance with some embodiments (n=4 mice per group; "n.s." indicates not significant, by Student's t-test).

It was found that the microglia-specific levels of Aβ are significantly higher in 5XFAD animals than WT controls, with levels at 27.2 pg/$10^4$ microglia in 5XFAD mice and 9.78 pg/$10^4$ microglia in WT control mice (see, e.g., FIGS. 52A and 52B, p<0.05 by Student's t-test, n=8 for 5XFAD and n=4 for WT mice). $A\beta_{1-42}$ was below detectable levels for both flicker and control groups in these animals. Overall, the transformation of microglia in visual cortex induced by 40-Hz stimulation appeared similar to that which occurred in hippocampal CA1. Additionally, synaptophysin levels did not change between dark and 40-Hz flicker conditions, indicating that microglia activation did not significantly increase engulfment of synapses (see, e.g., FIGS. 53A and 53B, "n.s." indicates not significant, n=2 sections from 4 mice per group). Taken together, the data disclosed herein demonstrate that 40-Hz oscillations induced non-invasively via sensory stimulation may effectively reduce Aβ abundance and promote microglia/Aβ interactions in an AD mouse model. Furthermore 40-Hz stimulation may reduce Aβ in two distinct brain circuits, suggesting a general mechanism by which gamma oscillations reduce amyloid abundance and enhance microglia phagocytosis in various brain regions.

Figures 54A, 54B:
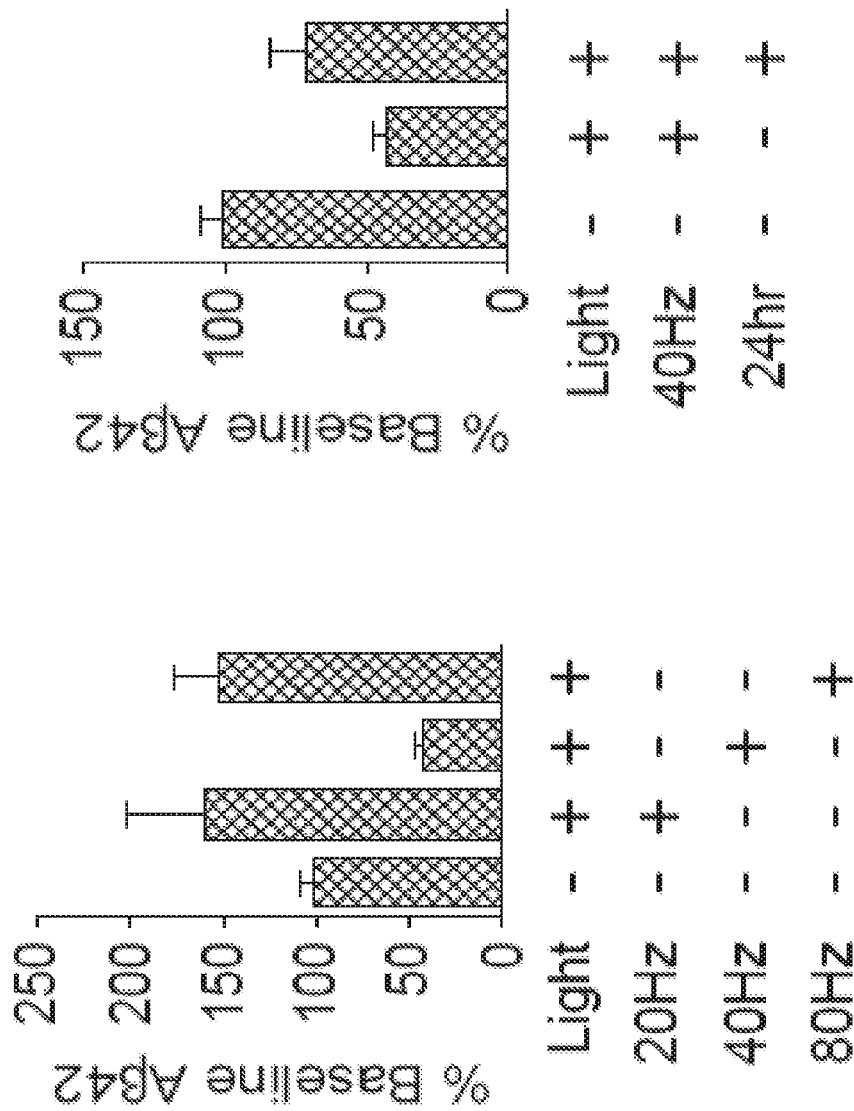
FIG. 54A is a bar graph illustrating a decrease in the Aβ peptide isoform $A\beta_{1-42}$ following stimulation of the visual cortex of a subject with gamma oscillations in accordance with some embodiments.
FIG. 54B is a bar graph illustrating levels of the Aβ peptide isoform $A\beta_{1-42}$ after stimulation of the visual cortex of a subject with gamma oscillations and again twenty-four hours after the stimulation in accordance with some embodiments.

In a further experiment, $A\beta_{1-42}$ levels were assessed following one hour of exposure to the dark (no light), a 20-Hz flashing light, a 40-Hz flashing light, or an 80-Hz flashing light, wherein 20 Hz and 80 Hz are harmonics of 40 Hz. However, only the 40-Hz flashing light flicker reduced $A\beta_{1-42}$ levels significantly. FIG. 54A is a bar graph illustrating a decrease in the Aβ peptide isoform $A\beta_{1-42}$ following stimulation of the visual cortex of a subject with gamma oscillations in accordance with some embodiments.

Another study was conducted to assess the timing of the reduction of $A\beta_{1-42}$ levels. For one hour, mice were exposed to either no light or a 40-Hz flashing light. The $A\beta_{1-42}$ levels were determined following one hour of treatment and again 24 hours after treatment completion. FIG. 54B is a bar graph illustrating levels of the Aβ peptide isoform $A\beta_{1-42}$ after stimulation of the visual cortex of a subject with gamma oscillations and again twenty-four hours after the stimulation in accordance with some embodiments. Although Aβ levels remained reduced twenty four hours after the treatment, the reduction was smaller than immediately after treatment.

Visual Stimulation at Gamma Frequency Did not Affect Aβ Levels in the Hippocampus.

Figure 55A:
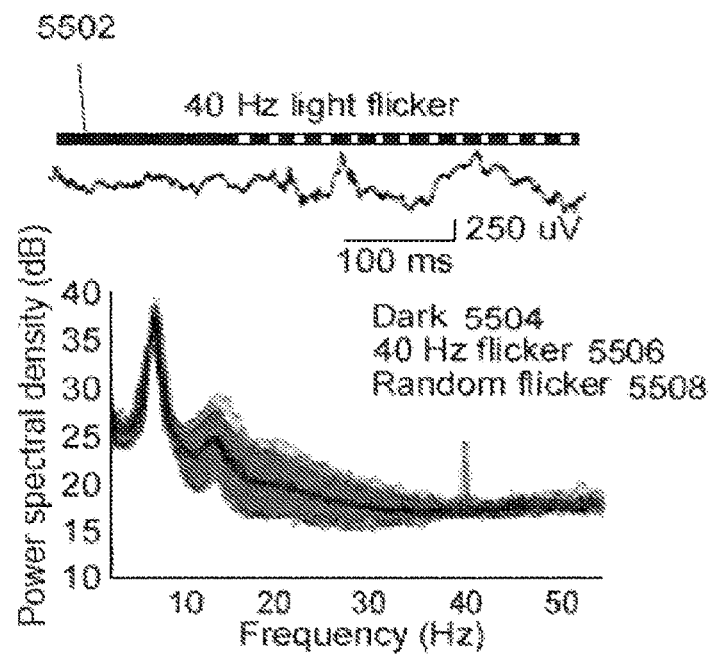
FIG. 55A includes an electrical trace of a local field potential in the hippocampus before and during 40-Hz light flicker and a plot of power spectral densities in accordance with some embodiments.

To determine if visual stimulation by light flicker could affect brain circuits implicated in AD, in some embodiments, the effects of light flicker on hippocampus, one of the brain regions affected early in the course of AD in humans were examined. FIG. 55A includes an electrical trace of a local field potential in the hippocampus before and during 40-Hz light flicker 5502 and a plot of power spectral densities in accordance with some embodiments. Mean (solid line) and standard deviation (shaded area) of power spectral density during dark 5504, 40-Hz light flicker 5506, and random light flicker 5508 in CA1 (n=two 5XFAD and three WT mice).

Figure 55B:
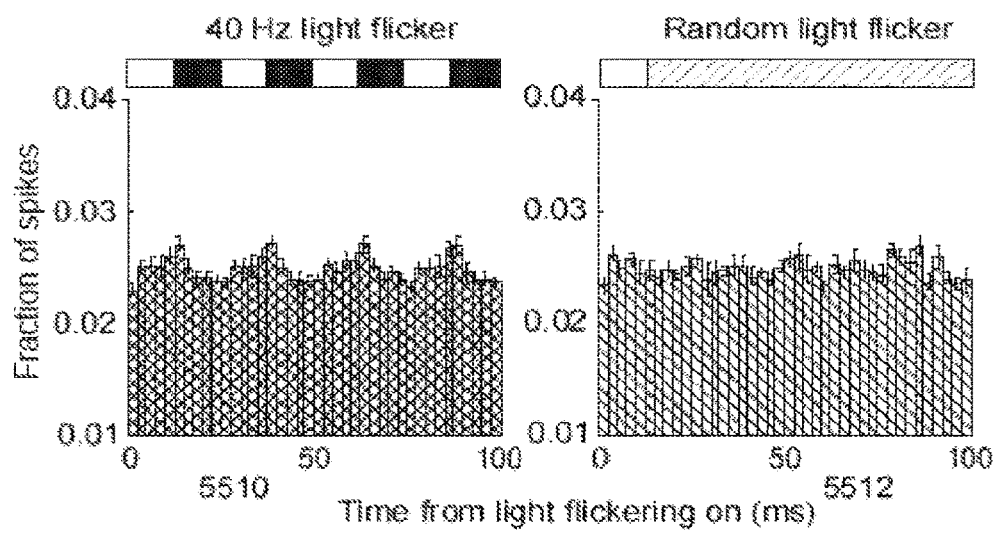
FIG. 55B is a series of histograms of fractions of spikes in the hippocampus as a function of time for 4 cycles of 40-Hz light flicker and the equivalent period of time for random light flicker, respectively, in accordance with some embodiments.

FIG. 55B is a series of histograms of fractions of spikes in the hippocampus as a function of time for 4 cycles of 40-Hz light flicker 5510 and the equivalent period of time for random light flicker 5512, respectively, in accordance with some embodiments (n=two 5XFAD and three WT mice, bar indicates mean and error bars indicate SEM across animals). Bar above indicates when light was on (white) or off (black). For random stimulation, spiking was aligned to the start of the light turning on, additional periods with light occurred at random intervals indicated by grey. Using the same approach to examine the effects of light flicker in CA1 as disclosed herein in visual cortex, it was found that light flickering at 40 Hz increased power in the LFPs recorded at 40 Hz (see, e.g., FIG. 55A and graph 5510 in FIG. 55B), while random interval light flickering (random flicker) and dark did not (see, e.g., FIG. 50D, graph 4310 in FIG. 43C). Spiking was also modulated by the 40-Hz flicker frequency during 40 H stimulation, however, the modulation appeared smaller than in visual cortex (see, e.g., FIG. 55B, hippocampus, FIG. 44A, visual cortex).

Figures 56A, 56B:
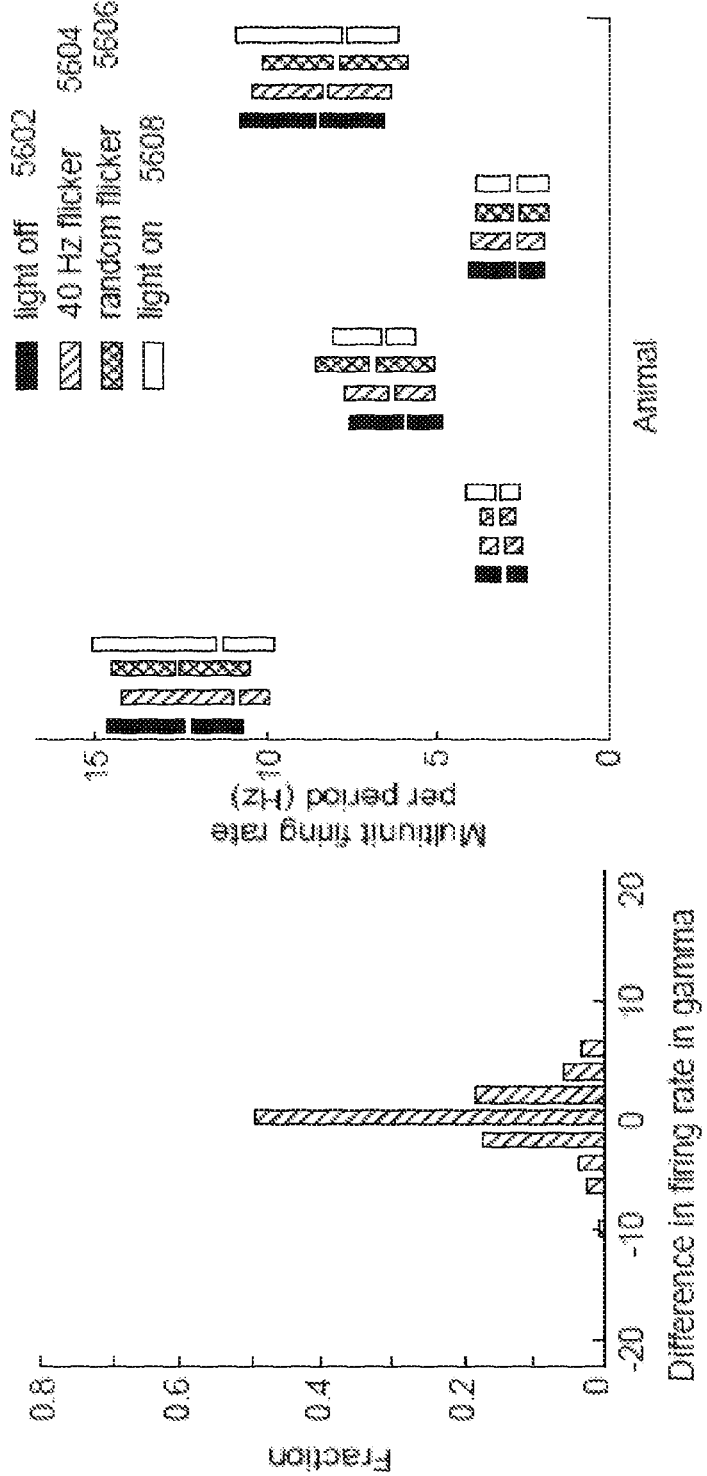
FIG. 56A is a histogram illustrating the difference in firing rates between 40-Hz light flicker and random light flicker in accordance with some embodiments.
FIG. 56B is a plot illustrating multi-unit firing rates in CA1 during 40-Hz light flicker in accordance with some embodiments.

FIG. 56A is a histogram illustrating the difference in firing rates between 40-Hz light flicker and random light flicker in accordance with some embodiments (bottom n=168 stimulation periods from 5 recording sessions in two 5XFAD and three WT mice). FIG. 56B is a plot illustrating multi-unit firing rates in CA1 during 40-Hz light flicker 5604, random light flicker 5605, dark 5602, or light 5608 periods in accordance with some embodiments. Box and whisker plots show median (white lines in box) and quartiles (top and bottom of box). In all animals firing rates between 40-Hz flicker and random flicker conditions were not significantly different showing that the random stimulation condition serves as a control for spiking activity (ranksum tests for each of 5 recordings from two 5XFAD and three WT animals, p>0.2, median and quartiles shown in figure, n=22, 54, 42, 71, 55 40-Hz flicker periods and 12, 34, 32, 54, 36 random flicker periods per recording). There were no significant differences in firing rates between 40-Hz flicker and light conditions indicating that 40-Hz light flicker generally did not cause neuronal hyper-excitability (ranksum tests for each of 5 recordings from two 5XFAD and three WT animals, p>0.3, median and quartiles shown in figure, n=22, 54, 42, 71, 55 40 Hz periods and 12, 34, 33, 54, 35 light periods per recording).

As in visual cortex, differences in multi-unit firing rates between 40 Hz and random flicker periods tended to be near zero (see, e.g., FIG. 56A), and in comparing these periods within animals, no significant differences were found (see, e.g., FIG. 56B, ranksum tests for each of 5 recording session from four 5XFAD mice, p>0.06, median and quartiles shown in figure, n=22, 54, 42, 71, 55 40-Hz flicker periods and 12, 34, 32, 54, 36 random flicker periods per recording).

Figure 57A:
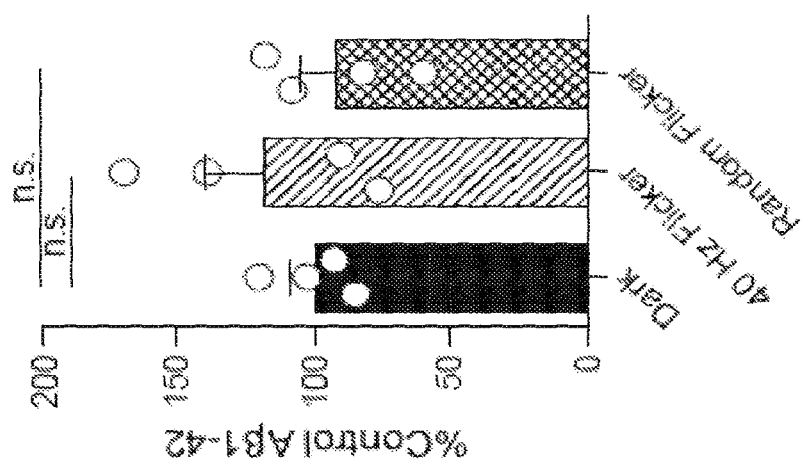
FIG. 57A is a bar graph depicting relative $A\beta_{1-40}$ levels in 5XFAD visual cortex in accordance with some embodiments.
Figure 57B:
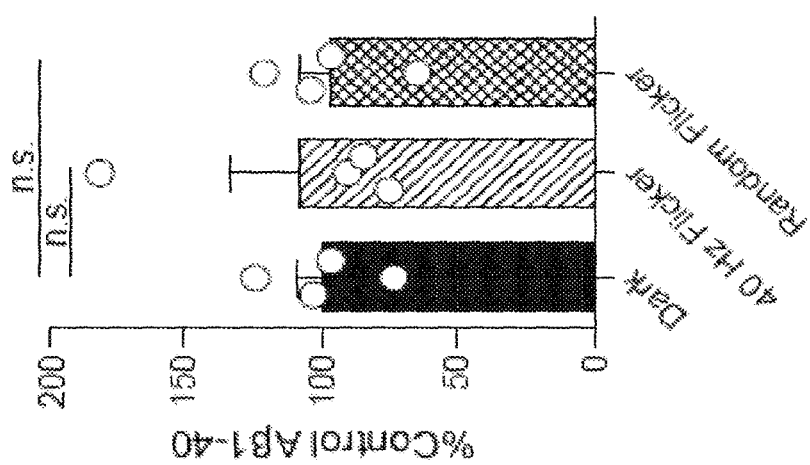
FIG. 57B is a bar graph depicting relative $A\beta_{1-42}$ levels in 5XFAD visual cortex in accordance with some embodiments.

In some embodiments, the effect of visual light flicker on levels of Aβ in hippocampus was examined, using the same approach used in visual cortex. FIG. 57A is a bar graph depicting relative $A\beta_{1-40}$ levels in 5XFAD visual cortex, and FIG. 57B is a bar graph depicting relative $A\beta_{1-42}$ levels in 5XFAD visual cortex in accordance with some embodiments (n=4 mice per group; "n.s." indicates not significant). In contrast to what was observed in visual cortex, in CA1 a significant difference in $A\beta_{1-40}$ and $A\beta_{1-42}$ levels one hour after 40-Hz flicker or random stimulation was not found. Aβ levels following 40-Hz flicker or random flicker were not significantly different from the dark condition: $A\beta_{1-40}$ levels were 108.4% and 96.82% of the dark condition following 40 Hz and random flicker, respectively, and $A\beta_{1-42}$ levels were 118.8% and 92.15% of the dark condition following 40-Hz and random flicker, respectively (see, e.g., FIGS. 57A and 57B, "n.s." indicates not significant, n=4 mice per group). Thus, one hour of 40-Hz light flicker did not significantly reduce levels of Aβ in hippocampus.

Chronic Visual Stimulation at Gamma Frequency Decreased Plaque Load in the Visual Cortex.

The affected amyloid abundance in pre-plaque 5XFAD mice when 40-Hz oscillations are driven either optogenetically or by visual stimulation via light flicker have been examined and disclosed herein. Next, the aim was to determine whether this treatment was effective in animals that already show plaque load. To this end, in some embodiments, six-month-old 5XFAD mice were used, as they develop extensive amyloid plaque pathology in many brain regions including visual cortex. A test was conducted to see what happens to the advanced Aβ-related pathology following non-invasive gamma stimulation. To investigate the duration of Aβ reduction in response to one hour of 40-Hz flicker, in some embodiments, Aβ levels were measured in the visual cortex 4, 12, and 24 hours after one hour of 40-Hz flicker or dark conditions.

Figures 58A, 58B:
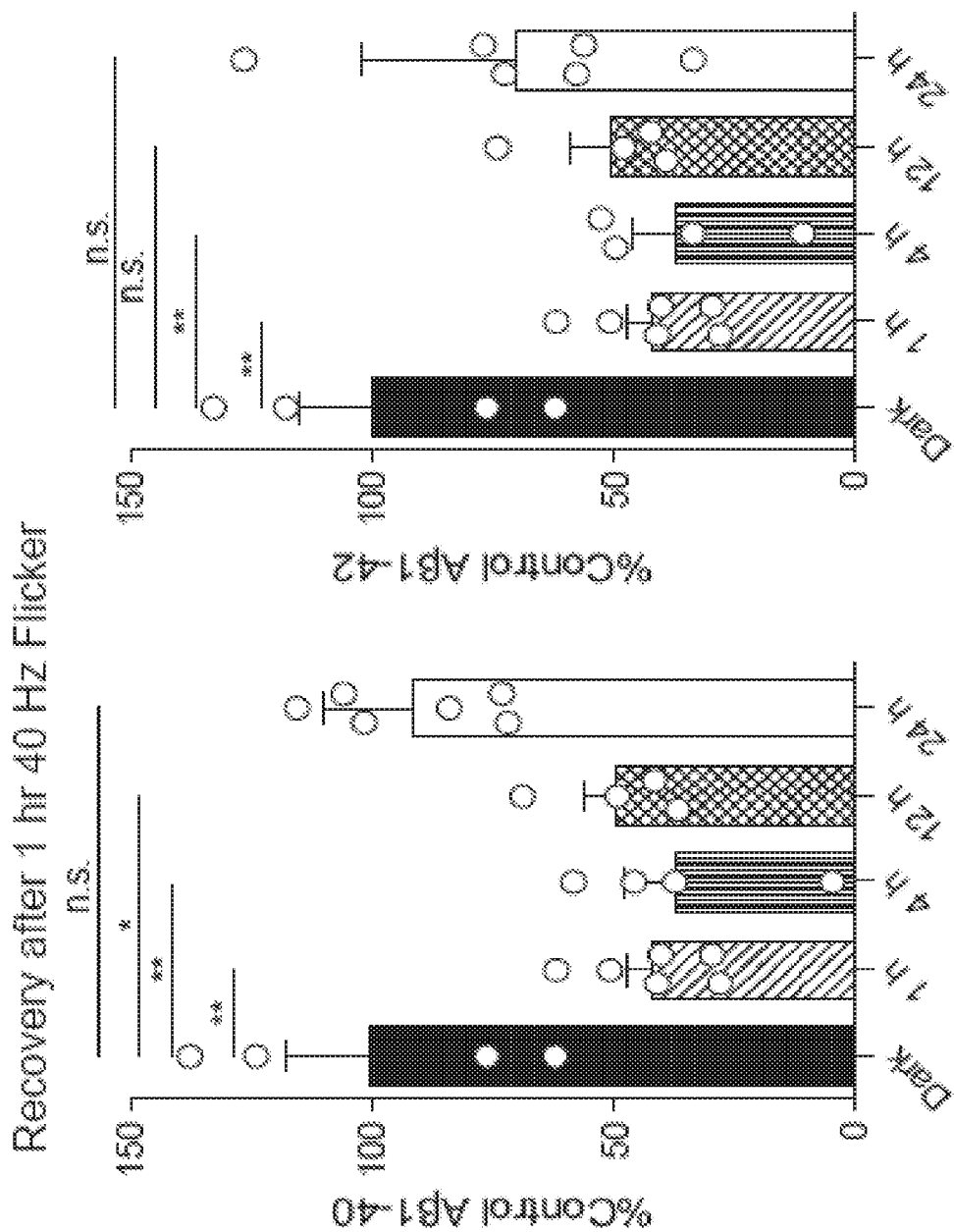
FIG. 58A is a bar graph depicting relative $A\beta_{1-40}$ levels in 5XFAD visual cortex with recovery after 40-Hz light flicker in accordance with some embodiments.
FIG. 58B is a bar graph depicting relative $A\beta_{1-42}$ levels in 5XFAD visual cortex with recovery after 40-Hz light flicker in accordance with some embodiments.

FIGS. 58A and 58B are bar graphs depicting relative Aβ1-40 and $A\beta_{1-42}$ levels, respectively, of 5XFAD visual cortex 1, 4, 12, and 24 hours following one hour of dark or 40-Hz flicker treatment in accordance with some embodiments (n=4 mice per group for 4 and 12 hour wait, n=6 for 1 and 24 hour wait, n=12 for dark; "n.s." indicates not significant, one asterisk indicates p<0.05 and two asterisks indicate p<0.01, by one-way ANOVA). The results showed that after 4 hours, $A\beta_{1-40}$ levels were reduced by 63.4% and $A\beta_{1-42}$ levels were reduced by 63.2% compared to dark controls (see, e.g., FIG. 58, p<0.01, n=4 mice per group). By 12 hours, $A\beta_{1-40}$ levels were reduced by 50.9% while $A\beta_{1-42}$ levels were not significantly different from dark controls (see, e.g., FIG. 58, "n.s." indicates not significant and p<0.01, n=4 mice per group). Finally, 24 hours following one hour of 40-Hz flicker treatment, soluble $A\beta_{1-40}$ and $A\beta_{1-42}$ levels were not significantly different in 40-Hz flicker compared to dark control conditions (see, e.g., FIG. 58, "n.s." indicates not significant, n=6 mice per group for 24 hours and n=4 mice per group for dark). These results indicate that the effects of 40-Hz flicker treatment are transient.

Therefore, to disrupt advanced plaque pathology, in some embodiments, mice were treated for one hour each day for seven days with 40-Hz flicker or, for control, with dark conditions. FIG. 59A is a schematic diagram depicting six-month-old mice exposed to one hour of flicker per day for seven days in accordance with some embodiments. FIG. 59B is a bar graph illustrating relative $A\beta_{1-42}$ levels in visual cortices of six-month-old 5XFAD mice after seven days of one hour/day under dark or 40-Hz flicker conditions in accordance with some embodiments (n=13 mice per group, two asterisks indicate p<0.01 and three asterisks indicate p<0.001, Student's t-test). FIG. 59C is a bar graph illustrating relative $A\beta_{1-40}$ levels in visual cortices of six-month-old 5XFAD mice after seven days of one hour/day under dark or 40-Hz flicker conditions in accordance with some embodiments (n=13 mice per group, one asterisk indicates p<0.01 and two asterisks indicate p<0.01, by Student's t-test). FIGS. 59B and 59C show mean and SEM. Circles superimposed on bars in the bar graphs indicate individual data points in each group.

At the conclusion of the seven-day period, the visual cortex was analyzed by ELISA and immunostaining. In some embodiments, the tissue was lysed in phosphate-buffered saline (PBS) to extract the PBS soluble Aβ fraction and it was found that seven days of one hour 40-Hz flicker reduced soluble $A\beta_{1-40}$ and $A\beta_{1-42}$ levels by 60.5% and 51.7% respectively, in six-month-old 5XFAD mice, as measured by ELISA (see, e.g., FIGS. 59B and 59C, p<0.05 and p<0.01 by Student's t-test, n=13 mice per group). Tissue was further treated with guanidine hydrochloric acid (HCl) to extract the insoluble $A\beta_{1-40}$ and $A\beta_{1-42}$ fraction, which constitutes aggregated amyloid plaques. Insoluble $A\beta_{1-40}$ and $A\beta_{1-42}$ levels were reduced by 43.7% and 57.9% respectively, indicating that 40-Hz flicker disrupted the insoluble Aβ aggregates already formed in the six-month-old mice (see, e.g., FIGS. 59B and 59C, p<0.01 and p<0.001 by Student's t-test, n=13 mice per group).

Figure 60A:
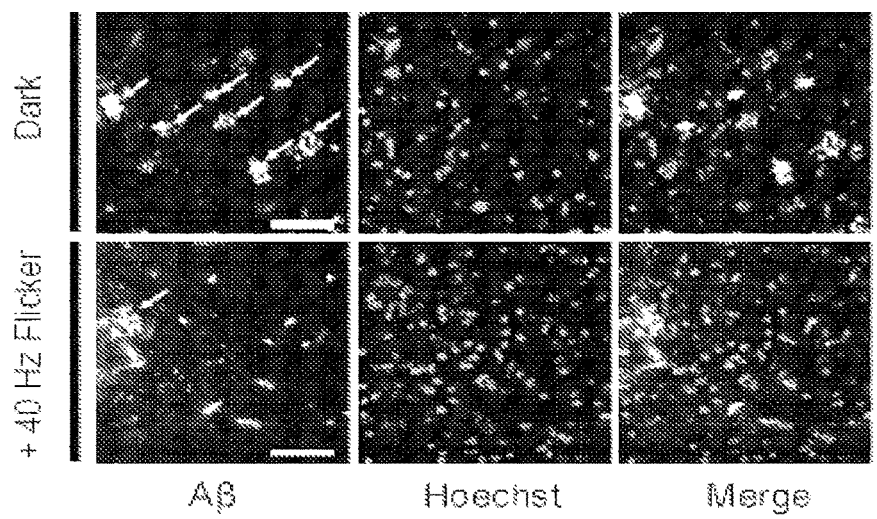
FIG. 60A is a series of immunofluorescence images illustrating immunohistochemistry with anti-Aβ antibody in visual cortices of six-month-old 5XFAD mice after seven days of one hour/day under dark or 40-Hz flicker conditions in accordance with some embodiments.
Figure 60B:
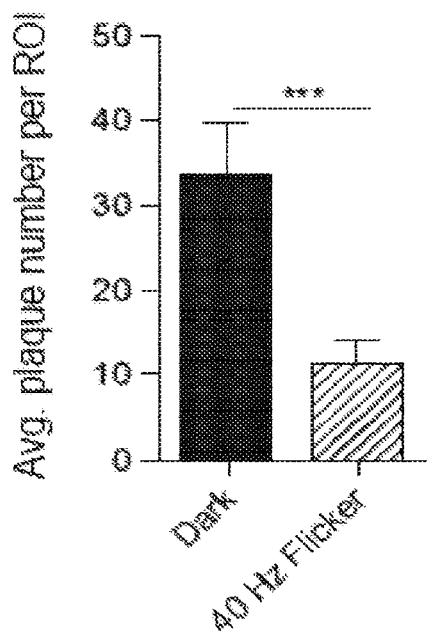
FIG. 60B is bar graph depicting the number of Aβ-positive plaque deposits after seven days of one hour/day under dark or 40-Hz flicker conditions in visual cortices of six-month-old 5XFAD mice in accordance with some embodiments.
Figure 60C:
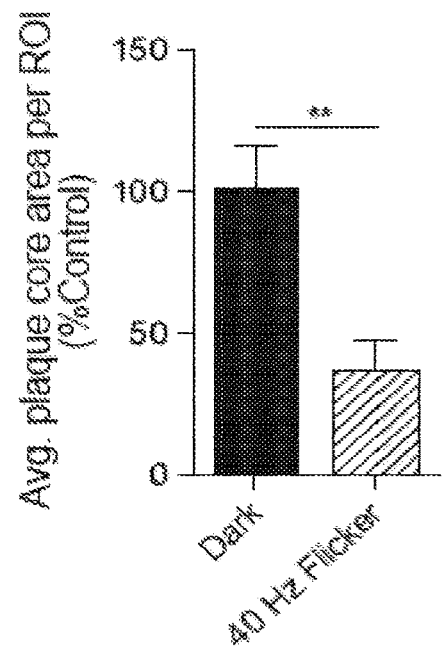
FIG. 60C is a bar graph depicting the area of Aβ-positive plaques after seven days of one hour/day under dark or 40-Hz flicker conditions in visual cortices of six-month-old 5XFAD mice in accordance with some embodiments.

To determine how plaque load, specifically, was affected, in some embodiments, immunohistochemical characterization was performed using an Aβ antibody (Cell Signaling Technology; D54D2). FIG. 60A is a series of immunofluorescence images illustrating immunohistochemistry with anti-Aβ (D5452) antibody in visual cortices of six-month-old 5XFAD mice after seven days of one hour/day under dark (top) or 40-Hz flicker (bottom) conditions in accordance with some embodiments (scale bar=50 μm). Aβ signals that appeared intracellular were excluded. FIG. 60B is bar graph depicting the number of Aβ-positive plaque deposits after seven days of one hour/day under dark or 40-Hz flicker conditions in visual cortices of six-month-old 5XFAD mice in accordance with some embodiments (n=8 mice per group, three asterisks indicate p<0.001, by Student's t-test). FIG. 60C is a bar graph depicting the area of Aβ-positive plaques after seven days of one hour/day under dark or 40-Hz flicker conditions in visual cortices of six-month-old 5XFAD mice in accordance with some embodiments (n=8 mice per group; two asterisks indicate p<0.01 by Mann Whitney test). FIGS. 60B and 60C show mean and SEM.

Plaque abundance was quantified by counting the number of Aβ+ deposits greater than or equal to about 10 μm in diameter. The 40-Hz flicker reduced the plaque number to 11.0 compared to 33.5 in dark controls (see, e.g., FIGS. 60A and 60B, p<0.01 by Student's t-test, n=8 mice per group). In addition, plaque size (measured as the area of the dense plaque region) after one week of 40-Hz flicker treatment, decreased by approximately 63.7% compared to dark controls (see, e.g., FIGS. 60A and 60C, p<0.01 by Mann Whitney test, n=8 mice per group). Taken together, these experiments identified a completely non-invasive treatment with a profound effect on amyloid plaque pathology.

To determine if 40-Hz flicker improves another key AD-related pathology, tau phosphorylation was investigated using the TauP301S tauopathy mouse model. Four-month-old TauP301S Tg mice, which show phosphorylated tau localized to the cell body at this age, were treated with either 40-Hz flicker or dark control conditions for one hour daily for seven days. To examine how 40-Hz flicker altered tau phosphorylation, immunohistochemical characterization of the visual cortex was performed using pTau antibodies against three different epitopes of pTau (S202, S396, and S400/T403/S404; 11834S, 9632S, 11837S) and dendritic marker MAP2 as a control.

Figure 61A:
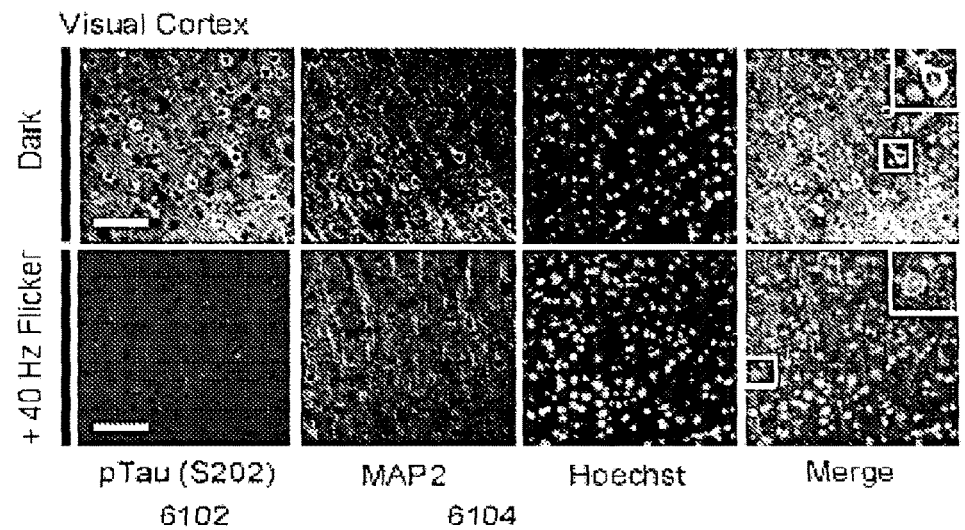
FIG. 61A is a series of immunofluorescence images illustrating immunohistochemistry with anti-phosphoTau (S202) and anti-MAP2 antibodies in four-month-old P301S mice after seven days of one hour/day under dark or 40-Hz flicker conditions in accordance with some embodiments.
Figure 61B:
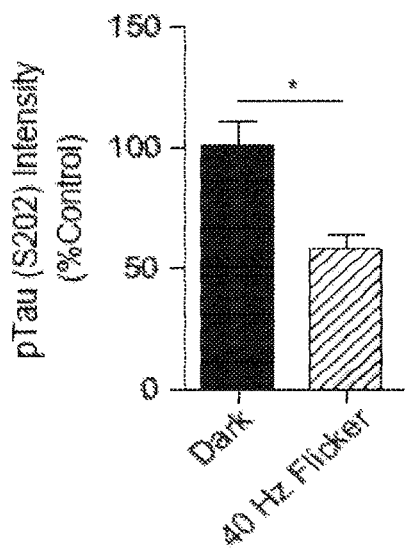
FIG. 61B is a bar graph depicting relative phosphoTau (pTau) (S202) intensity levels of P301S visual cortex after seven days of one hour/day under dark and 40-Hz flicker conditions in accordance with some embodiments.
Figure 61C:
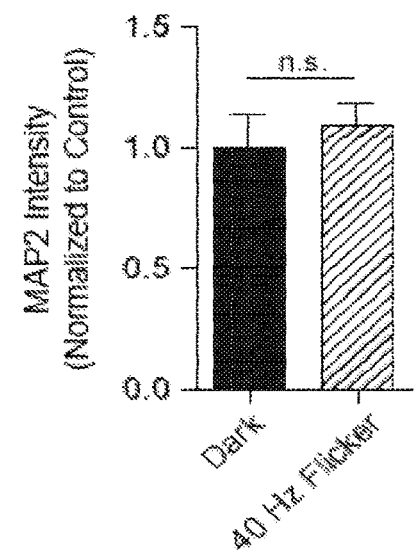
FIG. 61C is a bar graph depicting relative MAP2 intensity levels of P301S visual cortex after seven days of one hour/day under dark and 40-Hz flicker conditions in accordance with some embodiments.

FIG. 61A is a series of immunofluorescence images illustrating immunohistochemistry with anti-pTau 6102 (S202) and anti-MAP2 6104 antibodies in four-month-old P301S mice after seven days of one hour/day under dark or 40-Hz flicker conditions in accordance with some embodiments. Images were taken with 40× objective (scale bar=50 μm; insets include 100× rendering of representative cell body under dark and 40-Hz flicker conditions). FIG. 61B is a bar graph depicting relative pTau (S202) intensity levels of P301S visual cortex after seven days of one hour/day under dark and 40-Hz flicker conditions in accordance with some embodiments (n=8 mice per group; one asterisk indicates p<0.05 by Student's t-test). FIG. 61C is a bar graph depicting relative MAP2 intensity levels of P301S visual cortex after seven days of one hour/day under dark and 40-Hz flicker conditions in accordance with some embodiments (n=8 mice per group; "n.s." indicates not significant, by Student's t-test). FIGS. 61B and 61C show mean and SEM.

Figure 62B:
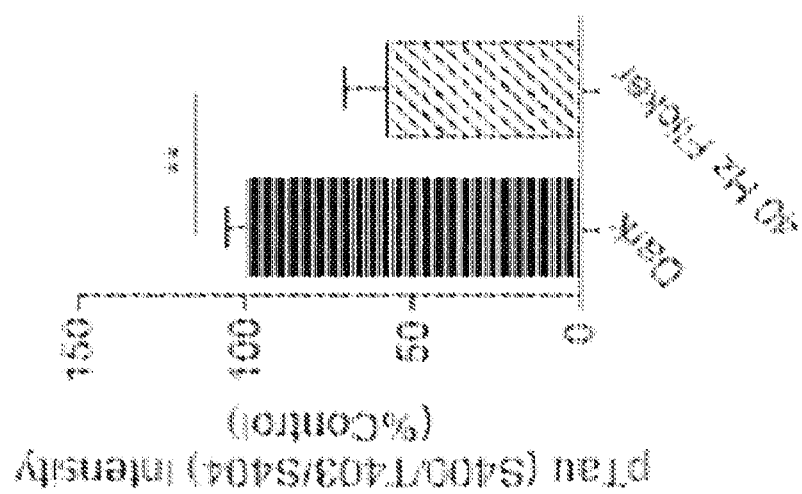
FIG. 62B is a bar graph depicting relative pTau (S400/T403/S404) fluorescence intensity levels of P301S visual cortex after seven days of one hour/day under dark and 40-Hz flicker conditions in accordance with some embodiments.
Figure 62A:
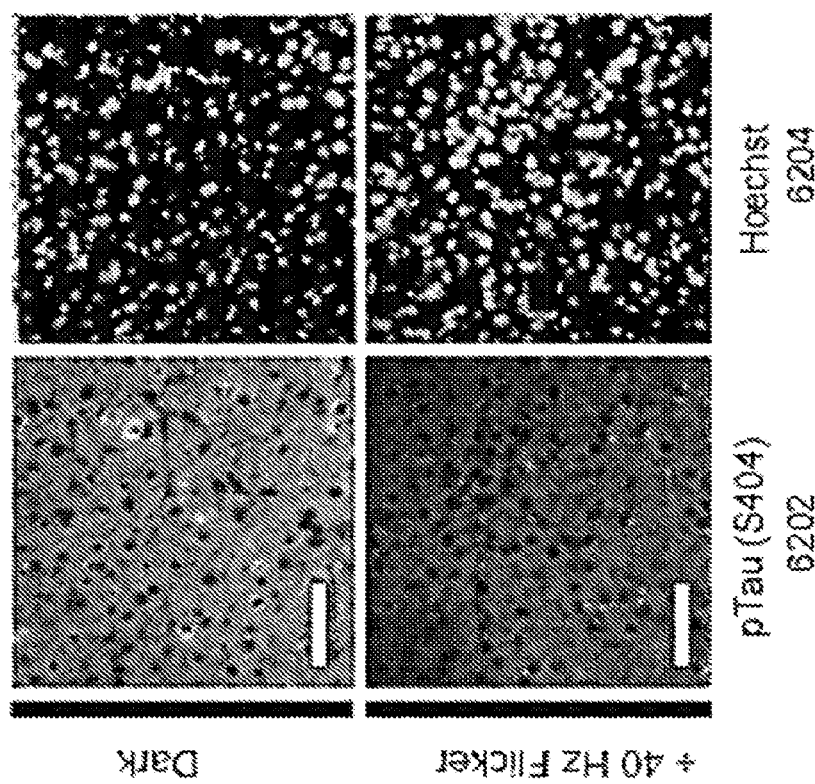
FIG. 62A is a series of immunofluorescence images illustrating immunohistochemistry with anti-pTau 6202 (S404) antibodies in 4-month-old P301S mice after seven days of one hour/day under dark and 40-Hz flicker conditions in accordance with some embodiments.

FIG. 62A is a series of immunofluorescence images illustrating immunohistochemistry with anti-pTau 6202 (S404) antibodies in 4-month-old P301S mice after seven days of one hour/day under dark and 40-Hz flicker conditions in accordance with some embodiments (scale bar=50 μm). FIG. 62B is a bar graph depicting relative pTau (S400/T403/S404) fluorescence intensity levels of P301S visual cortex after seven days of one hour/day under dark and 40-Hz flicker conditions in accordance with some embodiments (n=8 mice per group; two asterisks indicate p<0.01, by Student's t-test). FIG. 62B shows mean and SEM.

FIG. 63A is a series of immunofluorescence images illustrating immunohistochemistry with anti-pTau 6302 (S396) antibodies in four-month-old P301S mice after seven days of one hour/day under dark and 40-Hz flicker conditions in accordance with some embodiments (scale bar=50 μm). FIG. 63B is a bar graph depicting relative pTau (S396) fluorescence intensity levels of P301S visual cortex after seven days of one hour/day under dark and 40-Hz flicker conditions in accordance with some embodiments (n=8 mice per group; four asterisks indicate p<0.0001, by Student's t-test).

The results showed that the signal intensity of the pTau (S202) was reduced by 41.2% and pTau(S400/T403/S404) by 42.3% in the 40-Hz flicker conditions compared to dark controls (see, e.g., FIGS. 61A-B, 62A-B, p<0.01 by Student's t-test, n=2 sections from 8 mice per group), while MAP2 levels were unchanged (see, e.g., FIGS. 61A and 61C, "n.s." indicates not significant, n=2 sections from 4 mice per group). Staining with an antibody against pTau (S396) showed a trend in the same direction: 40-Hz flicker reduced pTau (S396) levels by 14.4% compared to dark controls (see, e.g., FIGS. 63A-B, "n.s." indicates not significant, n=2 sections from 8 mice per group). Moreover, less punctate and cell-body localization of pTau signal in response to 40-Hz flicker compared to the dark controls were observed. Although significant changes in tau phosphorylation were seen, no discernable difference in the levels of insoluble tau between 40-Hz flicker treated and dark control groups were observed.

Figure 64:
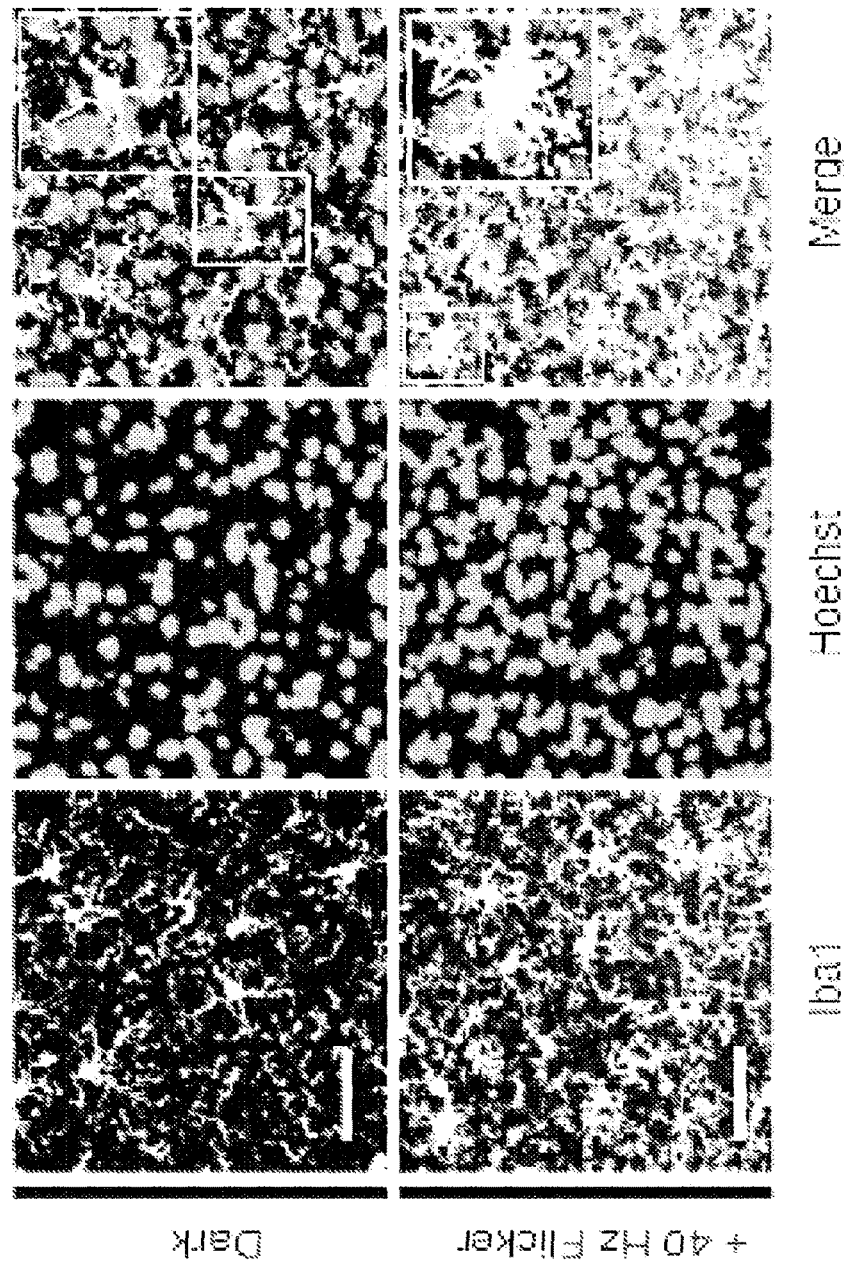
FIG. 64 is a series of immunofluorescence images illustrating immunohistochemistry with anti-Iba1 antibodies in four-month-old P301S mice after seven days of one hour/day under dark and 40-Hz flicker conditions in accordance with some embodiments.

The consequence of 40-Hz flicker on microglia in the TauP301S mouse model was evaluated. FIG. 64 is a series of immunofluorescence images illustrating immunohistochemistry with anti-Iba1 (019-19741) antibodies in four-month-old P301S mice after seven days of one hour/day under dark and 40-Hz flicker conditions in accordance with some embodiments. Images were taken with 40× objective (scale bar=50 μm; insets include 100× rendering of representative microglia in EYFP and 40-Hz stimulation conditions).

Figure 65:
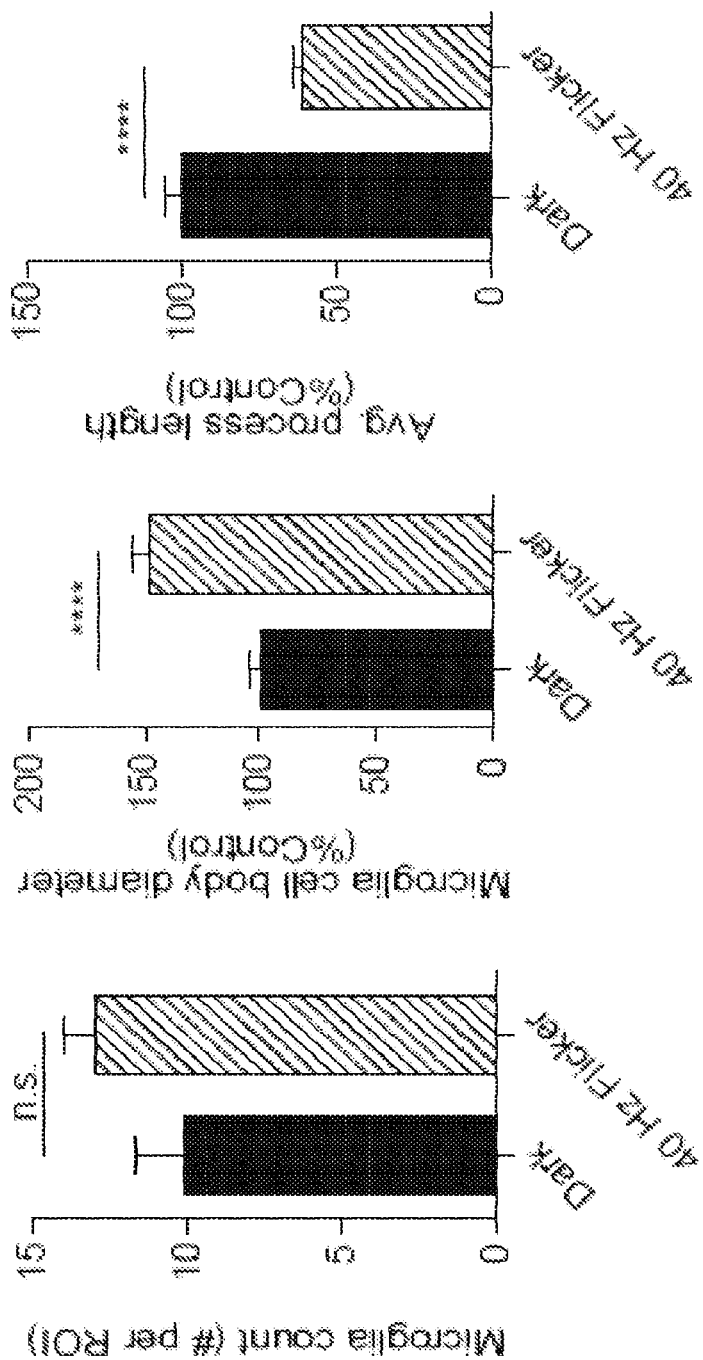
FIG. 65A is a bar graph depicting the number of microglia after seven days of one hour/day under dark and 40-Hz flicker conditions in accordance with some embodiments.
FIG. 65B is a bar graph depicting the diameter of microglial cell bodies normalized to control after seven days of one hour/day under dark and 40-Hz flicker conditions in accordance with some embodiments.
FIG. 65C is a bar graph depicting the average length of microglia primary processes normalized to control after seven days of one hour/day under dark and 40-Hz flicker conditions in accordance with some embodiments.

FIG. 65A is a bar graph depicting the number of microglia after seven days of one hour/day under dark and 40-Hz flicker conditions in accordance with some embodiments (n 8 mice per group; "n.s." indicates not significant, by Student's t-test). FIG. 65B is a bar graph depicting the diameter of microglial cell bodies normalized to control after seven days of one hour/day under dark and 40-Hz flicker conditions in accordance with some embodiments (n 8 mice per group; four asterisks indicate p<0.0001 by Student's t-test). FIG. 65C is a bar graph depicting the average length of microglia primary processes normalized to control after seven days of one hour/day under dark and 40-Hz flicker conditions in accordance with some embodiments (n 8 mice per group; four asterisks indicate p<0.0001 by Student's t-test).

In some embodiments, microglia with an anti-Iba1 antibody in visual cortex sections of the TauP301S mouse was labeled following seven days of one hour daily 40-Hz flicker or dark conditions (see, e.g., FIG. 64). In some embodiments, a trend was observed towards a 29.50% increase in microglia number in 40-Hz flicker conditions compared to dark controls (see, e.g., FIGS. 64 and 65A, "n.s." indicates not significant, n=3 mice per group) consistent with observations made in the 5XFAD model (see, e.g., FIG. 50A). In addition, the microglial cell body diameter increased by 49.00% following 40-Hz flicker in the visual cortex compared to dark controls (see, e.g., FIGS. 64 and 65B, p<0.0001 by Student's t-test, n=3 mice per group). The length of microglia primary processes was reduced by 39.08% in 40-Hz flicker group compared to dark controls (see, e.g., FIGS. 64 and 65C, p<0.0001 by Student's t-test, n=3 mice per group).

Taken together these data, from multiple models of AD pathology and in WT animals, demonstrate that 40-Hz oscillations may mitigate amyloid pathology, as measured by a reduction in Aβ levels, and may reduce tau phosphorylation. Furthermore, 40 Hz visual flicker may drive a distinct morphological transformation of microglia in both amyloidosis and tauopathy models of AD pathology.

Figure 66:
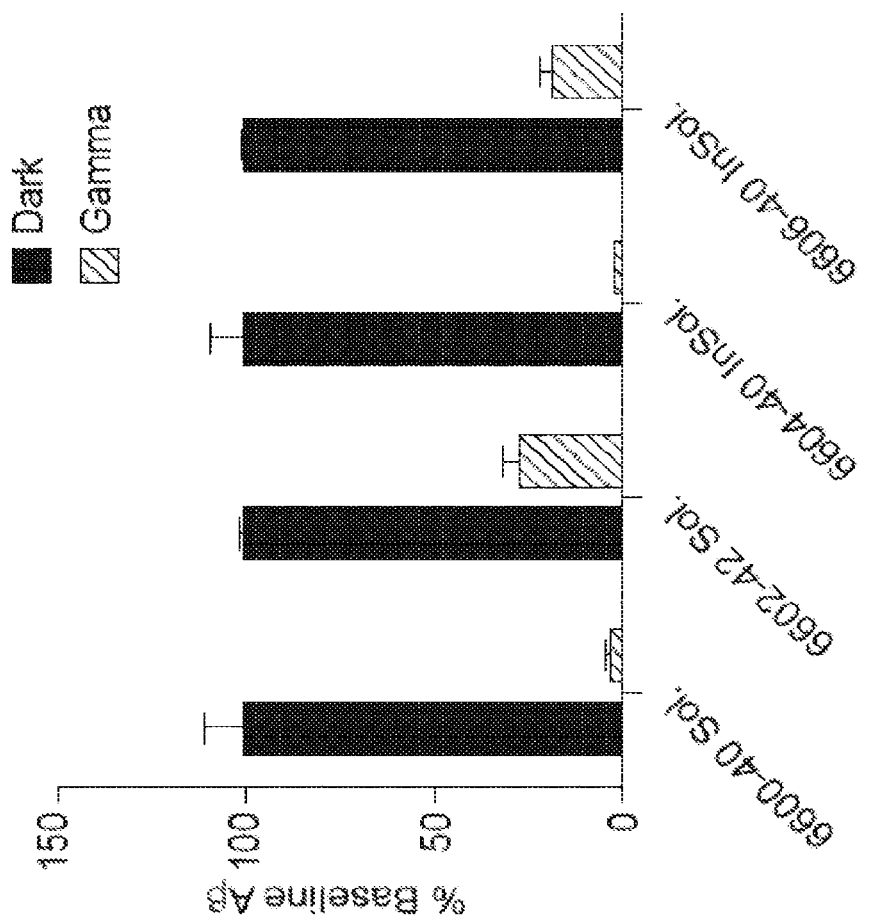
FIG. 66 is a plot illustrating levels of soluble and insoluble Aβ peptide isoforms $A\beta_{1-40}$ and $A\beta_{1-42}$ in the visual cortex of a subject with and without visual gamma stimulation in accordance with some embodiments.

In another experiment, a subset of aged mice (i.e., six months old) were exposed to visual gamma stimulation for seven days. The remaining mice were kept in the dark. FIG. 66 is a plot illustrating the levels of both soluble Aβ peptide and insoluble Aβ peptide (i.e., plaques) in the visual cortex of the mice. As shown in FIG. 66, the levels of each of soluble isoform $A\beta_{1-40}$ 6600, soluble isoform $A\beta_{1-42}$ 6602, insoluble isoform $A\beta_{1-40}$ 6604, and insoluble isoform $A\beta_{1-42}$ 6606 were significantly reduced in the mice exposed to the visual gamma stimulation.

Figures 67A, 67B:
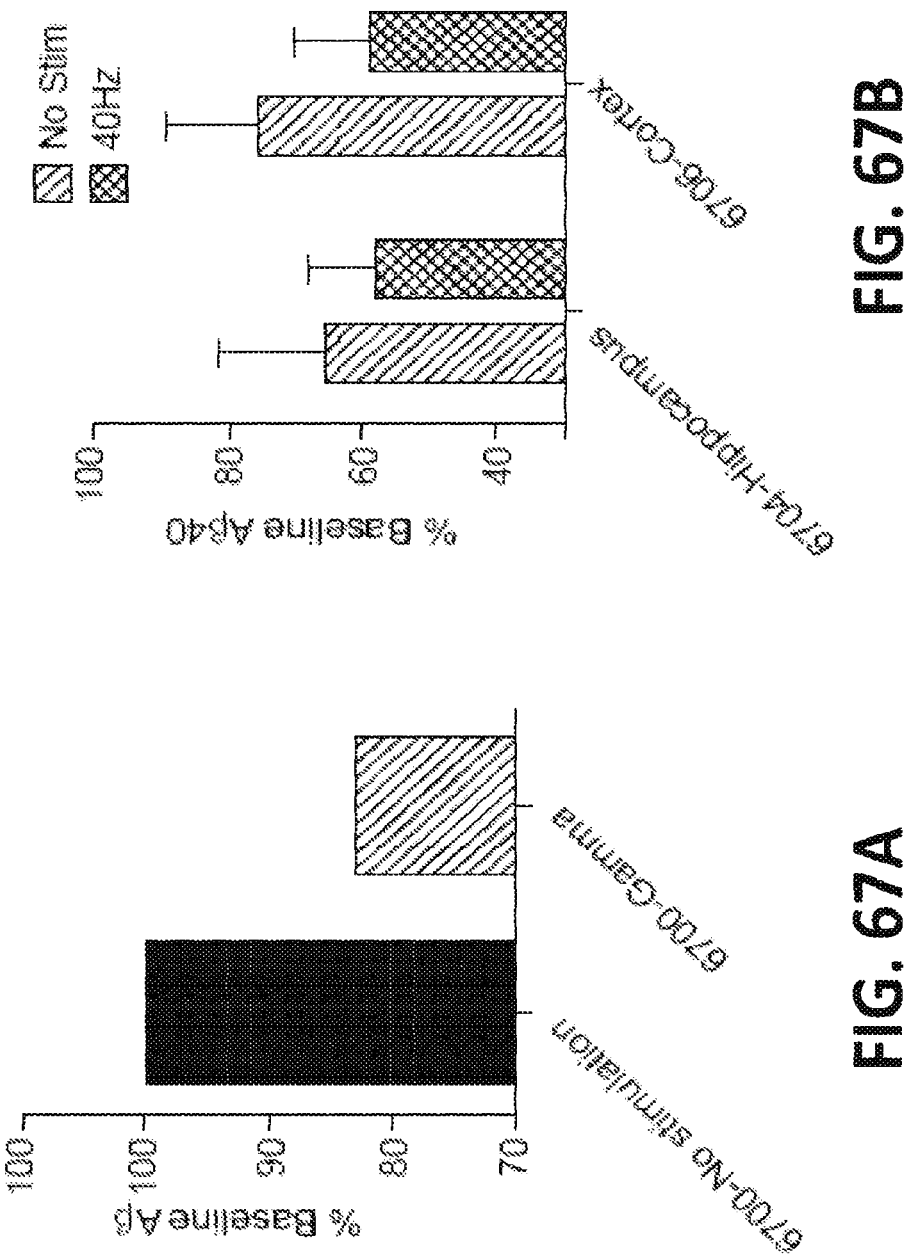
FIGS. 67A-67B are plots illustrating whole brain Aβ peptide levels with and without transcranial gamma stimulation of a subject in accordance with some embodiments.

FIGS. 67A-67B are plots illustrating Aβ peptide levels with and without transcranial gamma stimulation of a subject in accordance with some embodiments. In FIG. 67A, whole brain Aβ peptide levels stayed the same with no stimulation 6700 but fell following one hour of transcranial gamma stimulation 6702 (n=1 animal per group). In FIG. 67B, whole brain Aβ peptide levels were reduced following 40z transcranial stimulation at the hippocampus 6704 and at the cortex 6706 of a 5xFAD mouse in accordance with some embodiments.

Gamma oscillations have long been thought to be associated with higher cognitive functions and sensory responses. In some embodiments, driving FS-PV-interneurons using optogenetic methods enhanced LFPs at 40 Hz in mice. As disclosed herein, it has been demonstrated that in some embodiments, driving 40-Hz oscillations and phase locked spiking, using optogenetics or a non-invasive light flickering treatment in the 5XFAD mouse model, resulted in marked reduction of Aβ peptides in at least two different brain regions. This reduction was not due to decreased spiking activity because Aβ peptide levels were significantly lower in response to 40-Hz stimulation than to a random stimulation condition that produced similar amounts of multi-unit spiking activity without enhancing 40-Hz oscillations. Pyramidal cell firing rates may differ between these conditions but firing of FS-PV-interneurons or other cell types masked this change. In some embodiments, random optogenetic stimulation of FS-PV-interneurons provided the same amount of direct stimulation of FS-PV-interneurons yet did not reduce amyloid. In fact, optogenetic stochastic stimulation more than tripled amyloid levels while stochastic visual flicker produced no significant change, which may indicate that some aspects of the random stimulation have neurotoxic effects. While in some embodiments, random stimulation did not result in increased gamma power, a trend of small increases in power was noticed in a wide range of frequencies, from around 20 Hz to greater than 60 Hz. In some embodiments, a trend for increased amyloid levels with 20-Hz and 80-Hz light flicker was noticed. Taken together, these results may suggest that driving activity at some frequencies below or above 40 Hz may increase amyloid levels. These results point to a need to understand how patterns of spiking activity affect molecular pathways and disease pathology.

The robust reduction of total amyloid levels is likely mediated by both decreased amyloidogenesis, involving reduced EEA1/Rab5-positive early endosomes, and increased endocytosis of amyloid by microglia. Importantly, Gene Set Enrichment Analysis (GSEA) statistical analysis (The Broad Institute, Cambridge, Mass.) disclosed herein showed that the classical macrophage pro-inflammatory M1 or anti-inflammatory M2 cellular state did not correlate with either up- or down-regulated gene expression profiles following neuronal stimulation by 40-Hz oscillations. Indeed, the expression levels of pro-inflammatory genes Il6, Il1b, Itgam and anti-inflammatory gene Igf1 were not changed after stimulation. Instead, a number of microglia pro-phagocytic genes as well as cell adhesion/migration regulator Spp1 were activated upon 40-Hz stimulation. Thus, it appears that driving 40 Hz gamma oscillations induces an overall neuroprotective response by recruiting both neurons and microglia. The fact that GABA-A antagonist treatment completely abrogated the effects of 40-Hz stimulation on reducing Aβ levels strongly suggests that GABAergic signaling, most likely involving FS-PV-interneurons, is critical for those effects. Furthermore, in some embodiments, 40-Hz flicker stimulation reduced Aβ in multiple mouse models including APP/PS1 and WT mice in addition to the 5XFAD mouse. This replication in multiple mouse models shows that these findings may not be specific to one animal model and, importantly, may extend to situations where APP is expressed by its physiological promoter and Aβ is generated from endogenous APP as in the WT animals. In addition, in some embodiments, it was found that 40-Hz oscillations reduced pTau in a mouse model of tauopathy, TauP301S, showing that the protective effects of gamma stimulation generalize not only to other mouse models but also to other pathogenic proteins. In summary, the findings disclosed herein uncover previously unknown cellular and molecular processes mediated by gamma oscillations and establish a functional connection between brain gamma rhythms, microglia function, and AD-related pathology. In some embodiments, the findings of deficits in gamma oscillations converge with evidence of gamma deficits in different mouse models of AD (hAPP and apoE4) and reports that gamma is altered in humans with AD. By seeking converging evidence from multiple mouse models of AD, including Tg and knock-in models, it may be demonstrated that these results are not due solely to overexpression of transgenes or to other side effects particular to one model. Together these results from mice and humans show that multiple molecular pathways that contribute to Aβ pathology converge to alter gamma oscillations in AD. The findings disclosed herein hold promise for a novel therapeutic intervention against AD.

One theory of AD pathogenesis points to microglia malfunction, specifically microglia's failure to clear out pathological molecules, as a key mechanism of disease progression. Therefore, interventions that recruit microglia back to an endocytotic state, as 40-Hz stimulation does, have strong therapeutic potential. In the experiments described further herein, driving gamma oscillations optogenetically or via light flicker did not cause neuronal hyperactivity. Because this approach is fundamentally different from prior AD therapies, driving such patterned neural activity to trigger endogenous repair would provide a novel therapeutic approach to AD.

Visual Stimulation at Gamma Frequency had Positive Effects on Subject Behavior.

A study was conducted to examine whether gamma exposure and/or administration in accordance with some embodiments causes any stress to a subject. FIG. 68A is a flow diagram illustrating the study. As shown at 6800 in FIG. 68A, WT mice were exposed to either normal room light (N=8) or a 40-Hz light flicker (N=8) in accordance with some embodiments for one hour per day for seven consecutive days, Days 1-7. On Day 8, shown at 6802, blood was collected from the mice, and the blood plasma was separated to examine corticosterone levels. In mice, corticosterone is a main glucocorticoid involved in stress responses.

Figure 68B:
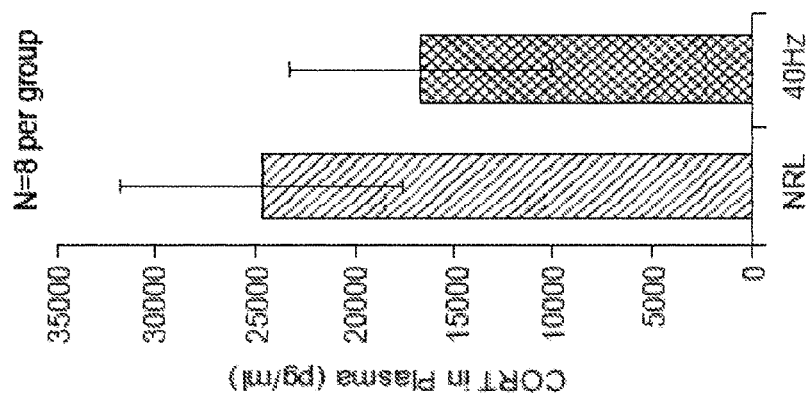
FIG. 68B is a bar graph depicting levels of corticosterone indicating stress response in the subjects.
Figure 68A:
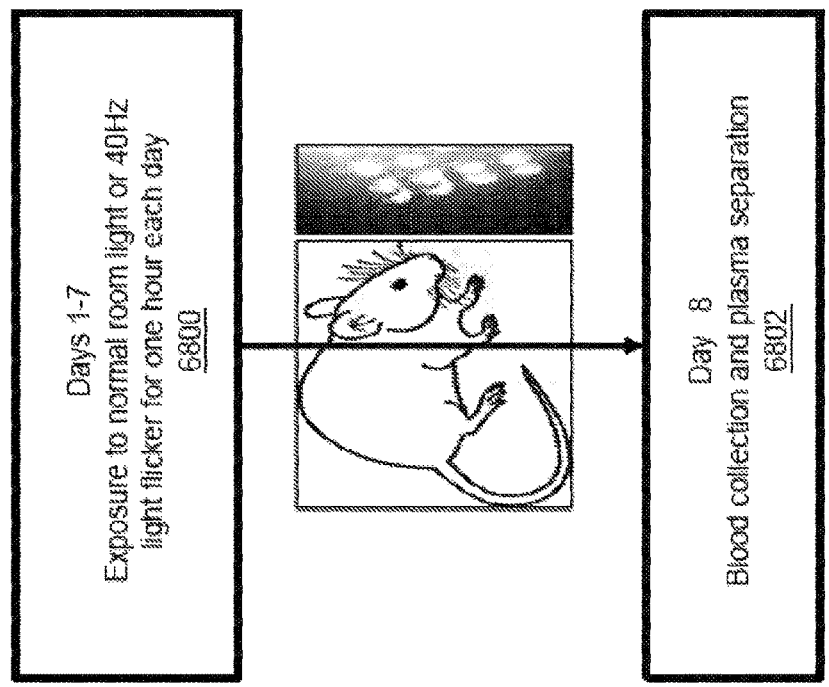
FIG. 68A is a flow diagram illustrating a study conducted to examine whether gamma exposure and/or administration in accordance with some embodiments causes stress to subjects.

FIG. 68B is a bar graph depicting levels (pg/ml) of corticosterone (CORT) in the plasma collected from the eight mice exposed to normal room light (NRL) and the eight mice exposed to the 40-Hz light flicker (40-Hz). No increase in corticosterone was observed in the mice exposed to the 40-Hz light flicker. Instead, the group of mice exposed to the 40-Hz light flicker had lower levels of corticosterone compared to the control group. For N=8 independent measures per group, the T-distribution and the p-value for corticosterone levels were calculated to be:

$$T(14)=0.827; p=0.422 \qquad (1)$$

Another study was conducted to examine whether gamma exposure and/or administration in accordance with some embodiments reduces anxiety in a subject. FIG. 69A is a flow diagram illustrating the study. As shown at 6900 in FIG. 69A, WT mice were exposed to either normal room light (N=10) or a 40-Hz light flicker (N=1) in accordance with some embodiments for one hour per day for seven consecutive days, Days 1-7. On Day 8, shown at 6902, a ten-minute session of elevated plus maze was conducted.

The elevated plus maze is a test used to measure anxiety in laboratory animals. The behavioral model is based on the general aversion of rodents to open spaces, which leads to thigmotaxis, a preference for remaining in enclosed spaces or close to the edges of a bounded space. FIG. 69B is an image illustrating an elevated plus maze apparatus. The apparatus is plus-shaped with two open arms (vertical) and two enclosed arms (horizontal). Anxiety is expressed by the animal spending more time in the enclosed arms.

Figure 69D:
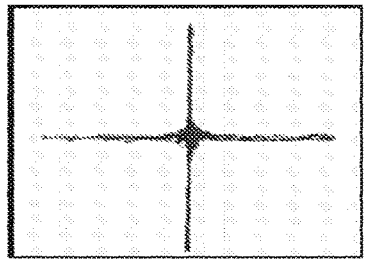
FIGS. 69C and 69D are images illustrating representative tracks of the subjects during an elevated plus maze session.
Figure 69C:
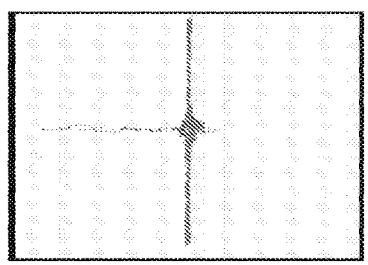
Figure 69B:
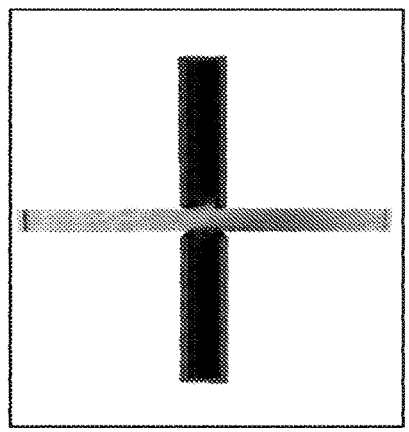
FIG. 69B is an image illustrating an elevated plus maze apparatus.
Figure 69A:
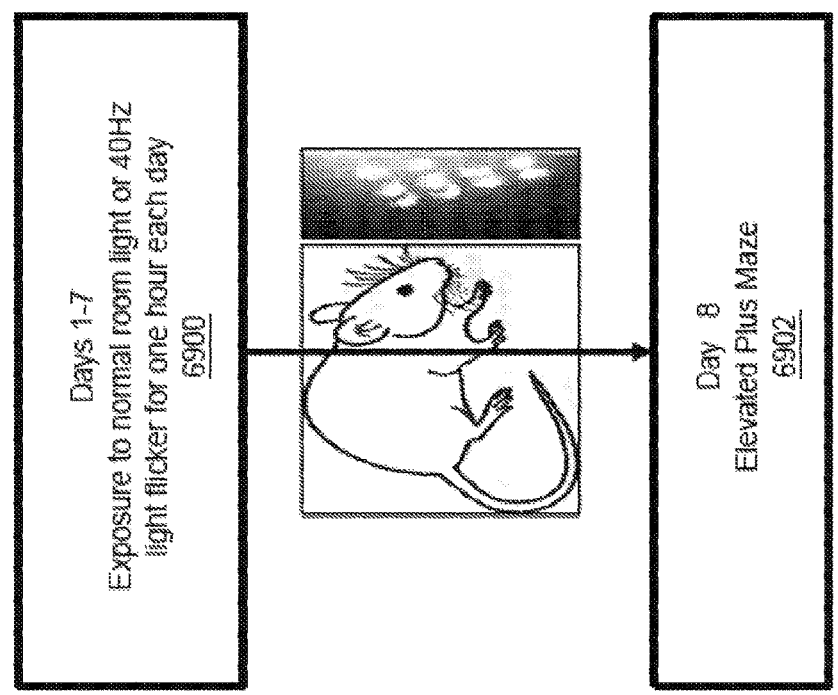
FIG. 69A is a flow diagram illustrating a study conducted to examine whether gamma exposure and/or administration in accordance with some embodiments reduces anxiety in subjects.

FIGS. 69C and 69D are images illustrating representative tracks of the subjects during the elevated plus maze session. In FIG. 69C, a mouse exposed to normal room light tended to stay in the enclosed arms, indicating more anxiety, whereas in FIG. 69D, a mouse exposed to the 40-Hz light flicker explored in both the open arms and enclosed arms, indicating relatively less anxiety in accordance with some embodiments.

Figure 70:
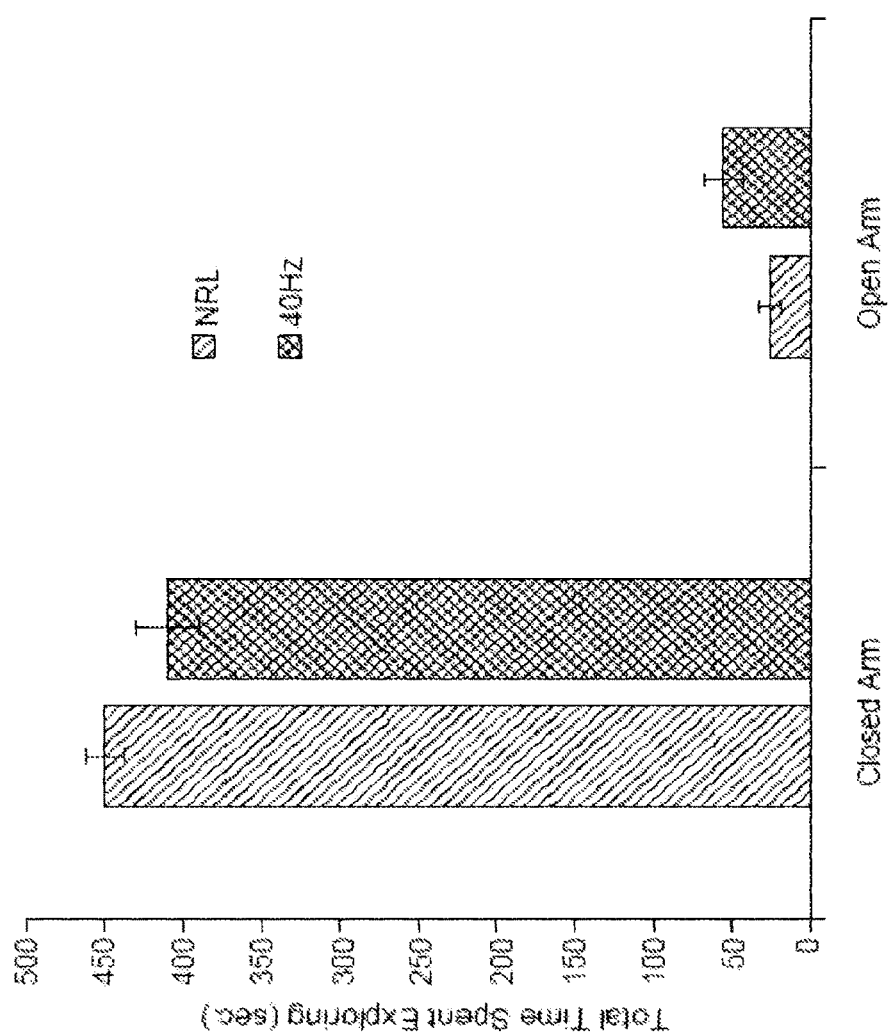
FIG. 70 is a bar graph depicting the average time the subjects spent exploring in open arms and closed arms during the elevated plus maze session.

FIG. 70 is a bar graph depicting total time spent exploring in open arms and closed arms by the ten mice exposed to normal room light (NRL) and the ten mice exposed to the 40-Hz light flicker (40-Hz) in accordance with some embodiments. The mice exposed to the 40-Hz light flicker spent less total time in the closed arms and more total time in the open arms, indicating less anxiety compared to the control group in accordance with some embodiments. For N=10 independent measures per group, the T-distribution and the p-value for total time spent exploring the closed arms were calculated to be:

$$T(18)=-1.652; p=0.11 \qquad (2)$$

For N=10 independent measures per group, the T-distribution and the p-value for total time spent exploring the open arms were calculated to be:

$$T(18)=-2.136; p=0.047 \qquad (3)$$

Another study was conducted to examine whether gamma exposure and/or administration in accordance with some embodiments reduces stress and/or anxiety in a subject. FIG. 71A is a flow diagram illustrating the study. At 7100 in FIG. 71A, WT mice were exposed to either normal room light (N=8) or a 40-Hz light flicker (N=8) in accordance with some embodiments for one hour per day for seven consecutive days, Days 1-7. On Day 8, shown at 7102, a five-minute open field test was conducted.

The open field test is an experiment used to assay general locomotor activity levels and anxiety in laboratory animals. The behavioral model is based on anxiety caused by the conflicting drives of rodents to avoid brightly lit areas but also explore a perceived threatening stimulus. FIG. 71B is an image illustrating an open field arena. The open field arena has walls to prevent escape and may be marked with a grid or monitored using infrared beams or video cameras integrated with software systems. Increased anxiety will result in less locomotor motion and preference for the edges of the field, whereas decreased anxiety leads to increased exploratory behavior in accordance with some embodiments.

Figure 71D:
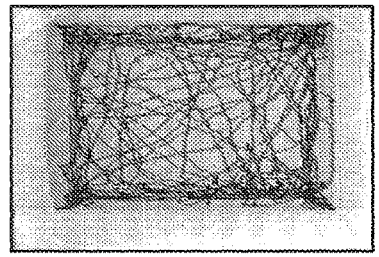
FIGS. 71C and 71D are images illustrating representative tracks of the subjects during an open field test.
Figure 71B:
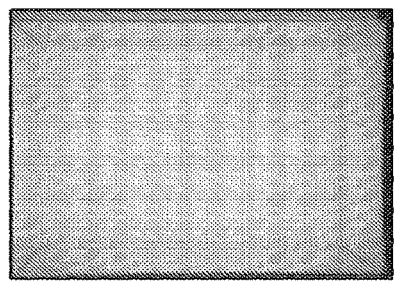
FIG. 71B is an image illustrating an open field arena.
Figure 71C:
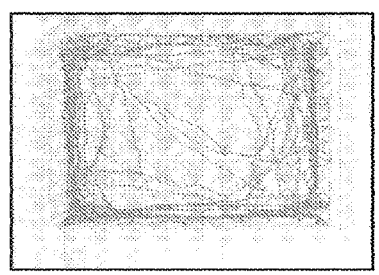
Figure 71A:
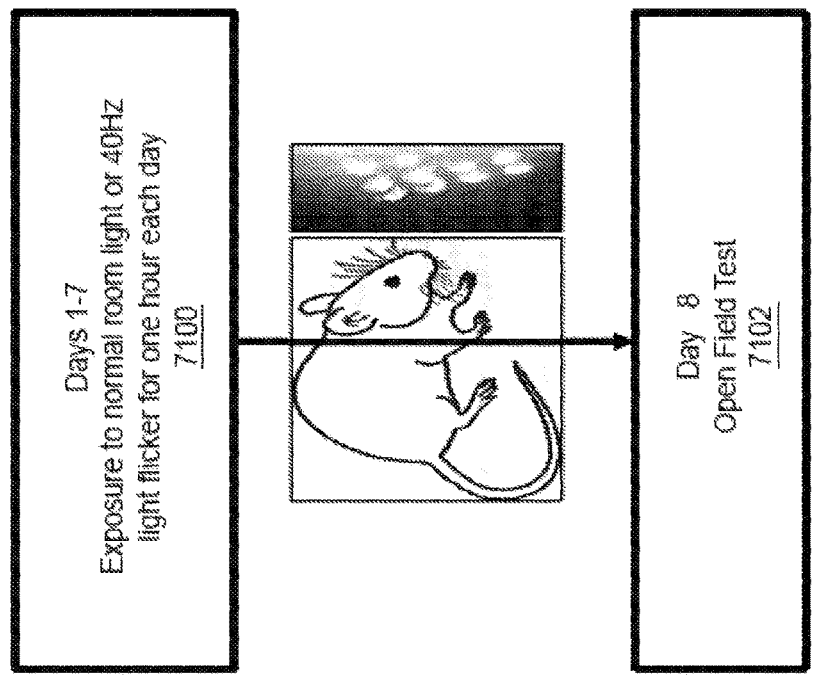
FIG. 71A is a flow diagram illustrating a study conducted to examine whether gamma exposure and/or administration in accordance with some embodiments reduces stress and/or anxiety in subjects.

FIGS. 71C and 71D are images illustrating representative tracks of the subjects during the open field test. In FIG. 71C, a mouse exposed to normal room light tended to prefer the edges of the arena, indicating more stress and/or anxiety, whereas in FIG. 71D, a mouse exposed to the 40-Hz light flicker explored more in the center of arena, indicating relatively less stress and/or anxiety in accordance with some embodiments.

Figure 72A:
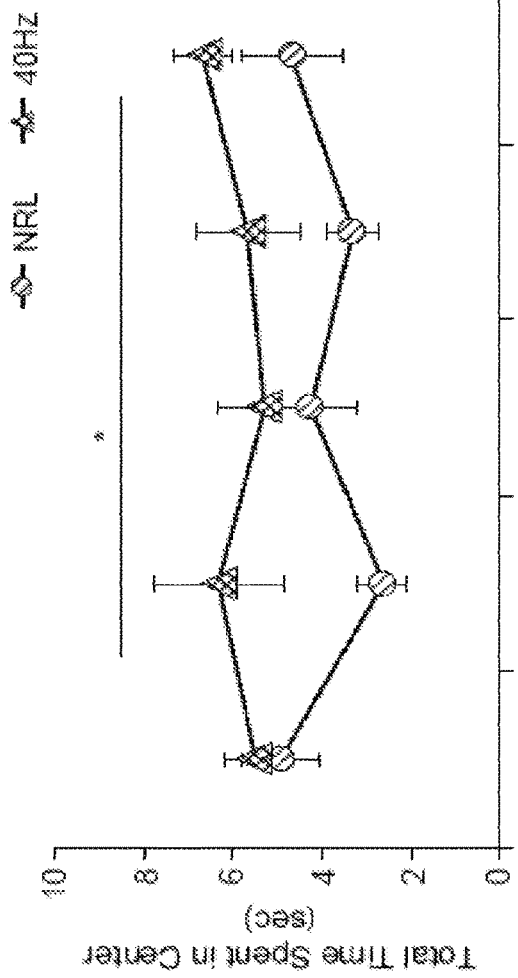
FIG. 72A is a plot depicting the average amount of time the subjects spent in the center of the open field during each minute of the open field test.
Figure 72B:
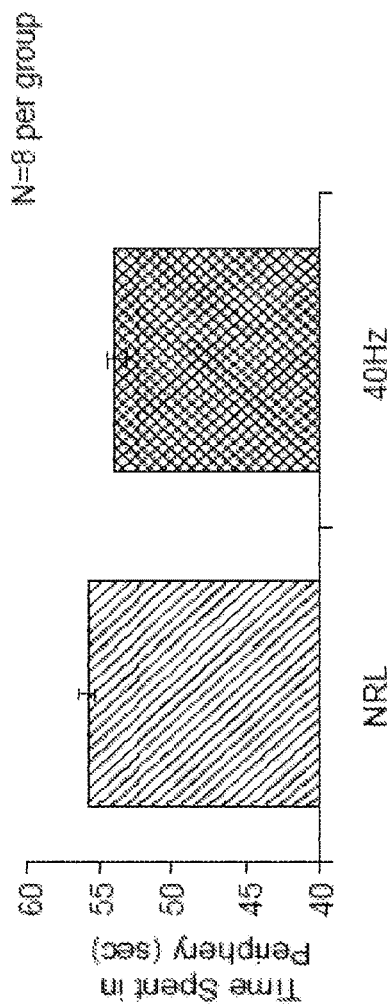
FIG. 72B is a bar graph depicting the average total time the subjects spent in the periphery of the open field during the open field test.

FIGS. 72A and 72B are graphs depicting total time spent exploring the center and the periphery of the open field arena by the eight mice exposed to normal room light (NRL) and the eight mice exposed to the 40-Hz light flicker (40-Hz) in accordance with some embodiments. FIG. 72A is a plot of the average amounts of seconds spent in the center of the arena for each of the five minutes. FIG. 72B is a bar graph of the total time spent in the periphery of the arena for the entire five-minute duration, averaged for each minute.

On average, the mice exposed to the 40-Hz light flicker spent more time in the center of the arena, significantly so during Minutes 2, 4, and 5, thus indicating less stress and/or anxiety compared to the control group, which also is consistent with the elevated plus maze results in accordance with some embodiments. Repeated measures analysis of variance (RM ANOVA) was performed. For N=8 independent measures per group, the F-distribution and the p-value for mean times spent exploring the open field arena were calculated to be:

$$F(1,14)=4.860; p=0.045 \qquad (4)$$

Figure 73C:
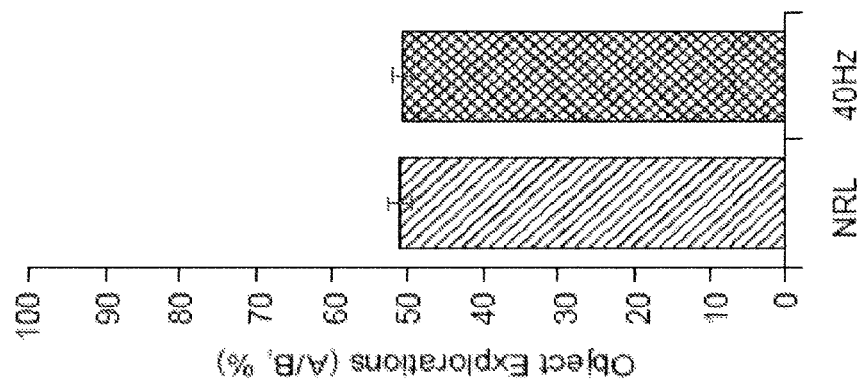
FIG. 73C is a bar graph depicting the average amount of time the subjects spent exploring a first novel object compared to a second novel object according to the schematic diagram of FIG. 73A.
Figure 73A:
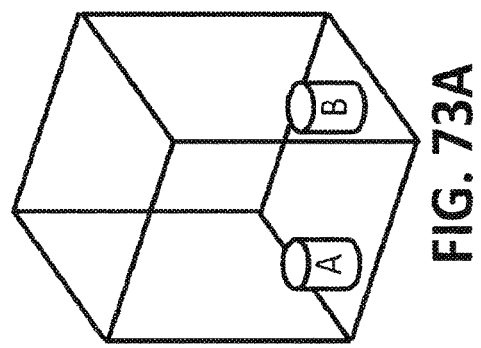
FIGS. 73A and 73B are schematic diagrams illustrating a study conducted to examine whether gamma exposure and/or administration in accordance with some embodiments alters innate novelty seeking behavior in subjects.
Figure 73B:
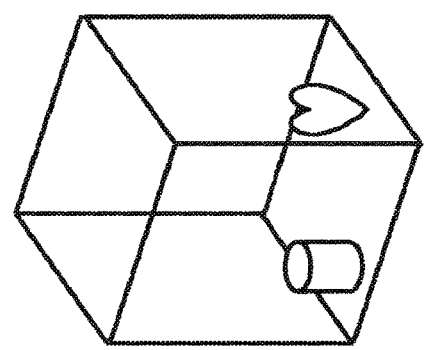

Another study was conducted to examine whether gamma exposure and/or administration in accordance with some embodiments alters innate novelty seeking behavior in a subject. FIGS. 73A and 73B are schematic diagrams illustrating the study using a novel recognition task. In FIG. 73A, two novel objects are provided in a familiar arena. In FIG. 73B, one familiar object and one novel object are provided in the familiar arena. Wild type mice were exposed to either normal room light (N=8) or a 40-Hz light flicker (N=8) in accordance with some embodiments for one hour per day for seven consecutive days, Days 1-7.

On Day 8, the mice were exposed to the scenario in FIG. 73A, two novel objects in a familiar arena, for five minutes. FIG. 73C is a bar graph depicting the percentage of time spent exploring new object A to the percentage of time spent exploring new object B for the eight mice exposed to normal room light (NRL) and the eight mice exposed to the 40-Hz light flicker (40-Hz) in accordance with some embodiments. As illustrated by FIG. 73C, equal preference was shown to each object by each group. That is, no difference was observed in the object exploration between the groups.

Figure 74:
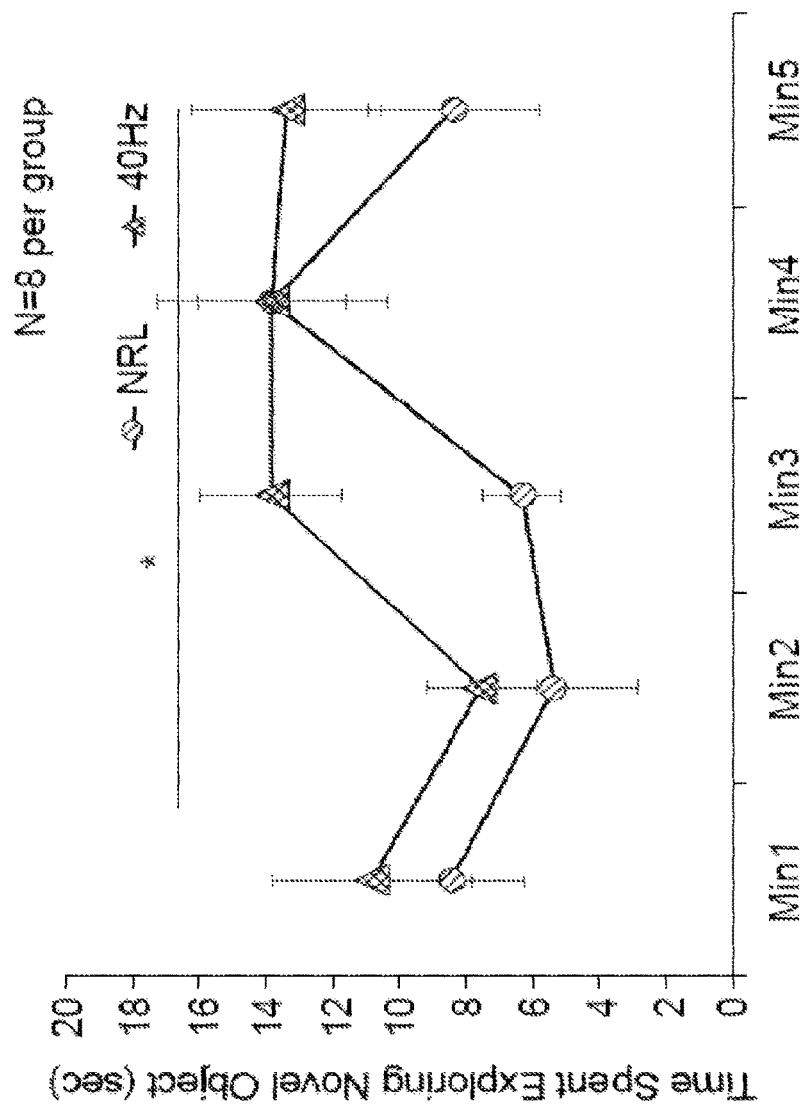
FIG. 74 is a plot depicting the average amount of time during each minute the subjects spent exploring a novel object according to the schematic diagram of FIG. 73B.

Then, the mice were exposed to the scenario in FIG. 73B, one familiar object and one novel object in the familiar arena, for five minutes. FIG. 74 is a plot depicting the average amounts of seconds spent exploring the novel object for each of the five minutes. On average, the mice exposed to the 40-Hz light flicker spent significantly higher amounts of time exploring the novel object, especially during Minutes 1-3 and 5, thus indicating increased novelty seeking behavior compared to the control group in accordance with some embodiments. Friedman's non-parametric RM ANOVA was performed. For N=8 independent measures per group, the test statistic $\chi^2$ and the p-value for mean times spent exploring the novel object were calculated to be:

$$\chi^2(4, n=16)=16.088; p=0.003 \tag{5}$$

The Mann-Whitney U test was performed for mean times spent exploring the novel object during Minute 3. For N=8 independent measures per group, the U-value, the Z-value, and the p-value were calculated to be:

$$U=58.00; Z=2.731; p=0.005 \tag{6}$$

Figure 75B:
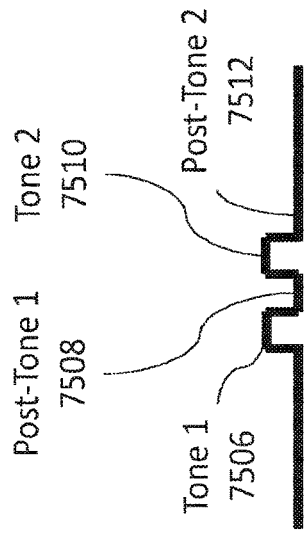
FIG. 75B is a stimulus diagram illustrating a tone test with altered contexts as a function of time.
Figure 75A:
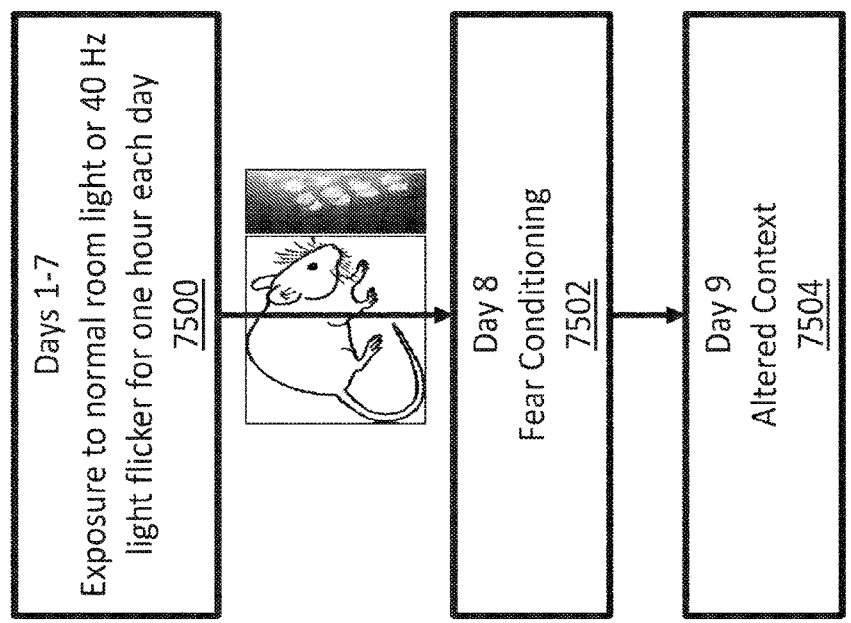
FIG. 75A is a flow diagram illustrating a study conducted using a fear conditioning paradigm to examine whether gamma exposure and/or administration in accordance with some embodiments impacts learning and memory in subjects.

Another study was conducted to examine whether gamma exposure and/or administration in accordance with some embodiments impacts learning and memory in a subject. FIG. 75A is a flow diagram illustrating the study using a fear conditioning paradigm. As shown at 7500 in FIG. 75A, WT mice were exposed to either normal room light or a 40-Hz light flicker in accordance with some embodiments for one hour per day for seven consecutive days, Days 1-7. On Day 8, shown at 7502, the mice were subjected to a mild two-tone-shock pairing. Specifically, the mice were introduced into a new arena in which a first tone was paired with a foot shock. The mice became conditioned to associate a context (i.e., tone) with an aversive experience (i.e., foot shock). For this original context, the T-distribution and the p-value for total time spent freezing were calculated to be:

$$T(24)=0.577; p=0.569 \tag{7}$$

On Day 9, shown at 7504, a tone test was conducted in an altered context. FIG. 75B is a stimulus diagram illustrating the tone test as a function of time, including a first-tone context 7506, a post-first-tone context 7508, a second-tone context 7510, and a post-second-tone context 7512. For the test, the mice were returned to the arena in which the first tone was paired with the foot shock. When the first-tone context 7506 was applied, the mice exposed to the 40-Hz light flicker spent more time freezing, presumably in anticipation of the foot shock, thus indicating a measure of memory. The mice exposed to the 40-Hz light flicker also spent more time freezing during the second-tone context 7510 than the control group, but less time freezing during either post-tonal context.

FIGS. 76A and 76B are bar graphs demonstrating enhanced memory in accordance with some embodiments. As shown in FIG. 76A, the percentages of time spent freezing during the first-tone context 7506 and the second-tone context 7510 were greater for the mice exposed to the 40-Hz light flicker compared to the control group, indicating enhanced memory association in accordance with some embodiments. In addition, the mice exposed to the 40-Hz light flicker exhibited stronger extinction post-tone presentation in accordance with some embodiments. As shown in FIG. 76B, the percentages of time spent freezing during the post-first-tone context 7506 and the post-second-tone context 7510 were greater for the control group compared to the mice exposed to the 40-Hz light flicker, indicating enhanced memory specificity in accordance with some embodiments.

For the pre-tonal context, RM ANOVA was performed between groups and the F-distribution and the p-value for mean times spent freezing were calculated to be:

$$F(1,24)=3.106; p=0.091 \tag{8}$$

For the first-tone context, the T-distribution and the p-value for total time spent freezing were calculated to be:

$$T(24)=-2.155; p=0.041 \tag{9}$$

For the second-tone context, the T-distribution and the p-value for total time spent freezing were calculated to be:

$$T(24)=-1.433; p=0.164 \tag{10}$$

For the tone contexts, RM ANOVA was performed between groups and the F-distribution and the p-value for mean times spent freezing were calculated to be:

$$F(1,24)=4.559; p=0.043 \tag{11}$$

For the post-first-tone context, the T-distribution and the p-value for total time spent freezing were calculated to be:

$$T(24)=1.874; p=0.073 \tag{12}$$

For the post-second-tone context, the T-distribution and the p-value for total time spent freezing were calculated to be:

$$T(24)=2.223; p=0.036 \tag{13}$$

For the post-tonal contexts, RM ANOVA was performed between groups and the F-distribution and the p-value for mean times spent freezing were calculated to be:

$$F(1,24)=6.646; p=0.017 \tag{14}$$

Another study was conducted to examine whether gamma exposure and/or administration in accordance with some embodiments improves memory in a subject. FIG. 77A is a flow diagram illustrating the study. As shown at 7700 in FIG. 77A, WT mice were exposed to either normal room light or a 40-Hz light flicker in accordance with some embodiments for one hour per day for seven consecutive days, Days 1-7. On Day 8, shown at 7702, a Morris water maze test was conducted.

The Morris water navigation task or maze is a test used to study spatial memory and learning in laboratory animals. The behavioral procedure involves placing a subject in a large circular pool with an invisible or visible platform that allows the subject to escape the water using a praxic strategy (remembering movements required to reach the platform), a taxic strategy (using visual cues to locate the platform), or a spatial strategy (using distal cues as points of reference). FIG. 77B is a diagram illustrating a Morris water maze. The maze includes a circular pool of water divided into directional quadrants and a platform 7704 hidden in the South-West (SW) quadrant.

Figure 78B:
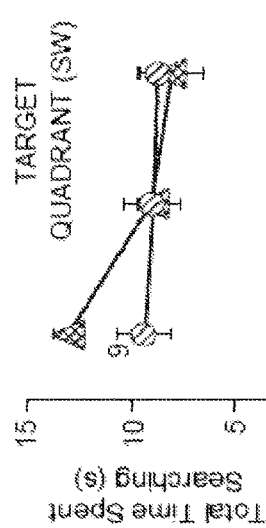
FIG. 78B is a plot depicting the average amount of time the subjects spent searching for the removed platform in the target quadrant during each half minute.
Figure 78C:
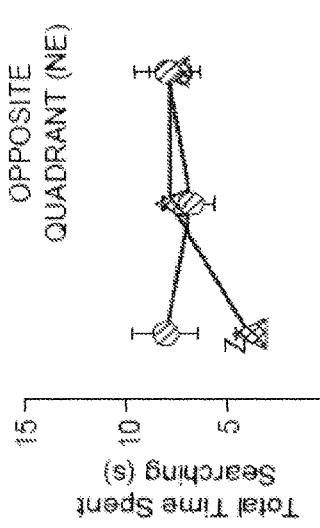
FIG. 78C is a plot depicting the average amount of time the subjects spent searching for the removed platform in the opposite quadrant during each half minute.
Figure 78A:
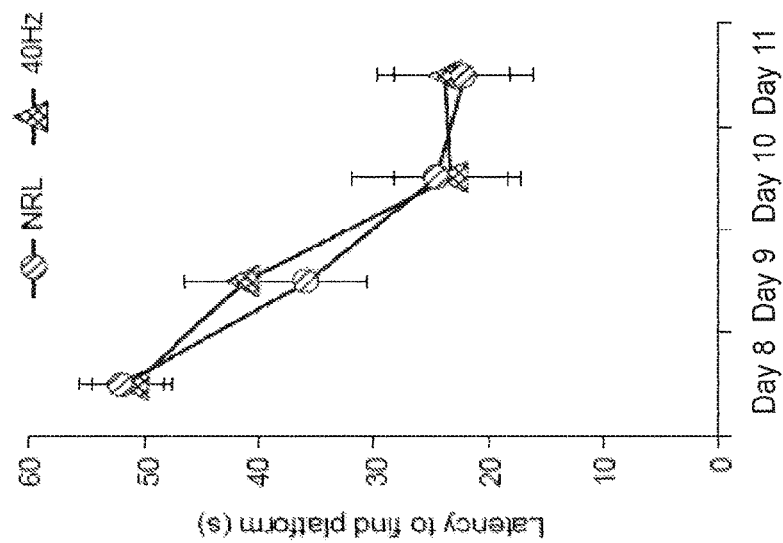
FIG. 78A is a plot depicting the average amount of time the subjects spent finding the hidden platform in the Morris water maze test on each day.

For weak training, the Morris water maze test was repeated twice per day for four consecutive days, Days 8-11. FIG. 78A is a plot depicting latency to find the platform by the mice exposed to normal room light (NRL) and the mice exposed to the 40-Hz light flicker (40-Hz) in accordance with some embodiments.

On Day 12, a probe test was conducted by removing the hidden platform from the Morris water maze. FIGS. 77C and 77D are images illustrating representative tracks of the subjects during the probe test. In FIG. 77C, a mouse exposed to normal room light appears to have searched for the platform throughout the pool, whereas in FIG. 77D, a mouse exposed to the 40-Hz light flicker appears to have searched more methodically and primarily in the SW quadrant in accordance with some embodiments. FIG. 78B is a plot depicting the total time (seconds per each half minute) spent searching for the platform in the target quadrant (i.e., the SW quadrant), whereas FIG. 78C is a plot depicting the total time (seconds per each half minute) spent searching for the platform in the opposite quadrant (i.e., the NE quadrant).

The mice exposed to the 40-Hz light flicker spent more time than the control group searching in the target quadrant and less time than the control group searching in the opposite quadrant, indicating enhancement of spatial memory in accordance with some embodiments.

Figure 79A:
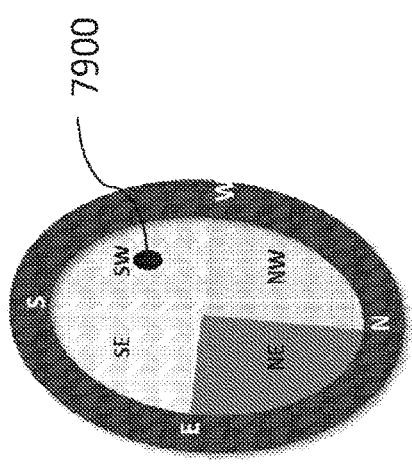
FIG. 79A is a diagram illustrating a Morris water maze test with a platform hidden in a first quadrant.
Figure 79B:
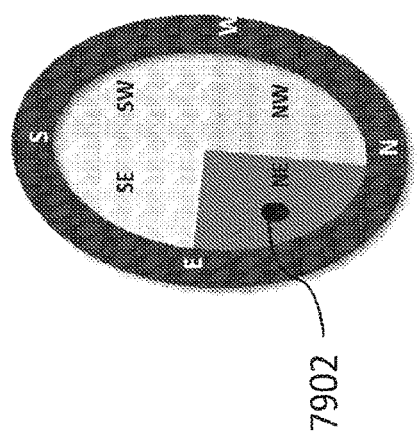
FIG. 79B is a diagram illustrating a Morris water maze test with a platform hidden in a second quadrant, opposite the first quadrant, for reversal learning.

Reversal learning was conducted using the same groups of mice from the Morris water maze trials and probe test. FIG. 79A is a diagram illustrating a Morris water maze with a platform 7900 hidden in the SW quadrant as in the trials. FIG. 79B is a diagram illustrating a Morris water maze with a platform 7902 hidden in the opposite NE quadrant for reversal learning.

Figure 79C:
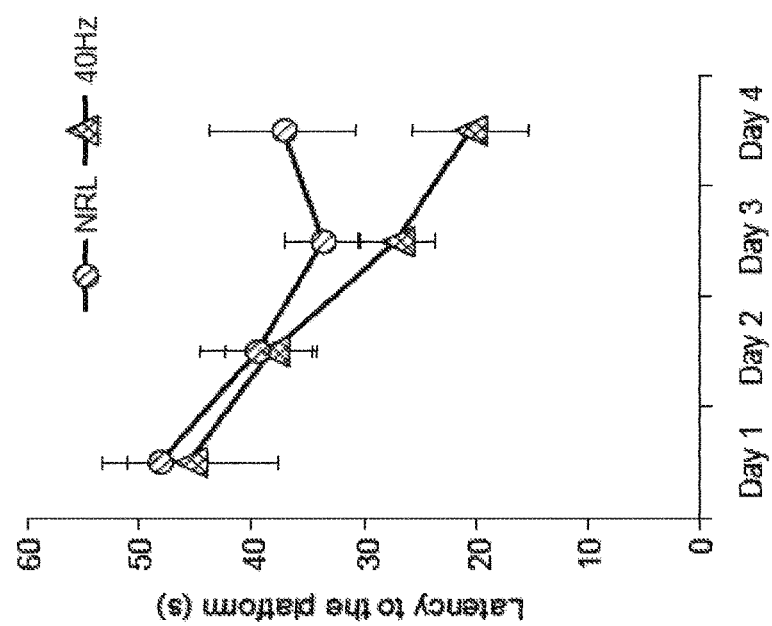
FIG. 79C is a plot depicting the average amount of time the subjects spent finding the hidden platform in the Morris water maze reversal learning test on each day.

For weak training, reversal learning was repeated twice per day for four consecutive days, Days 14-17. FIG. 79C is a plot depicting latency to find the platform by the mice exposed to normal room light (NRL) and the mice exposed to the 40-Hz light flicker (40-Hz) in accordance with some embodiments. Despite receiving no further 40-Hz exposure after Day 7, the mice exposed to the 40-Hz light flicker showed increased behavioral flexibility.

Another study was conducted to examine whether chronic gamma exposure and/or administration in accordance with some embodiments influences spatial learning and memory in a subject. FIG. 80A is a flow diagram illustrating the study. As shown at 8000 in FIG. 80A, C57BL/6 mice were exposed to either normal room light (N=7) or a 40-Hz light flicker (N=7) in accordance with some embodiments for one hour per day for two weeks. During the third week, shown at 8002, the mice continued to be exposed to either normal room light or a 40-Hz light flicker for one hour each morning and then also subjected to a Morris water maze test each afternoon.

FIG. 80B is a plot depicting the latency to find the platform by the mice exposed to normal room light (NRL) and the mice exposed to the 40-Hz light flicker (40-Hz) on Days 1-4 of the third week. Following the third week, a probe test was conducted by removing the hidden platform. FIG. 80C is a bar graph depicting the total time (seconds per 30-second trial) spent searching for the platform in the target quadrant during the probe test. Similar to one week of treatment, chronic three week treatment enhanced spatial learning in accordance with some embodiments.

Figures 81A, 81B:
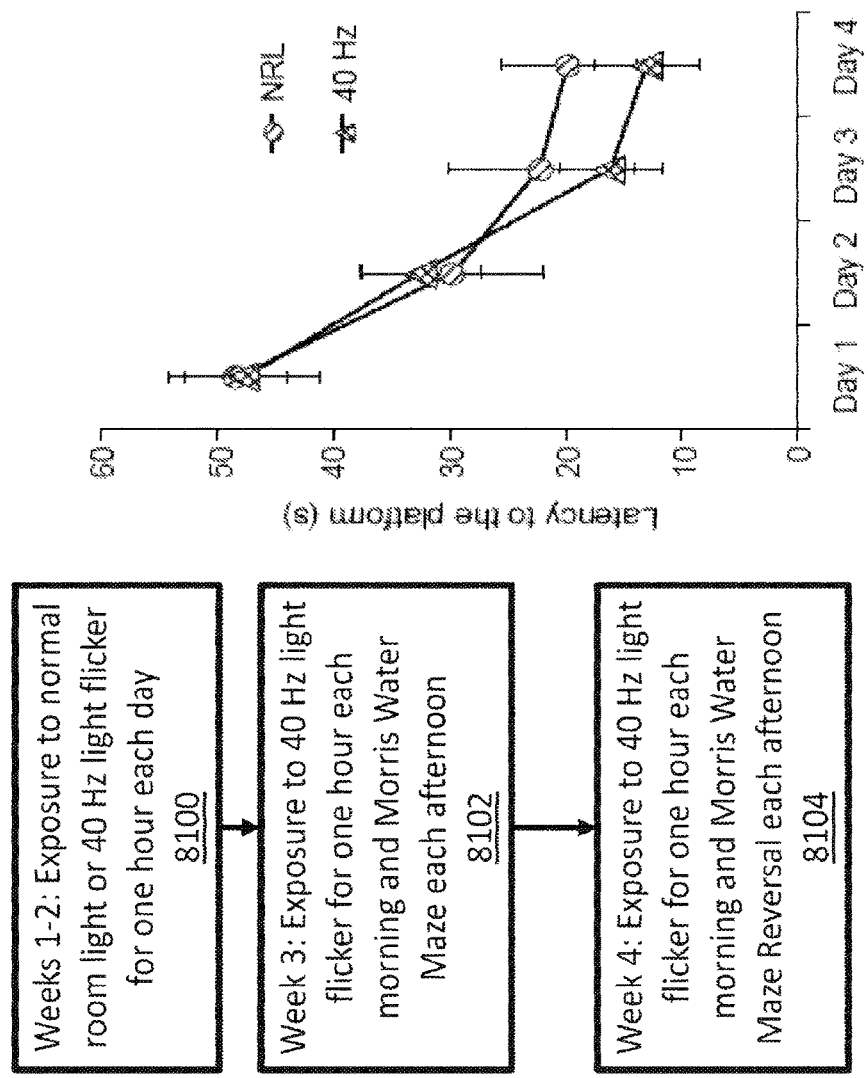
FIG. 81A is a flow diagram illustrating the study of FIG. 80A expanded to include reversal learning.
FIG. 81B is a plot depicting the average amount of time the subjects spent finding the hidden platform in the Morris water maze reversal learning test on each day.

Reversal learning was conducted using the same groups of mice from FIGS. 80A-80C. FIG. 81A is a flow diagram illustrating the expanded study. As shown at 8100 in FIG. 81A, the C57BL/6 mice were exposed to either normal room light or a 40-Hz light flicker in accordance with some embodiments for one hour per day for two weeks. During the third week, shown at 8102, the mice continued to be exposed to either normal room light or a 40-Hz light flicker for one hour each morning and then also subjected to a Morris water maze test each afternoon. During the fourth week, shown at 8104, the mice continued to be exposed to either normal room light or a 40-Hz light flicker for one hour each morning and then also subjected to a Morris water maze reversal test each afternoon. FIG. 81B is a plot depicting the latency to find the platform by the mice exposed to normal room light (NRL) and the mice exposed to the 40-Hz light flicker (40-Hz) on Days 1-4 of the fourth week in accordance with some embodiments.

Figure 82B:
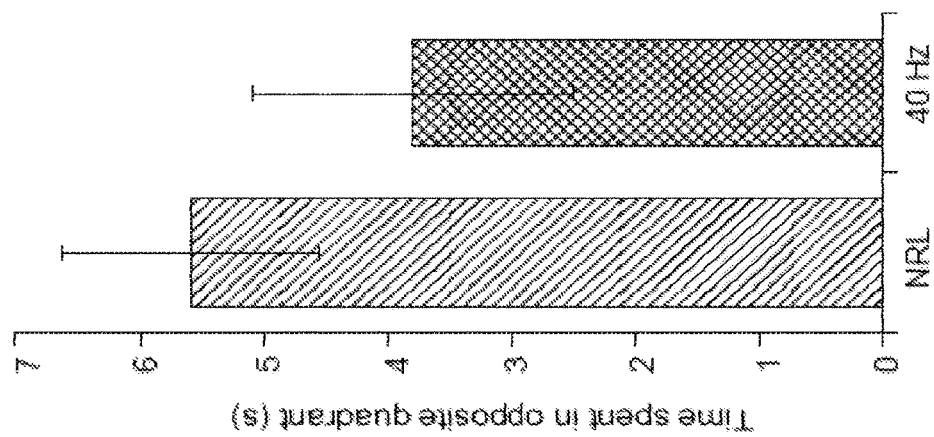
FIG. 82B is a bar graph depicting the average amount of time the subjects spent searching for the removed platform in the opposite quadrant.
Figure 82A:
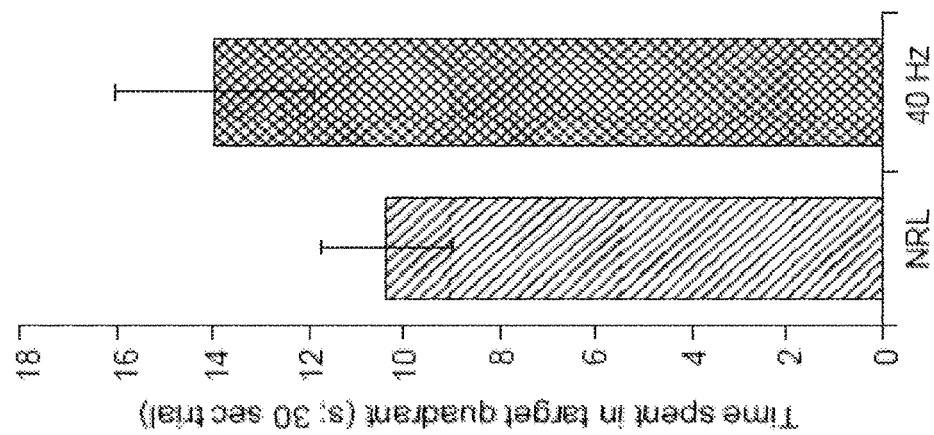
FIG. 82A is a bar graph depicting the average amount of time the subjects spent searching for the removed platform in the target quadrant during a thirty-second trial.

Following the fourth week, a probe test was conducted by removing the hidden platform. FIG. 82A is a bar graph depicting the total time (seconds per 30-second trial) spent searching for the platform in the target quadrant during the probe test. FIG. 82B is a bar graph depicting the time spent in the opposite quadrant during the probe test. The mice exposed to the 40-Hz light flicker showed strong cognitive flexibility.

Visual Stimulation at Gamma Frequency Provided Anatomical, Morphology, Cellular, and Molecular Benefits.

A study was conducted to examine the effect of gamma exposure and/or administration in accordance with some embodiments on DNA damage and neuronal loss in the visual cortex of a subject. For the study, an inducible mouse model of p25 accumulation (i.e., a creatine kinase carboxyl-terminal fragment p25 Tg mouse (CK-p25 Tg mouse)) was used. The CK-p25 Tg mouse model displays key pathological hallmarks of AD, including profound neuronal loss in the forebrain, increased Aβ peptide production, tau pathology, DNA damage, and severe cognitive impairment. In this model, increased Aβ peptide levels are observed prior to neuronal loss; furthermore, reducing Aβ peptide production ameliorates memory deficits in the CK-p25 Tg mouse model, indicating that this event operates synergistically with the carboxyl-terminal fragment p25, leading to the manifestation of neurodegeneration and memory impairment.

Figure 83:
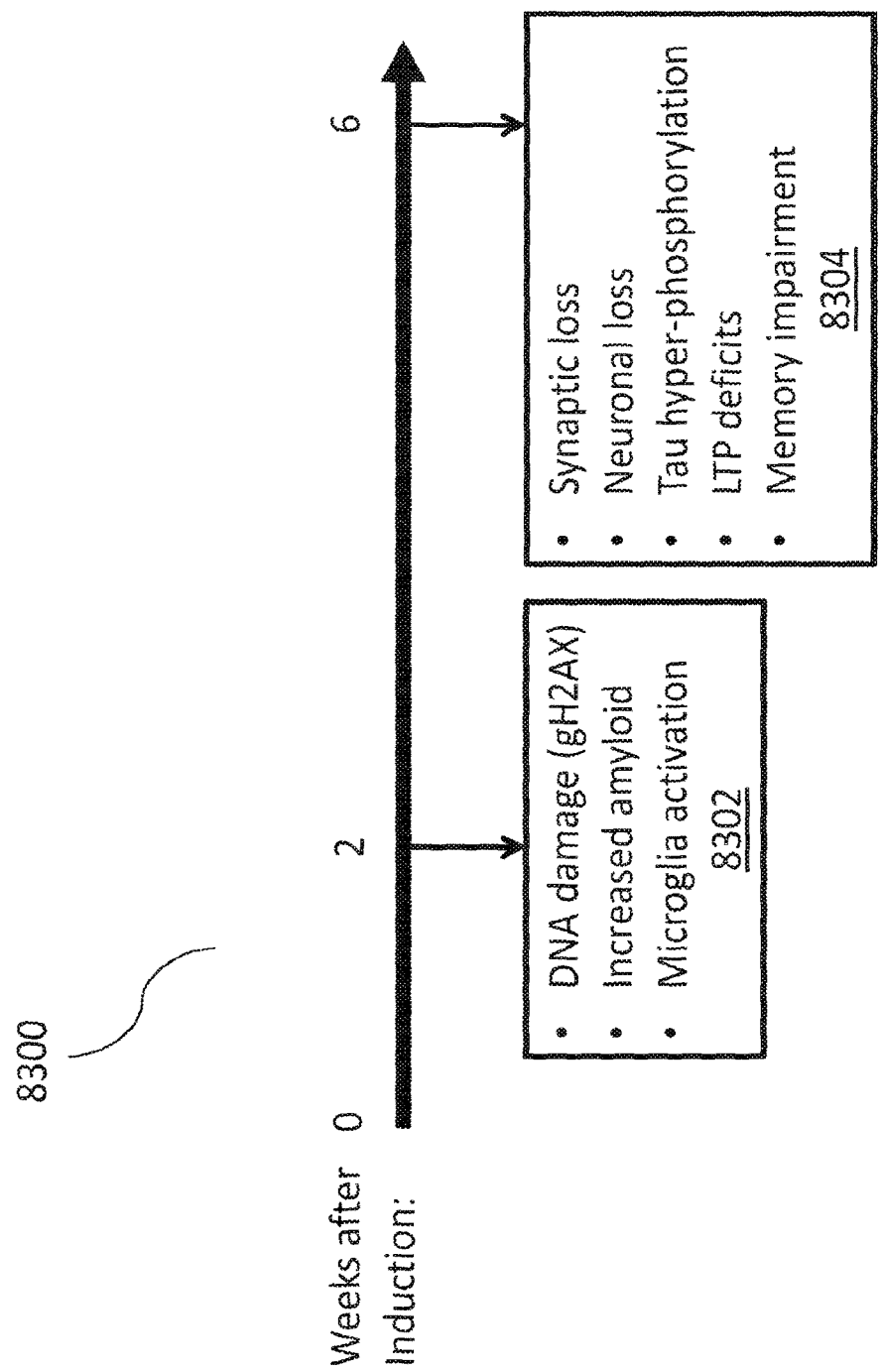
FIG. 83 is a timeline diagram of a study conducted to examine the effect of gamma exposure and/or administration in accordance with some embodiments on deoxyribonucleic acid (DNA) damage and neuronal loss in the visual cortex of a subject.

FIG. 83 is a timeline diagram 8300 illustrating changes in CK-p25 Tg mice. After two weeks 8302, the mice exhibit DNA damage (e.g., biomarker γH2AX), increased Aβ peptide, and microglia activation. After six weeks 8304, the mice exhibit synaptic loss, neuronal loss, tau hyper-phosphorylation, long-term potentiation deficits, and memory impairment.

Figure 84:
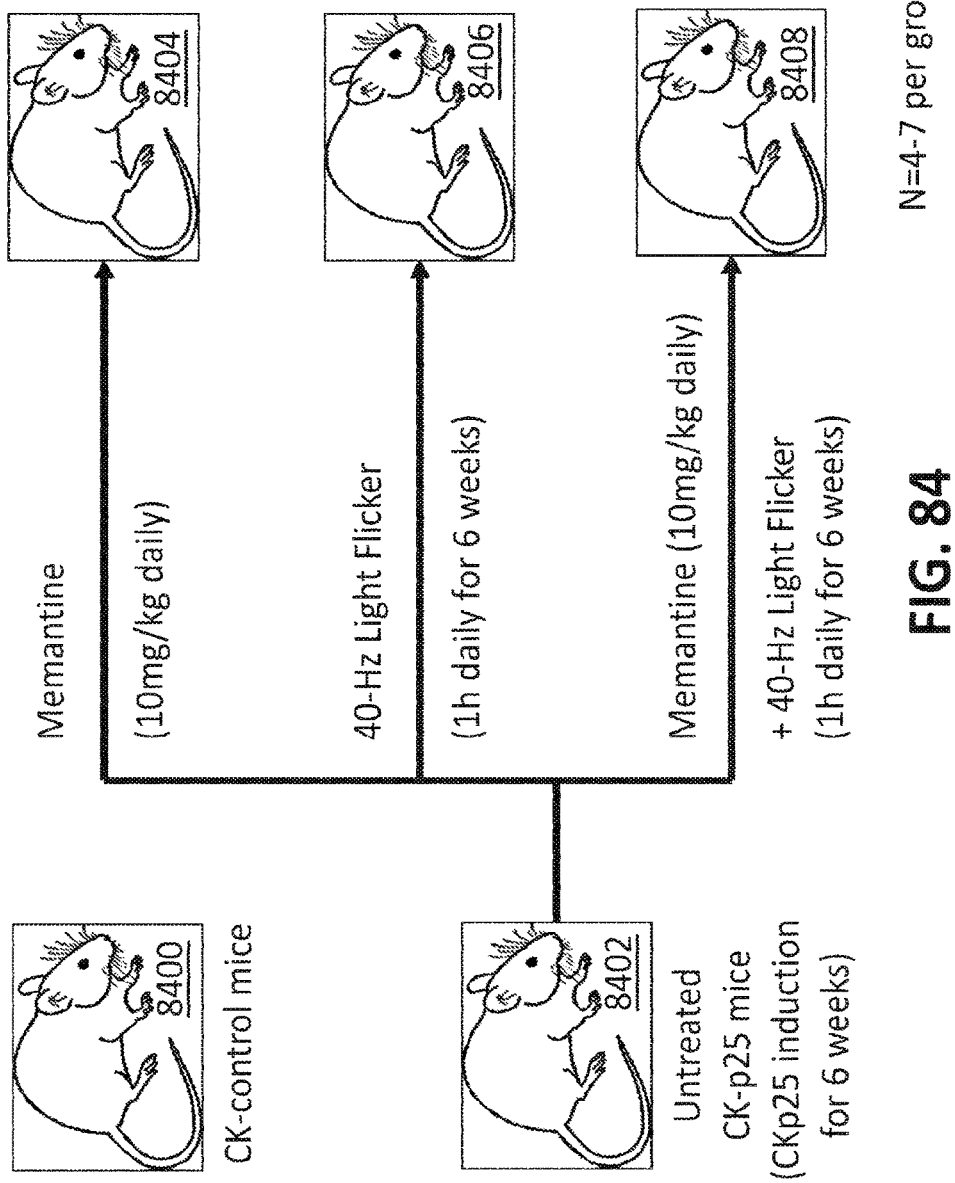
FIG. 84 is a diagram illustrating groups of subjects for studies conducted to examine the effect of gamma exposure and/or administration in accordance with some embodiments.

A study was conducted to compare groups of mice under different treatment regimens. FIG. 84 is a diagram of the groups including CK-control mice 8400, untreated CK-p25 Tg mice 8402, CK-p25 Tg mice treated with memantine (10 mg/kg daily) 8404, CK-p25 Tg mice exposed to the 40-Hz light flicker (one hour daily for 6 weeks) in accordance with some embodiments 8406, and CK-p25 Tg mice treated with memantine and also exposed to the 40-Hz light flicker 8408. Memantine is a medication used with limited success to treat severe AD by blocking NMDA receptors, thereby acting on the glutamatergic system.

Figure 85:
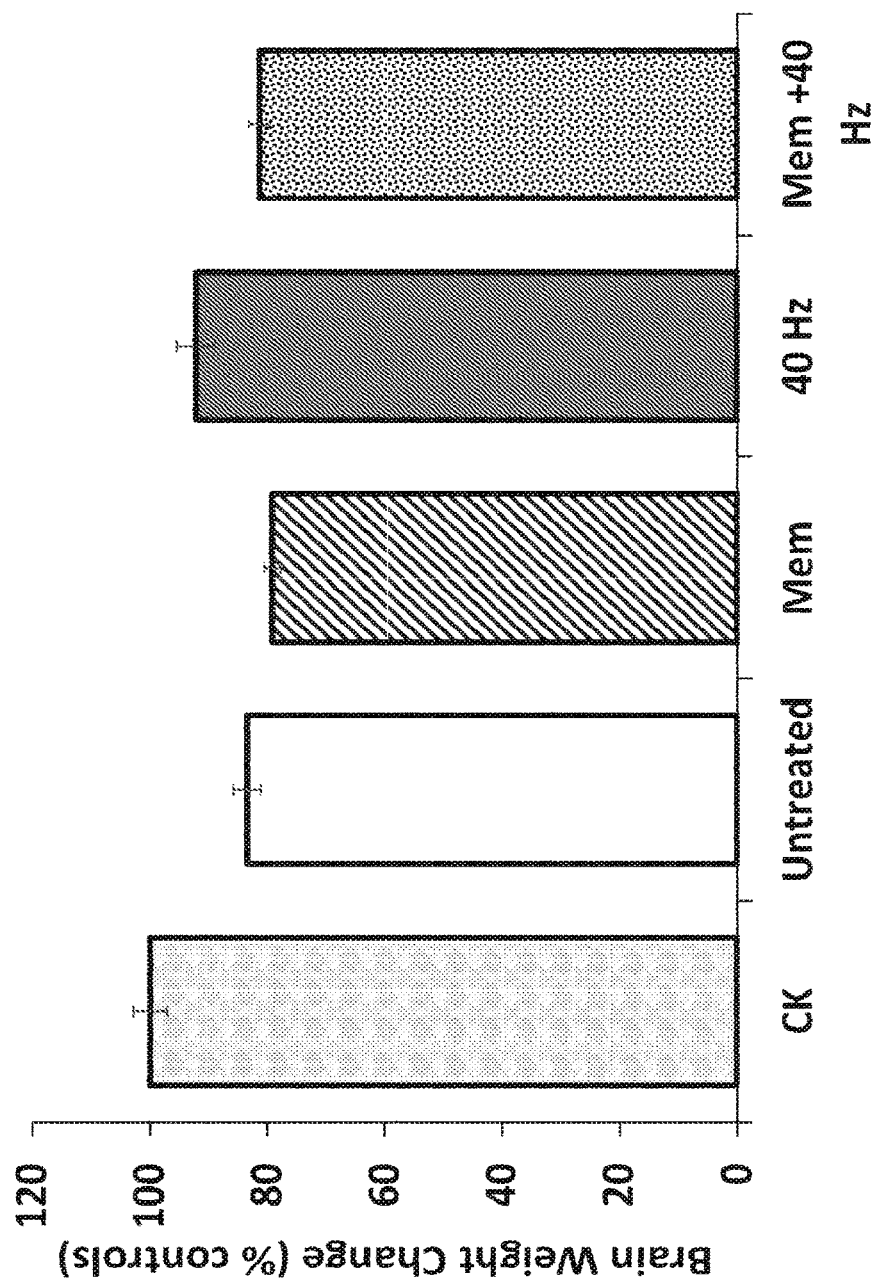
FIG. 85 is bar graph comparing brain weight change across the groups of subjects in FIG. 84 in accordance with some embodiments.

Gamma exposure and/or administration in accordance with some embodiments was shown to preserve and/or reduce changes to brain anatomy. For example, gamma exposure reduced and/or prevented CKp-25-induced loss of brain weight. FIG. 85 is bar graph comparing brain weight change in CK-control mice, untreated CK-p25 Tg mice, CK-p25 Tg mice treated with memantine, CK-p25 Tg mice exposed to the 40-Hz light flicker in accordance with some embodiments, and CK-p25 Tg mice treated with both memantine and the 40-Hz light flicker. Brain weight loss was pronounced in untreated CK-p25 Tg mice, CK-p25 Tg mice treated with memantine, and CK-p25 Tg mice treated with both memantine and the 40-Hz light flicker. However, CK-p25 Tg mice exposed to the 40-Hz light flicker in accordance with some embodiments retained more brain weight.

Figure 86:
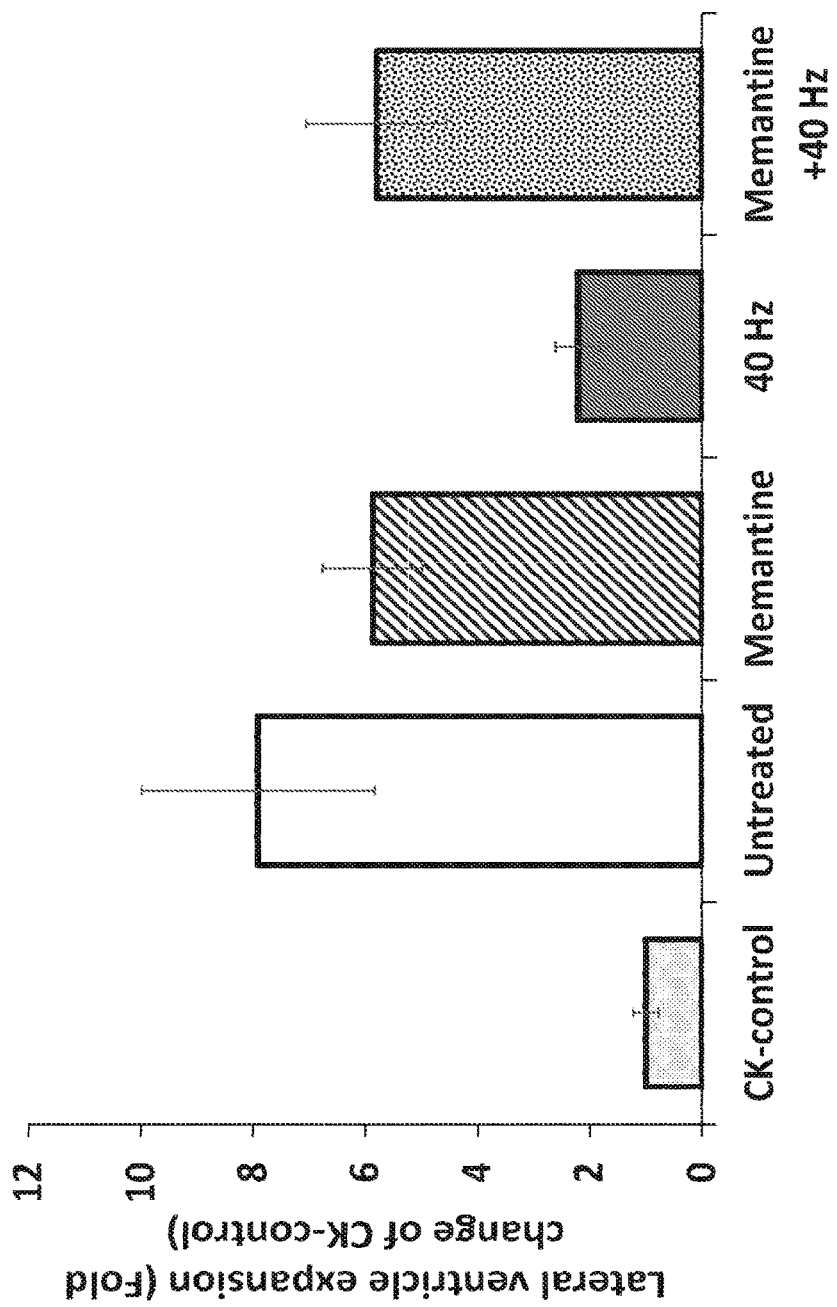
FIG. 86 is bar graph comparing fold change of lateral ventricle expansion across the groups of subjects in FIG. 84 in accordance with some embodiments.

Gamma exposure and/or administration in accordance with some embodiments was shown to preserve and/or reduce changes to brain morphology. For example, gamma exposure reduced and/or prevented CKp-25-induced abnormal lateral ventricle expansion in subjects. FIG. 86 is bar graph comparing fold change of lateral ventricle expansion in CK-control mice, untreated CK-p25 Tg mice, CK-p25 Tg mice treated with memantine, CK-p25 Tg mice exposed to the 40-Hz light flicker in accordance with some embodiments, and CK-p25 Tg mice treated with both memantine and the 40-Hz light flicker with expansion in the CK-control mice as a baseline. Lateral ventricle expansion was pronounced in untreated CK-p25 Tg mice, CK-p25 Tg mice treated with memantine, and CK-p25 Tg mice treated with both memantine and the 40-Hz light flicker. Lateral ventricles in CK-p25 Tg mice exposed to the 40-Hz light flicker in accordance with some embodiments expanded much less than the lateral ventricles in the other CK-p25 Tg mice.

Figure 87A:
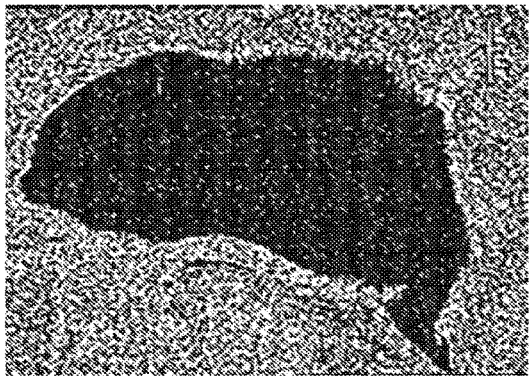
FIGS. 87A-87E are images illustrating lateral ventricles representative of the groups of subjects in FIG. 84 in accordance with some embodiments.
Figure 87B:
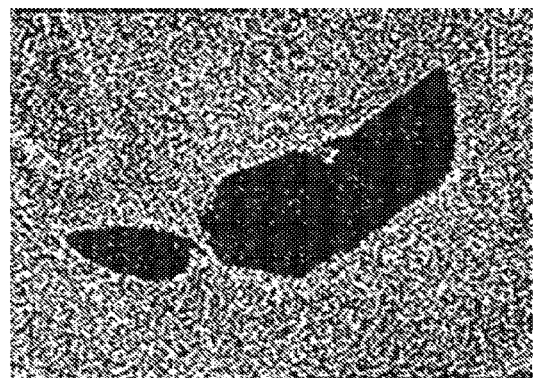
Figure 87C:
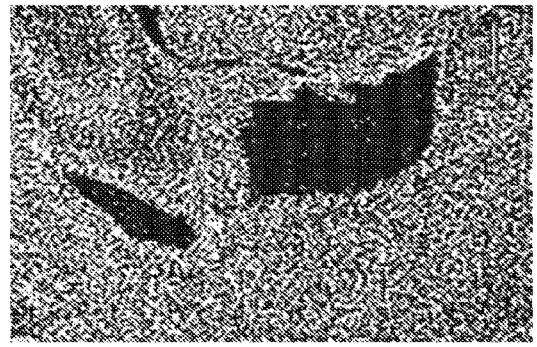
Figure 87D:
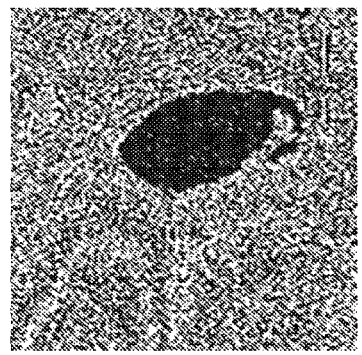
Figure 87E:
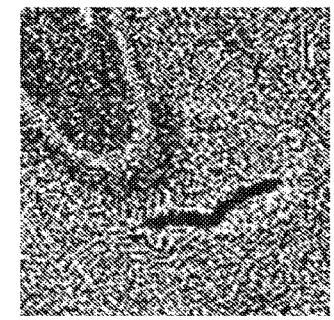

FIGS. 87A-87E are images illustrating lateral ventricles representative of subjects in each group. The lateral ventricles were largest in untreated CK-p25 Tg mice (FIG. 87A), CK-p25 Tg mice treated with memantine (FIG. 87B), and CK-p25 Tg mice treated with both memantine and the 40-Hz light flicker (FIG. 87C). As shown in FIG. 87D, the lateral ventricles of CK-p25 Tg mice exposed to the 40-Hz light flicker in accordance with some embodiments expanded much less. FIG. 87E is an example of the baseline lateral ventricle size in CK-control mice.

Figures 88A, 88B, 88C:
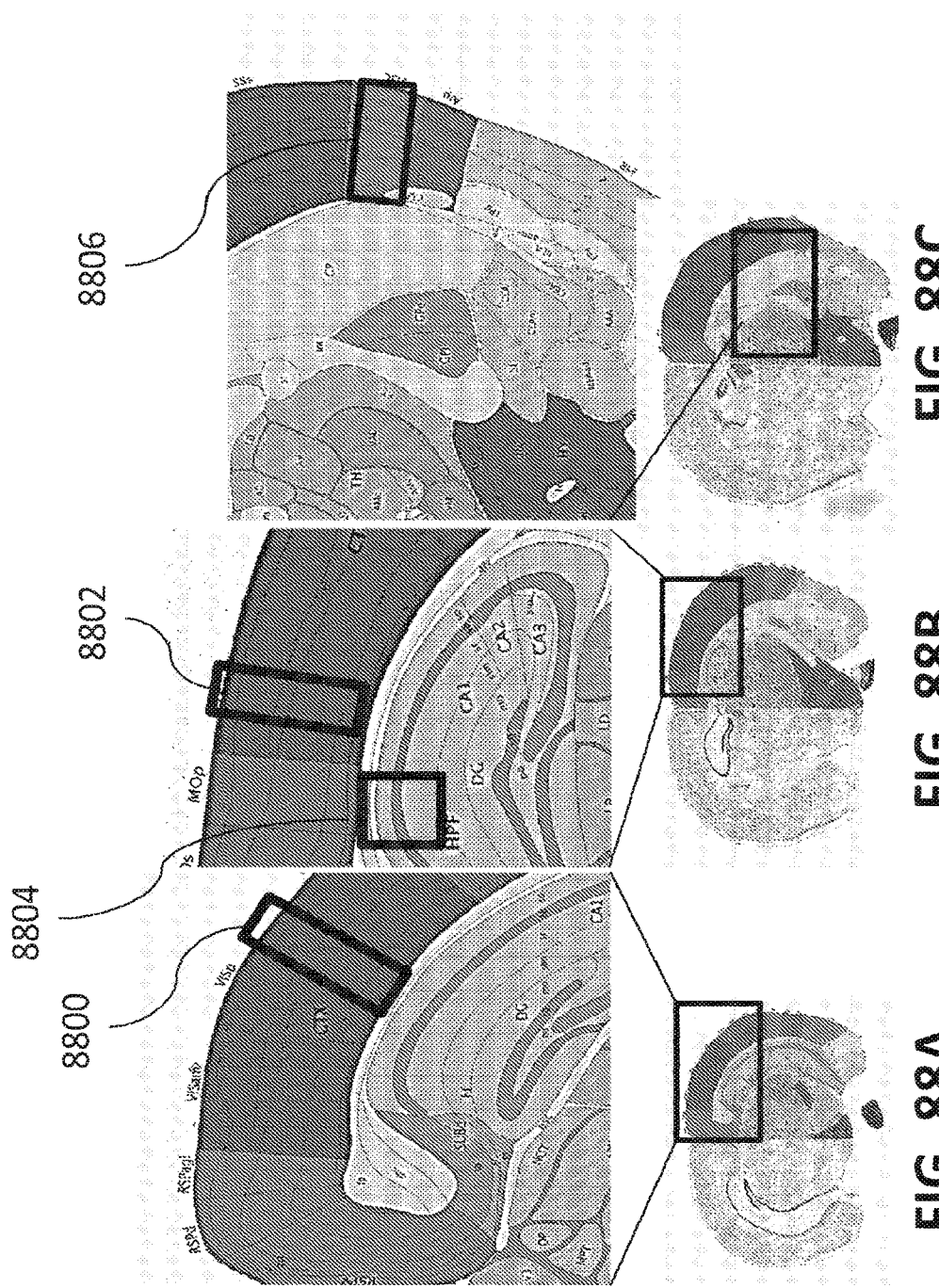
FIGS. 88A-88C are brain anatomy diagrams illustrating brain regions of interest in accordance with some embodiments.

FIGS. 88A-88C are brain anatomy diagrams illustrating brain regions of interest for molecular characterization in accordance with some embodiments. FIG. 88A includes the visual cortex (V1) 8800, the somatosensory cortex (SS1) 8802, the hippocampus 8804, and the insular cortex 8806.

Gamma exposure and/or administration in accordance with some embodiments was shown to preserve and/or reduce changes to cortical and neuronal layers in the visual cortex. For example, gamma exposure reduced and/or prevented CKp-25-induced cortical and neuronal layer loss in the visual cortex of subjects.

Figure 89:
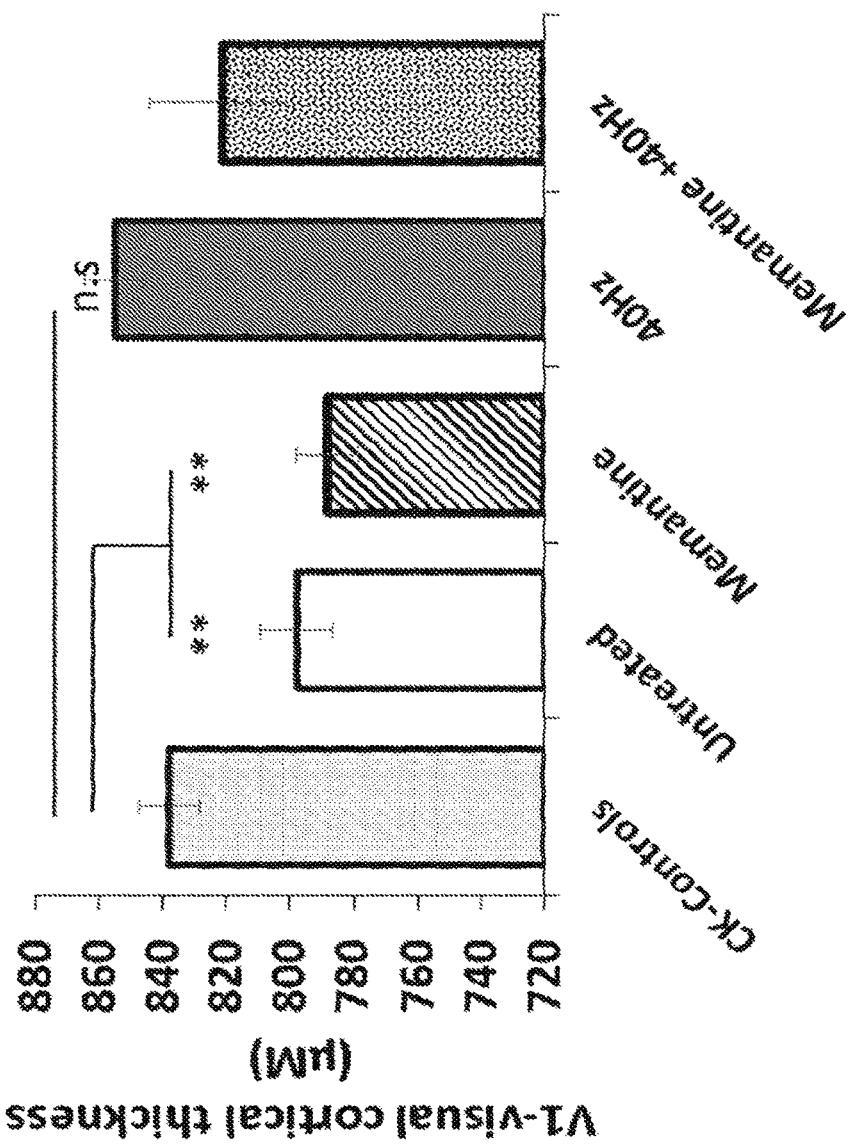
FIG. 89 is a bar graph depicting average thickness of the V1-cortical layer across the groups of subjects in FIG. 84 in accordance with some embodiments.
Figure 90:
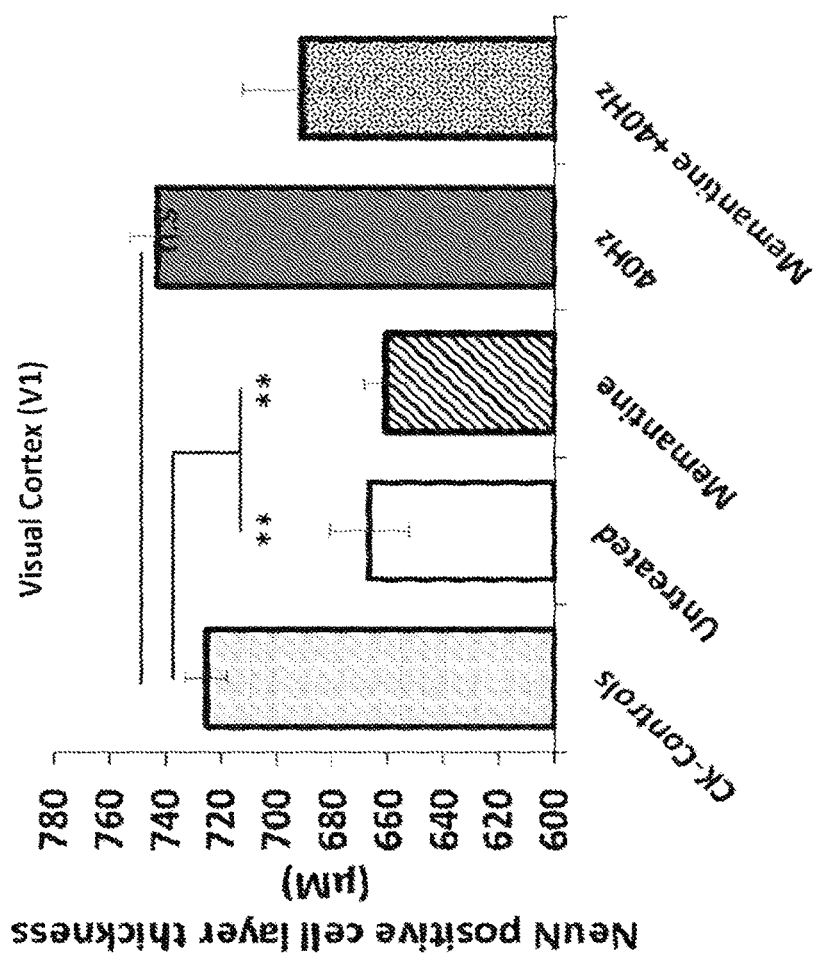
FIG. 90 is a bar graph depicting average thickness of the V1-NeuN-positive cell layer across the groups of subjects in FIG. 84 in accordance with some embodiments.

Cortical layer loss was gauged using nuclear staining with Hoechst labels (i.e., blue fluorescent dyes used to stain DNA). Neuronal layer loss was gauged using NeuN, a neuronal nuclear antigen that is commonly used as a biomarker for neurons. FIG. 89 is a bar graph depicting average thickness of the V1-cortical layer in each group, and FIG. 90 is a bar graph depicting average thickness of the V1-NeuN-positive cell layer in each group.

Figure 91:
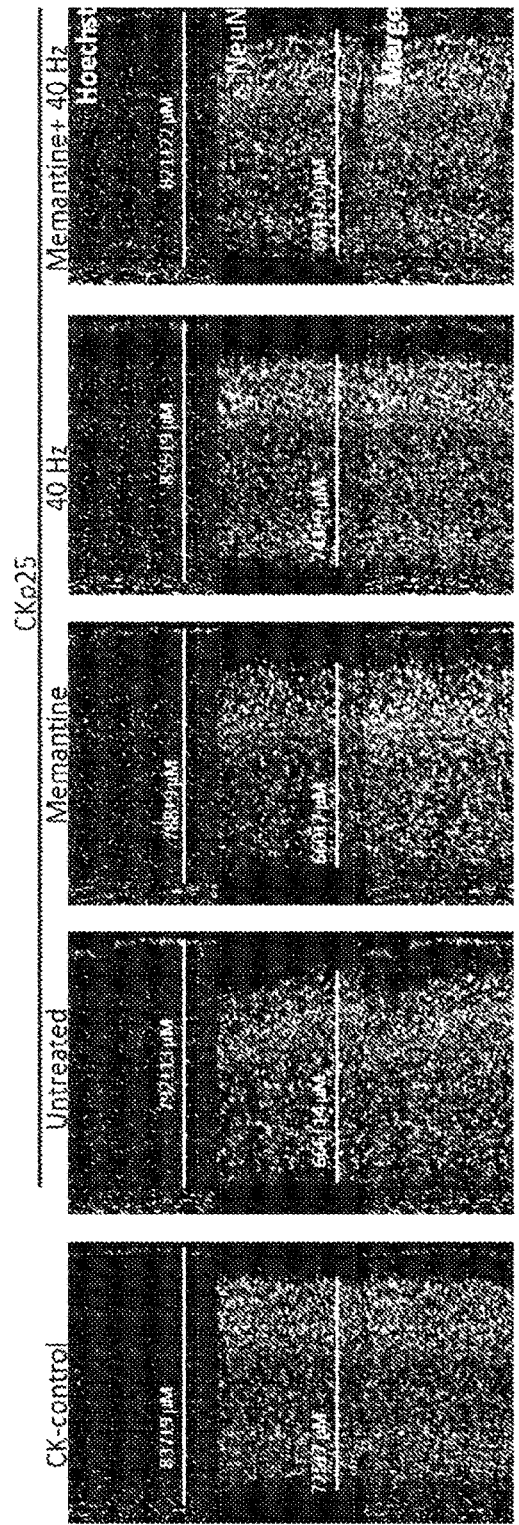
FIGS. 91A-91E are images illustrating cells with Hoechst labels and/or NeuN labels representative of the groups of subjects in FIG. 84 in accordance with some embodiments.

FIGS. 91A-91E are images illustrating cells with Hoechst labels and/or NeuN labels representative of subjects in each group. FIG. 91A is an example of the thickness of the baseline V1-cortical layer (e.g., 837±9 μM) and V1-neuronal layer (e.g., 725±7 μM) in CK-control mice.

The V1-cortical layers were progressively thinner in CK-p25 Tg mice exposed to the 40-Hz light flicker in accordance with some embodiments (FIG. 91D, e.g., 855±9 μM); CK-p25 Tg mice treated with both memantine and the 40-Hz light flicker (FIG. 91E, e.g., 821±22 μM); untreated CK-p25 Tg mice (FIG. 91B, e.g., 792±13 μM); and CK-p25 Tg mice treated with memantine (FIG. 91C, e.g., 788±9 μM).

The V1-neuronal layers in CK-p25 Tg mice exposed to the 40-Hz light flicker in accordance with some embodiments were actually thicker than in the CK-control mice (FIG. 91D, e.g., 743±9 μM), but then progressively thinner than in the CK-control mice in CK-p25 Tg mice treated with both memantine and the 40-Hz light flicker (FIG. 91E, e.g., 691±20 μM); untreated CK-p25 Tg mice (FIG. 91B, e.g., 666±14 μM); and CK-p25 Tg mice treated with memantine (FIG. 91C, e.g., 660±7 μM).

Gamma exposure and/or administration in accordance with some embodiments was shown to preserve and/or reduce changes to cortical and neuronal layers in the somatosensory cortex. For example, gamma exposure reduced and/or prevented CKp-25-induced cortical and neuronal layer loss in the somatosensory cortex of subjects.

Figure 92:
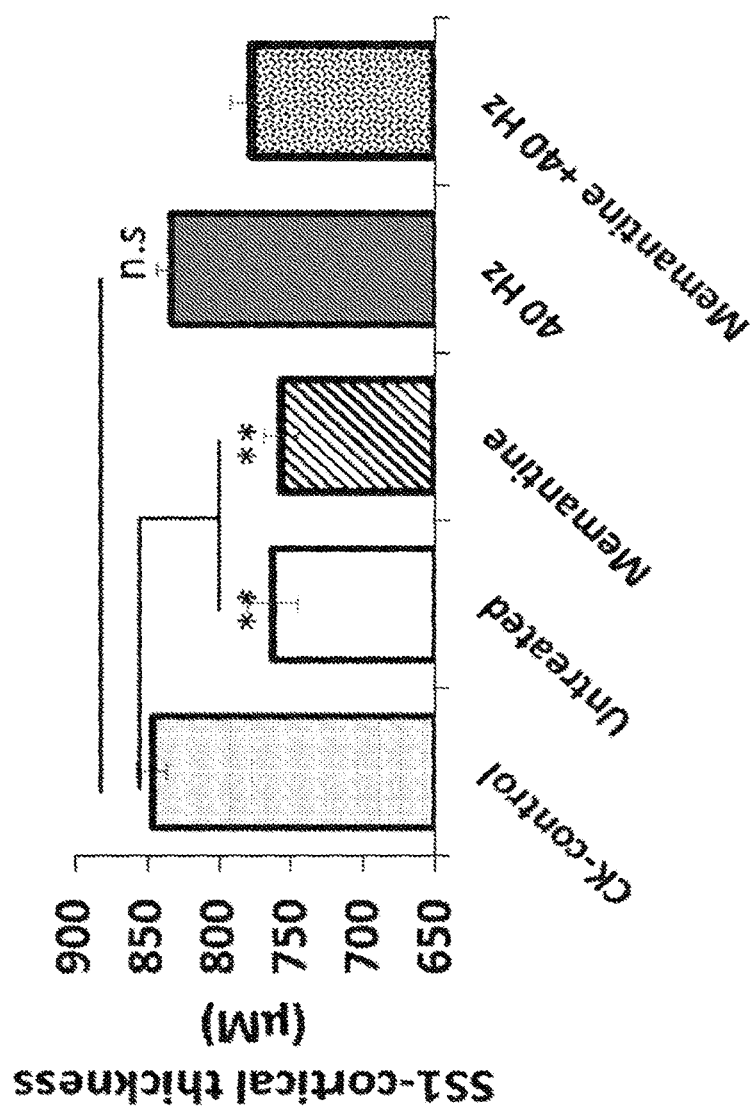
FIG. 92 is a bar graph depicting average thickness of the SS1-cortical layer across the groups of subjects in FIG. 84 in accordance with some embodiments.
Figure 93:
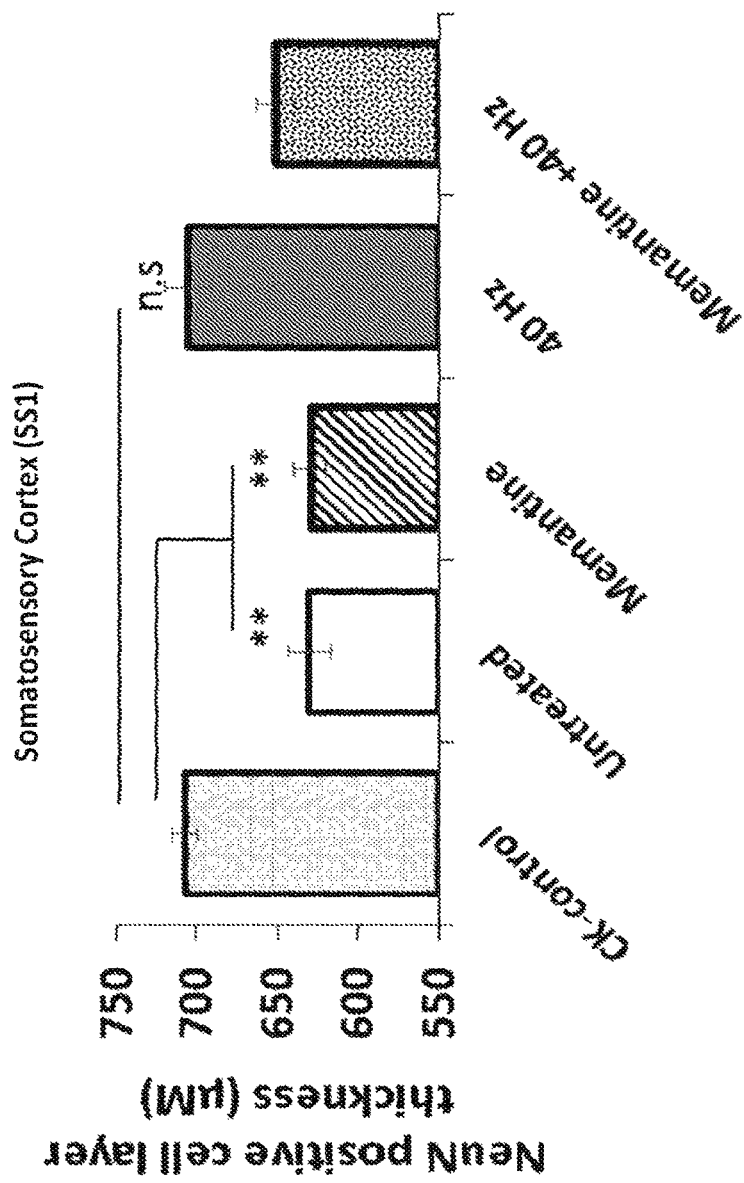
FIG. 93 is a bar graph depicting average thickness of the SS1-NeuN-positive cell layer across the groups of subjects in FIG. 84 in accordance with some embodiments.

FIG. 92 is a bar graph depicting average thickness of the SS1-cortical layer in each group, and FIG. 93 is a bar graph depicting average thickness of the SS1-NeuN-positive cell layer in each group.

Figure 94:
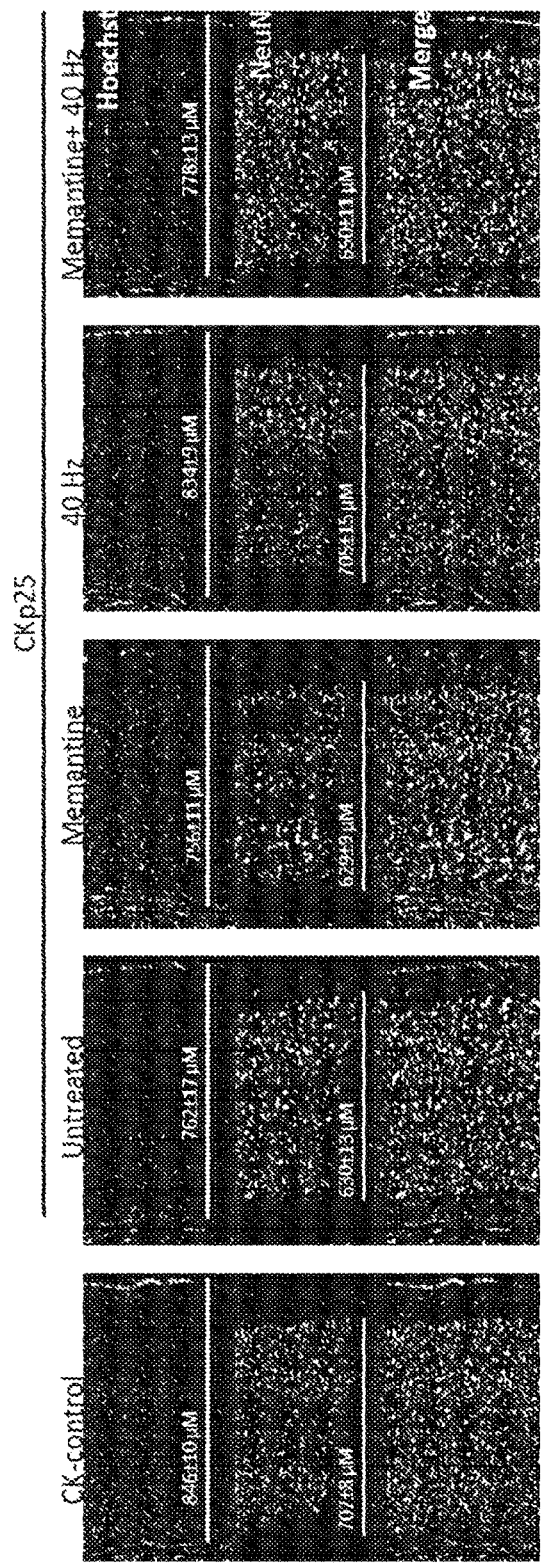
FIGS. 94A-94E are images illustrating cells with Hoechst labels and/or NeuN labels across the groups of subjects in FIG. 84 in accordance with some embodiments.

FIGS. 94A-94E are images illustrating cells with Hoechst labels and/or NeuN labels representative of subjects in each group. FIG. 94A is an example of the thickness of the baseline SS1-cortical layer (e.g., 846±10 μM) and SS1-neuronal layer (e.g., 707±8 μM) in CK-control mice.

The SS1-cortical layers were progressively thinner in CK-p25 Tg mice exposed to the 40-Hz light flicker in accordance with some embodiments (FIG. 94D, e.g., 834±9 μM); CK-p25 Tg mice treated with both memantine and the 40-Hz light flicker (FIG. 94E, e.g., 778±13 μM); untreated CK-p25 Tg mice (FIG. 94B, e.g., 762±17 μM); and CK-p25 Tg mice treated with memantine (FIG. 94C, e.g., 756±11 μM).

The SS1-neuronal layers in CK-p25 Tg mice exposed to the 40-Hz light flicker in accordance with some embodiments were nearly the same thickness as that in the CK-control mice (FIG. 94D, e.g., 705±15 μM). However, the SS1-neuronal layers were progressively thinner in CK-p25 Tg mice treated with both memantine and the 40-Hz light flicker (FIG. 94E, e.g., 650±11 μM); untreated CK-p25 Tg mice (FIG. 94B, e.g., 630±13 μM); and CK-p25 Tg mice treated with memantine (FIG. 94C, e.g., 629±9 μM).

Gamma exposure and/or administration in accordance with some embodiments was shown to preserve and/or reduce changes to cortical and neuronal layers in the insular cortex. For example, gamma exposure reduced and/or prevented CKp-25-induced cortical and neuronal layer loss in the insular cortex of subjects.

Figure 95:
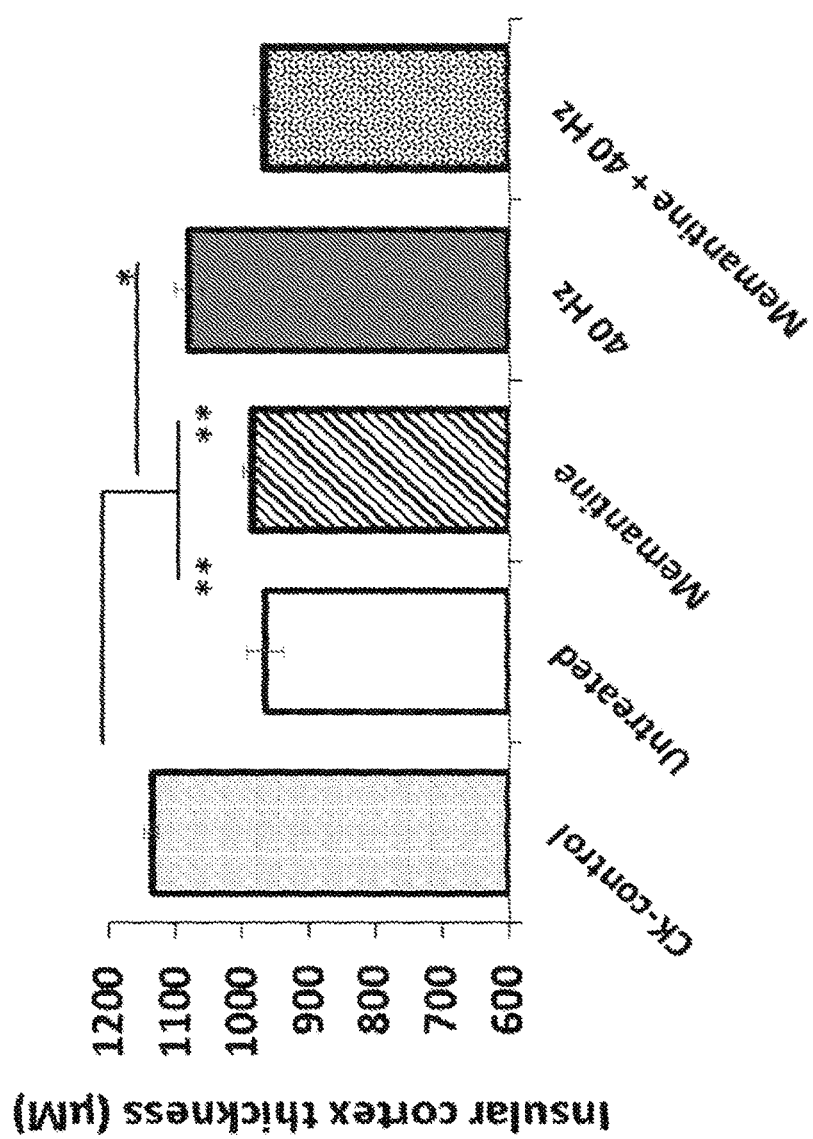
FIG. 95 is a bar graph depicting average thickness of the cortical layer of the insular cortex across the groups of subjects in FIG. 84 in accordance with some embodiments.
Figure 96:
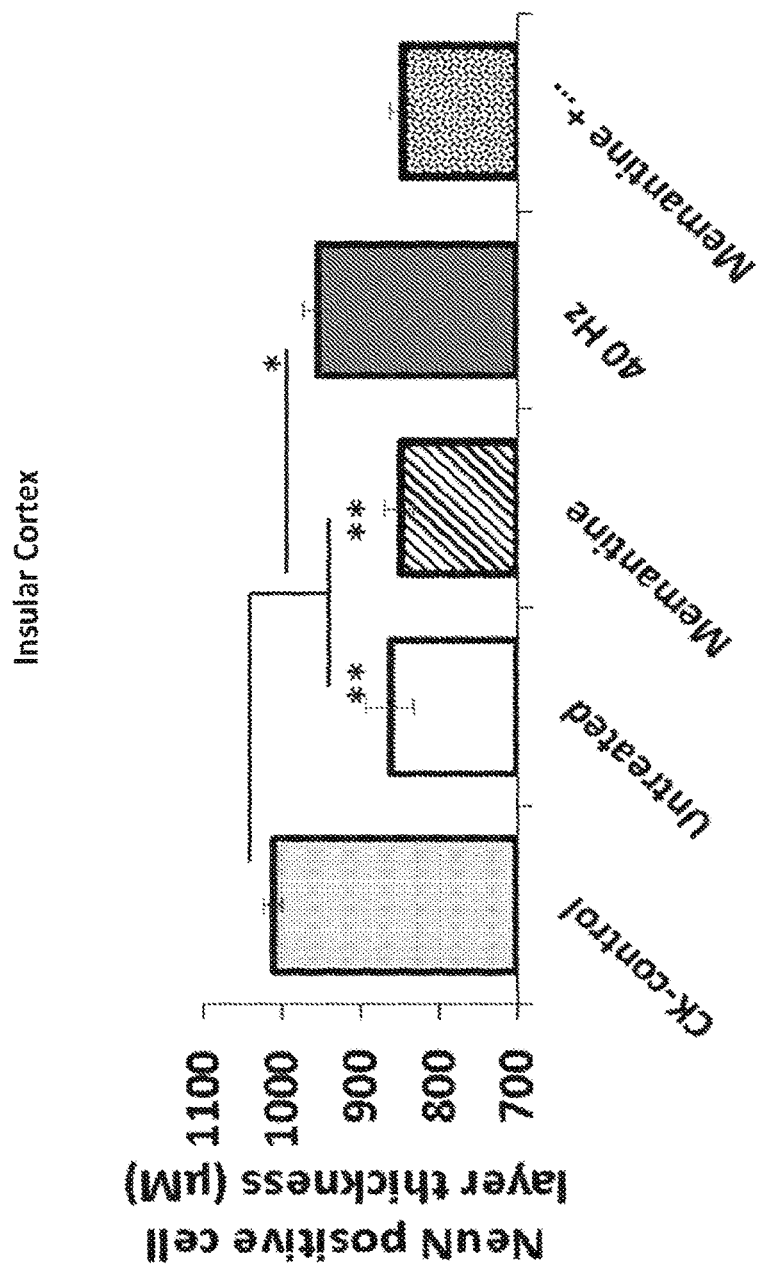
FIG. 96 is a bar graph depicting average thickness of the NeuN-positive cell layer of the insular cortex across the groups of subjects in FIG. 84 in accordance with some embodiments.

FIG. 95 is a bar graph depicting average thickness of the cortical layer of the insular cortex in each group, and FIG. 96 is a bar graph depicting average thickness of the NeuN-positive cell layer of the insular cortex in each group.

Figure 97:
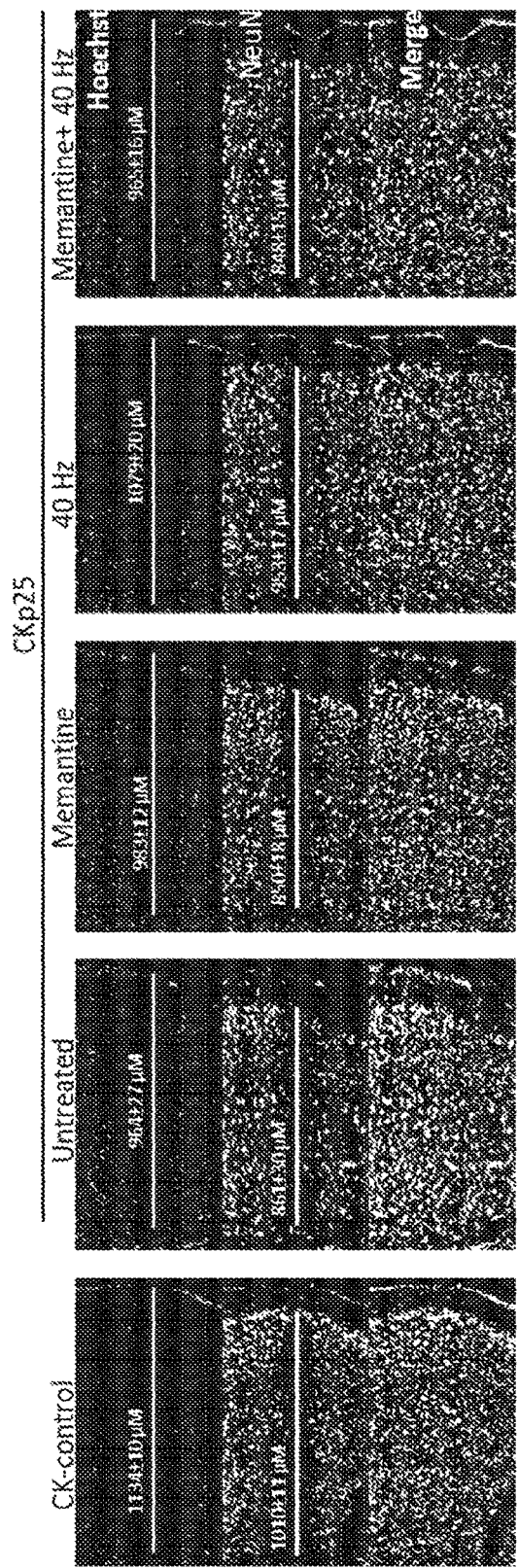
FIGS. 97A-97E are images illustrating cells with Hoechst labels and/or NeuN labels representative of the groups of subjects in FIG. 84 in accordance with some embodiments.

FIGS. 97A-97E are images illustrating cells with Hoechst labels and/or NeuN labels representative of subjects in each group. FIG. 97A is an example of the thickness of the baseline cortical layer (e.g., 1134±10 μM) and neuronal layer (e.g., 1010±11 μM) of the insular cortex in CK-control mice.

The cortical layers were progressively thinner in the insular cortices of CK-p25 Tg mice exposed to the 40-Hz light flicker in accordance with some embodiments (FIG. 97D, e.g., 1079±20 μM); CK-p25 Tg mice treated with memantine (FIG. 97C, e.g., 983±12 μM); CK-p25 Tg mice treated with both memantine and the 40-Hz light flicker (FIG. 97E, e.g., 965±16 μM); and untreated CK-p25 Tg mice (FIG. 97B, e.g., 764±27 μM).

The neuronal layers were progressively thinner in the insular cortices of CK-p25 Tg mice exposed to the 40-Hz light flicker in accordance with some embodiments (FIG. 97D, e.g., 953±17 μM); untreated CK-p25 Tg mice (FIG. 97B, e.g., 861±30 μM); CK-p25 Tg mice treated with memantine (FIG. 97C, e.g., 850±18 μM); and CK-p25 Tg mice treated with both memantine and the 40-Hz light flicker (FIG. 97E, e.g., 848±15 μM).

Gamma exposure and/or administration in accordance with some embodiments was shown to preserve and/or reduce changes to the number of neurons and/or damage of DNA. For example, gamma exposure reduced CKp-25-induced neuron loss and DNA damage in the visual cortex of subjects.

Figure 98:
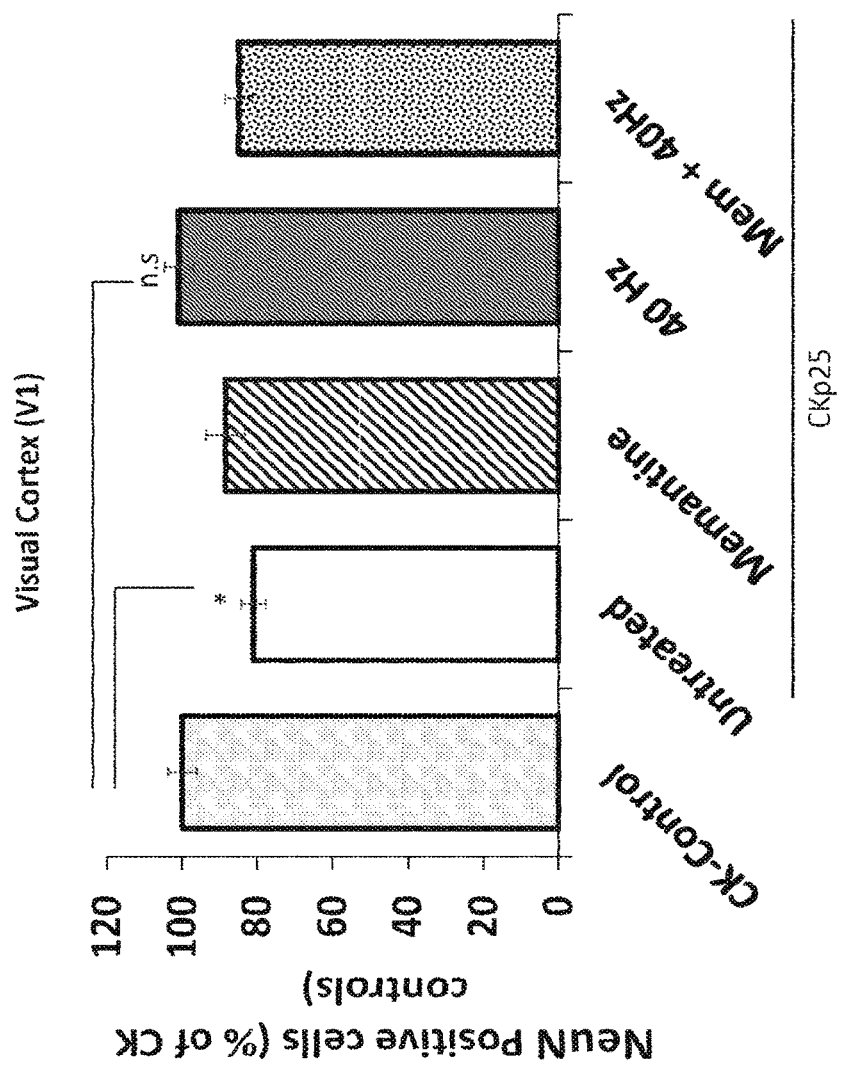
FIG. 98 is a bar graph comparing the amount of visual cortex NeuN-positive cells across the groups of subjects in FIG. 84 in accordance with some embodiments.

FIG. 98 is a bar graph comparing the amount of NeuN-positive cells as a percentage of the NeuN-positive cells in CK-control mice for the CK-control mice, untreated CK-p25

Tg mice, CK-p25 Tg mice treated with memantine, CK-p25 Tg mice exposed to the 40-Hz light flicker in accordance with some embodiments, and CK-p25 Tg mice treated with both memantine and the 40-Hz light flicker. Thus, the percentage of the CK-control mice NeuN-positive cells are 100% in the CK-control mice, but only about 80% in untreated CK-p25 Tg mice, corroborating neuronal loss in the CK-p25 Tg mouse model. Treatment with memantine prevented some neuronal loss in CK-p25 Tg mice compared to the untreated group. Exposure to the 40-Hz light flicker in accordance with some embodiments prevented most neuronal loss in CK-p25 Tg mice. Thus, FIG. 98 illustrates how 40-Hz visual flicker treatment in accordance with some embodiments can preserve neurons in the visual cortex. However, combination of memantine and exposure to the 40-Hz light flicker failed to prevent as much neuronal loss.

Figure 99:
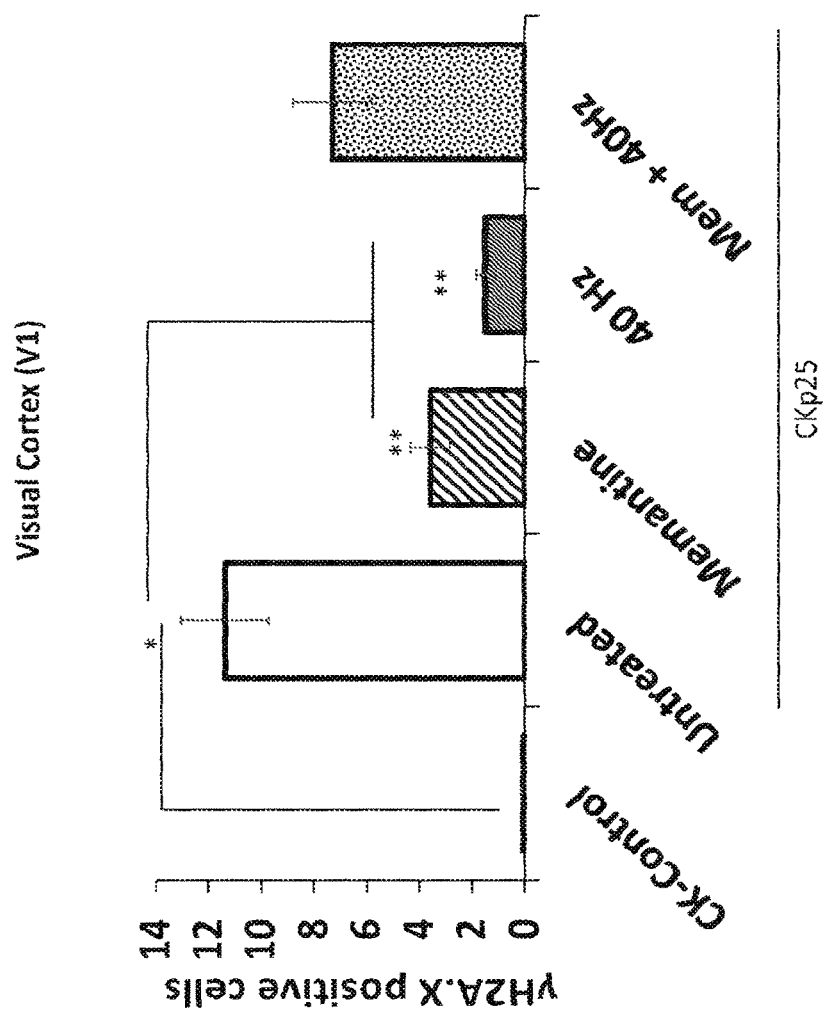
FIG. 99 is bar graph comparing the amount of visual cortex γH2AX-positive cells across the groups of subjects in FIG. 84 in accordance with some embodiments.

DNA double strand breaks (DSB) are one example of DNA damage in eukaryotic cells, causing genomic instability, leading to tumorigenesis and possibly accelerated aging. Phosphorylated histone H2AX ($\gamma$H2AX) was used as a biomarker of cellular response to DSB. FIG. 99 is bar graph comparing the amount of $\gamma$H2AX-positive cells in CK-control mice, untreated CK-p25 Tg mice, CK-p25 Tg mice treated with memantine, CK-p25 Tg mice exposed to the 40-Hz light flicker in accordance with some embodiments, and CK-p25 Tg mice treated with both memantine and the 40-Hz light flicker. Cells positive for $\gamma$H2AX were almost non-existent in CK-control mice, but very high in untreated CK-p25 Tg mice, indicating high amounts of DSB and other DNA damage. Treatment with memantine reduced the amount of $\gamma$H2AX-positive cells in CK-p25 Tg mice compared to the untreated group. Exposure to the 40-Hz light flicker in accordance with some embodiments resulted in even greater reductions of $\gamma$H2AX-positive cells in CK-p25 Tg mice. Thus, FIG. 99 illustrates how 40-Hz visual flicker treatment in accordance with some embodiments can reduce DNA damage in the visual cortex. However, combination of memantine and exposure to the 40-Hz light flicker significantly increased the number of $\gamma$H2AX-positive cells in CK-p25 Tg mice.

Figure 100:
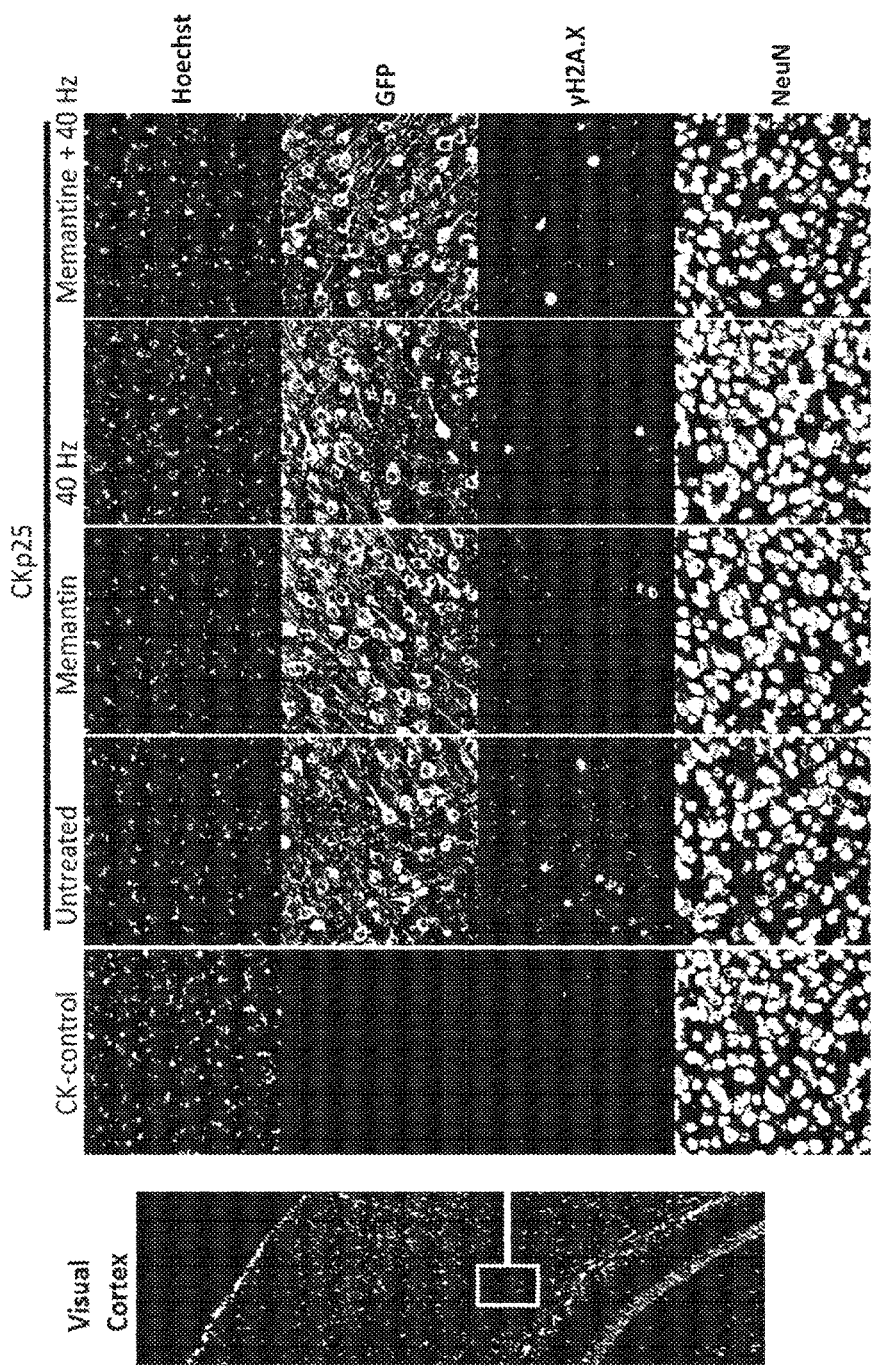
FIG. 100 is a series of images illustrating visual cortex samples representative of the groups of subjects in FIG. 84 in accordance with some embodiments.

FIG. 100 is a series of images illustrating visual cortex samples representative of subjects in each group labeled with Hoechst stain (indicating cortical cells), green fluorescent protein or GFP (indicating CK-p25), $\gamma$H2AX (indicating DSB), or NeuN (indicating neurons).

Figure 101:
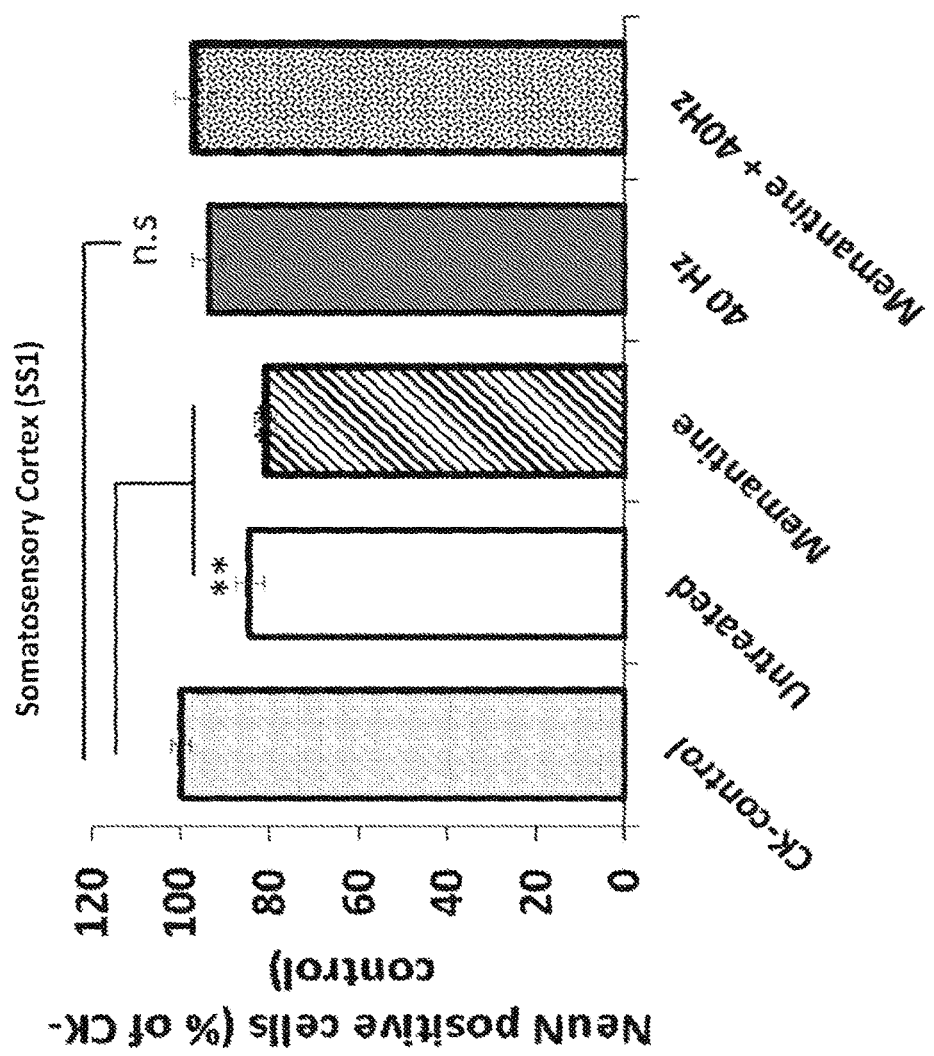
FIG. 101 is a bar graph comparing the amount of somatosensory cortex NeuN-positive cells across the groups of subjects in FIG. 84 in accordance with some embodiments.

Gamma exposure also reduced CKp-25-induced neuron loss and DNA damage in the somatosensory cortex of subjects. FIG. 101 is a bar graph comparing the amount of NeuN-positive cells as a percentage of the NeuN-positive cells in CK-control mice for the CK-control mice, untreated CK-p25 Tg mice, CK-p25 Tg mice treated with memantine, CK-p25 Tg mice exposed to the 40-Hz light flicker in accordance with some embodiments, and CK-p25 Tg mice treated with both memantine and the 40-Hz light flicker. Thus, the percentage of the CK-control mice NeuN-positive cells are 100% in the CK-control mice, but closer to 80% in untreated CK-p25 Tg mice, corroborating neuronal loss in the CK-p25 Tg mouse model. Treatment with memantine failed to prevent any neuronal loss in CK-p25 Tg mice compared to the untreated group except for in combination with exposure to the 40-Hz light flicker, which prevented most neuronal loss in CK-p25 Tg mice. Thus, FIG. 101 illustrates how 40-Hz visual flicker treatment in accordance with some embodiments can preserve neurons in the somatosensory cortex.

Figure 102:
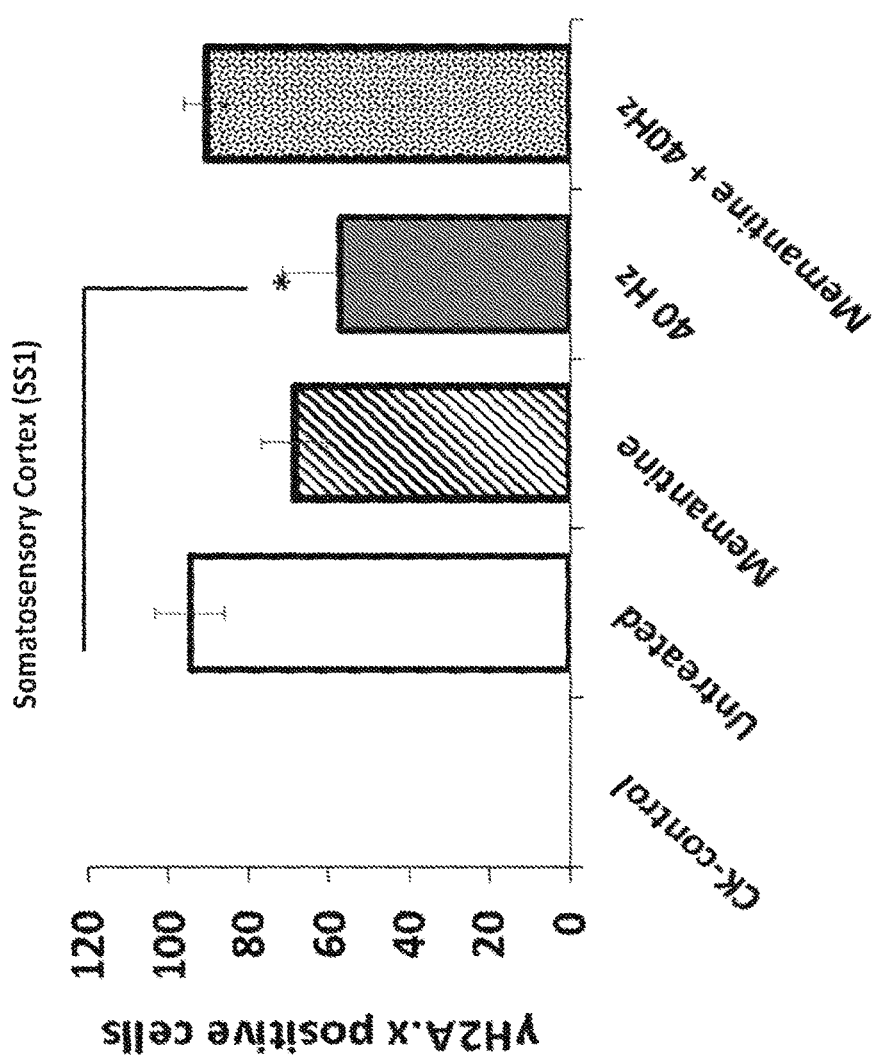
FIG. 102 is bar graph comparing the amount of somatosensory cortex γH2AX-positive cells across the groups of subjects in FIG. 84 in accordance with some embodiments.

FIG. 102 is bar graph comparing the amount of $\gamma$H2AX-positive cells in CK-control mice, untreated CK-p25 Tg mice, CK-p25 Tg mice treated with memantine, CK-p25 Tg mice exposed to the 40-Hz light flicker in accordance with some embodiments, and CK-p25 Tg mice treated with both memantine and the 40-Hz light flicker. Cells positive for $\gamma$H2AX were non-existent in CK-control mice, but very high in untreated CK-p25 Tg mice, indicating high amounts of DSB and other DNA damage. Treatment with memantine reduced the amount of $\gamma$H2AX-positive cells in CK-p25 Tg mice compared to the untreated group. Exposure to the 40-Hz light flicker in accordance with some embodiments resulted in even greater reductions of $\gamma$H2AX-positive cells in CK-p25 Tg mice. Thus, FIG. 102 illustrates how 40-Hz visual flicker treatment in accordance with some embodiments can reduce DNA damage in the somatosensory cortex. However, combination of memantine and exposure to the 40-Hz light flicker significantly increased the number of $\gamma$H2AX-positive cells in CK-p25 Tg mice.

Figure 103:
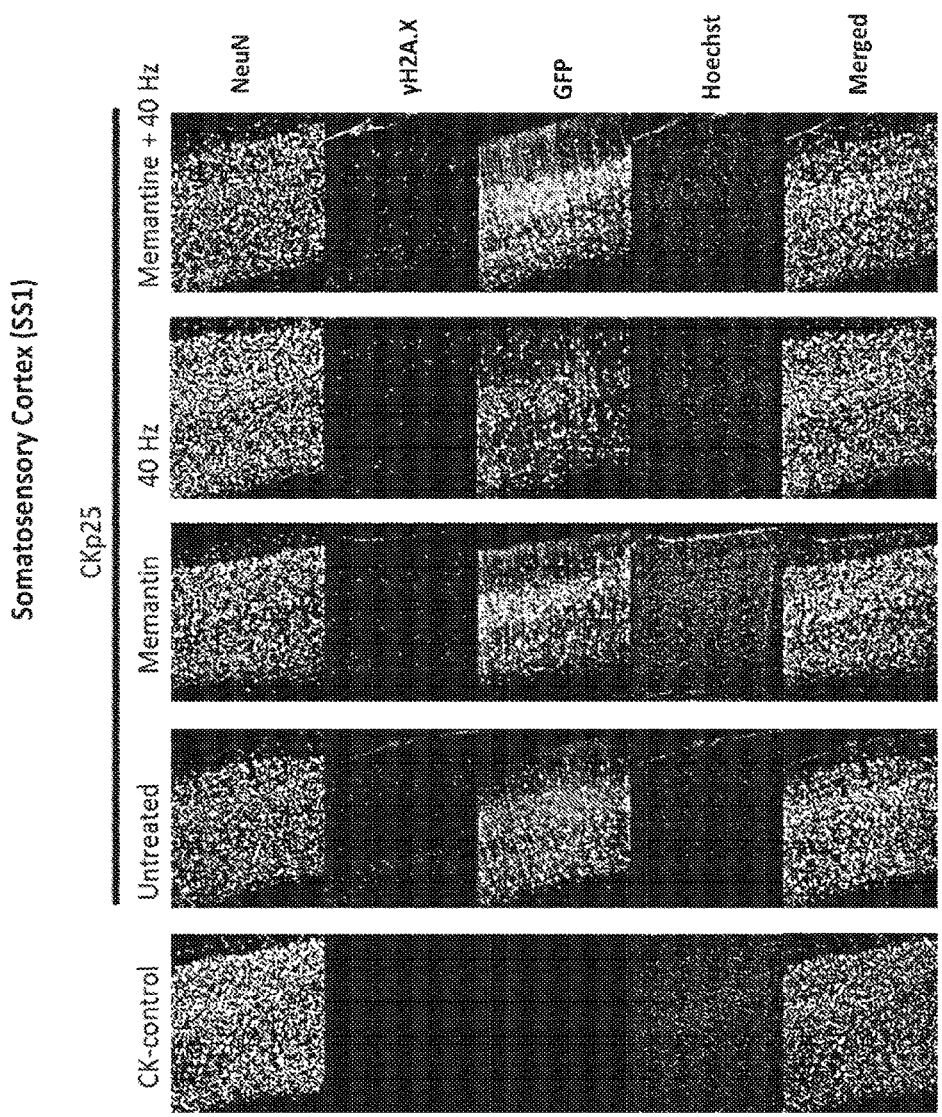
FIG. 103 is a series of images illustrating somatosensory cortex samples representative of the groups of subjects in FIG. 84 in accordance with some embodiments.

FIG. 103 is a series of images illustrating somatosensory cortex samples representative of subjects in each group labeled with NeuN (indicating neurons), $\gamma$H2AX (indicating DSB), GFP (indicating CK-p25), and/or Hoechst stain (indicating cortical cells).

Figure 104:
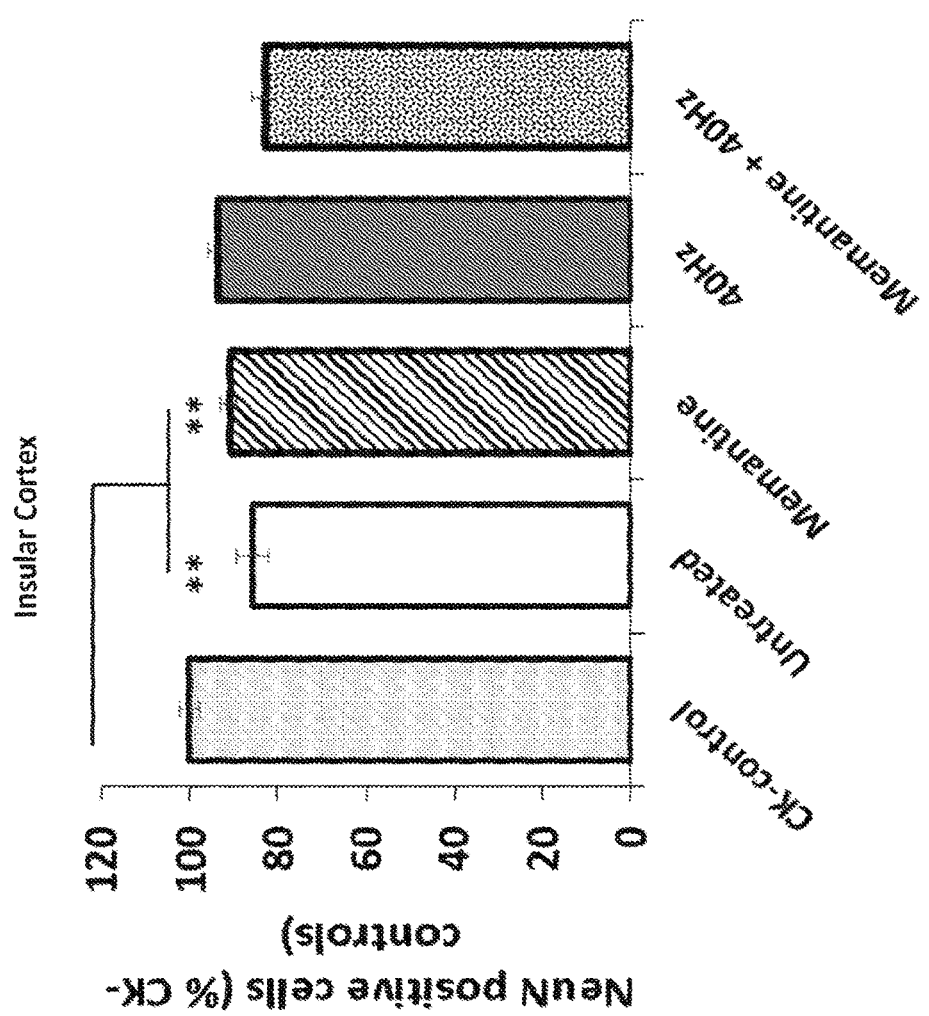
FIG. 104 is a bar graph comparing the amount of insular cortex NeuN-positive cells across the groups of subjects in FIG. 84 in accordance with some embodiments.

Gamma exposure also reduced CKp-25-induced neuron loss and DNA damage in the insular cortex of subjects. FIG. 104 is a bar graph comparing the amount of NeuN-positive cells as a percentage of the NeuN-positive cells in CK-control mice for the CK-control mice, untreated CK-p25 Tg mice, CK-p25 Tg mice treated with memantine, CK-p25 Tg mice exposed to the 40-Hz light flicker in accordance with some embodiments, and CK-p25 Tg mice treated with both memantine and the 40-Hz light flicker. Thus, the percentage of the CK-control mice NeuN-positive cells are 100% in the CK-control mice, but closer to 80% in untreated CK-p25 Tg mice, corroborating neuronal loss in the CK-p25 Tg mouse model. Treatment with memantine prevented some neuronal loss in CK-p25 Tg mice compared to the untreated group except for in combination with exposure to the 40-Hz light flicker, which prevented the least neuronal loss in CK-p25 Tg mice. Thus, FIG. 104 illustrates how 40-Hz visual flicker treatment in accordance with some embodiments can preserve neurons in the insular cortex.

Figure 105:
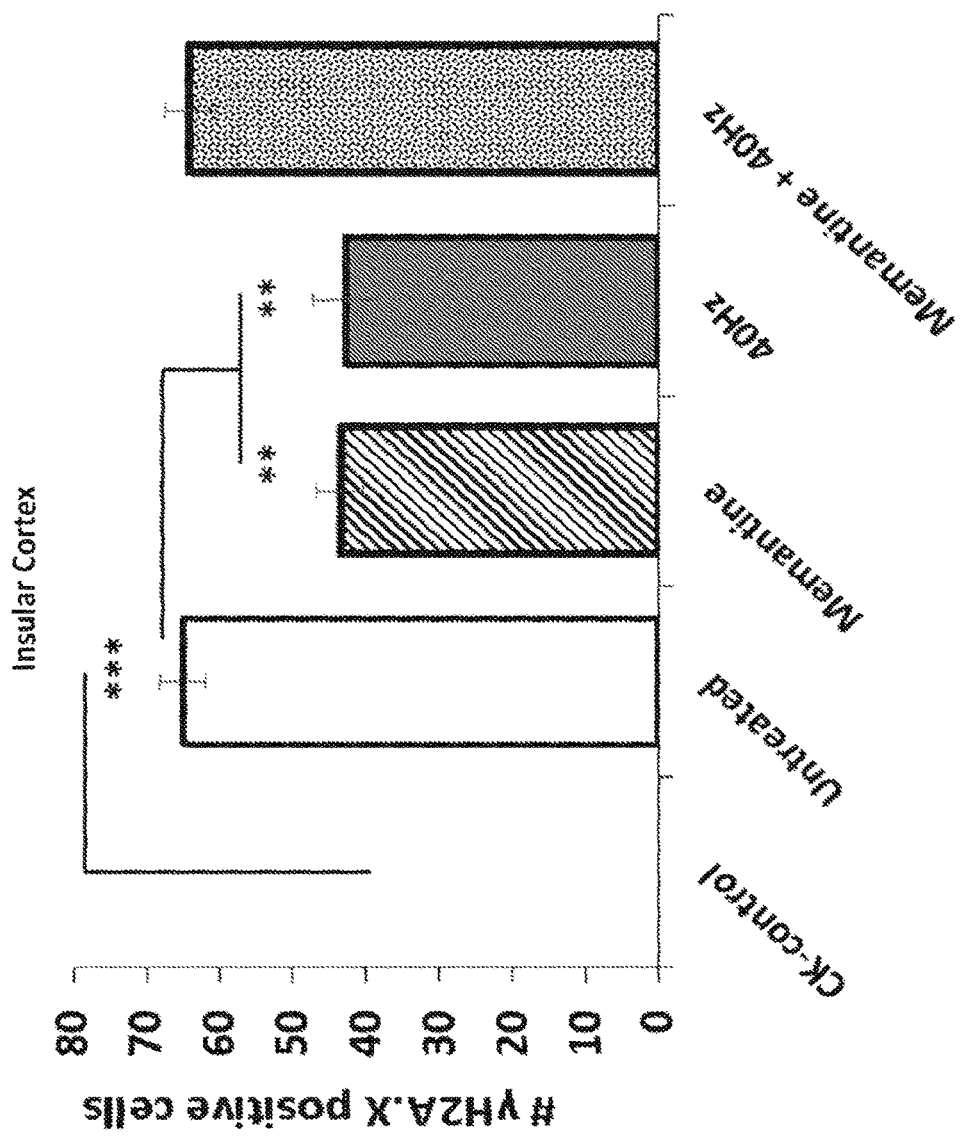
FIG. 105 is bar graph comparing the amount of insular cortex γH2AX-positive cells across the groups of subjects in FIG. 84 in accordance with some embodiments.

FIG. 105 is bar graph comparing the amount of $\gamma$H2AX-positive cells in CK-control mice, untreated CK-p25 Tg mice, CK-p25 Tg mice treated with memantine, CK-p25 Tg mice exposed to the 40-Hz light flicker in accordance with some embodiments, and CK-p25 Tg mice treated with both memantine and the 40-Hz light flicker. Cells positive for $\gamma$H2AX were non-existent in CK-control mice, but very high in untreated CK-p25 Tg mice, indicating high amounts of DSB and other DNA damage. Treatment with memantine reduced the amount of $\gamma$H2AX-positive cells in CK-p25 Tg mice compared to the untreated group. Exposure to the 40-Hz light flicker in accordance with some embodiments resulted in similar reductions of $\gamma$H2AX-positive cells in CK-p25 Tg mice. Thus, FIG. 105 illustrates how 40-Hz visual flicker treatment in accordance with some embodiments can reduce DNA damage in the insular cortex. However, combination of memantine and exposure to the 40-Hz light flicker significantly increased the number of $\gamma$H2AX-positive cells in CK-p25 Tg mice.

Figure 106:
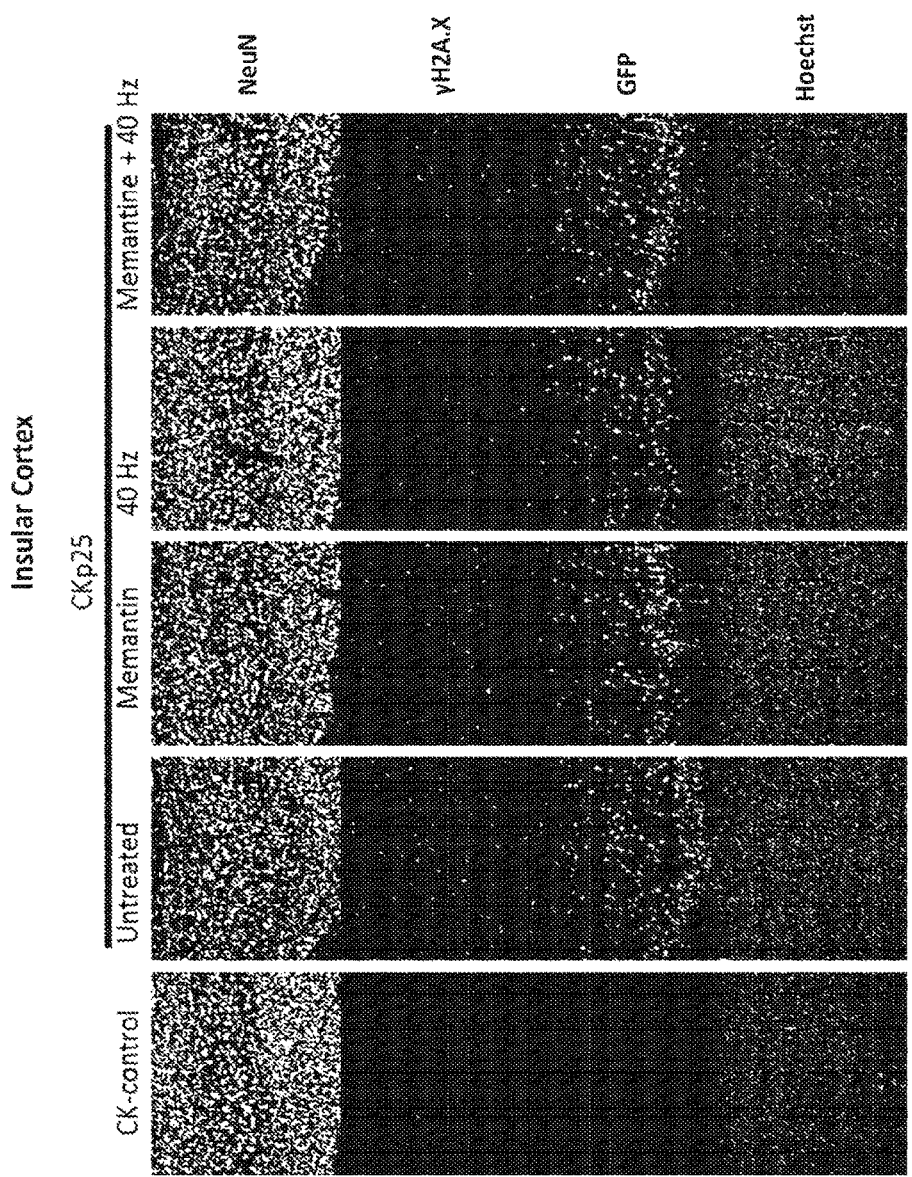
FIG. 106 is a series of images illustrating insular cortex samples representative of the groups of subjects in FIG. 84 in accordance with some embodiments.

FIG. 106 is a series of images illustrating insular cortex samples representative of subjects in each group labeled with NeuN (indicating neurons), $\gamma$H2AX (indicating DSB), GFP (indicating CK-p25), or Hoechst stain (indicating cortical cells).

Gamma exposure also reduced CKp-25-induced neuron loss and DNA damage in the hippocampus of subjects. FIG.

Figure 107:
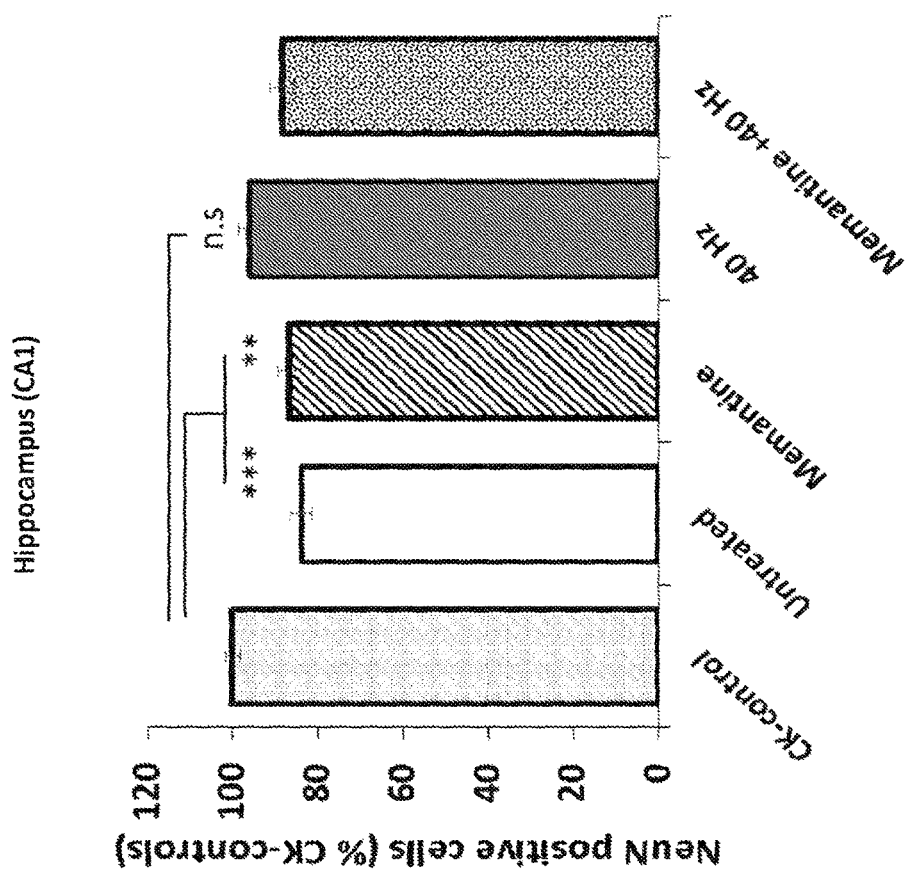
FIG. 107 is a bar graph comparing the amount of hippocampus NeuN-positive cells across the groups of subjects in FIG. 84 in accordance with some embodiments.

107 is a bar graph comparing the amount of NeuN-positive cells as a percentage of the NeuN-positive cells in CK-control mice for the CK-control mice, untreated CK-p25 Tg mice, CK-p25 Tg mice treated with memantine, CK-p25 Tg mice exposed to the 40-Hz light flicker in accordance with some embodiments, and CK-p25 Tg mice treated with both memantine and the 40-Hz light flicker. Thus, the percentage of the CK-control mice NeuN-positive cells are 100% in the CK-control mice, but closer to 80% in untreated CK-p25 Tg mice, corroborating neuronal loss in the CK-p25 Tg mouse model. Treatment with memantine with or without exposure to the 40-Hz light flicker prevented some neuronal loss in CK-p25 Tg mice compared to the untreated group, which prevented the least neuronal loss in CK-p25 Tg mice. Thus, FIG. 107 illustrates how 40-Hz visual flicker treatment in accordance with some embodiments can preserve neurons in the hippocampus.

Figure 108:
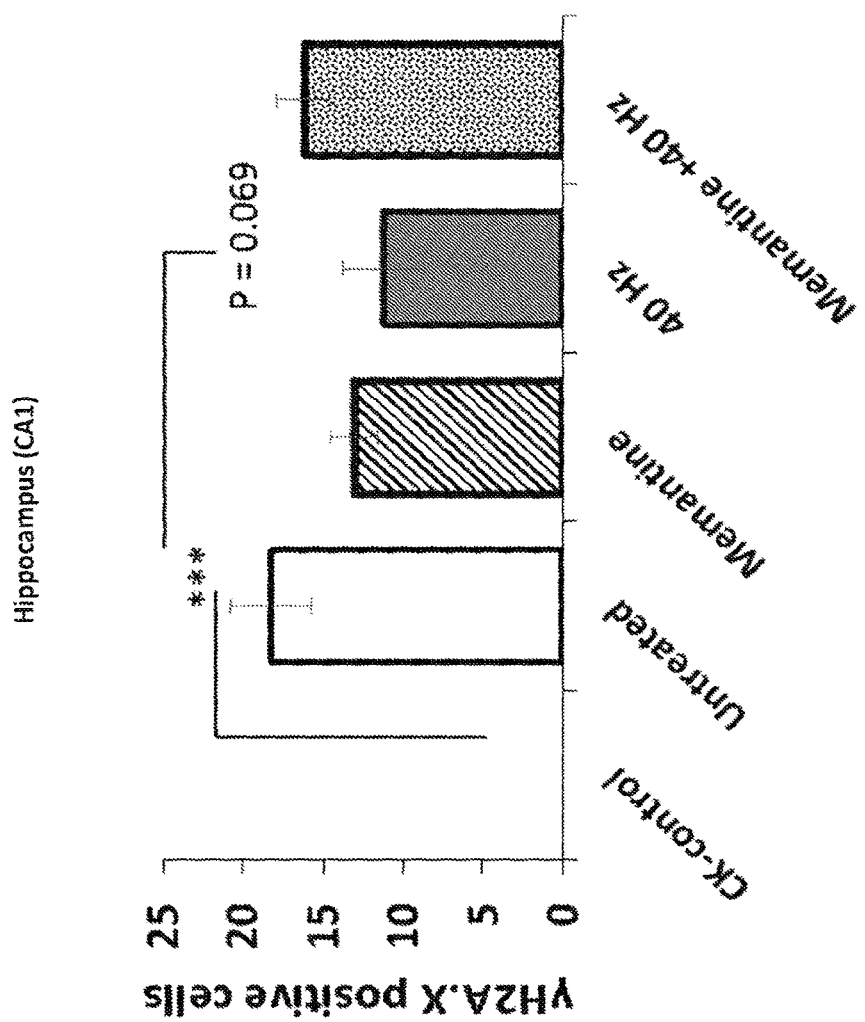
FIG. 108 is bar graph comparing the amount of hippocampus γH2AX-positive cells across the groups of subjects in FIG. 84 in accordance with some embodiments.

FIG. 108 is bar graph comparing the amount of γH2AX-positive cells in CK-control mice, untreated CK-p25 Tg mice, CK-p25 Tg mice treated with memantine, CK-p25 Tg mice exposed to the 40-Hz light flicker in accordance with some embodiments, and CK-p25 Tg mice treated with both memantine and the 40-Hz light flicker. Cells positive for γH2AX were non-existent in CK-control mice, but very high in untreated CK-p25 Tg mice, indicating high amounts of DSB and other DNA damage. Treatment with memantine reduced the amount of γH2AX-positive cells in CK-p25 Tg mice compared to the untreated group. Exposure to the 40-Hz light flicker in accordance with some embodiments resulted in better reductions of γH2AX-positive cells in CK-p25 Tg mice. Thus, FIG. 108 illustrates how 40-Hz visual flicker treatment in accordance with some embodiments can reduce DNA damage in the hippocampus. However, combination of memantine and exposure to the 40-Hz light flicker significantly increased the number of γH2AX-positive cells in CK-p25 Tg mice.

Figure 109:
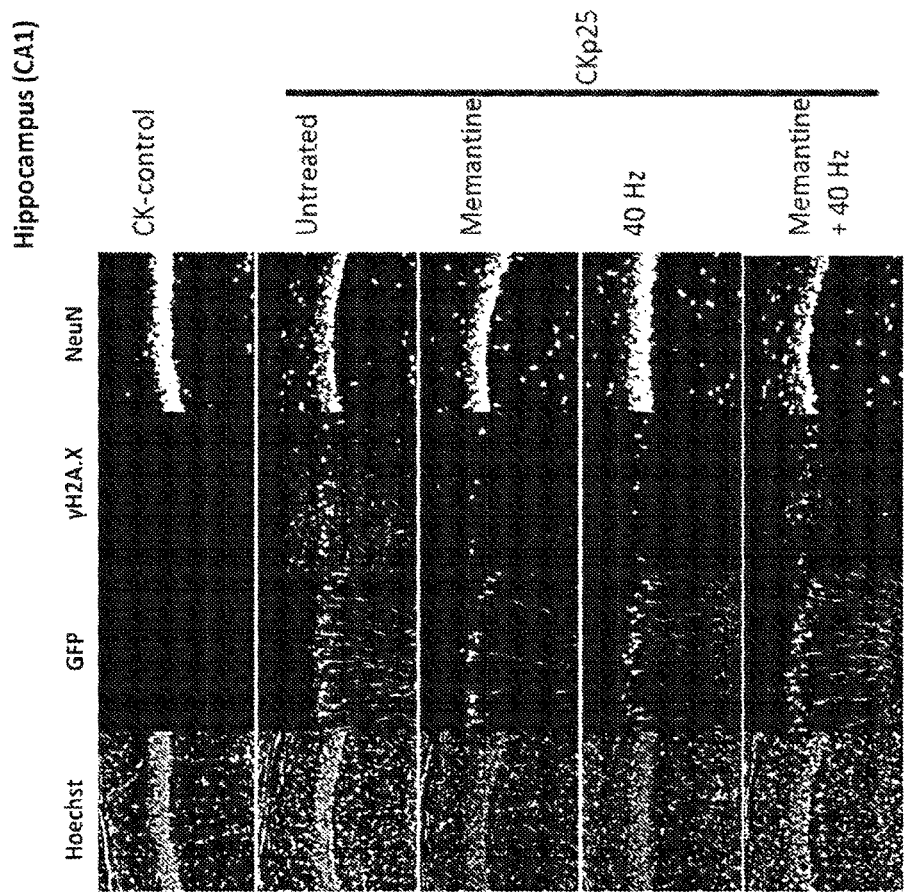
FIG. 109 is a series of images illustrating hippocampus samples representative of the groups of subjects in FIG. 84 in accordance with some embodiments.

FIG. 109 is a series of images illustrating hippocampus samples representative of subjects in each group labeled with Hoechst stain (indicating cortical cells), GFP (indicating CK-p25), γH2AX (indicating DSB), or NeuN (indicating neurons).

Gamma exposure and/or administration in accordance with some embodiments was shown to preserve synapses and/or reduce synaptic losses. Changes in synaptic connectivity may be quantified using specific markers for glutamatergic synapses (e.g., VGluT1, VGluT2, PSD95, and GluR2) and GABAergic synapses (e.g., GAD and VGAT).

Figure 110:
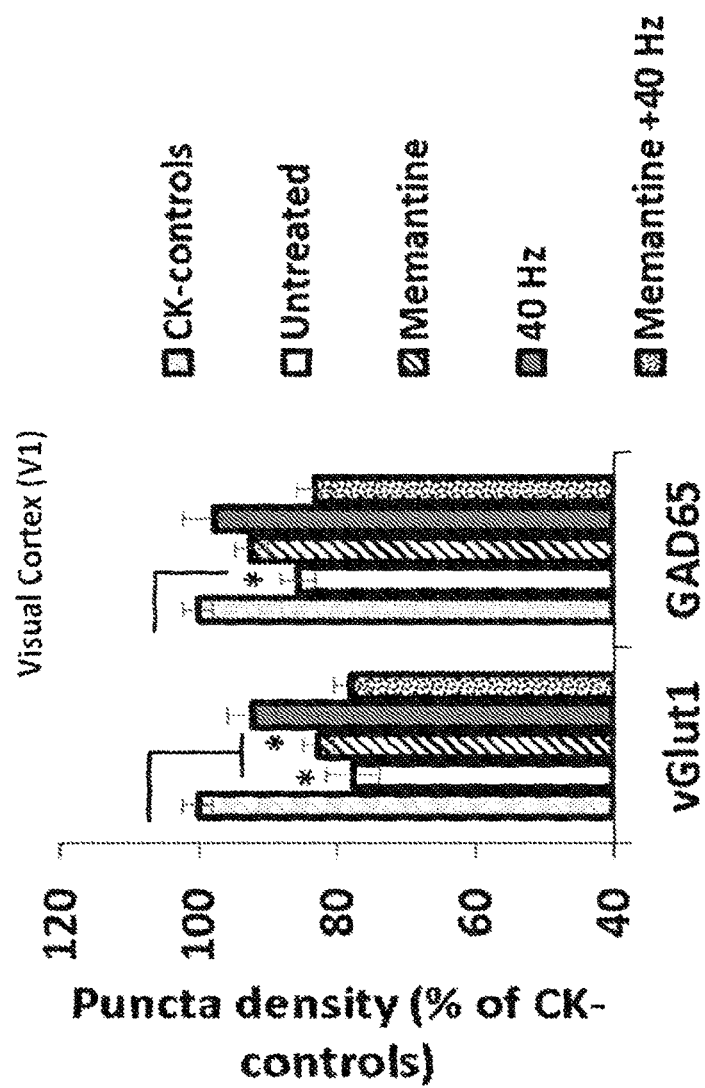
FIG. 110 is a bar graph comparing the visual cortex puncta density across the groups of subjects in FIG. 84 in accordance with some embodiments.

For example, gamma exposure reduced CKp-25-induced synaptic loss in the visual cortex of subjects. FIG. 110 is a bar graph comparing the puncta density of glutamatergic synapses (using VGluT1) and GABAergic synapses (using GAD65) as a percentage of the baseline synaptic puncta density in CK-control mice for the CK-control mice, untreated CK-p25 Tg mice, CK-p25 Tg mice treated with memantine, CK-p25 Tg mice exposed to the 40-Hz light flicker in accordance with some embodiments, and CK-p25 Tg mice treated with both memantine and the 40-Hz light flicker.

Figure 111:
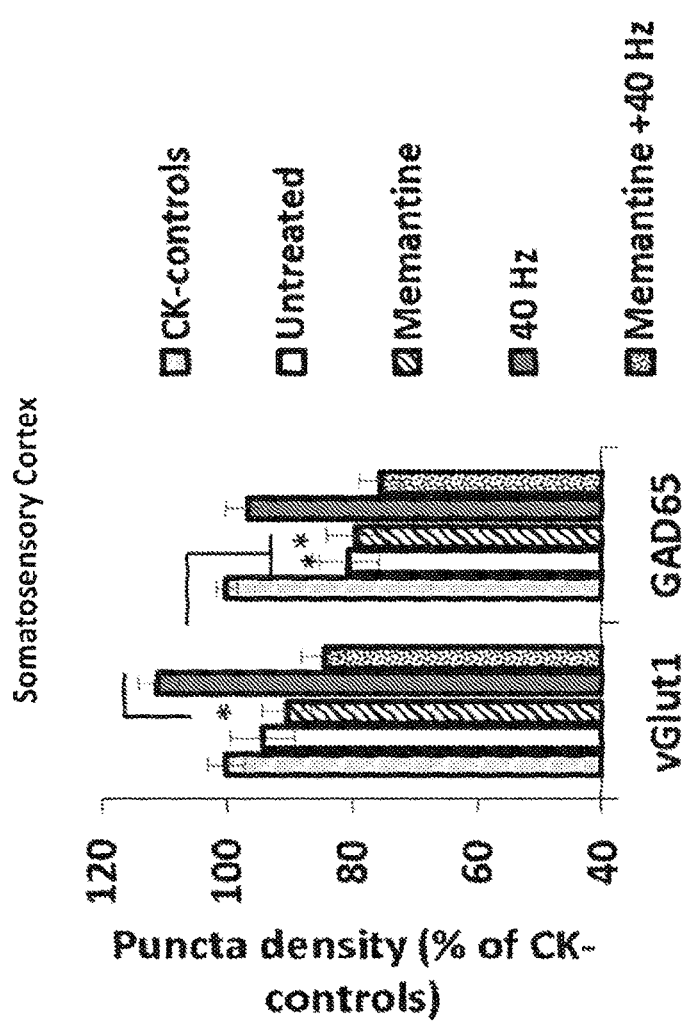
FIG. 111 is a bar graph comparing the somatosensory cortex puncta density across the groups of subjects in FIG. 84 in accordance with some embodiments.

Gamma exposure also reduced CKp-25-induced synaptic loss and even increased synaptic puncta density in the somatosensory cortex of subjects. FIG. 111 is a bar graph comparing the puncta density of glutamatergic synapses (using VGluT1) and GABAergic synapses (using GAD65) as a percentage of the baseline synaptic puncta density in CK-control mice for the CK-control mice, untreated CK-p25 Tg mice, CK-p25 Tg mice treated with memantine, CK-p25 Tg mice exposed to the 40-Hz light flicker in accordance with some embodiments, and CK-p25 Tg mice treated with both memantine and the 40-Hz light flicker.

Figure 112:
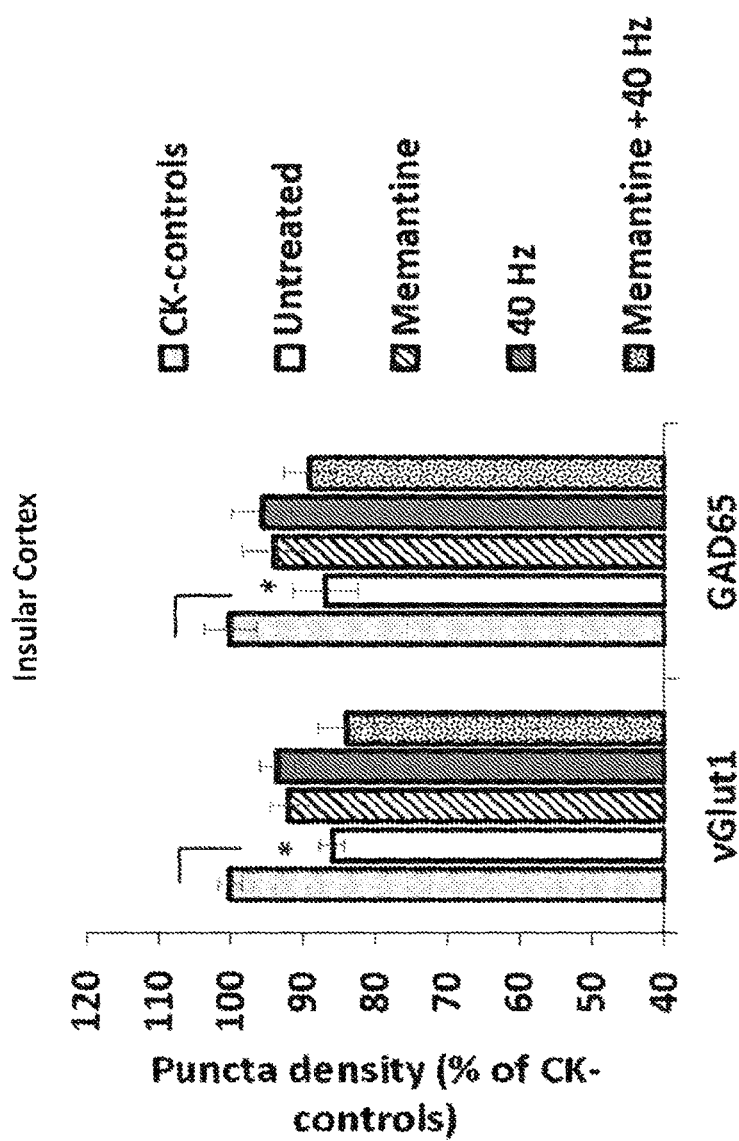
FIG. 112 is a bar graph comparing the insular cortex puncta density across the groups of subjects in FIG. 84 in accordance with some embodiments.

Gamma exposure also reduced CKp-25-induced synaptic loss in the insular cortex of subjects. FIG. 112 is a bar graph comparing the puncta density of glutamatergic synapses (using VGluT1) and GABAergic synapses (using GAD65) as a percentage of the baseline synaptic puncta density in CK-control mice for the CK-control mice, untreated CK-p25 Tg mice, CK-p25 Tg mice treated with memantine, CK-p25 Tg mice exposed to the 40-Hz light flicker in accordance with some embodiments, and CK-p25 Tg mice treated with both memantine and the 40-Hz light flicker.

FIG. 113A is an image illustrating a representative sample with a Hoechst stain (indicating cortical cells). FIG. 113B is an image illustrating VGluT1 (indicating glutamatergic synapses) in the representative sample. FIG. 113C is an image illustrating GAD65 (indicating GABAergic synapses) in the representative sample. FIG. 113D is a merged image illustrating Hoechst stain, VGluT1, and GAD65 in the representative sample. FIGS. 113E and 113F illustrate a method of puncta quantification using GAD65. FIG. 113E is a binary image of the GAD65 converted from FIG. 113C. ImageJ software (available from the U.S. National Institutes of Health, Bethesda, Md.) was used to quantify the binary image, as shown in FIG. 113F.

A study was conducted to examine whether gamma exposure and/or administration in accordance with some embodiments affects brain vasculature. Mice were placed in a dark box and exposed to either 40-Hz light-emitting diode (LED) flicker or constant light off (dark) for one hour. Following stimulation, the mice were sacrificed and perfused. Brain sections were stained with lectin linked to a fluorophore to fluorescently tag blood vessels. Using confocal imaging, changes in vasculature size (i.e., blood vessel diameter) were measured. Vasodilation was observed following one hour of 40-Hz LED flicker.

FIG. 128A is a series of representative immunofluorescence images illustrating enlarged vasculature in the visual cortex in accordance with some embodiments. FIG. 128B is a bar graph depicting blood vessel diameter in the visual cortex and illustrating an increase in blood vessel diameter following gamma exposure in accordance with some embodiments.

Thus, gamma exposure and/or administration was demonstrated to provide anatomical (e.g., prevention and/or reduction of brain weight loss and enlargement of vasculature), morphology (e.g., prevention and/or reduction of aberrant ventricle expansion and cortical layer thickness loss), cellular (e.g., prevention and/or reduction of neuronal loss), and molecular (e.g., prevention and/or reduction of DNA damage and synaptic loss) benefits.

Furthermore, gamma exposure and/or administration was shown to be neuroprotective. Following gamma treatment, the CK-p25 Tg mouse model—which otherwise exhibits increased Aβ peptide levels, profound neuronal loss, DNA damage, synaptic loss, tau hyper-phosphorylation, long-term potentiation deficits, and severe cognitive/memory impairment—showed relative preservation of neuronal structure and/or function (e.g., maintenance/prevention of disease measures and/or reduced/slowed disease progression) and, in some cases, suggested improvement of neuronal structure and/or function.

Auditory Stimulation at Gamma Frequency Non-Invasively Induced Microglial Changes in Subjects.

In some embodiments, gamma exposure and/or administration includes auditory stimulation. The auditory stimulation may include sound pulses or clicks. A sound stimulus may include a click train of about 35 sound pulses or clicks per second (clicks/s) to about 45 clicks/s. FIG. 114 is a stimulus diagram illustrating a click-train stimulus in accordance with some embodiments. The stimulus in FIG. 114 has a click frequency of 40 clicks/s, with 25 ms between each click, and each click having a duration of 1 ms.

In some embodiments, a sound stimulus has a frequency of about 10 Hz to about 100 kHz, about 12 Hz to about 28 kHz, about 20 Hz to about 20 kHz, and/or about 2 kHz to about 5 kHz. For example, each sound pulse or click in a click train may have a frequency of about 10 kHz.

In some embodiments, a sound stimulus has a sound pressure level of about 0 dB to about 85 dB, about 30 dB to about 70 dB, and/or about 60 dB to about 65 dB. For example, each sound pulse or click in a click train may have a sound pressure level of about 65 dB.

Auditory gamma stimulation was shown to induce microglial cell-state changes in subjects according to some embodiments. A study was conducted to examine whether auditory gamma exposure and/or administration induces microglial activation in the auditory cortex of subjects in accordance with some embodiments. A 40-Hz click-train stimulus similar to FIG. 114 was used, the stimulus having a click frequency of about 40 clicks/s with each click having a duration of about 1 ms at a tone of about 10 kHz and about 60-65 dB. The click-train stimulus was hypothesized to entrain PV+ interneurons in the auditory cortex, thereby exogenously regulating gamma oscillations in the auditory cortex.

Figure 115:
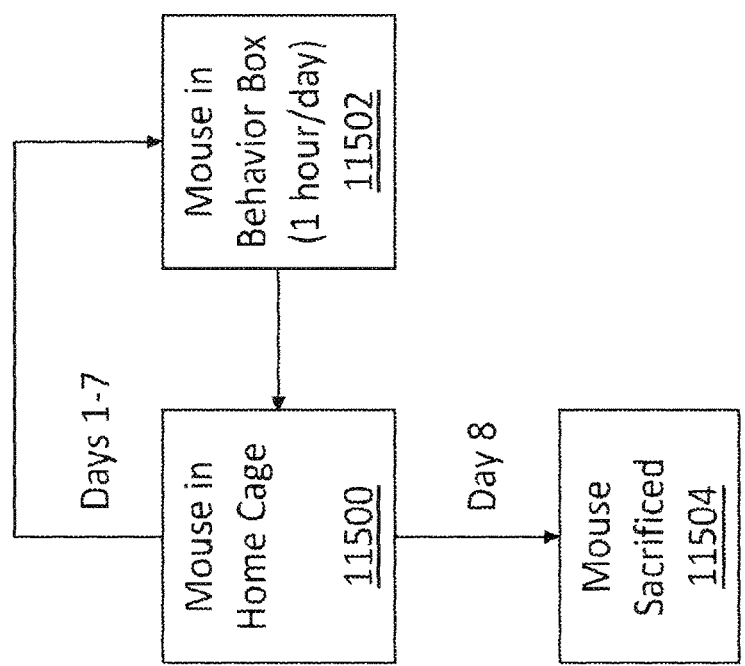
FIG. 115 is a flow diagram illustrating a study conducted to examine whether auditory gamma exposure and/or administration in accordance with some embodiments induces microglial activation in the auditory cortices of subjects.

FIG. 115 is a flow diagram illustrating the study. In FIG. 115, WT mice were housed in their home cage 11500. For one hour per day, for seven consecutive days (Days 1-7), the mice were moved to a behavior box (i.e., a soundproof chamber) 11502. While in the behavior box 11502, a first group of mice was exposed to silence, and a second group of mice was exposed to the click-train stimulus in accordance with some embodiments. After each hour in the behavior box 11502, the mice were returned to their home cage 11500. On Day 8, the mice were sacrificed for tissue collection and staining 11504.

Figures 116A, 116B, 116C:
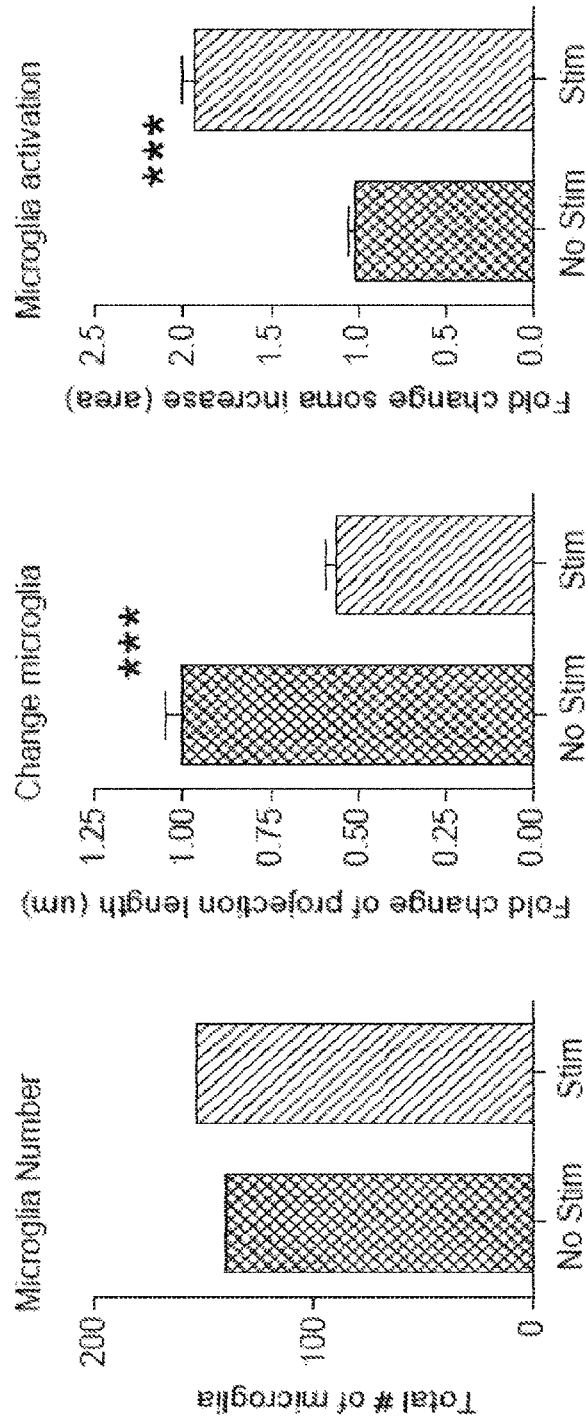
FIG. 116A is a bar graph depicting the average number of microglia in the auditory cortices of subjects in accordance with some embodiments.
FIG. 116B is a bar graph depicting fold change of microglial projection length in the auditory cortices of subjects in accordance with some embodiments.
FIG. 116C is a bar graph depicting the average fold change of soma size of microglia in the auditory cortices of subjects in accordance with some embodiments.

The tissue was examined for a level of microglial cells, morphologic changes in the microglial cells, and microglial activation, as indicated by soma size. FIG. 116A is a bar graph depicting the average number of microglia in mice exposed to silence (No Stim) compared to mice exposed to the click-train stimulus (Stim). More microglial cells were observed in the mice exposed to the click-train stimulus in accordance with some embodiments. FIG. 116B is a bar graph depicting the average fold change of projection length of microglia in mice exposed to silence (No Stim) compared to mice exposed to the click-train stimulus (Stim). The average fold change of the length of the microglia projections was significantly less in the mice exposed to the click-train stimulus in accordance with some embodiments. FIG. 116C is a bar graph depicting the average fold change of soma size of microglia in mice exposed to silence (No Stim) compared to mice exposed to the click-train stimulus (Stim). The average fold change of the soma size of the microglia was significantly greater in the mice exposed to the click-train stimulus, indicating greater microglial activation in accordance with some embodiments.

Figures 117A, 117B:
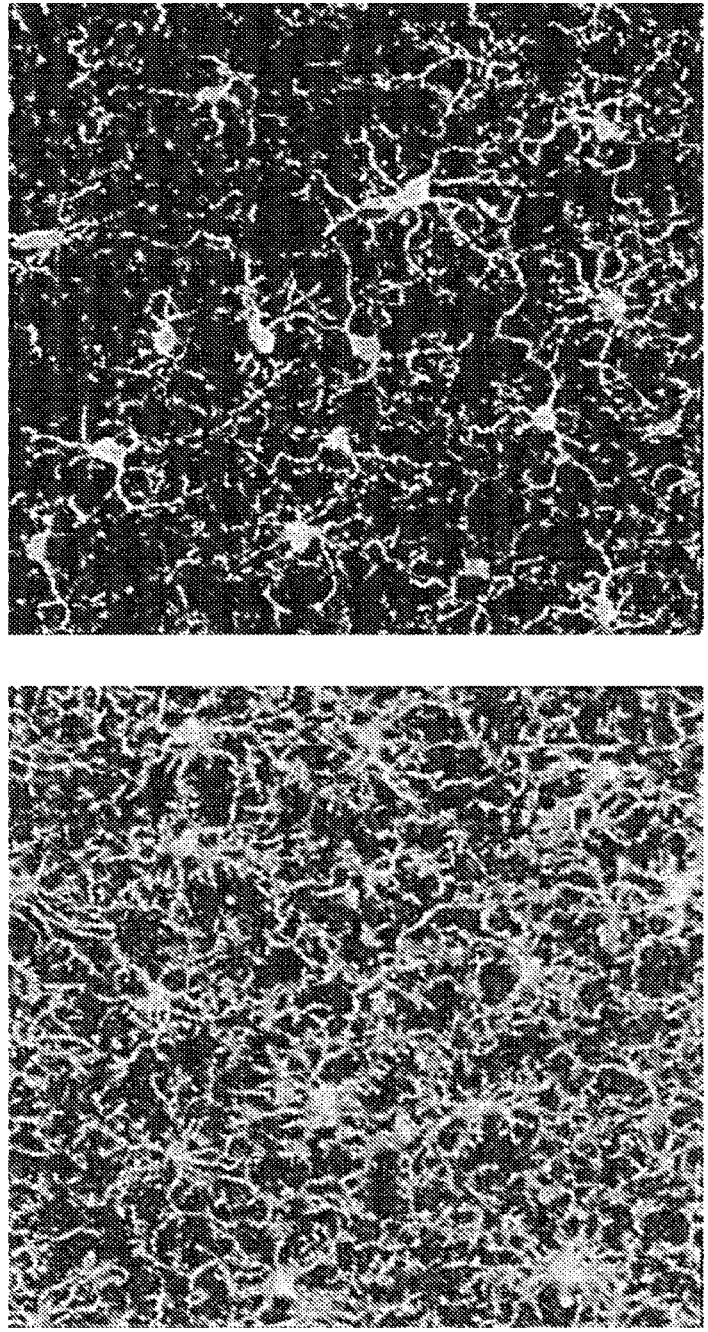
FIGS. 117A and 117B are representative images of microglia in the auditory cortices of subjects in accordance with some embodiments.

FIG. 117A is a representative image of the microglial cells in mice exposed to silence. FIG. 117B is a representative image of the microglial cells in mice exposed to the click-train stimulus in accordance with some embodiments. The projections and soma of the microglia are visibly different between FIG. 117A and FIG. 117B in accordance with some embodiments. FIG. 118A is a magnified image from FIG. 117B of a microglial cell from a mouse exposed to the click-train stimulus in accordance with some embodiments. One projection 11800 of the microglial cell has been highlighted. Meanwhile, FIG. 118B is a magnified image from FIG. 117A of a microglial cell from a mouse exposed to silence. One projection 11802 of the microglial cell has been highlighted to show its length relative to the comparatively shorter projection 11800 of the microglial cell from a mouse exposed to the click-train stimulus in accordance with some embodiments.

Figure 119B:
Figure 119A:
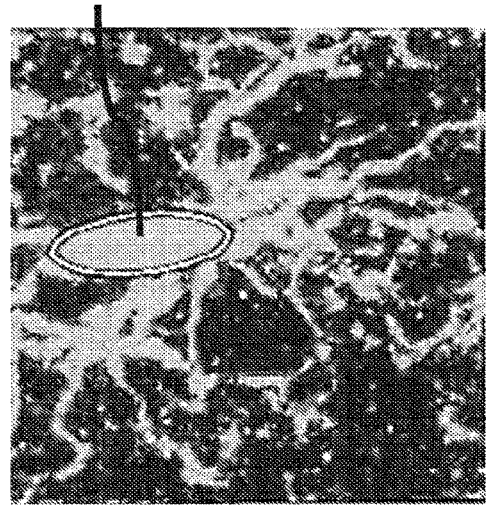

FIG. 119A is a magnified image from FIG. 117B of a microglial cell from a mouse exposed to the click-train stimulus in accordance with some embodiments. The area of soma 11900 of the microglial cell has been highlighted. Meanwhile, FIG. 119B is a magnified image from FIG. 117A of a microglial cell from a mouse exposed to silence. The area of soma 11902 of the microglial cell has been highlighted to show its size relative to the comparatively larger soma 11900 of the microglial cell from a mouse exposed to the click-train stimulus, thus indicating greater microglial activation in accordance with some embodiments.

Auditory gamma stimulation was shown to induce microglial activation-like phenotype in subjects according to some embodiments. The study of FIG. 115 was repeated with 5XFAD Tg mice in accordance with some embodiments. The tissue was examined for a level of microglial cells, morphologic changes in the microglial cells (e.g., projection length), and microglial activation (e.g., as indicated by soma size). FIG. 120A is a bar graph depicting the average number of microglia per field of image in mice exposed to silence (No Stim) compared to mice exposed to the click-train stimulus (Stim). Significantly more microglial cells were observed in the mice exposed to the click-train stimulus in accordance with some embodiments. FIG. 120B is a bar graph depicting the average fold change in soma size of microglia in mice exposed to silence (No Stim) compared to mice exposed to the click-train stimulus (Stim). The average fold change in soma size was significantly greater in the mice exposed to the click-train stimulus, indicating greater microglial activation in accordance with some embodiments. FIG. 120C is a bar graph depicting the average fold change in projection length of microglia in mice exposed to silence (No Stim) compared to mice exposed to the click-train stimulus (Stim). The average fold change in projection length was significantly less in the mice exposed to the click-train stimulus in accordance with some embodiments.

FIG. 121A is a representative image of the microglial cells in mice exposed to silence. FIG. 121B is a representative image of the microglial cells in mice exposed to the click-train stimulus in accordance with some embodiments. The projections and soma of the microglia are visibly different between FIG. 121A and FIG. 121B with comparatively shorter projection length and larger soma size in the microglia from a mouse exposed to the click-train stimulus in accordance with some embodiments.

Auditory Stimulation at Gamma Frequency Non-Invasively Reduces Aβ in the Auditory Cortex and Hippocampus of Subjects.

Auditory gamma stimulation was shown to decrease levels of Aβ in subjects according to some embodiments. The study of FIG. 115 was repeated with six-month 5XFAD Tg mice in accordance with some embodiments. On Day 8 the auditory cortex and hippocampus were dissected. ELISA was used to measure levels of soluble and insoluble Aβ isoforms, including isoform Aβ$_{1-40}$ peptide and isoform Aβ$_{1-42}$ peptide. Insoluble Aβ was treated with 5M guanidine-HCl for three hours in order to solubilize plaques.

Auditory gamma stimulation was shown to decrease levels of soluble Aβ in subjects according to some embodiments. FIG. 122A is a bar graph depicting much smaller levels of soluble isoform Aβ$_{1-42}$ peptide in the auditory cortex of mice exposed to the click-train stimulus (Stim) relative to levels of soluble isoform Aβ$_{1-42}$ peptide in the auditory cortex of mice exposed to silence (No Stim) in accordance with some embodiments.

FIG. 122B is a bar graph depicting smaller levels of soluble isoform Aβ$_{1-40}$ peptide in the auditory cortex of mice exposed to the click-train stimulus (Stim) relative to levels of soluble isoform Aβ$_{1-40}$ peptide in the auditory cortex of mice exposed to silence (No Stim) in accordance with some embodiments.

FIG. 122C is a bar graph depicting much smaller levels of soluble isoform Aβ$_{1-42}$ peptide in the hippocampus of mice exposed to the click-train stimulus (Stim) relative to levels of soluble isoform Aβ$_{1-42}$ peptide in the hippocampus of mice exposed to silence (No Stim) in accordance with some embodiments.

FIG. 122D is a bar graph depicting smaller levels of soluble isoform Aβ$_{1-40}$ peptide in the hippocampus of mice exposed to the click-train stimulus (Stim) relative to levels of soluble isoform Aβ$_{1-40}$ peptide in the hippocampus of mice exposed to silence (No Stim) in accordance with some embodiments.

Auditory gamma stimulation was shown to decrease levels of insoluble Aβ in subjects according to some embodiments. FIG. 123A is a bar graph depicting much smaller levels of insoluble isoform Aβ$_{1-42}$ peptide in the auditory cortex of mice exposed to the click-train stimulus (Stim) relative to levels of insoluble isoform Aβ$_{1-42}$ peptide in the auditory cortex of mice exposed to silence (No Stim) in accordance with some embodiments.

FIG. 123B is a bar graph depicting smaller levels of insoluble isoform Aβ$_{1-40}$ peptide in the auditory cortex of mice exposed to the click-train stimulus (Stim) relative to levels of insoluble isoform Aβ$_{1-40}$ peptide in the auditory cortex of mice exposed to silence (No Stim) in accordance with some embodiments.

FIG. 123C is a bar graph depicting much smaller levels of insoluble isoform Aβ$_{1-42}$ peptide in the hippocampus of mice exposed to the click-train stimulus (Stim) relative to levels of insoluble isoform Aβ$_{1-42}$ peptide in the hippocampus of mice exposed to silence (No Stim) in accordance with some embodiments.

FIG. 123D is a bar graph depicting smaller levels of insoluble isoform Aβ$_{1-40}$ peptide in the hippocampus of mice exposed to the click-train stimulus (Stim) relative to levels of insoluble isoform Aβ$_{1-40}$ peptide in the hippocampus of mice exposed to silence (No Stim) in accordance with some embodiments.

Figure 124A:
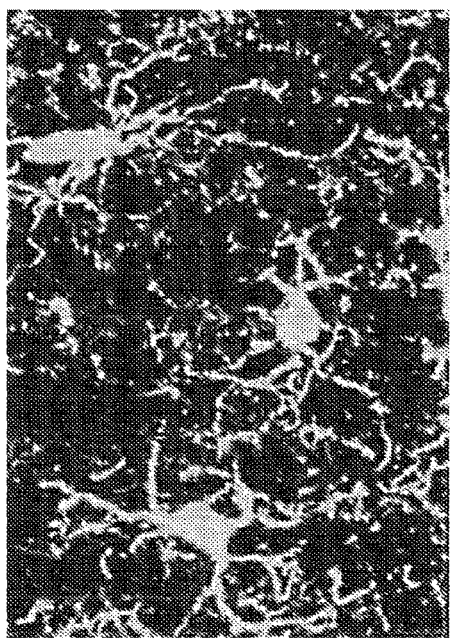
Figure 124B:
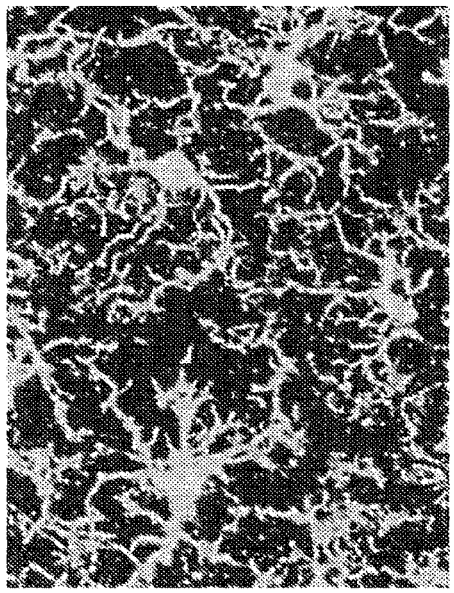

FIG. 124A is a representative image of the microglial cells in 5XFAD mice exposed to the click-train stimulus in accordance with some embodiments. FIG. 124B is a representative image of the microglial cells in 5XFAD mice exposed to silence. The projections and soma of the microglia are visibly different between FIG. 124A and FIG. 124B with comparatively shorter projection length and larger soma size in the microglia from a 5XFAD mouse exposed to the click-train stimulus in accordance with some embodiments.

Figure 124C:
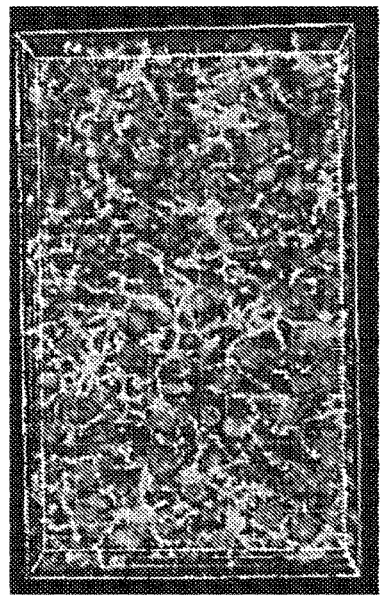
Figure 124D:
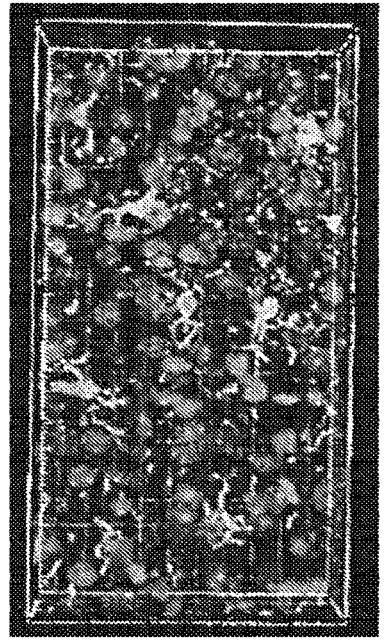

FIG. 124C is a representative image of the microglial cells in WT mice exposed to silence. FIG. 124D is a representative image of the microglial cells in WT mice exposed to the click-train stimulus in accordance with some embodiments. The projections and soma of the microglia are visibly different between FIG. 124C and FIG. 124D with comparatively shorter projection length and larger soma size in the microglia from a WT mouse exposed to the click-train stimulus in accordance with some embodiments.

Thus, according to some embodiments, non-invasive auditory stimulation at a gamma frequency promoted gamma oscillations and a profound reduction in AD-associated pathology in the auditory cortex and the hippocampus.

Auditory Stimulation at Gamma Frequency had Positive Effects on Subject Behavior.

Auditory gamma stimulation was shown to improve recognition in subjects according to some embodiments. FIG. 125A is a flow diagram illustrating a novel object recognition test performed using 5XFAD mice exposed to the click-train stimulus in accordance with some embodiments and 5XFAD mice exposed to silence. The test assesses an ability of a subject to recognize novel from familiar objects (i.e., recognition memory) based on the tendency of rodents to spend more time exploring a novel object than a familiar object. A recognition index RI was used to compare the subjects:

$$RI = \frac{\text{(time with new object)}}{\text{(time with new object)} + \text{(time with familiar object)}} \quad (15)$$

In FIG. 125A, 5XFAD mice were habituated to an environment 12500. At time T1, two novel objects were introduced 12502. Then at time T2, following one hour of rest, the mice were exposed to one familiar object and one novel object 12504, 12506 for one hour. FIG. 125B is a bar graph depicting the results of the novel object recognition test in which the mice exposed to the click-train stimulus had higher RI, indicating that the mice exposed to the click-train stimulus spent much more time with the new object than the familiar object due to better recognition memory in accordance with some embodiments.

Auditory gamma stimulation was shown to improve discrimination in subjects according to some embodiments. FIG. 126A is a flow diagram illustrating a novel object location test performed using 5XFAD mice exposed to the click-train stimulus in accordance with some embodiments and 5XFAD mice exposed to silence. The test assesses spatial memory and/or discrimination based on the tendency of rodents to spend more time exploring a newly located object. A recognition index RI was used to compare the subjects:

$$RI = \frac{\text{(time with newly located object)}}{\text{(time with newly located object)} + \text{(time with previously located object)}} \quad (16)$$

In FIG. 126A, 5XFAD mice were habituated to an environment 12600. At time T1, two objects were introduced at first locations 12602. Then at time T2, following one hour of rest, the mice were exposed to one of the objects at its first location and the other object located at a new second location 12604, 12606 for one hour. FIG. 126B is a bar graph depicting the results of the novel object location test in which the mice exposed to the click-train stimulus had higher RI, indicating that the mice exposed to the click-train stimulus spent much more time with the object that moved than the object that stayed in the same location due to better spatial memory and/or discrimination in accordance with some embodiments.

Auditory gamma stimulation was shown to improve spatial memory in subjects according to some embodiments. A Morris water maze test was performed using 5XFAD mice exposed to the click-train stimulus in accordance with some embodiments and 5XFAD mice exposed to silence. As described above, the test assesses spatial and/or reference memory based on distal cues used by subjects to navigate from start locations around the perimeter of an open swimming arena to locate a submerged escape platform. The test was assessed across repeated trials, and spatial and/or reference memory was determined by preference for the platform area when the platform is absent.

FIG. 127A is a plot depicting average latency to find the platform by the mice exposed to silence (No Stim) and the mice exposed to the click-train stimulus (Stim) on each day in accordance with some embodiments. FIG. 127B is a bar graph depicting the results of a probe test in which the platform was removed. The mice exposed to the click-train stimulus spent more time searching for the missing platform in the target quadrant than did the mice exposed to silence, thus indicating that the mice exposed to the click-train stimulus had better spatial and/or reference memory in accordance with some embodiments.

Thus, according to some embodiments, non-invasive auditory stimulation at a gamma frequency induced microglial activation, reduced AD-associated (e.g., Aβ) pathology, and significantly ameliorated cognitive deficits (in, e.g., recognition, discrimination, and spatial memory). With easy and accessible options for administration (including self-administration), auditory gamma stimulation has the potential for vast commercial applications, including but not limited to applications for home or mobile use (e.g., using noise-canceling headphones). In addition to self-administration potential, clinicians and/or researchers may administer a stimulation paradigm to subjects ranging from animal models to human patients in accordance with some embodiments. Clinicians and/or researchers may find it useful to combine auditory gamma stimulation with various forms of monitoring. For example, a therapeutic session may include locating a subject in a sound proof room or supplying the subject with noise-canceling headphones or another device to limit interference. The subject may be monitored during the stimulation using, for example, functional magnetic resonance imaging (fMRI) for any beneficial brain-state changes.

Experimental Methods

Animals

All animal work was approved by the Committee for Animal Care of the Division of Comparative Medicine (Massachusetts Institute of Technology, Cambridge, Mass.). Adult (three-month-old) male double Tg 5XFAD Cre mice were produced by crossing 5XFAD Tg mice with the Tg PV or CW2 promoter driven Cre line. Adult (5-month-old) male and female APP/PS1 mice were gifted from the Tonegawa Laboratory (Massachusetts Institute of Technology, Cambridge, Mass.). Adult (4-month-old) male TauP301S mice were obtained from the Jackson Laboratory. Aged WT mice (8-month-old, C57Bl/6) were obtained from the Jackson Laboratory (Bar Harbor, Me.). Mice were housed in groups of 3-5 on a standard 12 hours light/12 hours dark cycle, and all experiments were performed during the light cycle. Food and water were provided ad libitum unless otherwise noted. Littermates were randomly assigned to each condition by the experimenter. Experimenter was blind to animal genotypes during tissue processing and electrophysiological recording and analysis. No animals were excluded from analysis.

AAV Vectors

Adeno-associated viral particles of serotype 5 were obtained from the Vector Core Facility (The University of North Carolina, Chapel Hill, N.C.). The AAV5 virus contained ChR2 fused to enhanced yellow fluorescent protein (EYFP) in a double-floxed, inverted, open-reading-frame (DIO) driven by the EF1α promoter (see, e.g., FIG. 9). An AAV DIO EYFP construct was used as a control.

Surgical Procedures

Three-month-old 5XFAD/PV-Cre or CW2 mice were anesthetized with an intraperitoneal injection of a mixture of ketamine (1.1 mg kg$^{-1}$) and xylazine (0.16 mg kg$^{-1}$). A small craniotomy was made 2.0 mm posterior to bregma and 1.8 mm lateral to the midline on the left side. Virus was delivered through a small durotomy by a glass micropipette attached to a Quintessential Stereotaxic Injector™ (available from Stoelting Co., Wood Dale, Ill.). The glass micropipette was lowered to 1.2 mm below the brain surface. A bolus of 1 μl of virus (AAV DIO ChR2-EYFP or AAV DIO EYFP; 2×1012 viral molecules per ml) was injected into the CA1 region of the hippocampus at 0.075 μl min$^{-1}$. The pipette remained in place for 5 min following the injection before being retracted from the brain. A unilateral optical fiber implant (300 μm core diameter, available from Thorlabs Inc., Newton, N.J.) was lowered to 0.9 mm below the brain surface about the injection site. Two small screws anchored at the anterior and posterior edges of the surgical site were bound with dental glue to secure the implant in place. For electrophysiological recordings adult (three-month-old) male 5XFAD/PV-Cre bi-transgenic mice and 5XFAD negative littermates (for CA1 recordings), or 5XFAD and their WT littermates (for visual cortex recordings) mice were anesthetized using isoflurane and placed in a stereotactic frame. The scalp was shaved, ophthalmic ointment (e.g., Puralube® Vet Ointment (Dechra Pharmaceuticals PLC, Northwich, United Kingdom)) was applied to the eyes, and Betadine® antiseptic (available from Purdue Products L.P., Stamford, Conn.) and 70% ethanol were used to sterilize the surgical area. For CA1 recordings, a craniotomy (in mm, from bregma: −2 A/P, 1.8 M/L) was opened to deliver 1 μL of virus to CA1 (as described above). The target craniotomy site for LFP recordings was marked on the skull (in mm, from bregma: −3.23 A/P, 0.98 M/L for CA1 and 2.8 A/P, 2.5 M/L for visual cortex), three self-tapping screws (e.g., F000CE094, available from Morris Precision Screws and Parts, Southbridge, Mass.) were attached to the skull, and a custom stainless steel head plate was affixed using dental cement (e.g., C&B Metabond®, available from Parkell Inc., Edgewood, N.Y.). On the day of the first recording session, a dental drill was used to open the LFP craniotomies (e.g., 300-400 μm diameter) by first thinning the skull until approximately 100 μm thick, and then using a 30 gauge needle to make a small aperture. The craniotomy was then sealed with a sterile silicone elastomer (e.g., Kwik-Sil™ adhesive, available from World Precision Instruments, Inc., Sarasota, Fla.) until recording that day and in between recording sessions.

Optogenetic Stimulation Protocol

Two to four weeks following virus injection and implant placement, which provides time for the mice to recover and undergo behavior training for animals used for electrophysiology, and the virus to express in the neurons, hippocampal CA1 neurons were optogenetically manipulated. A 200 mW 4793 nm DPSS laser was connected to a patch cord with a fiber channel/physical contact connector at each end. During the experiment, 1 mW (measured from the end of the fiber) of optical stimulation was delivered for one hour. For molecular and biochemical analyses, each animal received one of three stimulation protocols: 8 Hz, 40 Hz, or random stimulation (light pulses were delivered with a random interval determined by a Poisson process with an average frequency of 40 Hz) or for electrophysiological recordings each animal received all stimulation conditions interleaved during recordings.

Visual Stimulation Protocol

Fifteen minutes prior to the experiment 5XFAD mice were treated with saline (Control) or picrotoxin (0.18 mg/kg). For molecular and biochemical analyses mice were then placed in a dark chamber illuminated by an LED bulb and exposed to one of five stimulation conditions: dark, light, 20-Hz flicker, 40-Hz flicker, or 80-Hz flicker (12.5 ms light on, 12.5 ms light off) for one hour (see, e.g., FIG. 43A). For electrophysiological recordings each animal received dark, light, 40-Hz flicker, or random (light pulses were delivered with a random interval determined by a Poisson process with an average interval of 40 Hz) stimulation conditions interleaved in 10 s blocks during recordings.

Behavior Training and Virtual Reality Environment (VR) for Electrophysiology

For CA1 recordings, headfixed animals ran on an 8" spherical treadmill supported by an air cushion through a virtual reality environment, as described in Harvey et al. The motion of the spherical treadmill was measured by an optical mouse and fed into virtual reality software, running in the MATLAB® computing environment (software version 2013b, available from MathWorks, Natick, Mass.). The virtual environment consisted of a linear track with two small enclosures at the ends where the animal could turn. Animals were rewarded with sweetened condensed milk (diluted 1:2 in water) at each end of the track for alternating visits to each end of the track. Animals learned to run on the virtual linear track over approximately one week. The animals were left to recover from the surgery for one week, and habituated to handling for one to two days before behavioral training began. To learn to maneuver on the treadmill and get comfortable in the testing environment, on the first two days of training the animals were placed on the spherical treadmill with the virtual reality system off and were rewarded with undiluted sweetened condensed milk. On the second day of training on the spherical treadmill, animals' food was restricted to motivate them to run. Animals were restricted to no more than 85% of their baseline weight and typically weighed over 88% of their baseline weight. From the third day until the end of training (typically 5-seven days) the animals were placed on the treadmill for increasing amounts of time (30 min to 2 hours) running in the VR linear track. Animals were rewarded with diluted (1:2) sweetened condensed milk at the end of the linear track after traversing the length of the track. Between recording sessions, animals were given refresher training sessions to maintain behavioral performance. For visual cortex recordings, animals ran on the spherical treadmill while exposed to dark, light, or light flickering conditions (described below in data acquisition). Prior to recordings animals learned to maneuver on the treadmill and get comfortable in the testing environment by being placed on the spherical treadmill (with the virtual reality system off) and receiving reward of undiluted sweetened condensed milk.

Electrophysiology Data Acquisition

For optogenetic stimulation of CA1 during recording, a 300 µm core optical fiber was advanced through the craniotomy used to deliver virus to CA1 to a depth of 900 µm into the brain. Light pulses that were 1 ms and 1 mW (measured from the end of the fiber) were delivered via a 473 nm DPSS (diode pumped solid state) laser (as described above). To avoid photoelectric artifacts, neural activity was recorded with glass electrodes. LFP electrodes were pulled from borosilicate glass pipettes (e.g., available from Warner Instruments, Hamden, Conn.) on a filament-based micropipette puller (e.g., a P-97 FlamingBrown™ micropipette puller, available from Sutter Instrument Co., Novato, Calif.), to a fine tip, which was then manually broken back to a diameter of approximately 10-20 µm and then filled with sterile saline. For CA1 recordings the LFP electrode was advanced through the LFP recording craniotomy at an angle 60 degrees posterior to the coronal plane and 45 degrees inferior to the horizontal plane until clear electrophysiological signatures of the hippocampal stratum pyramidale layer were observed (approximately 600-1000 µV theta waves while the animal was running, clearly distinguishable SWR during immobility, multiple spikes greater than 150 µN, see, e.g., FIGS. 2A-2B). For visual cortex recordings the LFP electrode was advanced vertically through the LFP recording craniotomy to a depth of 600-900 µm and multiple spikes greater than 150 µV were observed. Data was acquired with a sampling rate of 20 kHz and bandpass filtered 1 Hz-1 kHz. Animals ran on the spherical treadmill or rested for prolonged periods. For optogenetic simulation sessions, data was recorded for 30 minutes before any stimulation began. Then stimulation was delivered at gamma (40 Hz), random (as described under optogenetic stimulation), or theta (8 Hz) frequency for 10 s periods interleaved with 10 s baseline periods (no stimulation). In two animals, stimulation of each type or baseline was delivered for 5 min periods instead of 10 s periods. Each 30 minutes of stimulation recordings were followed by 5-30 minutes of recording with no stimulation. For visual light flicker simulation sessions, LED strip lights surrounding the animal lights were flickered at gamma (40 Hz), random (described above in Visual stimulation protocol), theta (8 Hz), or 20 Hz frequency for 10 s periods, or were on continuously for 10 s periods, interleaved with 10 s periods with lights off. A few recordings were made above the brain surface during light flicker to ensure that the lights did not create electrical or photoelectric noise during recording. Recording sessions were terminated after approximately 3-5 hours. Animals were 3-4 months old at the time of recording. Analysis of electrophysiology recordings Spike Detection Spikes were detected by thresholding the 300-6000 Hz bandpassed signal. Threshold was the median of the filtered signal plus five times a robust estimator of the standard deviation of the filtered signal (median/0.675) to avoid contamination of the standard deviation measure by spikes (see, e.g., Rossant et al., "Spike Sorting for Large, Dense Electrode Arrays," bioRxiv doi: dx_doi_org_10.1101_015198 (Feb. 16, 2015)).

Local Field Potential (LFP)

Recorded traces were downsampled to 2 kHz and then bandpass-filtered between 1 to 300 Hz.

Theta and SWR Detection

Activity across the hippocampal network changes markedly when animals run or sit quietly and these changes are often referred to as different network states. These network states are clearly distinguishable by the presence or absence of LFP oscillations in different frequency bands. When animals ran, large theta (4-12 Hz) oscillations in CA1 were observed as others have shown (see, e.g., FIG. 2A). When animals sat quietly, theta oscillations were no longer visible and SWRs, high frequency oscillations of 150-250 Hz that last around 50-100 ms and are associated with bursts of population activity (see, e.g., FIG. 2B), were recorded. SWRs were detected (see, e.g., FIGS. 4A, 4B, 5A, 5B, 6A, 6B, 7B, and 8) when the envelope amplitude of the filtered trace was greater than four standard deviations above the mean for at least 15 ms. The envelope amplitude was calculated by taking the absolute value of the Hilbert transform of the filtered LFP. It has been confirmed that results disclosed herein held when using a higher threshold for SWR detection, 6 standard deviations above the mean, which detects larger SWRs (see, e.g., FIGS. 6C and 7C). To detect theta (see, e.g., FIGS. 3A and 3C), the LFP was bandpass filtered for theta (4-12 Hz), delta (1-4 Hz), and beta (12-30 Hz) using an FIR equiripple filter. The ratio of theta to delta and beta ('theta ratio') was computed as the theta envelope amplitude divided by the sum of the delta and beta envelope amplitudes. Theta periods were classified as such when the theta ratio was greater than one standard deviation above mean for at least two seconds and the ratio reached a peak of at least two standard deviations above mean. Non-theta periods were classified as such when the theta ratio was less than one for at least two seconds. SWRs, theta periods, and non-theta periods were visually inspected to ensure that these criteria accurately detected SWRs, theta periods, and non-theta periods, respectively.

Power Spectrum

Spectral analysis was performing using multitaper methods (e.g., Chronux open source software, available from the Mitra Lab in Cold Spring Harbor Laboratory, Cold Spring Harbor, N.Y., time-bandwidth product=3, number of tapers=5). For examining power spectra without stimulation (see, e.g., FIGS. 3A and 3C), only theta periods were included: theta periods greater than 5 seconds long were divided into 5 second trials and the average power spectral density was computed for each animal over these trials. For examining power spectra during optogenetic (see, e.g., FIGS. 13A and 6C) and visual stimulation (see, e.g., FIGS. 43B and 43C), data was divided into 10 second trials of each stimulation condition or baseline periods, and the average power spectral density was computed for each animal over these trials.

Gamma During SWRs

Spectrograms were computed using multitaper methods (e.g., Chronux open source software, available from the Mitra Lab in Cold Spring Harbor Laboratory, Cold Spring Harbor, N.Y.). The spectrogram was computed for each SWR including a window of 400 ms before and after the peak of the SWR. Then a z-scored spectrogram was computed in each frequency band using the mean and standard deviation of the spectrogram computed across the entire recording session to create a normalized measure of power in units of standard deviation (see, e.g., FIGS. 4A, 4B, 5A, and 5B). Instantaneous frequency of gamma oscillations during SWRs was computed by bandpass filtering the LFP for 10-50 Hz, taking the Hilbert transform, then taking the reciprocal of the difference in peaks of the transformed signal (see, e.g., FIGS. 4A, 5A, and 6B). Gamma power before, during, and after SWRs was computed by filtering the LFP for low gamma (20-50 Hz) and taking the amplitude of the envelope of the Hilbert transform to get the mean gamma power in 100 ms bins centered on the SWR peak. This was normalized by the mean and standard deviation of the amplitude of the envelope for the entire recording session to get z-scored gamma power for each bin around each SWR (see, e.g., FIGS. 6A and 7B). Phase modulation by gamma during SWRs was computed by bandpass filtering the LFP for gamma (20-50 Hz), taking the Hilbert transform, and determining the phase of the resulting signal for each spike that occurred during SWRs (see, e.g., FIG. 7E). To measure differences in phase modulation between 5XFAD and WT animals, resampling was used with replacement: a subset of 100 spikes from each recording was randomly selected to create a phase modulation distribution and this was repeated 500 times for each recording (see, e.g., FIGS. 6C and 7A). The depth of modulation was then measured for the spike-gamma phase distribution by computing the difference between the peak and trough divided by the sum of the peak and trough for each distribution (see, e.g., FIGS. 6C and 7A). Differences in firing during stimulation: To plot stimulus-evoked multiunit firing histograms, spikes were binned in 2.5 ms bins for the 100 ms after the start of each light on pulse and the fraction of spikes in each bin was computed. Mean and SEM was then computed across all light on periods. To compute differences in multi-unit firing rate between conditions, firing rates were computed for each 10 second period of stimulation or baseline (total number of spikes divided by duration of period). Differences in firing rate were taken between nearby periods of the relevant type of stimulation (firing rate in gamma stimulation period minus baseline or random periods for optogenetic stimulation, firing rate in gamma stimulation period minus baseline, continuous on, or random periods for light flicker stimulation). Differences from all animals were plotted in histograms (see, e.g., FIGS. 14A and 44A) and the median and quartiles of differences per animals were plotted in box plots (see, e.g., FIGS. 13B and 44A).

Immunohistochemistry

Mice were perfused with 4% paraformaldehyde under deep anesthesia, and the brains were post-fixed overnight in 4% paraformaldehyde. Brains were sectioned at 40 µm using a vibratome (e.g., Leica VT100S, available from Leica Biosystems, Buffalo Grove, Ill.). Sections were permeabilized and blocked in PBS containing 0.2% Triton X-100 and 10% normal donkey serum at room temperature for one hour. Sections were incubated overnight at 4° C. in primary antibody in PBS with 0.2% Triton X-100 and 10% normal donkey serum. Primary antibodies were anti-EEA1 (BD Transduction Laboratories™ EEA1 (641057), available from BD Biosciences, San Jose, Calif.), anti-β-amyloid (e.g., β-amyloid (D54D2) XP®, available from Cell Signaling Technology, Danvers, Mass.), anti-Iba1 (e.g., 019-19741, available from Wako Chemicals, Richmond, Va.), anti-parvalbumin (e.g., ab32895, available from Abcam, Cambridge, Mass.), anti-Rab5 (ADI-KAp-GP006-E, available from Enzo Life Sciences Inc., Farmingdale, N.Y.). To confirm ELISA experiments, the anti-Aβ antibody D54D2 was used because it allowed for co-labeling with EEA1 and the anti-Aβ antibody 12F4 was used because it does not react with APP allowing a determination as to whether the labeling was specific to Aβ. For co-labeling experiments, the anti-Aβ antibody 12F4 (805501, available from BioLegend, San Diego, Calif.) was used. Primary antibodies were visualized with Alexa-Fluor 488 and Alex-Fluor 647 secondary antibodies (Molecular Probes), neuronal nuclei with Hoechst 33342 (94403, available from Sigma-Aldrich, St. Louis, Mo.). Images were acquired using a confocal microscope (LSM 710; Zeiss™) at identical settings for all conditions. Images were quantified using ImageJ 1.42q by an experimenter blind to treatment groups. For each experimental condition, at least 2 coronal sections from at least 3 animals were used for quantification. For hippocampal CA1 imaging, the analysis was restricted to the pyramidal cell layer, except in the case of Iba1+ cells analysis, where the whole field of view was required to image an adequate number of cells. ImageJ was used to measure the diameter of Iba1+ cell bodies and to trace the processes for length measurement. In addition, the Coloc2 plug-in was used to measure co-localization of Iba1 and Aβ. Imaris ×64 8.1.2 (available from Bitplane, Belfast, United Kingdom) was used for 3-D rendering. For counting the "plaque number," deposits greater than or equal to 10 μm were included.

Clarity

Fixed brains were sliced into 100 uM coronal sections on a vibratome (e.g., Leica VT100S, available from Leica Biosystems, Buffalo Grove, Ill.) in 1×PBS. Sections containing visual cortex were selected, with reference to the Allen Mouse Brain Atlas, and incubated in clearing buffer (pH 8.5-9.0, 200 mM sodium dodecylsulfate, 20 mM lithium hydroxide monohydrate, 4 mM boric acid in ddH2O) for 2 hours, shaking at 55° C. Cleared sections were washed 3×10 mins in 1×PBST (0.1% Triton-X100/1×PBS) and put into blocking solution (2% bovine serum albumin/1×PBST) overnight, shaking at RT. Subsequently, three one hour washes in 1×. PBST were performed, shaking at RT. Sections were then incubated at 4° C. for 2 days, shaking, with anti-β-amyloid (805501, available from BioLegend, San Diego, Calif.) and anti-Iba1 (Wako Chemicals, Richmond, Va.; 019-19741) primary antibodies, diluted to 1:100 in 1×PBST. Another set of 3×1 h washes in 1×PBST was conducted before sections were incubated for 9 hours, shaking at RT, in 1:100 1×PBS diluted secondary antibody mixture. Fragmented Donkey Anti-Rabbit Alexa Fluor® 488 (ab175694) and Anti-Mouse 568 (ab150101) secondary antibodies (both available from Abcam, Cambridge, Mass.) were used to visualize the primary antibody labeling. Halfway through this incubation period, Hoechst 33258 (Sigma-Aldrich; 94403) was spiked into each sample at a 1:250 final dilution. Sections were then washed overnight in 1×PBS, shaking at RT. Prior to mounting for imaging, slices were incubated in RIMS (Refractive Index Matching Solution: 75 g Histodenz, 20 mL 0.1M phosphate buffer, 60 mL ddH2O) for one hour, shaking at RT. Tissue sections were mounted onto microscopy slides with coverslips (e.g., VistaVision™, available from VWR International, LLC, Radnor, Pa.) using Fluoromount G Mounting Medium (Electron Microscopy Sciences, Hatfield, Pa., USA). Images were acquired on a Zeiss™ LSM 880 microscope with the accompanying Zen Black 2.1 software (Carl Zeiss Microscopy, Jena, Germany). Section overview and cellular level images used for 3-D reconstruction were taken using a Plan-Apochromat 63×/1.4 Oil DIC objective. Imaris ×64 8.1.2 (Bitplane™ (Zurich, Switzerland) was used for 3-D rendering and analysis.

Western Blot

Hippocampal CA1 whole cell lysates were prepared using tissue from three-month-old male 5XFAD/PV-Cre mice. Tissue was homogenized in 1 ml RIPA (50 mM Tris HCl pH 8.0, 150 mM NaCl, 1% Np-40, 0.5% sodium deoxycholate, 0.1% SDS) buffer with a hand homogenizer (Sigma-Aldrich (St. Louis, Mo.)), incubated on ice for 15 min, and rotated at 4° C. for 30 min. Cell debris was isolated and discarded by centrifugation at 14,000 rpm for 10 minutes. Lysates were quantitated using a nanodrop and 25 μg protein was loaded on a 10% acrylamide gels. Protein was transferred from acrylamide gels to PVDF membranes (e.g., Invitrogen™, available from Thermo Fisher Scientific, Waltham, Mass.) at 100 V for 120 min. Membranes were blocked using bovine serum albumin (5% w/v) diluted in TBS: Tween. Membranes were incubated in primary antibodies overnight at 4° C. and secondary antibodies at room temperature for 90 minutes. Primary antibodies were anti-APP (Invitrogen™ PAD CT695, available from Thermo Fisher Scientific, Waltham, Mass.), anti-APP (A8967, available from Sigma-Aldrich, St. Louis, Mo.), anti-β-Actin (ab9485, available from Abcam, Cambridge, Mass.). Secondary antibodies were horseradish peroxidase-linked (e.g., available from GE Healthcare, Marlborough, Mass.). Signal intensities were quantified using ImageJ 1.46a and normalized to values of β-actin. Tau protein solubility was examined using sequential protein extraction. The detergent insoluble tau fraction was probed using an antibody against Tau5 (e.g., AHB0042, available from Thermo Fisher Scientific, Waltham, Mass.).

ELISA

Hippocampal CA1 or VC was isolated from male mice, lysed with PBS or 5M Guanidine HCl, and subjected to Aβ measurement with the use of mouse/human $A\beta_{1-40}$ or $A\beta_{1-42}$ ELISA kit (e.g., Invitrogen™ available from Thermo Fisher Scientific, Waltham, Mass.) according to the manufacturer's instructions. The tissue was lysed in phosphate-buffered saline (PBS) to extract the PBS soluble Aβ fraction. The soluble Aβ fraction likely contained monomeric and oligomeric Aβ Tissue was further treated with guanidine hydrochloric acid (HCl) to extract the insoluble Aβ fraction.

Genome-Wide RNA Sequencing

Total RNA was extracted from hippocampal CA1 isolates using the RNeasy kit (available from Qiagen, Hilden, Germany). Purified mRNA was used for RNA-seq library preparation using the BIOO NEXTflex™ kit (BIOO#5138-08) as per the manufacturer's instructions. Briefly, 1 μg of total mRNA was subject to a sequential workflow of poly-A purification, fragmentation, first flex strand and second strand synthesis, DNA end-adenylation, and adapter ligation. The libraries were enriched by 15 cycles of PCR reactions and cleaned with Agencourt® AMPure XP magnetic beads (available from Beckman Coulter Genomics, Danvers, Mass.). The quality of the libraries was assessed using an Advanced Analytical-fragment Analyzer. The barcoded libraries were equally mixed for sequencing in a single lane on the Illumina HiSeq 2000 platform at the MIT BioMicro Center (Massachusetts Institute of Technology, Cambridge, Mass.). The raw fastq data of 50-bp single-end sequencing reads were aligned to the mouse mm9 reference genome using TopHat 2.0 software (available from the Center for Computational Biology at Johns Hopkins University, Baltimore, Md., for aligning RNA-seq reads to mammalian-sized genomes using an ultra-high-throughput short read aligner Bowtie, and then analyzing the mapping results to identify splice junctions between exons). The mapped reads were processed by Cufflinks 2.2 software (available from the Trapnell Lab at the University of Washington, Seattle, Wash.) with UCSC mm9 reference gene annotation to estimate transcript abundances, and test for differential expression. Relative abundance of transcript was measured by Fragments Per Kilobase of exon per Million fragments mapped (FPKM). Gene differential expression test between treated and untreated groups was performed using the Cuffdiff module (for finding significant changes in transcript expression, splicing, and promoter use, included as part of Cufflinks 2.2 software (available from the Trapnell Lab at the University of Washington, Seattle, Wash.)) with an adjusted p-value<0.05 for statistical significance (GEO accession: GSE77471).

To understand the cellular and molecular mechanisms from the RNA-seq data, 14 of publicly available RNA-seq datasets were processed for cell-type specific analysis. Additionally, 60 publicly available neuron-, microglia-, and macrophage-specific RNA-seq datasets under different chemical and genetic perturbations were downloaded and processed using TopHat Cufflinks 2.2 software (available from the Trapnell Lab at the University of Washington, Seattle, Wash.) for GSEA statistical analysis. Gene set enrichment analysis (GSEA) was used to determine whether a defined gene set from the RNA-seq data is significantly enriched at either direction of a ranked gene list from a particular perturbation study. Genes detected in the public RNA-seq datasets were ranked by log 2 values of fold change (case versus control), from positive to negative values. A defined gene set (in this case, up- or down-regulated genes upon gamma treatment) was considered significantly correlated with a perturbation-induced transcriptomic changes (either up- or down-regulation), when both nominal p-value and FDR q-value were less than 0.05. The sign of calculated normalized enrichment score (NES) indicates whether the gene set is enriched at the top or the bottom of the ranked list. The heatmap for differentially expressed genes was generated using a custom R script, and z-score values across all libraries for each gene were calculated based on the gene FPKM values. The box plots for cell-type specificity analysis were also generated by R program, based on gene FPKM values.

Quantitative RT-PCR

The CA1 was isolated from the hippocampus of three-month-old male 5XFAD/PV-Cre mice. Tissue was rapidly frozen using liquid nitrogen and stored at −80° C., and RNA extracted using the RNeasy kit according to the manufacturer's protocol (Qiagen (Hilden, Germany)). RNA (3 µg) was DNase I treated (4 U, Worthington Biochemical Corporation (Lakewood, N.J.), purified using RNA Clean and Concentrator-5 Kit (Zymo Research (Irvine, Calif.)) according to manufacturers' instructions and eluted with 14 µl DEPC-treated water. For each sample, 1 µg RNA was reverse transcribed in a 20 µl reaction volume containing random hexamer mix and Superscript III reverse transcriptase (50 U, Invitrogen™ available from Thermo Fisher Scientific, Waltham, Mass.) at 50° C. for one hour. First strand cDNAs were diluted 1:10 and 1 µl were used for RT-qPCR amplification in a 20 µl reaction (SsoFast™ EvaGreen® Supermix, Bio-Rad) containing primers (0.2 µM). Relative changes in gene expression were assessed using the $2^{-\Delta\Delta C_t}$ method.

Isolation of microglia from visual cortex. The V1 region was rapidly dissected and placed in ice cold Hanks' Balanced Salt Solution (HBSS) (Gibco™ 14175-095, available from Life Technologies). The tissue was then enzymatically digested using the Neural Tissue Dissociation Kit (P) (130-092-628, Miltenyi Biotec, Cambridge, Mass.) according to the manufacturer's protocol, with minor modifications. Specifically, the tissue was enzymatically digested at 37° C. for 15 minutes instead of 35 minutes and the resulting cell suspension was passed through a 40 µm cell strainer (352340, Falcon Cell Strainers, Sterile, Corning, N.Y.) instead of a MACS® SmartStrainer, 70 µm. The resulting cell suspension was then stained using allophycocyanin (APC)-conjugate CD11b mouse clone M1/70.15.11.5 (130-098-088, Miltenyi Biotec, Cambridge, Mass.) and phycoerythrin (PE)-conjugated CD45 antibody (e.g., BD Pharmingen™, 553081). Fluorescence-activated cell sorting (FACS) was then used to purify CD11b and CD45 positive microglial cells. The cells were sorted directly into 1×PBS (see, e.g., FIG. 52A).

Statistics

For electrophysiological data that was not normally distributed, results are presented as medians and quartiles unless otherwise noted. Two-sided Wilcoxon rank sum tests for equal medians were performed to determine if distributions were significantly different or Wilcoxon signed rank tests were performed to determine if distributions were significantly different from zero as these do not assume data is normally distributed. Variability was similar between the groups that were statistically compared. The Bonferroni method was used to correct for multiple comparisons. Molecular and biochemical results are presented as mean and SEM. Percentages stated in the disclosure are group means. All statistical analysis was performed using Prism GraphPad software (GraphPad software Inc., La Jolla, Calif.). Normality was determined using the D'Agostino & Pearson omnibus normality test. Variability was similar between the groups that were statistically compared. Comparison data for normally distributed data consisting of two groups was analyzed by two-tailed unpaired t tests. Comparison of data for normally distributed data consisting of three or more groups was analyzed by one-way ANOVA followed by Tukey's multiple comparisons test. Comparison data for non-normally distributed data was carried out using Mann Whitney tests. The statistical test, exact P values, and sample size (n) for each experiment is specified in the figure legend. Molecular and biochemical analysis was performed using a minimum of three biological replicates per condition.

Auditory Gamma Stimulus Generation

The following script composed in the MATLAB® programming language (available from MathWorks, Natick, Mass.) illustrates one way to generate an auditory click-train stimulus in accordance with some embodiments:

```
click_freq=input('Specify Number of Clicks Per Second: ');%Obtain desired
    number of clicks per second from the keyboard
click_duration =input('Specify Click Duration in Milliseconds: ');%Obtain
    desired click duration from the keyboard
sound_freq=input('Specify Sound Frequency in Hertz: ');%Obtain desired sound
    frequency in Hertz from the keyboard
sound_duration =input ('Specify Sound Duration in Seconds: ');%Obtain desired
    sound duration from the keyboard
%audio_sample_rate=input ('Specify Audio Sample Rate in Hertz: ');%Obtain
    desired audio sample rate from the keyboard
audio_file_name =input ('Specify Audio File Name and Extension: ');%Obtain
    desired audio file name from the keyboard
rfreq=2*pi*sound_freq;%Convert sound frequency to radian frequency
%% audio_sample_rate = double(sound_freq*8);
%%
%% if audio_sample_rate < 8192
%%    audio_sample_rate = 8192
%% end
audio_sample_rate = 200000;
```

-continued

```
%Ts=linspace (0, sound_duration,audio_sample_rate*sound_duration);%Specify
    sample times over 4 seconds (default sample rate in 8192 Hz)
Ts=0:1/audio_sample_rate:sound_duration;
sound_signal=cos(rfreq*Ts);%Calculate the cosine for the entire sound duration
pulse_width = click_duration/1000;% pulse width
D_1 = pulse width/2:1/click_freq:max(Ts);% 50Hz repetition freq; note: starting
    D at width/2 instead of 0 to shift the pulse train to the right by width/2 and
    thus start the train at 0
pulse_train_mask = pulstran(Ts, D_1, 'rectpuls', pulse_width):
%Mask the sound signal with the pulse train mask
sound_signal_masked = sound_signal.*pulse_train_mask;
%Play the click sound
soundsc(sound_signal_masked, audio_sample_rate);
%Save the audio file
audiowrite(audio_file_name, sound_signal_masked, audio_sample_rate);
```

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will see, e.g., the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method for treating Alzheimer's disease in a subject in need thereof, the method comprising:
   inducing synchronized gamma oscillations in at least one brain region of the subject, wherein inducing synchronized gamma oscillations comprises non-invasively delivering a visual or auditory signal having a frequency of approximately 35 Hz to approximately 45 Hz to the subject to treat Alzheimer's disease.

2. The method of claim 1, wherein the synchronized gamma oscillations have a frequency of about 40 Hz.

3. The method of claim 1, wherein delivering the visual or auditory signal to the subject to treat Alzheimer's disease comprises inducing the synchronized gamma oscillations in a cell-type specific manner.

4. The method of claim 3, wherein delivering the visual or auditory signal to the subject to treat Alzheimer's disease comprises inducing synchronized activation of fast-spiking-parvalbumin (FS-PV)-interneurons.

5. The method of claim 1, wherein delivering the visual or auditory signal to the subject to treat Alzheimer's disease comprises inducing the synchronized gamma oscillations in a brain-region specific manner.

6. The method of claim 5, wherein delivering the visual or auditory signal to the subject to treat Alzheimer's disease comprises inducing synchronized activation in at least one of the hippocampus region and a sensory cortex region.

7. The method of claim 6, wherein the sensory cortex region comprises the visual cortex or the auditory cortex.

8. The method of claim 1, wherein the subject is a human.

9. The method of claim 1, wherein delivering the visual or auditory signal to the subject to treat Alzheimer's disease comprises maintaining or reducing an amount of amyloid-β (Aβ) peptide in at least one brain region of the subject, and wherein the Aβ peptide includes at least one of isoform $A\beta_{1-40}$ peptide and isoform $A\beta_{1-42}$ peptide.

10. The method of claim 9, wherein the Aβ peptide includes at least one of soluble Aβ peptide and insoluble Aβ peptide.

11. The method of claim 1, wherein delivering the visual or auditory signal to the subject to treat Alzheimer's disease comprises reducing production of Aβ peptide in the at least one brain region of the subject.

12. The method of claim 11, wherein delivering the visual or auditory signal to the subject to treat Alzheimer's disease comprises reducing an amount of at least one of C-terminal fragments (CTFs) and N-terminal fragments (NTFs) of amyloid precursor protein (APP) in the at least one brain region of the subject.

13. The method of claim 12, wherein delivering the visual or auditory signal to the subject to treat Alzheimer's disease comprises reducing cleavage of APP into CTFs and NTFs by at least one of β-secretase (BACE1) and γ-secretase in the at least one brain region of the subject.

14. The method of claim 11, wherein delivering the visual or auditory signal to the subject to treat Alzheimer's disease comprises reducing a number of endosomes in the at least one brain region of the subject.

15. The method of claim 14, wherein the endosomes are positive for at least one of early endosomal antigen 1 (EEA1) and Ras-related protein encoded by the RAB5A gene (Rab5).

16. The method of claim 1, wherein delivering the visual or auditory signal to the subject to treat Alzheimer's disease comprises promoting clearance of Aβ peptide in the at least one brain region of the subject.

17. The method of claim 16, wherein delivering the visual or auditory signal to the subject to treat Alzheimer's disease comprises increasing uptake of Aβ peptide by microglia in the at least one brain region of the subject.

18. The method of claim 1, wherein delivering the visual or auditory signal to the subject to treat Alzheimer's disease comprises upregulating at least one differentially expressed gene involved in the activity of the microglial cells in the at least one brain region of the subject.

19. The method of claim 18, wherein the at least one differentially expressed gene includes at least one of Nr4a1, Arc, Npas4, Cd68, B2m, Bsr2, Icam1, Lyz2, Irf7, Spp1, Csf1r, and Csf2ra.

20. The method of claim 1, wherein delivering the visual or auditory signal to the subject to treat Alzheimer's disease comprises increasing a number of microglial cells, inducing a morphologic change in the microglial cells consistent with a neuroprotective state, or promoting activity of the microglial cells in at least one brain region of the subject, wherein the morphologic change in the microglial cells consistent with the neuroprotective state includes at least one of an increase in cell body size and a decrease in process length.

21. The method of claim 1, wherein delivering the visual or auditory signal to the subject comprises: stimulating the subject with a plurality of light pulses, thereby inducing synchronized gamma oscillations in the visual cortex of the subject; or stimulating the subject with a plurality of sound pulses, thereby inducing the synchronized gamma oscillations the hippocampus and/or auditory cortex of the subject.

22. The method of claim 1, wherein delivering the visual or auditory signal to the subject comprises delivering the visual or auditory signal for about one hour.

23. The method of claim 1, wherein delivering the visual or auditory signal to the subject comprises repeatedly delivering the visual or auditory signal at least once per day over a time period, the time period being at least one of 2 days, 3 days, 4 days, 5 days, 6 days, one week, two weeks, three weeks, and one month.

24. A method for treating Alzheimer's disease in a subject in need thereof, the method comprising:
non-invasively delivering a visual or auditory signal having a frequency of approximately 35 Hz to approximately 45 Hz to the subject via a stimulus-emitting device so as to induce synchronized gamma oscillations in the at least one brain region of the subject to treat Alzheimer's disease.

25. The method of claim 24, wherein the stimulus-emitting device is at least one of a haptic device, a light-emitting device, and a sound-emitting device.

26. The method of claim 25, wherein:
the stimulus-emitting device is at least one of the light-emitting device and the sound-emitting device;
the light-emitting device includes a light occlusion device for reducing ambient light to at least one eye of the subject, the light occlusion device comprising a light-emitting unit for emitting the visual signal to the at least one eye of the subject so as to induce the synchronized gamma oscillations in at least one of the visual cortex and the hippocampus of the subject; and
the sound-emitting device includes a noise-canceling device for reducing ambient noise to at least one ear of the subject, the noise-canceling device comprising a speaker unit for emitting the auditory signal to the at least one ear of the subject so as to induce the synchronized gamma oscillations in at least one of the auditory cortex and the hippocampus of the subject.

27. The method of claim 1, wherein delivering the visual or auditory signal to the subject to treat Alzheimer's disease comprises reducing tau phosphorylation in at least one brain region of the subject.

28. The method of claim 24, wherein delivering the visual or auditory signal to the subject to treat Alzheimer's disease comprises one or more of:
a) maintaining or reducing an amount of amyloid-β (Aβ) peptide in at least one brain region of the subject;
b) increasing a number of microglial cells, inducing a morphologic change in the microglial cells consistent with a neuroprotective state, or promoting activity of the microglial cells in at least one brain region of the subject; and
c) reducing tau phosphorylation in at least one brain region of the subject.

* * * * *